US012779019B2

(12) United States Patent
Haaber et al.

(10) Patent No.: US 12,779,019 B2
(45) Date of Patent: Nov. 3, 2026

(54) **TREATING AND PREVENTING *E COLI* INFECTIONS**

(71) Applicant: SNIPR Biome ApS, Copenhagen Ø (DK)

(72) Inventors: Jakob Krause Haaber, Copenhagen Ø (DK); Szabolcs Semsey, Copenhagen Ø (DK); Mette Grove, Copenhagen Ø (DK); Birgitte Damholt, Copenhagen Ø (DK); Dziuginta Jasinskyte, Copenhagen Ø (DK); Yilmaz Emre Gençay, Copenhagen Ø (DK)

(73) Assignee: SNIPR BIOME APS, Copenhagen Ø (DK)

(*) Notice: Subject to any disclaimer, the term of this patent is extended or adjusted under 35 U.S.C. 154(b) by 243 days.

(21) Appl. No.: 18/778,686

(22) Filed: Jul. 19, 2024

(65) Prior Publication Data

US 2025/0049895 A1 Feb. 13, 2025

Related U.S. Application Data

(62) Division of application No. 17/812,359, filed on Jul. 13, 2022, now Pat. No. 12,076,375.

(30) Foreign Application Priority Data

Jun. 29, 2022 (GB) ...................................... 2209518

(51) Int. Cl.
*A61K 38/46* (2006.01)
*A61K 35/76* (2015.01)
*A61P 31/04* (2006.01)
*C12N 15/113* (2010.01)

(52) U.S. Cl.
CPC ............ *A61K 38/465* (2013.01); *A61K 35/76* (2013.01); *A61P 31/04* (2018.01); *C12N 15/113* (2013.01); *C12N 2310/20* (2017.05)

(58) Field of Classification Search
CPC ....... A61K 38/465; A61K 35/76; A61P 31/04; C12N 15/113; C12N 2310/20
See application file for complete search history.

(56) References Cited

U.S. PATENT DOCUMENTS

| | | | |
|---|---|---|---|
| 9,701,964 | B2 | 7/2017 | Clube et al. |
| 10,195,273 | B2 | 2/2019 | Clube |
| 10,300,138 | B2 | 5/2019 | Clube |
| 10,300,139 | B2 | 5/2019 | Clube |
| 10,363,308 | B2 | 7/2019 | Clube et al. |
| 10,463,049 | B2 | 11/2019 | Clube et al. |
| 10,506,812 | B2 | 12/2019 | Clube |
| 10,524,477 | B2 | 1/2020 | Clube et al. |
| 10,561,148 | B2 | 2/2020 | Clube |
| 10,582,712 | B2 | 3/2020 | Clube et al. |
| 10,596,255 | B2 | 3/2020 | Clube |
| 10,603,379 | B2 | 3/2020 | Clube et al. |
| 10,624,349 | B2 | 4/2020 | Clube |
| 10,751,427 | B2 | 8/2020 | Clube |
| 10,760,075 | B2 | 9/2020 | Sommer et al. |
| 10,765,740 | B2 | 9/2020 | Clube |
| 10,920,222 | B2 | 2/2021 | Sommer et al. |
| 10,953,090 | B2 | 3/2021 | Clube et al. |
| 11,141,481 | B2 | 10/2021 | Clube |
| 11,147,830 | B2 | 10/2021 | Clube |
| 11,291,723 | B2 | 4/2022 | Clube |
| 11,351,252 | B2 | 6/2022 | Clube |
| 11,400,110 | B2 | 8/2022 | Clube |
| 11,421,227 | B2 | 8/2022 | Sommer et al. |
| 11,471,530 | B2 | 10/2022 | Clube |
| 11,471,531 | B2 | 10/2022 | Clube et al. |
| 11,485,973 | B2 | 11/2022 | Sommer et al. |
| 11,517,582 | B2 | 12/2022 | Clube et al. |
| 11,547,716 | B2 | 1/2023 | Clube |
| 11,578,333 | B2 | 2/2023 | Martinez et al. |
| 11,612,617 | B2 | 3/2023 | Clube |
| 11,629,350 | B2 | 4/2023 | Martinez et al. |
| 11,642,363 | B2 | 5/2023 | Clube et al. |
| 11,643,653 | B2 | 5/2023 | Sommer et al. |
| 11,788,085 | B2 | 10/2023 | Sommer et al. |
| 11,844,760 | B2 | 12/2023 | Clube et al. |
| 11,851,663 | B2 | 12/2023 | Martinez et al. |
| 11,891,629 | B2 | 2/2024 | Clube |
| 11,931,426 | B2 | 3/2024 | Clube |
| 12,076,375 | B2 | 9/2024 | Haaber et al. |
| 2002/0001590 | A1 | 1/2002 | Kelly et al. |
| 2002/0044922 | A1 | 4/2002 | Mardh |
| 2002/0058027 | A1 | 5/2002 | Nelson et al. |
| 2016/0333348 | A1 | 11/2016 | Clube et al. |

(Continued)

FOREIGN PATENT DOCUMENTS

| | | | |
|---|---|---|---|
| WO | 2000/69269 | A1 | 11/2000 |
| WO | 2001/93904 | A1 | 12/2001 |

(Continued)

OTHER PUBLICATIONS

Beghain, J. et al. (Jul. 2018, e-pub. Jun. 19, 2018), "ClermonTyping: An Easy-To-Use and Accurate In Silico Method For *Escherichia* Genus Strain Phylotyping," Microbial Genomics 4:1-8.

(Continued)

*Primary Examiner* — Paul J Holland

(74) *Attorney, Agent, or Firm* — MORRISON & FOERSTER LLP

(57) ABSTRACT

The invention relates to methods and compositions for treating or preventing an infection by *E coli* cells in human or animal subjects. The method comprises administering to the subject a plurality of transduction particles that encode a nuclease for targeting the genomes of B2 phylogroup *E coli* cells.

24 Claims, 2 Drawing Sheets

Specification includes a Sequence Listing.

(56) References Cited

U.S. PATENT DOCUMENTS

| | | | |
|---|---|---|---|
| 2017/0196225 | A1 | 7/2017 | Clube et al. |
| 2017/0246221 | A1 | 8/2017 | Clube et al. |
| 2018/0064114 | A1 | 3/2018 | Clube |
| 2018/0064115 | A1 | 3/2018 | Clube et al. |
| 2018/0070594 | A1 | 3/2018 | Clube et al. |
| 2018/0084785 | A1 | 3/2018 | Clube |
| 2018/0084786 | A1 | 3/2018 | Clube |
| 2018/0140698 | A1 | 5/2018 | Clube et al. |
| 2018/0146681 | A1 | 5/2018 | Clube |
| 2018/0273940 | A1 | 9/2018 | Sommer et al. |
| 2018/0303934 | A1 | 10/2018 | Clube et al. |
| 2018/0326057 | A1 | 11/2018 | Clube et al. |
| 2018/0326093 | A1 | 11/2018 | Clube |
| 2019/0133135 | A1 | 5/2019 | Clube |
| 2019/0134194 | A1 | 5/2019 | Clube et al. |
| 2019/0160120 | A1 | 5/2019 | Haaber |
| 2019/0230936 | A1 | 8/2019 | Clube |
| 2019/0240325 | A1 | 8/2019 | Clube |
| 2019/0240326 | A1 | 8/2019 | Clube |
| 2019/0321468 | A1 | 10/2019 | Clube |
| 2019/0321469 | A1 | 10/2019 | Clube et al. |
| 2019/0321470 | A1 | 10/2019 | Clube |
| 2020/0030444 | A1 | 1/2020 | Clube |
| 2020/0046773 | A1 | 2/2020 | Borody |
| 2020/0068901 | A1 | 3/2020 | Clube et al. |
| 2020/0077663 | A1 | 3/2020 | Clube et al. |
| 2020/0085066 | A1 | 3/2020 | Clube |
| 2020/0087660 | A1 | 3/2020 | Sommer et al. |
| 2020/0115716 | A1 | 4/2020 | Martinez et al. |
| 2020/0121787 | A1 | 4/2020 | Clube |
| 2020/0128832 | A1 | 4/2020 | Clube et al. |
| 2020/0164070 | A1 | 5/2020 | Clube |
| 2020/0205416 | A1 | 7/2020 | Clube |
| 2020/0254035 | A1 | 8/2020 | Haaber |
| 2020/0267992 | A1 | 8/2020 | Clube |
| 2020/0337313 | A1 | 10/2020 | Clube et al. |
| 2020/0390886 | A1 | 12/2020 | Clube |
| 2021/0009996 | A1 | 1/2021 | Sommer et al. |
| 2021/0060180 | A1 | 3/2021 | Clube |
| 2021/0113689 | A1 | 4/2021 | Clube |
| 2021/0145006 | A1 | 5/2021 | Clube |
| 2021/0147827 | A1 | 5/2021 | Clube |
| 2021/0147857 | A1 | 5/2021 | Clube |
| 2021/0163960 | A1 | 6/2021 | Martinez et al. |
| 2021/0189406 | A1 | 6/2021 | Martinez et al. |
| 2021/0198665 | A1 | 7/2021 | Sommer et al. |
| 2021/0230559 | A1 | 7/2021 | Clube |
| 2021/0238167 | A1 | 8/2021 | Glimcher et al. |
| 2021/0290654 | A1 | 9/2021 | Clube |
| 2021/0386773 | A1 | 12/2021 | Clube |
| 2022/0162270 | A1 | 5/2022 | Szabolcs |
| 2022/0233575 | A1 | 7/2022 | Clube et al. |
| 2022/0241318 | A1 | 8/2022 | Clube et al. |
| 2022/0259588 | A1 | 8/2022 | Sommer et al. |
| 2022/0273696 | A1 | 9/2022 | Clube |
| 2022/0275380 | A1 | 9/2022 | Porse |
| 2022/0282245 | A1 | 9/2022 | Sommer et al. |
| 2022/0290133 | A1 | 9/2022 | Sommer et al. |
| 2022/0362280 | A1 | 11/2022 | Clube |
| 2022/0387559 | A1 | 12/2022 | Haaber et al. |
| 2023/0193241 | A1 | 6/2023 | Clube et al. |
| 2023/0248822 | A1 | 8/2023 | Clube |
| 2023/0330167 | A1 | 10/2023 | Haaber |
| 2023/0364268 | A1 | 11/2023 | Clube |
| 2024/0082289 | A1 | 3/2024 | Clube et al. |
| 2024/0141365 | A1 | 5/2024 | Martinez et al. |

FOREIGN PATENT DOCUMENTS

| | | | |
|---|---|---|---|
| WO | 2002/07742 | A2 | 1/2002 |
| WO | 2019/243373 | A1 | 12/2019 |
| WO | 2021/092254 | A1 | 5/2021 |
| WO | 2022/063986 | A2 | 3/2022 |

OTHER PUBLICATIONS

Chen, S. et al. (Sep. 1, 2018). "Fastp: An Ultra-Fast All-In-One FASTQ Preprocessor," Bioinformatics 34(17):i884-i890.

Fagen, J.R. et al. (2017). "Advancing the Design and Delivery of CRISPR Antimicrobials," Current Opinion in Biomedical Engineering 4:57-64.

Flament-Simon, S.C. et al. (Apr. 4, 2020). "Clonal Structure, Virulence Factor-Encoding Genes and Antibiotic Resistance of *Escherichia coli*, Causing Urinary Tract Infections and Other Extraintestinal Infections in Humans in Spain and France During 2016," Antibiotics 9(161):1-17.

Gencay, Y. et al. (2023, e-pub. May 4, 2023). "Engineered Phage with Antibacterial CRISPR-Cas Selectively Reduce *E. coli* Burden in Mice," Nature Biotechnology, 23 pages.

Gibb, B. et al. (Jun. 30, 2021). "The Many Applications of Engineered Bacteriophages—An Overview," Pharmaceuticals 14(7):634, 19 pages.

Karch, H. et al. (Jul. 1999). "Epidemiology and diagnosis of Shiga toxin-producing *Escherichia coli* infections," Diagnostic Microbiology and Infectious Disease (34(3):229-243.

Letunic, I. et al. (2021, e-pub. Apr. 22, 2021). "Interactive Tree Of Life (iTOL) v5: An Online Tool For Phylogenetic Tree Display And Annotation," Nucleic Acids Research 49:W293-W296.

Matsushiro, A. et al. (Apr. 1999). "Induction Of Prophages Of Enterohemorrhagic *Escherichia coli* O157:H7 with Norfloxacin," Journal Of Bacteriology 181(7):2257-2260.

Nath, A et al. (May 17, 2022). "Phage Delivered CRISPR-Cas System to Combat Multidrug-Resistant Pathogens in Gut Microbiome," Biomedicine & Pharmacotherapy 151:113122, 13 pages.

Ondov, B.D. et al. (2016). "Mash: Fast Genome and Metagenome Distance Estimation Using MinHash," Genome Biol. 17:132, 14 pages.

Rousset, F. et al. (Nov. 7, 2018). "Genome-Wide CRISPR-dCas9 Screens in *E. coli* Identify Essential Genes and Phage Host Factors," PLO Genetics, pp. 1-28.

Safdar, N. et al. (Jun. 4, 2002). "The Commonality Of Risk Factors For Nosocomial Colonization and infection With Antimicrobial-Resistant *Staphylococcus aureus*, Enterococcus, Gram-Negative Bacilli, Clostridium difficile, and Candida," Ann. Intern. Med. 136(11):834-844.

Satlin, J.J. et al. (Dec. 1, 2018, e-pub. Nov. 13, 2018). "Colonization With Levofloxacin-Resistant Extended-Spectrum ß Lactamase-producing Enterobacteriaceae and Risk of Bacteremia in Hematopoietic Stem Cell Transplant Recipients," Clin. Infect. Dis. 67(11):1720-1728.

Satlin, M.J. et al. (Oct. 1, 2021, e-pub. May 6, 2021). "Colonization with Fluoroquinolone-Resistant Enterobacterales Decreases The Effectiveness Of Fluoroquinolone Prophylaxis In Hematopoietic Cell Transplant Recipients," Clin Infect Dis. 73(7):1257-1265.

Silva, J.B. (2016, e-pub. Jan. 10, 2016). "Host Receptors for Bacteriophage Adsorption," FEMS Microbiology Letters 363:1-11.

Simonsen, et al. (Oct. 2008). "Rapid Neighbour-Joining," Proceedings of the 8th Workshop in Algorithms in Bioinformatics (WABI), pp. 113-122.

Slutsker, L. et al. (Apr. 1998). "A Nationwide Case-Control Study Of *Escherichia coli* O157:H7 Infection In The United States," J. Infect. Dis. 177(4):962-966.

Souvorov, A. et al. (2018). "SKESA: Strategic K-Mer Extension For Scrupulous Assemblies," Genome Biology 19:153, 13 pages.

Tarr, P.I. et al. (Mar. 19-25, 2005). "Shiga-Toxin-Producing *Escherichia coli* and Haemolytic Uraemic Syndrome," Lancet 365(9464):1073-1086.

Wagner, P.L. (2002). "Bacteriophage Control of Shiga Toxin 1 Production and Release by *Escherichia coli*," Molecular Microbiology 44(4):957-970.

Wong, C.S. et al. (Jun. 29, 2000). "The Risk Of The Hemolytic-Uremic Syndrome After Antibiotic Treatment Of *Escherichia coli* O157:H7 Infections," N. Engl. J. Med. 342(26):1930-1936, 13 pages.

Yosef, I. et al. (Jun. 9, 2015). "Temperate and Lytic Bacteriophages Programmed To Sensitize and Kill Antibiotic-Resistant Bacteria," Proc. Natl. Acad. Sci. USA 112(23):7267-7272.

(56) References Cited

OTHER PUBLICATIONS

Zimmerhackl, L.B. (Jun. 29, 2000). "*E. coli*, Antibiotics, and The Hemolytic-Uremic Syndrome," N. Engl. J. Med. 342(26):1990-1991, 6 pages.

TREATING AND PREVENTING *E COLI* INFECTIONS

CROSS REFERENCE TO RELATED APPLICATIONS

This application is a divisional of U.S. application Ser. No. 17/812,359, filed on Jul. 13, 2022, which claims benefit of Great Britain Application No.: GB2209518.6, filed on Jun. 29, 2022, the disclosures of each of which are herein incorporated by reference in their entirety.

REFERENCE TO AN ELECTRONIC SEQUENCE LISTING

The content of the electronic sequence listing (786212001410seqlist.xml; Size: 181,625 bytes; and Date of Creation: Jul. 15, 2024) is herein incorporated by reference in its entirety.

TECHNICAL FIELD

The technology described herein relates to methods and compositions for treating or preventing an infection by *E coli* cells in human or animal subjects. The method comprises administering to the subject a plurality of transduction particles that encode a nuclease for targeting the genomes of B2 phylogroup *E coli* cells.

BACKGROUND

*E coli* infection has been identified as harmful or life-threatening in various settings, such as UTI infections, transplant patients, cancer patients and other patients that are immunocompromised or on immunosuppressant.

Nuclease targeting of *E coli*, such as by means of CRISPR/Cas systems, has been proposed with delivery using transduction particles that can target the nuclease to *E coli* cells for chromosomal or episomal cutting, thereby killing cells or reducing their growth or proliferation. Suitable transduction particles are phage or engineered particles (such as non-self-replicative transduction particles) comprising capsids that contain nucleic acid encoding at least crRNAs or gRNAs (or additionally a Cas nuclease) for targeting. Advantageously, selective targeting can be achieved which is not possible using conventional antibiotics, such as broad-spectrum antibiotics. Such selective targeting can avoid killing of beneficial species and strains in treated patients. Indeed, disturbances of the microbiome with broad-spectrum antibiotics is a risk-factor in the prophylactic management of cancer patients at risk of febrile neutropenia.

Bacteriophage (phage) therapy has been used prior to the broad availability of antibiotics, but has now re-gained interest due to the rise in bacterial antimicrobial resistance (AMR) combined with several successful individual case reports.

Bacteriophages (phages) are a phylum of viruses that infect bacteria, and are distinct from the animal and plant viruses. Phages can have either a “lytic” life cycle, a “lysogenic” life cycle that can potentially become lytic, or a “non-lytic” life cycle. Phages replicating through the lytic cycle cause lysis of the host bacterial cell as a normal part of their life cycles. Phages replicating through the lysogenic cycles are called temperate phages, and can either replicate by means of the lytic life cycle and cause lysis of the host bacterium, or they can incorporate their DNA into the host bacterial DNA and become noninfectious prophages.

The natural capability of phages to infect and kill bacteria, together with the specificity of the phage-bacterial interactions, is the basic phenomena on which the concept of phage therapy is built. Therefore, phages that possess lytic life cycle are suitable candidates for phage therapy.

International Patent Application No. WO 00/69269 discloses the use of certain phage strain for treating infections caused by Vancomycin-sensitive as well as resistant strains of *Enterococcus faecium*, and International Patent Application No. WO 01/93904 discloses the use of bacteriophage, alone or in combination with other anti-microbial means, for preventing or treating gastrointestinal diseases associated with the species of the genus *Clostridium*.

US Patent Application No. 2002/0001590 discloses the use of phage therapy against multi-drug resistant bacteria, specifically methicillin-resistant *Staphylococcus aureus*, and International Patent Application No. WO 02/07742 discloses the development of bacteriophage having multiple host range.

The use of phage therapy for the treatment of specific bacterial-infectious disease is disclosed, for example, in US Patent Application Nos. 2002/0044922; 2002/0058027 and International Patent Application No. WO 01/93904.

US20160333348 describes the use of CRISPR/Cas systems delivered to host bacterial cells using phage as vectors.

Amongst the several phylogroups of *E coli*, it has been observed that antibitic-resitant (eg, fluoroquinolone (FQ)-resistant) and multi-drug resistant (MDR) strains are frequently found in the B2 phylogroup. B2 strains ST131 and ST1193 have been found that are associated with antibiotic resistance. ST131 is a globally dominant multidrug resistant clone associated with high rates in rUTI. ST131 is a major contributor to hospital- and community-acquired UTI, as well as *E coli* bloodstream infections and infections in companion animals and poultry. Originally identified in 2008, ST131 is associated with the worldwide spread of the CTX-M-15 extended spectrum β-lactamase (ESBL) resistance gene. ST131 is now strongly associated with multidrug resistance (MDR), including resistance to fluoroquinolones. Recent reports have also identified strains that are resistant to last-line carbapenems. Sequence type 1193 has recently emerged as a new, virulent and resistant lineage among fluoroquinolone resistant *E coli*.

Classic antibiotics, such as FQ and broad-spectrum antibiotics are not, thus, sufficiently effective for combatting such infections. There is, therefore, a need to find alternative means to address these infections.

SUMMARY OF THE INVENTION

The invention provides means for treating or preventing B2 phylogroup *E coli* infections in humans and animals by combining the use of selective killing with nucleases targeted using specific types of transduction particles. The particles of the invention target by adhesion to LPS, LamB or Tsx, which has surprisingly been found highly advantageous for killing and inhibiting growth of B2 *E coli* cells of many different strains (including the potentially lethal ST131 and ST1193 strains). As exemplified herein, surprisingly more than 10 different ST131 strains were killed (plaques formed) and more than 10 different ST1193 strains were killed (plaques formed).

The invention finds utility, for example, to treat or prevent potentially life-threating B2 phylogroup *E coli* infections in patients, such as in immunosuppressed, cancer, transplant and UTI patients, who are susceptible to infection by B2 strains (and often by multiple different B2 strains). As demonstrated in the Examples, the invention is useful for preventing *E coli* B2 phylogroup bacteraemia (infection of the blood stream by *E coli*) in a subject.

To this end, the invention provides:

In a First Configuration

In a First Aspect:

A composition comprising a plurality of transduction particles for use in a method of treating or preventing an infection by *E coli* cells in a human or animal subject, wherein the method comprises administering the particles to the subject, wherein (a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

In a Second Aspect:

A composition comprising a plurality of transduction particles for use in a method of treating or preventing *E coli* bacteriaemia in a human or animal subject, wherein the method comprises administering the particles to the subject, wherein (a) each particle comprises a nucleic acid encoding a nuclease for targeting the genomes of cells of said *E coli*, wherein the said administered particles contact the cells and introduce therein the nucleic acid, wherein the nuclease is expressed in the cells and cuts genomic DNA of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

In a Second Configuration

In a First Aspect:

A method for treating or preventing an infection by *E coli* cells in a human or animal subject, the method comprising administering to the subject a plurality of transduction particles, wherein (a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

In a Second Aspect:

A method for treating or preventing an infection by *E coli* cells in a human or animal subject, the method comprising administering to the subject a plurality of transduction particles, wherein (a) each particle comprises a nucleic acid encoding a crRNA or guide RNA that is operable with a Cas nuclease for chromosomal targeting in the cells, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

In a Third Aspect:

A method for treating or preventing *E coli* bacteriaemia in a human or animal subject, the method comprising administering to the subject a plurality of transduction particles, wherein (a) each particle comprises a nucleic acid encoding a nuclease for targeting the genomes of cells of said *E coli*, wherein the said administered particles contact the cells and introduce therein the nucleic acid, wherein the nuclease is expressed in the cells and cuts genomic DNA of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

In a Fourth Aspect:

A method for treating or preventing *E coli* bacteriaemia in a human or animal subject, the method comprising administering to the subject a plurality of transduction particles, wherein (a) each particle comprises a nucleic acid encoding a crRNA or guide RNA that is operable with a Cas nuclease for chromosomal targeting in cells of said *E coli*, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

In a Third Configuration

In a First Aspect:

Use of a composition comprising a plurality of transduction particles in a method for treating or preventing an infection by phylogroup B2 *E coli* cells in a human or animal subject, the method comprising administering to the subject the composition, wherein (a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject; and (b) each particle comprises an adhesion moiety for recognising and binding to a cognate moiety selected from a LPS, LamB and Tsx displayed on the surface of the phylogroup B2 *E coli* cells.

In a Second Aspect:

Use of a composition comprising a plurality of transduction particles in a method for treating or preventing an infection by phylogroup B2 *E coli* cells in a human or animal subject, the method comprising administering to the subject the composition, wherein (a) each particle comprises a nucleic acid encoding a crRNA or guide RNA that is operable with a Cas nuclease for chromosomal targeting in the cells, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

In a Third Aspect:

Use of a composition comprising a plurality of transduction particles in a method for treating or preventing phylogroup B2 *E coli* bacteraemia in a human or animal subject, the method comprising administering to the subject the composition, wherein (a) each particle comprises a nucleic acid encoding a nuclease for targeting the genomes of cells of said *E coli*, wherein the said administered particles contact the cells and introduce therein the nucleic acid, wherein the nuclease is expressed in the cells and cuts genomic DNA of the cells, thereby killing the cells or reducing growth or proliferation of the cells in the subject; and (b) each particle comprises an adhesion moiety for recognising and binding to a cognate moiety selected from a LPS, LamB and Tsx displayed on the surface of the phylogroup B2 *E coli* cells.

In a Fourth Aspect:

Use of a composition comprising a plurality of transduction particles in a method for treating or preventing phylogroup B2 *E coli* bacteraemia in a human or animal subject, the method comprising administering to the subject the composition, wherein (a) each particle comprises a nucleic acid encoding a crRNA or guide RNA that is operable with a Cas nuclease for chromosomal targeting in cells of said *E coli*, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

DETAILED DESCRIPTION

Figure 1:
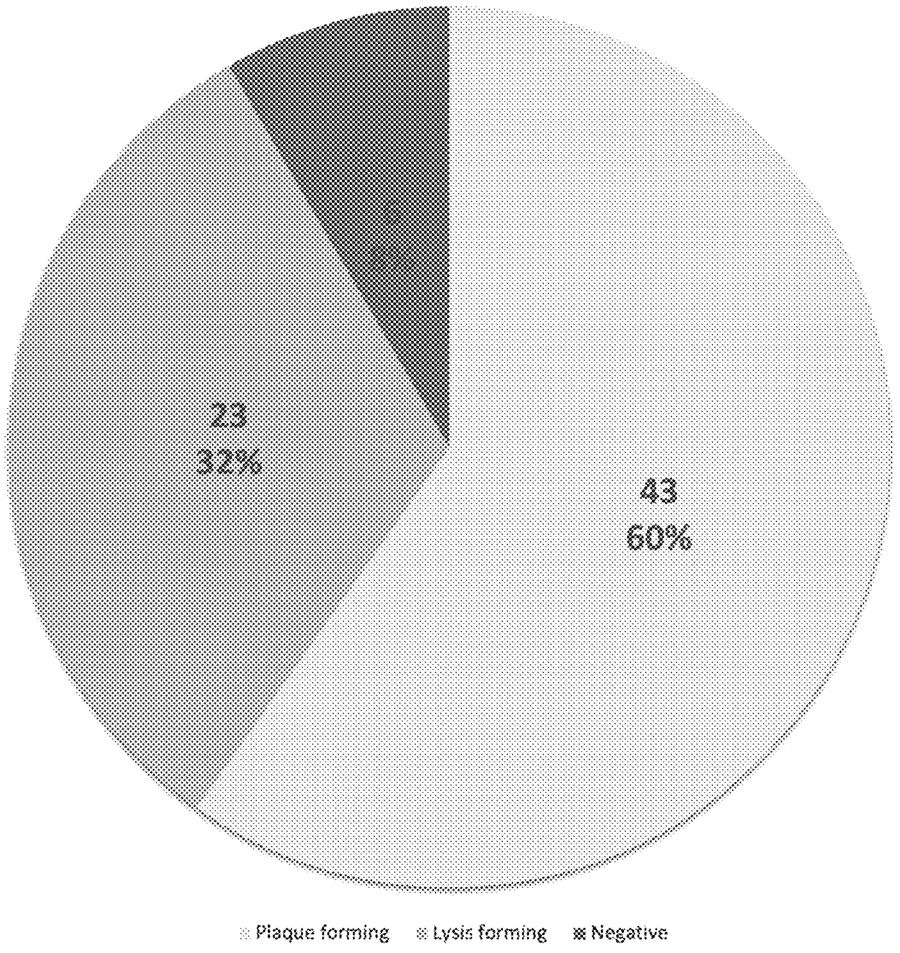
FIG. 1: Killing and growth inhibition activity of a composition of the invention when tested against *E coli* of several different phylogroups and different strains within each group (*E coli* taken from clinical samples); the composition was surprisingly highly effective at killing across many phylogroups (and particularly in the B2 phylogroup, where multiple strains-including those known to be potentially life-threatening and related with antibiotic resistance-were killed or whose growth was effectively inhibited). The 6 negatives comprised non *E coli* and non PQ resistant samples.

The invention finds application to combat harmful or life-threatening B2 *E coli* infections in various settings, such as UTI infections, transplant patients, cancer patients and other patients that are immunocompromised or on immunosuppressant.

Cancer treatment continues to advance and survival rates for people with hematological malignancies are increasing. However, this population is immunocompromised and chemotherapy regimens cause bone-marrow suppression and gastrointestinal mucositis with associated increased intestinal permeability. Translocation of gut bacteria, including *E coli*, from the gastrointestinal tract is a frequent cause of bloodstream infections (BSIs). The mortality-related to BSIs can be up to 50%; thus, antimicrobial prophylaxis is applied in people at risk of febrile neutropenia. There are no approved therapies for the prevention of BSIs in patients with hematological cancers, yet fluoroquinolones are used off-label in the United States. This antibiotic prophylaxis practice is at odds with the emerging paradigm that maintaining a normal microbiome is important for upholding immunological tonus potentially benefiting the outcome of oncology treatments. Indeed, disturbances of the microbiome with broad-spectrum antibiotics is a risk-factor in the prophylactic management of patients at risk of febrile neutropenia. Beyond the side effects of fluoroquinolones, including safety warnings and precautions, bacterial resistance is rising and approaching 60% in USA.

In immunocompromised patients with hematological malignancies at risk of developing neutropenia, *E coli* is responsible for 25.1-30% of all bacteraemia cases with a 35.8% 90-day mortality rate. Moreover, up to 65% of *E coli* isolated as the causative pathogen from BSIs in patients with hematological cancers undergoing hematopoietic stem cell transplantation (HSCT) were resistant to fluoroquinolones. Accordingly, novel narrow-spectrum treatment and prophylactic options are needed to prevent infections in these vulnerable patients. The invention addresses this need.

To this end, the invention provides compositions, methods and uses according to the above Configurations. There is, thus, provided the following description with numbered Embodiments.

1. A composition comprising a plurality of transduction particles for use in a method of treating or preventing an infection by *E coli* cells in a human or animal subject, wherein the method comprises administering the particles to the subject, wherein (a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of phylogroup B2 *E coli* cells.

2. A method for treating or preventing an infection by *E coli* cells in a human or animal subject, the method comprising administering to the subject a plurality of transduction particles, wherein the method comprises administering the particles to the subject, wherein (a) each particle comprises a nucleic acid encoding a nuclease for targeting the genomes of *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

Optionally, the genomic DNA is chromosomal DNA of the cells. Additionally or alternatively, the genomic DNA is plasmid DNA of the cells.

Optionally, each particle comprises a nucleic acid encoding a nuclease for chromosomal targeting, wherein the said administered particles contact the cells and introduce therein the nucleic acid, wherein the nuclease is expressed in the cells and cuts the chromosomes of the cells, thereby killing the cells or reducing growth or proliferation of the cells in the subject.

The human may be a male or female. The human may be an adult or child. The human may be 18 years of age or older, eg, 40, 50, 60, 70 80 or older. The human may be younger than 18, eg, a teenager, eg, a baby, eg, up to 5 years of age, eg, up to 2 years of age. The animal may be be a livestock or companion animal eg, a dog or cat). The animal may be a bird (eg, a poultry bird, eg, a chicken, turkey or duck, preferably a chicken), cow, sheep, goat or pig (eg, a neonatal swine or a swine under 6 months of age).

The infection may be a bloodstream infection. The infection may be a nosocomial infection.

In an example, each adhesion moiety is a tail fibre protein. In an example, each particle comprises a phage tail fibre that comprises or is fused to a said adhesion moiety. In an example, each adhesion moiety is an antibody fragment, eg, an antibody single variable domain. In an example, each adhesion moiety is a nanobody. In an example, each adhesion moiety comprises an antibody binding site that is capable of binding to the cognate moiety. For example, each adhesion moiety comprises an antibody single variable domain (ie, a dAb), such as a nanobody. In an example, each particle comprises one or more phage tail fibres or spikes, each fibre or spike comprising a said adhesion moiety.

For example, at least 2, 3 or 4 different types of said transduction particle are administered to the subject and each type comprises one or a plurality of types of tail fibres comprising adhesion moieties, wherein the other particle types do not comprise said one or plurality of tail fibre types. In an example, each type of said plurality of tail fibre types differs from the other types by the type of adhesion moiety it comprises.

Optionally, the particles comprise adhesion moieties for binding to LPS, LamB and Tsx. Optionally, the particles comprise adhesion moieties for binding to LamB and Tsx. Optionally, the particles comprise adhesion moieties for binding to LPS and Tsx. Optionally, the particles comprise adhesion moieties for binding to LPS and LamB.

In Gram-negative bacteria, the peptidoglycan layer is relatively thin and is located inward of the outer membrane, the major component of the cell wall. These two layers are connected by Braun's lipoproteins. The outer membrane is a sophisticated structure composed of a lipid bilayer ornamented with proteins, polysaccharides and lipids; the latter two molecules form the LPS layer. LPSs are complexes that consist of three parts: lipid A, the core polysaccharide and the O-polysaccharide. Lipid A is, in general, composed of fatty acids attached to glucosamine phosphate disaccharides. The core polysaccharide is connected to the lipid A through a ketodeoxyoctonate linker. The core polysaccharide and the O-polysaccharide (O-chain or O-antigen) contain several units of sugar residues extending outward to the outer membrane. Cells that contain all three components of the LPS are denominated as smooth(S) type and those that lack the O-polysaccharide portion are distinguished as rough (R) type.

Optionally, the LPS is smooth LPS or rough LPS.

For example, the particles comprise at least one type of particle whose adhesion moiety is capable of binding to O-antigen of LPS.

*E coli* is a very versatile species for which diversity has been explored from various perspectives highlighting, for example, phylogenetic groupings, pathovars as well as a wide range of O serotypes. The highly variable O-antigen, the most external part of the lipopolysaccharide component of the outer membrane of *E coli*, is linked to the innermost lipid A through the core region of LPS of which 5 different structures, denominated K-12, R1, R2, R3 and R4, have been characterized so far. Phylogroups B2 and C strains are mainly dominated by the R1 type. Strains within phylogroup B2 may carry a K-12 core, eg, belonging to the complex STc131, one of the major clone of extra-intestinal pathogenic *E coli* (ExPEC) strains.

Preferably, the LPS comprises a R1 core region. In an example, the LPS comprises a R2 core region. In an example, the LPS comprises a R3 core region. In an example, the LPS comprises a R4 core region. In an example, the LPS comprises a K-12 core region.

Optionally, the LamB comprises the amino acid of SEQ ID NO: 1 or an amino acid sequence that is at least 70, 80, 90 or 95% identical to SEQ ID NO: 1. Optionally, the Tsx comprises the amino acid of SEQ ID NO: 2 or an amino acid sequence that is at least 70, 80, 90 or 95% identical to SEQ ID NO: 2. Optionally, the LamB is encoded by the nucleotide sequence of SEQ ID NO: 3 or an amino acid sequence that is at least 70, 80, 90 or 95% identical to SEQ ID NO: 3. Optionally, the Tsx is encoded by the nucleotide sequence of SEQ ID NO: 4 or an amino acid sequence that is at least 70, 80, 90 or 95% identical to SEQ ID NO: 4.

The *Escherichia coli* tsx gene encodes an integral outer-membrane protein (Tsx) that functions as a substrate-specific channel for deoxynucleosides and the antibiotic albicidin. In an example, the Nucleoside-specific channel-forming protein Tsx of *E coli* has a Uniprot Accession Number of POA927 or is a homologue thereof. In an example, the maltose outer membrane porin (maltoporin) LamB of *E coli* has a Uniprot Accession Number of P02943 or is a homologue thereof.

Homologue: A gene, nucleotide or protein sequence related to a second gene, nucleotide or protein sequence by descent from a common ancestral DNA or protein sequence. The term, homologue, may apply to the relationship between genes separated by the event of or to the relationship between genes separated by the event of genetic duplication.

In an embodiment, the *E coli* cells comprise UPEC *E coli*. In an embodiment, the *E coli* cells comprise intestinal pathogenic *E coli* (ExPEC) cells.

3. The composition or method of Embodiment 1 or 2 respectively, wherein the method is for treating or preventing infection of the subject by an *E coli* strain selected from the group ST131, ST1193, ST648, ST315, ST405, ST361, ST88 and ST453.

In a preferred example, the strain is ST1193. In another preferred example, the strain is ST131.

4. The composition or method of any preceding Embodiment, wherein the method is for treating or preventing infection of the subject by a plurality of different phylogroup B2 strains of *E coli*; optionally wherein the plurality comprises *E coli* ST131 and ST1193 cells.

*E coli* ST131 and/or ST1193 have been found to be virulent and associated with fluoroquinolone resistance. As shown in the Example section herein, the invention is useful for treating or preventing infection by such strains. Optionally, said plurality of strains comprises *E coli* ST131 and/or ST1193 strains. Optionally, said plurality of strains comprises fluoroquinolone-resistant strains. For example, said plurality of strains comprises *E coli* ST131 and/or ST1193 fluoroquinolone-resistant strains. *E coli* strains B2-ST73 (CH24-30); B2-ST73 (CH24-103); B2-ST131 (CH40-30); B2-ST141 (CH52-5); B2-ST372 (CH103-9); B2-ST404 (CH14-27); B2-ST404 (CH14-807) and B2-ST1193 (CH14-64) have been found in UTI settings. In an embodiment (eg, wherein the subject is suffering from or at risk of UTI), the B2 *E coli* comprise one or more strains selected from B2-ST73 (CH24-30); B2-ST73 (CH24-103); B2-ST131 (CH40-30); B2-ST141 (CH52-5); B2-ST372 (CH103-9); B2-ST404 (CH14-27); B2-ST404 (CH14-807) and B2-ST1193 (CH14-64).

5. The composition or method of any preceding Embodiment, wherein the subject is a transplant or cancer patient (optionally a haematological cancer patient), or wherein the patient is suffering from or at risk of a urinary tract infection (UTI); and optionally wherein the transplant is a solid organ or stem cell transplant (optionally a haematopoietic cell transplant) or wherein the transplant is a transplant of a medical device.

For example, the subject is a haematological cancer patient suffering from neutropenia. For example, the subject is a haematopoietic stem cell transplant patient.

A suitable medical device may be, eg, heart device (eg, ventricular assist device, such as a left ventricular assist device (LVAD)), a catheter (eg, a biliary catheter) or a prosthesis (eg, a joint) prosthesis.

In an example, the patient is suffering from a sequestered B2 phylogroup *E coli* infection. In an example, the *E coli* are sequestered B2 phylogroup *E coli*.

For example, the subject is suffering from or at risk of acute bacterial sinusitis, pneumonia, urinary tract infections, chronic prostatitis or gastroenteritis caused by B2 phylogroup *E coli*. For example, the subject is a male human prostate surgery patient.

6. The composition or method of any preceding Embodiment, wherein the method is carried out prior to the subject receiving a transplant.

For example, the transplant is a solid organ or stem cell transplant (optionally a haematopoietic cell transplant).

7. The composition or method of any preceding Embodiment, wherein the B2 *E coli* cells comprise a strain of *E coli* that causes sepsis, septicaemia or diarrhoea in humans.

Enterohemorrhagic *Escherichia coli* (EHEC) serotype O157: H7 is a human pathogen responsible for outbreaks of bloody diarrhoea and haemolytic uremic syndrome (HUS) worldwide. Conventional antimicrobials trigger an SOS response in EHEC that promotes the release of the potent Shiga toxin that is responsible for much of the morbidity and mortality associated with EHEC infection. Cattle are a natural reservoir of EHEC, and approximately 75% of EHEC outbreaks are linked to the consumption of contaminated bovine-derived products. EHEC causes disease in humans but is asymptomatic in adult ruminants. Characteristics of *E. coli* serotype O157: H7 (EHEC) infection includes abdominal cramps and bloody diarrhoea, as well as the life-threatening complication haemolytic uremic syndrome (HUS). Currently there is a need for a treatment for EHEC infections (Goldwater and Bettelheim, 2012). The use of conventional antibiotics exacerbates Shiga toxin-mediated cytotoxicity. In an epidemiology study conducted by the Centers for Disease Control and Prevention, patients treated with antibiotics for EHEC enteritis had a higher risk of developing HUS (Slutsker et al., 1998). Additional studies support the contraindication of antibiotics in EHEC infection; children on antibiotic therapy for hemorrhagic colitis associated with EHEC had an increased chance of developing HUS (Wong et al., 2000; Zimmerhackl, 2000; Safdar et al., 2002; Tarr et al., 2005). Conventional antibiotics promote Shiga toxin production by enhancing the replication and expression of stx genes that are encoded within a chromosomally integrated lambdoid prophage genome. The approach of the present invention may rely on nuclease cutting of target cell genomic DNA. Stx induction also promotes phage-mediated lysis of the EHEC cell envelope, allowing for the release and dissemination of Shiga toxin into the environment (Karch et al., 1999; Matsushiro et al., 1999; Wagner et al., 2002). Thus, advantageously, the invention provides alternative means for treating B2 phylogroup EHEC in human and animal subjects. In an example, the subject (eg, a human) is suffering from or at risk of haemolytic uremic syndrome (HUS), eg, the subject is suffering from an *E coli* infection, such as an EHEC *E coli* infection.

8. The composition or method of any preceding Embodiment for preventing haemolytic uremic syndrome (HUS), a UTI infection, sepsis, septicaemia or diarrhoea in the subject.

The composition or method may be for treating or preventing a blood stream infection by pathogenic B2 phylogroup *E coli* cells in the subject.

9. The composition or method of any preceding Embodiment, wherein each particle comprises a phage capsid containing the nucleic acid; optionally wherein the capsid comprises capsid proteins of a T-even (optionally T4) or lambda phage.

As is known the to the skilled addressee, transduction particles are operable to infect their cognate host cells to introduce therein nucleic acid by transduction.

10. The composition or method of any preceding Embodiment, wherein each particle is a phage (optionally a lytic phage) or packaged phagemid.

11. The composition or method of any preceding Embodiment, wherein at least 2, 3 or 4 different types of transduction particle are administered to the subject.

For example, each particle types comprises a type of adhesion moiety or collection of adhesion moiety types that differs from the other types of particles.

In an example, 2 different types of transduction particle are administered to the subject. In an example, 3 different types of transduction particle are administered to the subject. In an example, 4 different types of transduction particle are administered to the subject. In an example, 5 different types of transduction particle are administered to the subject. In an example, 6 different types of transduction particle are administered to the subject.

12. The composition or method of any preceding Embodiment, wherein a first type of transduction particle and a second type of transduction particle are administered to the subject, wherein the first type of particle comprises a first adhesion moiety that is capable of recognising and binding to a first cognate moiety selected from the group LPS, LamB and Tsx displayed on B2 *E coli*, and the second type of particle comprises a second adhesion moiety that is capable of recognising and binding to a second cognate moiety selected from said group, wherein the first and second adhesion moieties different from each other.

For example, the first and second adhesion moieties different from each other by their tail fibres, optionally wherein the first adhesion moiety is cognate to LPS and the second moiety is cognate to LamB; or optionally wherein the first adhesion moiety is cognate to LPS and the second moiety is cognate to Tsx; optionally wherein the first adhesion moiety is cognate to Tsx and the second moiety is cognate to LamB.

For example, each particle comprises a phage capsid containing a said nucleic acid; wherein at least 2, 3 or 4 different types of transduction particle are administered to the subject; and wherein a first type of transduction particle and a second type of transduction particle are administered to the subject, wherein the first type of particle comprises a first adhesion moiety that is capable of recognising and binding to a first cognate moiety selected from the group LPS, LamB and Tsx displayed on B2 *E coli*, and the second type of particle comprises a second adhesion moiety that is capable of recognising and binding to a second cognate moiety selected from said group, wherein the first and second adhesion moieties different from each other.

For example, each particle comprises a phage capsid containing a said nucleic acid; wherein at least 2, 3 or 4 different types of transduction particle are administered to the subject; and wherein a first type of transduction particle and a second type of transduction particle are administered to the subject, wherein the first type of particle comprises a first adhesion moiety that is capable of recognising and binding to LPS displayed on B2 *E coli*, and the second type of particle comprises a second adhesion moiety that is capable of recognising and binding to LamB displayed on B2 *E coli*.

For example, each particle comprises a phage capsid containing a said nucleic acid; wherein at least 2, 3 or 4 different types of transduction particle are administered to the subject; and wherein a first type of transduction particle and a second type of transduction particle are administered to the subject, wherein the first type of particle comprises a first adhesion moiety that is capable of recognising and binding to Tsx displayed on B2 *E coli*, and the second type of particle comprises a second adhesion moiety that is capable of recognising and binding to LamB displayed on B2 *E coli*.

For example, each particle comprises a phage capsid containing a said nucleic acid; wherein at least 2, 3 or 4 different types of transduction particle are administered to the subject; and wherein a first type of transduction particle and a second type of transduction particle are administered to the subject, wherein the first type of particle comprises a first adhesion moiety that is capable of recognising and binding to LPS displayed on B2 *E coli*, and the second type of particle comprises a second adhesion moiety that is capable of recognising and binding to Tsx displayed on B2 *E coli*.

For example, each particle comprises a phage capsid containing a said nucleic acid; wherein at least 3 different types of transduction particle are administered to the subject; and wherein a first type of transduction particle, a second type of transduction particle and a third type of transduction particle are administered to the subject, wherein the first type of particle comprises a first adhesion moiety that is capable of recognising and binding to LPS displayed on B2 *E coli*, the second type of particle comprises a second adhesion moiety that is capable of recognising and binding to LamB displayed on B2 *E coli*, and the third type of particle comprises a second adhesion moiety that is capable of recognising and binding to Tsx displayed on B2 *E coli*.

For example, each particle comprises a phage capsid containing a said nucleic acid; wherein at least 4 different types of transduction particle are administered to the subject; and wherein a first type of transduction particle, a second type of transduction particle, a third type of transduction particle and a fourth type of transduction particle are administered to the subject, wherein the first type of particle comprises a first adhesion moiety that is capable of recognising and binding to LPS displayed on B2 *E coli*, the second type of particle comprises a second adhesion moiety that is capable of recognising and binding to LamB displayed on B2 *E coli*, the third type of particle comprises a second adhesion moiety that is capable of recognising and binding to Tsx displayed on B2 *E coli*, and the fourth type of particle comprises a second adhesion moiety that is capable of recognising and binding to LPS displayed on B2 *E coli*, wherein the adhesion moieties of said particles are different from each other.

For example, each particle comprises a phage capsid containing a said nucleic acid; wherein at least 4 different types of transduction particle are administered to the subject; and wherein a first type of transduction particle, a second type of transduction particle, a third type of transduction particle and a fourth type of transduction particle are administered to the subject, wherein the first type of particle comprises a first adhesion moiety that is capable of recognising and binding to LPS displayed on B2 *E coli*, the second type of particle comprises a second adhesion moiety that is capable of recognising and binding to LamB displayed on B2 *E coli*, the third type of particle comprises a second adhesion moiety that is capable of recognising and binding to Tsx displayed on B2 *E coli*, and the fourth type of particle comprises a second adhesion moiety that is capable of recognising and binding to LamB displayed on B2 *E coli*, wherein the adhesion moieties of said particles are different from each other.

For example, each particle comprises a phage capsid containing a said nucleic acid; wherein at least 4 different types of transduction particle are administered to the subject; and wherein a first type of transduction particle, a second type of transduction particle, a third type of transduction particle and a fourth type of transduction particle are administered to the subject, wherein the first type of particle comprises a first adhesion moiety that is capable of recognising and binding to LPS displayed on B2 *E coli*, the second type of particle comprises a second adhesion moiety that is capable of recognising and binding to LamB displayed on B2 *E coli*, the third type of particle comprises a second adhesion moiety that is capable of recognising and binding to Tsx displayed on B2 *E coli*, and the fourth type of particle comprises a second adhesion moiety that is capable of recognising and binding to Tsx displayed on B2 *E coli*, wherein the adhesion moieties of said particles are different from each other.

13. The composition or method of Embodiment 12, wherein the first and second cognate moieties are different from each other.

In an alternative, the first and second cognate moieties are identical. In an alternative, the first and second cognate moieties are LPS. In an alternative, the first and second cognate moieties are Tsx. In an alternative, the first and second cognate moieties are LamB.

14. The composition or method of any preceding Embodiment, wherein the nucleic acid of each particle comprises a nucleotide sequence (N1) encoding said nuclease, wherein each particle is a synthetic T-even phage (optionally a T4 phage) comprising an insertion of N1 into the genome of the phage, wherein the region is between the pin (protease inhibitor) gene and the iPII (internal protein) gene.

Optionally, the phage is (a) a synthetic T-even (eg, a T4) phage that comprises a deletion of DNA from, and/or an insertion of heterologous DNA into, a region of the genome of the phage corresponding to a region between coordinates
 (i) 1887 and 8983;
 (ii) 2625 and 8092;
 (iii) 1904 and 8113;
 (iv) 2668 and 7178;
 (v) 7844 and 11117;
 (vi) 8643 and 10313;
 (vii) 9231 and 13383;
 (viii) 9480 and 12224;
 (ix) 8454 and 17479; or
 (x) 9067 and 16673;

wherein coordinates are with reference to wild-type T4 phage genome (SEQ ID NO: 5);

15. The composition or method of any preceding Embodiment, wherein said nuclease is a guided nuclease, optionally a Cas, meganuclease, zinc finger nuclease or TALEN.

16. The composition or method of any preceding Embodiment, wherein the nuclease is a Type I, II, III, IV, V or VI nuclease, optionally a Cas9 or a Cas3.

17. The composition or method of any preceding Embodiment, wherein at least $1\times10^7$ PFU of particles are administered to the subject.

In an example, $1\times10^8$ to $1\times10^{13}$ PFU of particles are administered to the subject. In an example, $1\times10^8$ to $1\times10^{12}$ PFU of particles are administered to the subject. In an example, $1\times10^{10}$ to $1\times10^{12}$ PFU of particles are administered to the subject.

18. The composition or method of any preceding Embodiment, wherein the particles are administered to the subject at an MOI (multiplicity of infection) of at least 0.01.

Optionally, the particles are administered to the subject at an MOI of no more than 1. Optionally, the particles are administered to the subject at an MOI from 0.001 to 1. Optionally, the particles are administered to the subject at an MOI from 0.01 to 1. Optionally, the particles are administered to the subject at an MOI from 0.1 to 1.

19. The composition or method of any preceding Embodiment, wherein the strain or at least one strain is an antibiotic-resistant or MDR strain; and/or wherein the strain or at least one strain is a B2-I strain.

For example, the strain or at least one strain is a strain selected from B2-I (STc131), B2-II, B2-IX, and B2-VI.

For example, at least one MDR strain is resistant to fluoroquinolone and the strain is a beta-lactamase (ESBL)-producing *E coli.*

20. The composition or method of Embodiment 19, wherein the antibiotic is fluoroquinolone (optionally levofloxacin), carbapenem or vancomycin; and/or wherein the *E coli* are beta-lactamase (ESBL)-producing *E coli.*

Optionally, the antibiotic is selected from ciprofloxacin (eg, Cipro™), gemifloxacin (eg, Factive™), levofloxacin (eg, Levaquin™), moxifloxacin (eg, Avelox™), and ofloxacin.

For example, the *E coli* produce CTX-M-15. CTX-M-15 is the most abundant enzyme in ESBL-producing *E. coli* causing human infections.

Preferably, the antibiotic is fluoroquinolone (FQ). For example, the FQ is levofloxacin. Levofloxacin, sold under the brand name Levaquin™ among others, is an antibiotic medication. It is used to treat a number of bacterial infections including acute bacterial sinusitis, pneumonia, urinary tract infections, chronic prostatitis, and some types of gastroenteritis. Levofloxacin prophylaxis is recommended to prevent gram-negative bloodstream infections (BSIs) in patients with prolonged chemotherapy-induced neutropenia. However, increasing fluoroquinolone resistance may decrease the effectiveness of this approach (eg. Clin Infect Dis. 2021 Oct. 5; 73 (7): 1257-1265. doi: 10.1093/cid/ciab404, "Colonization With Fluoroquinolone-Resistant Enterobacterales Decreases the Effectiveness of Fluoroquinolone Prophylaxis in Hematopoietic Cell Transplant Recipients, Michael J Satlin et al). This study found that in the patients tested, nearly one-third of hematopoietic cell transplantation (HCT) recipients with pretransplant fluoroquinolone-resistant Enterobacterales (FQRE) colonization developed gram-negative bloodstream infections (BSIs) while receiving levofloxacin prophylaxis, and infections were typically caused by their colonizing strains. In contrast, levofloxacin prophylaxis was highly effective in patients not initially colonized with FQRE. The authors found that 23% of patients admitted for HCT were colonized with FQRE and *E. coli* was the predominant species. Patients with hematologic malignancies who receive intensive chemotherapy, including those undergoing hematopoietic cell transplantation (HCT), frequently develop severe neutropenia and gastrointestinal mucositis, placing them at high risk of developing bloodstream infections (BSIs) from gram-negative enteric bacteria (Enterobacterales). Neutropenic patients often suffer severe consequences from BSIs caused by Enterobacterales, with mortality rates as high as 15%-20%. Moreover, many fluoroquinolone-resistant Enterobacterales (FQRE) also harbor extended-spectrum β-lactamases (ESBLs); thus, breakthrough infections that occur despite fluoroquinolone prophylaxis may be resistant to first-line antimicrobial therapies for fever and neutropenia. Finally, adverse effects of fluoroquinolones have become increasingly apparent, including Clostridioides *difficile* infection, aortic dissection and rupture, dysglycemia, tendinopathy, QT interval prolongation, and mental status changes. Thus, fluoroquinolones should only be administered to patients when they are likely to provide clinical benefit to justify these potential adverse effects. Thus, Although fluoroquinolones may decrease the risk of gram-negative BSI in many patients, those who are colonized with FQRE may not benefit from fluoroquinolone prophylaxis.

The high rate and absence of risk factors for FQRE colonization suggest that FQRE are prevalent in the community. Indeed, a study of urinary isolates among outpatients in the United States demonstrated that 12% of *E. coli* isolates from young women and 29% of *E. coli* isolates from elderly women were fluoroquinolone resistant. A surveillance study of 1831 urinary *E. coli* isolates from 2017 found that one-quarter were FQ resistant. Furthermore, 13%-16% of men undergoing transrectal prostate biopsies were found to be colonized with fluoroquinolone-resistant *E. coli*. Nearly one-half of fluoroquinolone-resistant *E coli* isolates in the study were ST131, a common sequence type that has spread throughout the world and whose isolates are frequently fluoroquinolone resistant and ESBL producers.

Bacteraemia caused by extended-spectrum β-lactamase (ESBL)-producing Enterobacteriaceae (ESBL-E), such as *E coli*, is associated with inadequate empirical therapy and substantial mortality in neutropenic patients (see eg, "Colonization With Levofloxacin-resistant Extended-spectrum β-Lactamase-producing Enterobacteriaceae and Risk of Bacteremia in Hematopoietic Stem Cell Transplant Recipients", Satlin M J et al, Clin Infect Dis. 2018 Nov. 13: 67 (11): 1720-1728. doi: 10.1093/cid/ciy363). The study found that HSCT recipients who are colonized with levofloxacin-resistant ESBL-E pre-transplant and receive levofloxacin prophylaxis have high rates of bacteraemia from their colonizing strain during neutropenia. In this single-centre study of 312 HSCT recipients, it was found that 10% of patients were colonized with ESBL-E prior to their transplant. Nearly one-third of patients with pre-transplant ESBL-E colonization developed subsequent ESBL-E bacteraemia while neutropenic after their transplant, compared to <1% of patients who were not initially colonized with ESBL-E. Furthermore, the bloodstream and gastrointestinal ESBL-E had identical MLST and PFGE profiles in all cases, suggesting that these patients developed bacteraemia from their colonizing isolates.

In an example, the composition or method of the invention is for preventing the translocation of B2 phylogroup *E coli* from the gastrointestinal tract to the blood stream of the subject, thereby preventing or reducing bacteriaemia in the patient.

In an example, the composition or method of the invention is for preventing the translocation of B2 phylogroup *E coli* from the urinary tract to the blood stream of the subject, thereby preventing or reducing bacteriaemia in the patient.

In an example, the *E coli* are comprised by the gastrointestinal tract of the subject. Optionally, in these examples, the composition is administered orally to the subject.

In another example, the *E coli* are comprised by the urinary tract of the subject. For example, the infection is a kidney, bladder or urethra infection. Optionally, in these examples, the composition is administered to the urinary tract of the subject, such as by a catheter.

21. The composition or method of any preceding Embodiment, wherein (i) the nuclease is a Cas, (ii) each particle comprises a phage capsid containing the nucleic acid; and (iii) wherein a first type of transduction particle and a second type of transduction particle are administered to the subject, wherein the first type of particle comprises a first adhesion moiety that is capable of recognising and binding to a first cognate moiety selected from the group LPS, LamB and Tsx displayed on B2 strain *E coli*, and the second type of particle comprises a second adhesion moiety that is capable of recognising and binding to a second cognate moiety selected from said group, wherein the first and second adhesion moieties different from each other.

22. A method for treating or preventing an infection by *E coli* cells in a human or animal subject, the method comprising administering to the subject a plurality of transduction particles, wherein (a) each particle comprises a nucleic acid encoding a crRNA or guide RNA that is operable with a Cas nuclease for chromosomal targeting in the cells, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

Each nucleic acid preferably encodes a plurality of different cRNAs comprising spacer sequences that target *E coli* chromosomal genes. For example, Each nucleic acid preferably encodes a plurality of different cRNAs comprising spacer sequences that target 2, 3 or 4 *E coli* chromosomal genes selected from fimH, bolA, rpoH, IptA and murA.

Optionally, each crRNA or guide RNA comprises a spacer that targets an *E coli* gene selected from the group fimH, bolA, rpoH, IptA and murA. Optionally, each nucleic acid encodes a plurality of different cRNAs or guide RNAs, wherein the cRNAs or guide RNAs target at least 2, 3 or 4 (or targets all of) *E coli* genes selected from the group fimH, bolA, rpoH, IptA and murA. Optionally, each nucleic acid encodes a plurality of different cRNAs or guide RNAs, wherein the cRNAs or guide RNAs target fimH and bolA. Optionally, each nucleic acid encodes a plurality of different cRNAs or guide RNAs, wherein the cRNAs or guide RNAs target rpoH and lptA. Optionally, each nucleic acid encodes a plurality of different cRNAs or guide RNAs, wherein the cRNAs or guide RNAs target fimH and murA. Optionally, each crRNA or guide RNA comprises a spacer sequence that is complementary to an *E coli* gene selected from the group fimH, bolA, rpoH, IptA and murA. Optionally, each crRNA or guide RNA comprises a spacer sequence that is at least 80, 90 or 95% identical to a nucleotide sequence selected from the group SEQ ID NO: 6-10.

Optionally, each nucleic acid encodes a first crRNA, second crRNA, third crRNA, fourth crRNA and fifth cRNA, wherein the cRNAs are different from each other and each crRNA targets a B2 phylogroup *E coli* gene. Optionally, each nucleic acid encodes a first crRNA, second crRNA, third crRNA, fourth crRNA and fifth cRNA, wherein the cRNAs are different from each other and each crRNA is complementary to a B2 phylogroup *E coli* gene. Optionally, each nucleic acid encodes a first crRNA, second crRNA, third crRNA, fourth crRNA and fifth cRNA, wherein the cRNAs comprise respectively SEQ ID NO: 6, SEQ ID NO: 7, SEQ ID NO: 8, SEQ ID NO: 9 and SEQ ID NO: 10. Optionally, each nucleic acid encodes a first crRNA, second crRNA, third crRNA, fourth crRNA and fifth cRNA, wherein the cRNAs comprise respectively a nucleotide sequence that is at least 80% identical to SEQ ID NO: 6, a nucleotide sequence that is at least 80% identical to SEQ ID NO: 7, a nucleotide sequence that is at least 80% identical to SEQ ID NO: 8, a nucleotide sequence that is at least 80% identical to SEQ ID NO: 9 and a nucleotide sequence that is at least 80% identical to SEQ ID NO: 10. Optionally, each nucleic acid encodes a first crRNA, second crRNA, third crRNA, fourth crRNA and fifth cRNA, wherein the cRNAs comprise respectively a nucleotide sequence that is at least 90% identical to SEQ ID NO: 6, a nucleotide sequence that is at least 90% identical to SEQ ID NO: 7, a nucleotide sequence that is at least 90% identical to SEQ ID NO: 8, a nucleotide sequence that is at least 90% identical to SEQ ID NO: 9 and a nucleotide sequence that is at least 90% identical to SEQ ID NO: 10. Optionally, each nucleic acid encodes a first crRNA, second crRNA, third crRNA, fourth crRNA and fifth cRNA, wherein the cRNAs comprise respectively a nucleotide sequence that is at least 95, 96, 97, 98 or 99% identical to SEQ ID NO: 6, a nucleotide sequence that is at least 95, 96, 97, 98 or 99% identical to SEQ ID NO: 7, a nucleotide sequence that is at least 95, 96, 97, 98 or 99% identical to SEQ ID NO: 8, a nucleotide sequence that is at least 95, 96, 97, 98 or 99% identical to SEQ ID NO: 9 and a nucleotide sequence that is at least 95, 96, 97, 98 or 99% identical to SEQ ID NO: 10.

23. The method of Embodiment 22, wherein the method is according to any one of Embodiments 1-20, optionally except that the nuclease is an endogenous nuclease of the cells and is not encoded by the nucleic acid comprised by the particles.

24. A composition comprising a plurality of transduction particles for use in a method of treating or preventing an infection by *E coli* cells in a human or animal subject according to Embodiment 22 or 23, wherein (a) each particle comprises a nucleic acid encoding a crRNA or guide RNA that is operable with a Cas nuclease for chromosomal targeting in the cells, wherein the said administered particles contact the cells and introduce therein the nucleic acid, wherein the crRNA or guide RNA is expressed and guides the Cas nuclease wherein the nuclease cuts the chromosomes of the cells, thereby killing the cells or reducing growth or proliferation of the cells in the subject;

(b) the *E coli* cells are cells of *E coli* phylogroup B2; and (c) each particle comprises an adhesion moiety for recognising and binding to a cognate moiety selected from a LPS, LamB and Tsx displayed on the surface of the phylogroup B2 *E coli* cells.

25. A method of detecting the presence of a B2 phylogroup *E coli* in a sample, the method comprising contacting the sample comprising B2 phylogroup *E coli* with a composition comprising a plurality of transduction particles, wherein (a) each particle comprises a nucleic acid encoding a nuclease for targeting the genomes of said *E coli* cells, wherein the said administered particles contact the cells and introduce therein the nucleic acid, wherein the nuclease is expressed in the cells and cuts genomic DNA of the cells, thereby killing the cells or reducing growth or proliferation of the cells in the subject;

(b) each particle comprises an adhesion moiety for recognising and binding to a cognate moiety selected from a LPS, LamB and Tsx displayed on the surface of the phylogroup B2 *E coli* cells; and (c) the method comprises detecting that B2 phylogroup *E coli* cells have been killed or the growth or proliferation thereof has been reduced.

26. A method of detecting the presence of a B2 phylogroup *E coli* in a sample, the method comprising contacting the sample comprising B2 phylogroup *E coli* with a composition comprising a plurality of transduction particles, wherein (a) each particle comprises a nucleic acid comprising or encoding a detectable label, wherein the said administered particles contact the cells and introduce therein the nucleic acid, wherein optionally the label is expressed in the cells;

(b) each particle comprises an adhesion moiety for recognising and binding to a cognate moiety selected from a LPS, LamB and Tsx displayed on the surface of the phylogroup B2 *E coli* cells; and (c) the method comprises detecting B2 phylogroup *E coli* cells comprising the label.

27. The method of Embodiment 26 or 27, wherein the composition comprises the features of the composition of any one of Embodiments 1, 2-21 24 and 25.

28. The method of any one of Embodiments 26-28, wherein the *E coli* comprise one or more *E coli* strains selected from the group ST131, ST1193, ST648, ST315, ST405, ST361, ST88 and ST453.

29. The method of any one of Embodiments 26-29, wherein the sample is a patient sample (eg, blood, urine, stool or saliva sample), wherein the subject is a transplant or cancer patient (optionally a haematological cancer patient), or wherein the patient is suffering from or at risk of a urinary tract infection (UTI); and optionally wherein the transplant is a solid organ or stem cell transplant (optionally a haematopoietic cell transplant).

30. The method of any one of Embodiments 26-30, wherein the nucleic acid of each particle comprises a nucleotide sequence (N1) encoding said nuclease, or comprising or encoding the label wherein each particle is a synthetic T-even phage (optionally a T4 phage) comprising an insertion of N1 into the genome of the phage, wherein the region is between the pin (protease inhibitor) gene and the iPII (internal protein) gene.

31. The method of any one of Embodiments 26-31, wherein at least $1\times10^7$ PFU of particles are contacted with the sample.

32. The method of any one of Embodiments 26-32, wherein the particles are contacted with the sample at an MOI (multiplicity of infection) of at least 0.01.

Labelling for detection methods is routine for the skilled addressee. The label may, for example, be a fluorescence label, eg, GFP. The sample may be a blood, spit, sputum or cell sample.

It will be understood that particular embodiments described herein are shown by way of illustration and not as limitations of the invention. The principal features of this invention can be employed in various embodiments without departing from the scope of the invention. Those skilled in the art will recognize, or be able to ascertain using no more than routine study, numerous equivalents to the specific procedures described herein. Such equivalents are considered to be within the scope of this invention and are covered by the claims. All publications and patent applications mentioned in the specification are indicative of the level of skill of those skilled in the art to which this invention pertains. All publications and patent applications and all US equivalent patent applications and patents are herein incorporated by reference to the same extent as if each individual publication or patent application was specifically and individually indicated to be incorporated by reference. Reference is made to the publications mentioned herein and equivalent publications by the US Patent and Trademark Office (USPTO) or WIPO, the disclosures of which are incorporated herein by reference for providing disclosure that may be used in the present invention and/or to provide one or more features (eg, of a vector) that may be included in one or more claims herein.

The use of the word "a" or "an" when used in conjunction with the term "comprising" in the claims and/or the specification may mean "one," but it is also consistent with the meaning of "one or more," "at least one," and "one or more than one." The use of the term "or" in the claims is used to mean "and/or" unless explicitly indicated to refer to alternatives only or the alternatives are mutually exclusive, although the disclosure supports a definition that refers to only alternatives and "and/or." Throughout this application, the term "about" is used to indicate that a value includes the inherent variation of error for the device, the method being employed to determine the value, or the variation that exists among the study subjects.

As used in this specification and claim(s), the words "comprising" (and any form of comprising, such as "comprise" and "comprises"), "having" (and any form of having, such as "have" and "has"), "including" (and any form of including, such as "includes" and "include") or "containing" (and any form of containing, such as "contains" and "contain") are inclusive or open-ended and do not exclude additional, unrecited elements or method steps.

The term "or combinations thereof" or similar as used herein refers to all permutations and combinations of the listed items preceding the term. For example, "A, B, C, or combinations thereof is intended to include at least one of: A, B, C, AB, AC, BC, or ABC, and if order is important in a particular context, also BA, CA, CB, CBA, BCA, ACB, BAC, or CAB. Continuing with this example, expressly included are combinations that contain repeats of one or more item or term, such as BB, AAA, MB, BBC, AAABCCCC, CBBAAA, CABABB, and so forth. The skilled artisan will understand that typically there is no limit on the number of items or terms in any combination, unless otherwise apparent from the context.

Any part of this disclosure may be read in combination with any other part of the disclosure, unless otherwise apparent from the context.

All of the compositions and/or methods disclosed and claimed herein can be made and executed without undue experimentation in light of the present disclosure. While the compositions and methods of this invention have been described in terms of preferred embodiments, it will be apparent to those of skill in the art that variations may be applied to the compositions and/or methods and in the steps or in the sequence of steps of the method described herein without departing from the concept, spirit and scope of the invention. All such similar substitutes and modifications apparent to those skilled in the art are deemed to be within the spirit, scope and concept of the invention as defined by the appended claims.

The present invention is described in more detail in the following non-limiting Examples.

EXAMPLES

Example 1: Particle Composition for Surprisingly Targeting a Plurality of Different *E coli* Strains, Including B2 Phylogroup

Overview

Patient samples containing various different *E coli* strains were challenged with a particle composition. The composition comprised a plurality of transduction particles bearing adhesion moieties that are able to bind to LPS, LamB or Tsx present on *E coli* cells. The particles comprised capsids comprising phage capsid proteins, with the capsids containing nucleic acids encoding CRISPR/Cas systems for chromosomal targeting in *E coli*. Each nucleic acid encoded a plurality of different cRNAs comprising spacer sequences that target *E coli* chromosomal genes. The ability to kill or reduce growth of *E coli* in the samples was determined using a plaque assay as described below. Whole genome sequencing and genome assembly were used to assign susceptible *E coli* strains to phylogroups. It was surprisingly seen that use of such a particle composition was able to very effectively and extensively target a plurality of different *E coli* strains (these strains being clinically relevant from actual patient samples). Furthermore, advantageously a large number of different strains of the B2 phylogroup were targeted and killed. This is significant, because B2 *E coli* strains often display antibiotic resistance (such as MDR), eg, resistance to fluoroquinolone, that causes potentially life-threating infections in patients, such as in cancer, transplant and UTI patients. In addition to the B2 group, we surprisingly also were able to successfully kill or inhibit the growth of multiple strains of *E coli* phylo groups B1, D. F and G.

Patient Sampling

The samples tested (n=71) were obtained from two prospective observational studies enrolling adult (≥18 years) patients who were admitted to hospital for an autologous or allogenic hematopoietic cell transplantation (HCT) and who received levofloxacin (a fluoroquinolone, FQ) prophylaxis starting the day before the transplantation (Day-1) (Satlin 2021 and Satlin 2018). Trimethoprim-sulfamethoxazole (TMP-SMX) was administered to allogenic HCT recipients from 2 to 4 days prior to the HCT. The antibiotic treatments do not eradicate all *E coli* in the patients; for example, fluoroquinolone-resistant *E coli* would persist and thus sampling obtained *E coli* from patients. *E coli* isolates were derived from either anal swabs or fecal samples obtained upon admission for transplantation. The timing of sampling varied from Day-7 (7 days before transplantation) to Day 0 (the day of transplantation).

General Plaque Assay: Spotting for Coverage

This procedure describes the method to assess the coverage of phage particle lysates on a panel of bacterial strains.

| Section | Procedure |
|---|---|
| Step 1 | Prepare bacterial indicator strains by inoculating 5 μl of a frozen stock into 250 μl of LB broth on a 96 well plate. Incubate overnight at 37° C. and 250 rpm. This step is done the day before the assay is performed. |
| Step 2 | Pre-acclimatize the LB plates to room temperature. Melt and acclimatize the top agar to 55° C. and add $CaCl_2$ and $MgSO_4$ to a final concentration of 5 mM. |
| Step 3 | In a culture tube mix 100 ml of the overnight indicator strain with 3 ml of pre-warmed top agar. When working with many strains, the top agar can be distributed to culture tubes and kept at 60° C. before use. |
| Step 4 | Pour the mixture on top of the room temperature LB plate and distribute evenly by swirling. Let plates solidify in a biosafety cabinet or lab bench for 5-10 minutes. Keep the lids closed. While solidifying avoid stacking plates to keep the layer of the top agar even across the plate surface |
| Step 5 | In the meantime, dilute the sample(s) or the stock of phage to the required dilutions (10-fold dilutions). Use PBS for dilutions. |
| Step 6 | Spot dilutions 0 to −9, 5 μl of each on top of your overlays and let them dry for 20 minutes (or until the spots are completely absorbed by the agar) on a bench with the lids open. Incubate plates upside down at 37° C. overnight. |

-continued

| Section | Procedure |
|---|---|
| Step 7 | Evaluation of the results:<br>1. If visible plaques appear, they are counted, and phage concentration is calculated. The result is recorded as YES.<br>Calculation of phage concentration: number of plaques × 200 (to make it into ml) × dilution where you counted, i.e:<br>If counted 5 plaques on dilution-6: 5 × 200 × 1e6 = 1e9 pfu/ml<br>2. If there are no visible plaques, but inhibition of growth is observed the result is recorded as LZ (lysis zone) and the lowest dilution of inhibition is noted.<br>3. If no plaques or inhibition is observed, the result is recorded as NO |

Spotting was performed according to the above general plaque assay. Bacterial strains were prepared by inoculating 5 μl of a frozen stock into 250 μl of LB broth in a 96 well plate. The plate was incubated at 37° C. and 250 rpm overnight. Next day, in a culture tube 100 ml of the overnight strain was mixed with 3 ml of pre-warmed top agar (at 55° C.) containing 5 mM $CaCl_2$) and 5 mM $MgSO_4$. The mixture was poured on top of pre-acclimatized LB plate and distributed evenly by swirling. The plates were left on the lab bench for 5-10 minutes to solidify. In the meantime, the particle composition was diluted in PBS buffer from 100 to 109 and 5 μL of each serial dilution were spotted on top of the overlays. Plates were left on the bench with the lid open for 20 minutes or until the spots are completely absorbed by the agar, and then incubated upside down at 37° C. overnight.

Evaluation of the Results:

If visible plaques appeared, the results were recorded as positive, plaques were counted, and phage concentration was calculated. Calculation of phage concentration: number of plaques×200×dilution where plaques were observed. i.e: If counted 5 plaques on dilution−6:5×200×1e6=1e9 pfu/ml If there were no visible plaques, but inhibition of growth was observed, the result was recorded as lysis zone and the lowest dilution of inhibition is noted.

If no plaques or inhibition was observed, the results were recorded as negative.

Whole Genome Sequencing

DNA extraction was performed using Omega Bio-tek, Mag-Bind Bacterial DNA 96 Kit. The protocol was followed, and samples were eluted in 100 μL Elution Buffer.

Sequencing libraries were generated using Illumina Nextera XT, and sequencing was performed with paired ends on an Illumina MiSeq instrument with a V2 flow cell (300 cycles). The average sequencing depth for all samples was 48× (range: 31-72×)

Genome Assembly and Phylogenetic Tree Reconstruction

Raw data was trimmed for adaptor sequences and low-quality bases using fastp 0.22.0 (Chen et al 2018). Genomes were assembled using SKESA 2.4.0 (Souvorov et al 2018). The phylogroup of each sample was determined using EzClermont 0.7.0 (github.com/nickp60/EzClermont). Genomic distances were estimated using Mash 1.1 (Ondov et al 2016) with a kmer size of 17 and 1000 sketches. A neighbour joining tree was constructed using rapidnj 2.3.2 (Simonsen et al 2008). The final tree visualization was generated in Interactive Tree Of Life (iTOL) version 6.5.3 (Letunic et al 2021). Strain phylotyping was carried out in silico using the method disclosed in Microb Genom. 2018 July; 4 (7): e000192, Published online 2018 Jun. 19. doi: 10.1099/mgen.0.000192, PMCID: PMC6113867, PMID: 29916797, "Clermon Typing: an easy-to-use and accurate in silico method for *Escherichia* genus strain phylotyping, Johann Beghain et al. The set of primer sequences described in Table S1 (available in the online version of this article) was used.

Results

Figure 2:
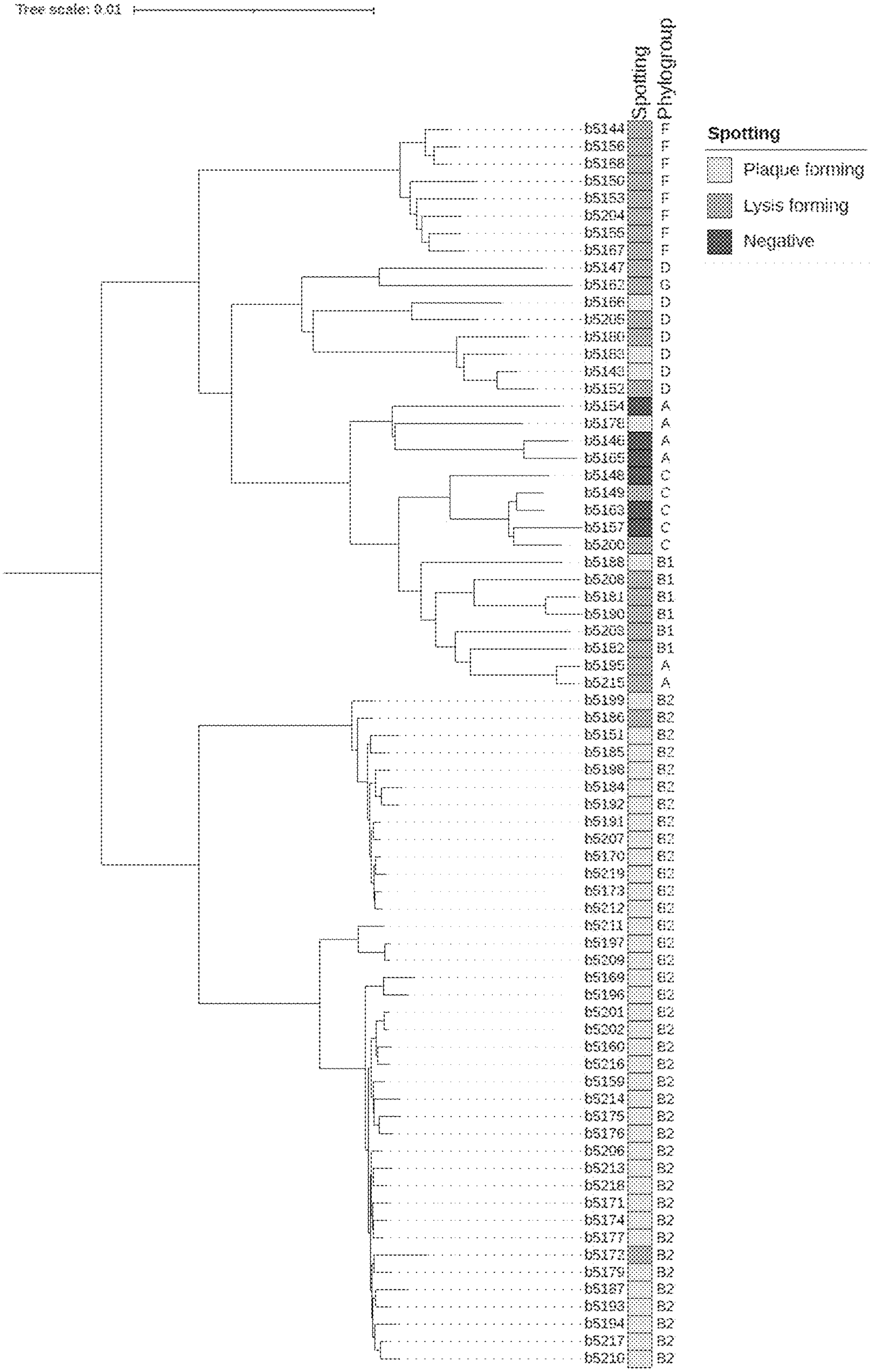
FIG. 2: Phylo-grouping of strains used in the study and showing particularly advantageous and extensive targeting of many clinical B2 phylogroup strains.

It was surprisingly seen that use of such a particle composition was able to very effectively and extensively target a plurality of different *E coli* strains (these strains being clinically relevant from actual patient samples), see FIG. 1. Furthermore (see FIG. 2), advantageously a large number of different strains of the B2 phylogroup were targeted and killed. This is significant, because B2 *E coli* strains often display antibiotic resistance (such as MDR), eg, resistance to fluoroquinolone, that causes potentially life-threating infections in patients, such as in cancer, transplant and UTI patients. More than 10 different ST131 strains were killed (plaques formed) and more than 10 different ST1193 strains were killed (plaques formed). Sequence type 1193 has recently emerged as a new, virulent and resistant lineage among fluoroquinolone resistant *E coli. Escherichia coli* ST131 is a globally dominant multidrug resistant clone associated with high rates of rUTI. Uropathogenic *E coli* (UPEC) are the primary cause of urinary tract infection (UTI), being responsible of ~90% of all cases. UPEC strains largely belong to the *E coli* phylogenetic groups B2 or D and are often clonal, with the most common sequence types (STs) isolated worldwide being ST69, ST73, ST95 and ST1312. The recently emerged and globally disseminated ST131 clone is a major contributor to hospital- and community-acquired UTI, as well as bloodstream infections and infections in companion animals and poultry. Originally identified in 2008, ST131 is associated with the worldwide spread of the CTX-M-15 extended spectrum B-lactamase (ESBL) resistance gene. Most ST131 strains are now strongly associated with multidrug resistance (MDR), including resistance to fluoroquinolones. Recent reports have also identified strains that are resistant to last-line carbapenems.

Significantly, we included clinical samples from patients that went on to develop *E coli* bacteraemia (despite pre-treatment with FQ/TMP-SMX). The composition could kill or reduce growth of *E coli* strains in these samples (and this is indicative of the possibility of using the composition for prophylaxis of bacteraemia in subjects). This included strains of the following Multi-Locus Sequence Typing (MLST) types (see FIG. 2): ST648, ST315, ST405, ST361, ST88, ST453, ST1193 and ST131.

In addition to the B2 group, we surprisingly also were able to successfully kill or inhibit the growth of multiple strains of *E coli* phylo groups B1, D, F and G.

REFERENCES

Shifu Chen, Yanqing Zhou, Yaru Chen, Jia Gu; fastp: an ultra-fast all-in-one FASTQ preprocessor, Bioinformatics, Volume 34, Issue 17, 1 Sep. 2018, Pages i884-1890, doi.org/10.1093/bioinformatics/bty560

Alexandre Souvorov, Richa Agarwala and David J. Lipman. SKESA: strategic k-mer extension for scrupulous assemblies. *Genome Biology* 2018 19:153. doi.org/10.1186/s13059-018-1540-z Ondov, B. D., Treangen, T. J., Melsted, P. et al. Mash: fast genome and metagenome distance estimation using MinHash. *Genome Biol* 17, 132 (2016). doi.org/10.1186/s13059-016-0997-x.

Martin Simonsen, Thomas Mailund and Christian N. S. Pedersen. Rapid Neighbour Joining. Proceedings of the 8th Workshop in Algorithms in Bioinformatics (WABI), LNBI 5251, 113-122, Springer Verlag, October 2008. doi: 10.1007/978-3-540-87361-7_10.

Letunic I and Bork P (2021) Nucleic Acids Res doi: 10.1093/nar/gkab301 Interactive Tree Of Life (iTOL) v5: an online tool for phylogenetic tree display and annotation Michael J. Satlin et al, Colonization with Fluoroquinolone-resistant Enterobacterales decreases the effectiveness of fluoroquinolone prophylaxis in hematopoietic cell transplant recipients. Clinical Infectious Diseases 2021.

Michael J. Satlin et al, Colonization with Levofloxacin-resistant extended-spectrum β-lactamase-producing Enterobacteriaceae and risk of bacteremia in hematopoietic cell transplant recipients. Clinical Infectious Diseases 2018.

SEQUENCES

Amino acid sequences are written in N- to C-terminal direction and DNA sequences are written in 5' to 3' direction.

PROTEIN

>LamB (SEQ ID NO: 1)

MMITLRKLPLAVAVAAGVMSAQAMAVDFHGYARSGIGWTGSGGEQQCFQTTGAQSKYRL

GNECETYAELKLGQEVWKEGDKSFYFDTNVAYSVAQQNDWEATDPAFREANVQGKNLIEW

LPGSTIWAGKRFYQRHDVHMIDFYYWDISGPGAGLENIDVGFGKLSLAATRSSEAGGSSSFAS

NNIYDYTNETANDVFDVRLAQMEINPGGTLELGVDYGRANLRDNYRLVDGASKDGWLFTA

EHTQSVLKGFNKFVVQYATDSMTSQGKGLSQGSGVAFDNEKFAYNINNNGHMLRILDHGAI

SMGDNWDMMYVGMYQDINWDNDNGTKWWTVGIRPMYKWTPIMSTVMEIGYDNVESQRT

GDKNNQYKITLAQQWQAGDSIWSRPAIRVFATYAKWDEKWGYDYNGDSKVNPNYGKAVP

ADFNGGSFGRGDSDEWTFGAQMEIWW

>Tsx (SEQ ID NO: 2)

MKKTLLAAGAVLALSSSFTVNAAENDKPQYLSDWWHQSVNVVGSYHTRFGPQIRNDTYLE

YEAFAKKDWFDFYGYADAPVFFGGNSDAKGIWNHGSPLFMEIEPRFSIDKLTNTDLSFGPFK

EWYFANNYIYDMGRNKDGRQSTWYMGLGTDIDTGLPMSLSMNVYAKYQWQNYGAANEN

EWDGYRFKIKYFVPITDLWGGQLSYIGFTNFDWGSDLGDDSGNAINGIKTRTNNSIASSHILA

LNYDHWHYSVVARYWHDGGQWNDDAELNFGNGNFNVRSTGWGGYLVVGYNF

DNA

>LamB (SEQ ID NO: 3)

ATGATGATTACTCTGCGCAAACTTCCTCTGGCGGTTGCCGTCGCAGCGGGCGTAATGTCT

GCTCAGGCAATGGCTGTTGATTTCCACGGCTATGCACGTTCCGGTATTGGCTGGACAGGT

AGCGGCGGTGAACAACAGTGTTTCCAGACTACCGGTGCTCAAAGTAAATACCGTCTTGG

CAACGAATGTGAAACTTATGCTGAATTAAAATTGGGTCAGGAAGTGTGGAAAGAGGGCG

ATAAGAGCTTCTATTTCGACACTAACGTGGCCTATTCCGTCGCGCAACAGAATGACTGGG

AAGCTACCGATCCGGCCTTCCGTGAAGCAAACGTGCAGGGTAAAAACCTGATCGAATGG

CTGCCAGGTTCCACCATCTGGGCAGGTAAGCGCTTCTACCAACGTCATGACGTTCATATG

ATCGACTTCTACTACTGGGATATTTCTGGTCCTGGTGCCGGTCTGGAAAACATCGATGTT

GGCTTCGGTAAACTCTCTCTGGCAGCAACCCGCTCCTCTGAAGCTGGTGGTTCTTCCTCTT

TTGCCAGCAACAATATTTATGACTATACCAACGAAACCGCGAACGACGTTTTCGATGTGC

GTTTAGCGCAGATGGAAATCAACCCGGGCGGCACATTAGAACTGGGTGTCGACTACGGT

CGTGCCAACCTGCGTGATAACTATCGTCTGGTTGATGGCGCATCGAAAGACGGCTGGTTA

TTCACTGCTGAACATACTCAGAGTGTCCTGAAGGGCTTTAACAAGTTTGTTGTTCAGTAC

GCTACTGACTCGATGACCTCGCAGGGTAAAGGTCTGTCGCAGGGTTCTGGCGTCGCGTTT

GATAACGAAAAATTTGCCTACAATATCAACAACAACGGTCACATGCTGCGTATCCTCGAC

CACGGTGCGATCTCCATGGGCGACAACTGGGACATGATGTACGTGGGTATGTACCAGGA

-continued

TATCAACTGGGATAACGACAACGGCACCAAGTGGTGGACCGTTGGTATTCGCCCGATGT

ACAAGTGGACGCCAATCATGAGCACCGTGATGGAAATCGGCTACGACAACGTCGAATCC

CAGCGCACCGGCGACAAGAACAATCAGTACAAAATTACCCTCGCACAACAATGGCAGGC

TGGCGACAGCATCTGGTCACGCCCGGCTATTCGTGTCTTCGCAACCTACGCCAAGTGGGA

TGAGAAATGGGGTTATGACTACAACGGCGATAGCAAGGTTAACCCGAACTACGGCAAAG

CCGTTCCTGCTGATTTCAACGGCGGCAGCTTCGGTCGTGGCGACAGCGACGAGTGGACCT

TCGGTGCCCAGATGGAAATCTGGTGGTAA

>Tsx (SEQ ID NO: 4)

ATGAAAAAAACATTACTGGCAGCCGGTGCGGTACTGGCGCTCTCTTCGTCTTTTACTGTC

AACGCAGCTGAAAACGACAAACCGCAGTATCTTTCCGACTGGTGGCACCAGAGCGTTAA

CGTTGTCGGAAGCTATCACACCCGTTTCGGACCGCAGATCCGCAACGATACCTACCTTGA

GTACGAAGCATTCGCTAAAAAAGACTGGTTCGACTTCTATGGTTATGCGGATGCGCCGGT

ATTCTTCGGCGGTAACTCCGATGCAAAAGGTATCTGGAACCACGGTTCTCCGCTGTTTAT

GGAAATCGAACCACGTTTCTCCATCGACAAGCTGACCAATACTGACCTTAGCTTCGGTCC

GTTCAAAGAGTGGTACTTCGCGAACAACTACATTTACGACATGGGTCGTAATAAAGATG

GTCGCCAGAGCACCTGGTACATGGGTCTGGGTACCGATATCGACACTGGCCTGCCGATG

AGCCTGTCCATGAACGTCTATGCGAAATACCAGTGGCAGAACTATGGCGCAGCGAACGA

AAACGAGTGGGACGGTTACCGTTTCAAAATTAAATACTTTGTGCCGATTACCGATCTGTG

GGGCGGTCAGCTGAGCTACATCGGCTTCACCAACTTCGACTGGGGTTCCGATTTAGGGGA

TGACAGCGGTAACGCAATCAACGGTATTAAGACCCGTACTAATAACTCTATCGCTTCCAG

CCATATTCTGGCTCTGAACTACGATCACTGGCACTACTCTGTCGTAGCTCGTTACTGGCAC

GACGGTGGTCAGTGGAACGACGATGCAGAACTGAACTTCGGCAACGGCAACTTCAACGT

TCGCTCTACCGGCTGGGGTGGTTACCTGGTAGTAGGTTACAACTTCTGA

>NC_000866.4 Enterobacteria phage T4, complete genome (SEQ ID NO: 5)

AATTTTCCTTATTAGGCCGCAAGGGCCTTCATAGTTTTAGCGATTTGGGAAACTTCATCATCACTTAAAG

AGTTGCGATAACCGATGAAGTCGGAAACAATACGGAATTTCTTGGTAAACTCAGCAACCATTTTATCACT

GTTTTTTGAAGCATTATTTGATAATACATCAAAAAGATTAGTTACTGTCCAAATGTCATGACCGATGGTA

TCTTTTCCACCATTAAAATATACACCCTGTAATGAACTAACCATATTAGCGAGTCGTGTATATTCTTCAG

AAACTTCATCTATACTGAAGTACTTCATCATAAAATCTAACTCAGGATACTTGATAATTTTATCAATATA

TCGTTTAGCTGAACTTGAATAACCTACATACTTATCATAATCTACATCATCAAAAGCATCTACATATAAA

TCACGCAAAGCTTCAAAAATACATTGGCACTGACCGAGTTCTTTTACCTTTTTCTGTAAAAGCGGACGAA

TAACATAAAATTCATTAATGCCAATAAGATTAGCCATACGAATCAAAATATTCATAGATGGATGACAAAG

AGATGTAGTACCATCCATAGAGAAAATATCAGAACGATGCATATACGCTACATAACCAGTAATTTCATCT

GCTTCTGATGTGAGGCGTAAATAATTCCTCTTTTCCCAGCGCCCGTCTTTAATTTCAAACTTAAACGCTG

TAGCAGCTTTAGGACGAGGAGCTTTACTTTTAACTACCTTTGGAATATAACTTTTTACTAAAGCTTCAAT

TTCTGACAAATAATGAATGTTAACTTCATCACTTTCAAACATCGCCATAATATCAGGAAGCAAATCAATC

TGCGATTCTACTTCTGGATTAATAAACAGAAGACGTTCGTTATGATGAATATTCAAAGTGTTATTAAATT

CACTATCATCTAACGCACGTGCTAATCCACGGACAATATTAACACGATTTTTAATATTATCAATAACGAT

ATTAATTTTTGTTGTATTAATACCAAACAGACGATAACTTGATGCAACGGCTGAAGTTTCATGACTTTGC

TTAATGCGCTTCAGTCGAGGGTCAAGATTTACTTCATACACAACTCCCGCGTTGCATAACTTACTGTCAG

-continued

GTTCAAACATGCTCTGCATCTTTTTATATGACAGATTTTTAGTCGTGAATTTGACTGAATTACTAATCAT

ATAATCTCGAGCAGAATACCCCATCTTCATCAATTCACGATATGTGTGACGAGGAGATGTAGATTCTTTA

AATCGTTTTACATCTTCATTAAATGCTTTCTCACTGAGTTCTTTAACTCGTTCAATAATATTTTTACGAG

TGCGATCATCCAGTGAAAGAGCCTCGCGAGATGGAGCAATATCAAGTGAACCCATTGGAAACTTAATGTA

ATTCACTTCATTGCGAATGCTTAGCCAGTTACGGTCTCTAATAACACCATCGATAGGATAAACAATACCA

CCGTAGATAGCATATAATCCACCACGATCAGGCCAGTATCTTTCTGGATTTACACCGTAATAGTCATCAA

AATCCGGAAAATAATCAATTTCGCGGTCAAGACCATTAATGATAGCCAAATCTTTGAACGGTCGCATGAT

ATAAGAAACTTCATAAGCAAAGTTTCTAAAGTCTTTTTCTTCAACTGGAACTACGATTTCAATACCAGTT

TTATCATCTGGACCCATTTCTTTTACGAATGTAGGTTTAATCTGTGGACCATCACCATCCATGTAAGCTA

CATAACCACGAATTTCACCTTTATGATACGAAGTAATACTAAACGTATCAGTATAACTAAACGGAGATTT

AGAACCTAAACCAAATCCGCCAATAAAGTCATTAGATTCAGCTTTAGATGAACTGAAGTATGAATTATAC

AACCCAGGAGAATTATCATCACCTTGAATATCAAAATCACTCATACCCGGACCAAAATCTCGACAAACAA

ATCGTGGGTCTAAACGTCCAGGAACTTGTATGATAAATTTTTCAGGATTTCCATTAAGTGCATGAGCATC

AATCATGTTAGTAATCAATTCACGGACTACTGCGCGAATCTTGTTTGTATACAAATCAGATGACAGAATT

TTAAATACTTTAGGAGATGCTGTGATGCTAAATGCTTTTGATTTAGAACCATTACCAAGAATTGTTTCTT

TTTCAGTGGTGATAATCATAATTTCCTCATTAATTCATATTACGCTTAATAACTTCAGCAACTTCTAGTA

GTTCATCTTTAGTTGCGGTGTCGGATTGAATTTTATCTCTAATATCTTTAAAGCGGGTTTTAAATTCTTC

GGCTTCTCCCATATCGAAAAAGCGTTGAATGATTCTATATTCTCGATGAACTGCTTTATCAAAAAGTTCT

AAATTTACTTTATATGATTTCATTTCAATATCCTCATTTGCCCAATTAATTATACCACATCCTTGTGGTA

AAGTAAACTACTGGCTCATCCATTCTTTACGAAGGTCAGCATTATCTCCCATGAGCATTTCAAAAAGCTC

TTTCCAGTTCTCAGGAAGTTTAACAACATCATATACTGGGTTTTGAATCATCTCACGATATTCAGATTTT

TCCAAAGAGCCAAGTCCCTTAATATAACGGATGCTATGTTTAGGTAGAGCATCTTTGGCACTCTCATATT

CAGCGACTGTATAAAACCATTCTTGTTTTTTACCGACCTGAGCGATGATTACAGGAGTTTTGACAAAGCG

AATTCGTCCTTGCTCAAACAATTCTGGCCAATTACTAAAAAATCCGAGCAGAGAAGGATAAATAGAACCT

AATCCAATAATCTCTTAATTATGAGGTATTTCTATAGATAGCCCGAAGGCTATCCATCGTGATCTGCGTC

TGTCATAATAGCGACATTCGCATAGTTCATTGAAGAGGATTTAATAGAACGACGAACATTGTTCTGCAAT

TTATATTTTTTCATATCAACGCTAGAAGAATCAATTTTTACAAATTTCATTATACACCTCATAGAACTTT

TCATCAGGAATCCAACCGCGTTTAAATTCATTAAATGCTCGGCCGAATAATTTTGAATTCACAGTTATAT

TATTAACTGATTTCCATTTAGCAACTCCCGTTCGTTTATAATGATCGGGGTCATATTTCGTGACGTACCA

TTCATATAAATTTGGTATTAATTTTACAGCCTCTGGATTTGTCGCTGATTTATTATACCATGGTTTCGCT

TTTTCAAGTTCAGCTGCTTTTGCAGTAGCAGCAACAGTATTTCCAACACCAACTAATTTTTCAGTTTTAA

TGCGTGGATCATTAACATGAAGACGAAAAACTTCGCCCTTTTCATTTTTAAAGCATGTCATGCCTTTAAT

TCCAGGAAGCTTAACACCTTTATTAACACCGCATCATTCCTTTGGGTTAAATGATCCTTTAATTAATAAG

GCGCATTTACCCGATTTAACTACTTCTCATTCAACAACTTTATCTTTCATAACGTTTTTTGACCATTCAG

ATACTGCTCTTTGATGGCTAAATTCTAGCAATTTCACTATAATTTGCACTAGAACGTAAACTATTTTTCA

GTGTTTCAACATTCTATTCATCGCATATGCCATTTCACGATTACGATGAATTTTATATAGTAGAAAATAG

TGCTAAAAAGTGTTCACGAAAAGTCATGTTTCACCAAATTTTCGTTATCATCAGAACCTCCCATTGATCT

TGGAAGGATATGATGAATTTCACCCTTAAATTTAGAAACGCGGGTTTTACCCCGCACTATTAAGTCATTA

TAGATTTTTTCGTAATTCACCTACTGTTATCCATTTACCATTAATCTGTACTTCATCATTTTCATTTACG

ATAATTGTATCGCCATTTAGCTCGAAAGTAAACCACTCGCCATCTTCTTTTTCTTCAAACGCTTTTTCAC

CGAGAACTAGACCAGTGATTGCGCAAATATCAAATAGTTCTTTGTTTTTAAGCATATCTGCATAAGACAT

-continued

ACCCCAACTGTTGAGAACTTTACCACGCAATGGATAACCACCGTGAAGTTCTTTATCACGAACATCAATA

AGATATCCGATAGCCGAATCACCCTCAGTCAAGAAAAGAGTAGTATCAGCATCTTTACCGCAAAGATTCG

CTTTGATATGTTTATGAACCTTAGCTTTAGAAGCCTTTTTAGCTGCTTTAGTTTCTGCTGCTTTTTCTGC

CGCCAATTTACGAGCCAAAGCAGCTTCAATAATCGGCATTAGAATTGCTTCATTATTTAGAATATCACGT

GAAATCTTTTTAGCATCAAGTTGAATATGACTACGAATTTCGCCAAATGGAGAAGTCAAACGCTCTTTAG

TTTGACGAATCAATCGCATGTTTTTCATATCACGAACAAACATAACGATAGTCAAACATTCTTTGACACG

TGCTTTAGTCACATCAATTTTGAACTTACGTTTGATTTGTGGAATAAGGTCTTCACAAATATCATCCATA

GCGCAGTCAATGTGATGGCCACCATTCTTAGTATGAATGTTATTGACGTATGTTAATTGACGAAAACCAT

CCGGTGAACGACCAACCGCAATAGAACAATTTTCTTGCTCTTGAACAATAGCATGTTCATCATACTGCCG

TGCATATTTCTTAAAATTGCCCTGAACCTTTTTACCATTAAAGGTAAATTGAATATCAGGATAAACTACA

GCAAGTGTCTGGAGACGATCCAGTGTAATGTCAAGATAAACTTGGGACAGCTCATTAGTTTCAAATGACA

TAAAATCAGGAATGAAAGTAACACGAGTTCCTTTCCATTTTCCAGGAATATCTTCCCATGATTTATTTTC

CATGCCATTTGAACAACGAACTACAATATTATTTTGACCGTCGCCAGTTTCACCGACAAACATCACAGAA

AAAATGTTTGTCAAACTAGAACCAACACCGTTCATACCGCCGGTGACGCGTTCTTTATCATCACCAAAGT

TACCACCTGCTTTTGGAATAGTCCATGCGGCAACAGGACCAGGAATTTCTTCACCGGTAGGTGTTTTAAC

CATCGCTTGTGGAATACCGCGACCGTTATCTTCAACTGTTACTTGATTGTTTTTAATAGTAACATTAATT

TTATTCGCGAATTTAAACTTAGTACGAATACCTTCATCTACTGAGTTATCGATAATTTCATCAATAAGCT

TAACAAGACCAGGTACATACTGAACACTTTCCCATTTACCAAACATAAAGCGCTCATGCGTTTCATTAGC

AGAAGAGCCAATGTACATGCCACTACGCTTTTTGATATGTTCAATATCGCTCAGAATTTTAATTTCATTC

TTAATCATCACTTATCCTCGTTTGGTTTCGGGAATATTATACTCCGGTAATCATAAAGCTAAAGGCCCGA

AGGCCTTTTATTTAAAACGAATAGTTGAATCCTTAAAGAACAGCCCAGAACATACTGTTCCTTCTACTTT

CTGCCCGGTAGGTCCAATAGCACGAAATCCAGTATGCTGGAAATCATTTTCAGAGCAACCGAACCAATTA

TATCCAGTGATTTCAATATTAGTAAAACCACTTGAAGACAAAACTTTGGTTGCATTAATCAGCATCAGTA

CTATTAATTAAAGACACTGCTAATACTAATGCTGCAATTGAACGACTAATATATTTCATAACTACCCTTT

AAGCAAGTCGTAAAATCCATTATTCCCATGCTTAGGAAGCGGAAACTAACCGAACAGCCAGCCGATGACA

ATCAGGACATACACCAGTATCTCTTCCAGAAATTTTCTTGATTTTTTCGTATTCTTTTGCACAGTCTTTG

GATTGACATTTATAATCATAAAGCGGCATAATTATTCCTTAAAGTAAGCTTTCAACATCTGATATAAAGA

CCACGCCTGATCATTATTTTCAATAGTAACTTTCATGACTGGGAATTCTGTGAAATCTTCTATTTGTTCT

TGCTCTTTCTCTTCCTGCTCTTGCTCTTCAACCGCCTGATATGGATTTTCCACTTCATCAAAGAACCCAG

CTTCGTTAGTAGAGAGCCAGATAAAGTTTTCGTCAAGGATATCACCGCCGGCACAACGTTTGAGTACACC

TATGGATGTCATAATTTTAGTAGGACGCCCAAGATAATCAGCATCTAAAATTTTAAAAGGCTCCATACCT

AAACGTCGTGCATAGATTCCGTTATCAGTATGGTCTTTAATAAAATTTTCTTGAGCTTGTTTATTTTTAA

ATTGATACCATTTATTAACTTCAAATTTAATAGCCATTAATAAATTTCCTTCCAGTAAGTTGTGCCGTCT

TCAGTAATTTCACGAAATACACCATAAATTGGCTGTTTATCACCGACTTTCTCATACACATAAACAGAAG

TCAAGTGAGTAAACTTGCTAGTATGTTCCTTTTGAACTACTACCAAATTTGGATCAAATAATACATCTTC

AAATTCATCATTAGTGCAATTCTGAACAATTTTACGTTTCATTACAATTTCCTCATTAATTGAACAGTGG

AGCGATACGTTTCAGAAGAGTATCAACACCTTTAGCGAATTTTCCATTTTATTCTCCAAGTTGTTTTCTG

TATCAGTAGTTGATATTGATATAGTACCATAATCAACTACTGATGTATATAGTTTTATGAAAAATTTAAA

CTTTATGCATAGAGAGCATTGCTATAGTGTTTAATCCAACTTTCAGGAATGACTTTGTATGTTCCTAAAA

ATACCACGTTGTACAACTTAACACCATCTTCTACCCATTGATCGGTAATGTATCCACACATAGCGCGAGT

-continued

ATAAACAACCCTTCCATCATCTTTAATAAAGTTAAATTCACAAGGAGCAATGAACTTGATAGCCTGACCG

AGTTTCCACTTAAAGTCTACACCTACATGCGAAGTATCAATCGTTTCAATTCCTTTAGCAGGAACAGCTT

TTAAAAACGCAGACTCAAGAAATTTCGCACGAACATAGCCAAACTGGGGTTTAGACTTTCCATCTTTAGG

AATGATACGCACTTTTACTTCAGAATCTTCATCTTTAACACCATGCTTAAGCTGAATGCTTACAACTTCG

ACCAATTTTCCTGCTGCTTTAGAACGGGATTTATCAGATACACGAGCTAATTCACCAATATTAATAATCA

TAGTTATCTCTCACTTGTTAAAAAGATTTTATACTCCACGGGACCATTATACTCTGGTCCCAAGAGTTTG

TAAACTATTAATTCAAAATAGCTACCACTGCACTACGAGGAACTACGGAGTACTCTCCAGCATGAACTAC

GTTCAGAAGTTCAACGCCATCTTCCAATCCATTGGTCAGTTACCCAACCACCAATCGGATTCGCAAATGG

ACGACGAATGTAAACTGCCTTACACAACAAATCAGTCGGGTCTTCAGGTTTTTCAATTTCTGTCAATAGA

TTAAAATCTTCTTCATAGATGATGAATGATGATACCCTTCCATAATAGTTTCTAATTTCCATGTACACTG

TACCAATGAGAATTCCACTATTAACACTAATGACAGTAAAAGGATATCCGCCAGTTGTACCAAGAAGTTC

CCAAAATTTGCTATCAGTCGTATTCGACATTGTCTGAAAATCAATTTCAGATGGTTTTTTCATTTGATAC

GCAGTATTAATTTTAATCATAATTTTCTCTTTAGTTTAAGGTAATAAAGCCTTTTAGTTCGGCATAGGAT

TTACGGAACATTACTTGATGCCCGCCAATGATAACTTGGTCATCTGGTACTTCGTATACAGCAAGATAAA

ATCCTTTCGAAGCTAATTCTTCACGCTCTTCTCGTGTGAACCATTTCATCATATCATATTCGCTAGCAAA

AGCAAAATGATAAAGAGCTACAAACCATCCGGGAATATGATATTCTACTCCAACATAATCTTTCTTGAAC

TTAGTATTAATTACGATATTAGCATTTTTAACTAATAGTTTGTCTTCGTGCGGCACAGGAATTCTTTTAT

TATCATTACTATGATGCATAAAATTAGGTCTGTCATAACCTACATGTAATAACCACTCTTCACTCCATGA

ATCTATTATACTTCTATACGGCGTTATTTGAACACAAAGATCTCGGCGTATTGTTATAGCGTCTTCATAA

TTAAGAATACTAAACGATGATTCAACACGATAAATTTTCATTTTATTATCCTCAGTAGCTATGGTGTTAT

AGTACCACAACTAACCGAGGAAGTAAACAACTTTTTATCGTTTTGTTGGAAGAGATAGAGGATCGCATTC

TTCCTCTGATGGAGCATCTTCAAGACCCATAGCATATCGCAAAGCATACTTCATCATCAGGATGTCTTTC

GCACAGTCATGAATAGAATCATGTGCAACGAATCCATCTAAAGTTCCCTTTGGAAGAGGACACGTTGTCA

TATCACGAACAAGCAGAAGTGCTTCAATTCTAGTACGAATATCACGCTGATTCCAAAATTTACAAGGTTC

TAACTTAAATGTATCAAGCTCATTCTCGGAAACGCCGTTAAGACGTTGAATATCGCGAATAAGATCGACT

AAAATTGGAAAATCAAACGACATTCCACGGCACCAGCCTTGAGATTTCCAAGGATCGATATTATGTGCAT

TGATGTAATCATTAAATTTTGCAATACCGTCGATAGTGCTTACATCTTCATCGGATGGTGCAATATTTTT

TCGAGCTTCAGGAGATTGATTCTTCCACCATTCGATAGTACTTTTAGTAAAAAGACGGTGTCCTTTTTGG

CTTTTTAAATCAAATTTGATTTTAATGCCACGTGAAACTAATTCATCGAATGTTTCAACTACTTCTGGAT

TAGGGTCAAAAGCAATTACAGCCAAATCAATAACCGCTGCTTTTTCACCACTTCCCATTGTTTCAAAATC

TATAATAAAATCAAACATTAAATTTTCCTCGCTAAATCACGAATTTGACCTACAGTATAGTCTTGAATAT

AAACTTTATTAATAGGCTCATCAATAAATTTTGCCATAGATTCAATATCTTTTTGTATTTCTTCAAGACT

GTATACTATCTTTGAAGCTTTTTCGCGAATAGTGATATTTTCAGGACCCGGATTTTCTTGAATGACAACT

TTAACATTTGTCATAAGAGATTTAAACTGGTACCAACTTAATTCAATCATTAATAATCGCCTCATAAAGA

TAGCTAATTTCGCCTAAAACATAATCATTGATTGTAACAGTTTTAACTTCACCGCAAAAGAATTCTAACG

CAATTAAATCTCGTTCAATTTCTTCTAATTGAAGCATCAACTTACTAGATTCAATTTTTACAGTTTCACG

ATTTTTGCTATAAGCTATTTCATAAATTTCGCTTACTTTATCTTGAAGAAGATAAAACTGATCTTTAGTT

ATTTCCACGAATAGCTTCCTCAAATTTAATCATACATAAAACACATCATAACGACCACGGGTGACACCAA

CATAAAGAAGTTGTTGAGCTAATTCAACATCTGCATAATGAATACAAGGCGTATAAATGAAAGCACGGTC

TACAGACATACCCTGCGCTTTATGGAATGTTGATGCAGGAAGTGCTTTCACTTTACTAAACTGTGATTTA

GCATCCCAAAAATCACTCCACGGAGCTTTTCCGCCTTTGTTCCAATTTTTATAAGTTTCTGCTGTTTTAG

-continued

CTAAAAATAGGTTAAACTTATACAATTCTTCGTCAGATGAAATTATTTTAATCTTTTCACGATAATATTC

ATCATCGCCATAAGTTTCTACTGTTAAATCCCAATGACGAATTAGATATTCTCCAGGAACACCACGGGCT

TTAACAAACGTTGATGTATACTCTGCTTCTATAATACGAACTAATTGTCCGTTATTAAAAATAATTTCTG

ACACAGGCTTTCCATCAATTTTATATGTTTTAAATAATGGTTCCTGCATTACAATAATTTCACCGACAAT

AAAATCTTTATCAGTTTCAAAAATCTTTTTACGAATAATGCTATTTAACTTGTCAACAGATTTATTCGTA

AATGCCATTACGCGATTTTCAAACAAATCATCTAGTGATTTGACGATTGAAAAATAATTTACCATAAAAT

CGCGTAAAGCGGTATCACCAGTAAATCCACGTACTCCATGCCCGTCAACAACTTTATCATAATTCCACTT

ACCGTTGCGAACGTCAGTAGCTACATCAATAATAGGAGCATTACTGCGTTTAACTTCAGTGAGTTCACAC

TGATAAAAATCTTTATGTGTAAAGAATGGACTGATATAAGCAGTATTTTCTCCTGGTTCAACAGGTCTGA

TTTGCTTATTATCCCCTATTCCAATTATAGTACACCAAGGTGGAATAGTTGAAAGCAGAATTTTAAATAG

CTTTCTATCATACATTGACACTTCGTCGCAGATTAATACTCTGCATTTGGCTAAATCAGGTACTTCTTTT

TGTTCAAAAAGAACATTTTCTTCATATGTTACTGGGTTAATTTTAAGAATACTATGAATAGTACTCGCTT

CTTTCCCTGATAGTTTTGAAAGAATCTTTTTAGCTGCATGTGTAGGAGCTGCTAAAATAATACCAGTTCC

ACCCGTAGATATTAAAGCTTCAATGATGAACTTAGTAAGAGTAGTCTTACCGGTACCAGCAGGTCCATTA

ATAGTTACATGATGTTTCTTTTCTTTAATAGCCTTCATAACAATGTTAAAGGCATTTTTCTGGCCTTCGG

TCAAATCATCAAATGTCATCGTAAATTCCCTGCAATTGGTATACTAACAATACGCCCAGTATCTAAAATT

CGCTGATATAATCTTTGCGTGTCTACGTCAGGCTTAACATGTTTAACTTCTATTTTATTAAACCAAAATT

TACGTGGAGTCTCAACTAATCTTGGAATTCCCTTACCTAAAGCTAATCGATACTGCTCTTTAAGAGTGGT

AAATACTTTATCAGCAATCTTCCATTCAAAAAATACAGCAGGACGATGTTCATCAAGCGGAACTGGCGCT

GTAAATCCGTCTTTGTCTCGGTAAACTATCGCATATACATAAACCATATTATCCTCGGATAAGTTTAAAA

ATTGAACAATTTAGCGGATATCCTCTTTTCAGTTTAAGTTTATCAATAAAAGACAAATTTTGATACCGCT

CTACACCTTGAATAATTTTATCACACATATCATATTGCATTTCTGCTTCTGACAACTTTTTCACAATTTT

CCAATCCGAGCCTTTAAGAAGAACGTTCAATTTAACAACTTCAGCGCCTTCTGCTATGCGAGAACCATCA

ATACGTGCTTTAAGTGCTATAATTCTCAGCTTAATGTCAGAGGTCTGTTTTGATTTAGAAAGCTGAGAAA

TGTGTTCAATTCGATTTTCACGTTTTTTCTGTATAGCTTTAATTTGATTATAAGTCTTTTTGATTTTAGC

CCATTTCTTTTCATCTAAATTTAGTTTATGAACTTTTTTCGCAGATGAACGACCAATTCGCAAAGCAAAT

AAATCACGCTTTTCAATCAACTCTTCTAAAGTATAATCAGAACGAAATGTATTATACTTTTTCTTTACTG

CAATAACATTCCCTTTAATGTATCCAACGTTATTATCAAAACGTTCTAATGATAATTTCTCTCCTTCAAT

ACGATTATCAAAAGGTTCTCCCGAGTAAGCACAAACTTTTTGATCTAAAATGTTCTTAATGTAATTGAAG

TCTAAGTTAAAATCTTTAGAACGTCTTTTTGCAGATGCCTGAGTATGCTCTAAACGACGTTTAATTTTAC

GAATTTGGTTATTAGACAGCTTCATATTTTTCTCACATCTTACGGACGGTTAACTACTTATACTATAACA

TTTTTACTTTAACTTGTAAACAACTTTATGAAAAATGCTTTAAAACTTTCATGGTATAATGAATCTAAGT

CCTTCCATTATAGATTAAATCCTTCAAAATCAAGAGTATAGATAGTGTATGTTGAACACTTTTTATACTC

ATATCTATCTGCAATTCTAAATACACTTCCAGCTGGTATCATTACTTCTTGTTCATCTGAAACTAATTCC

ATATTACGATAACGATGACTATCCGGAAACTTAAAGTTTGGATTGTATTCTTTACAGCGTAGAGCTTTTA

TAGCATACTCCTGGAAATTGAATACCATAGGAGCTTTGAATTCAAAAATAACTTGTGTGTTATACTCTAA

ACCAGAAGCAAAATGTAGAGCTATATTTTTATCATATGAAGCTGATACGACTTTATCAAATGTAATAATA

TCAATTCCTTGATTTAATACTTGTTTAGTCTCAGCTGGAACACCTCTCCAAAGAGGTTTATCGTTTGGAA

CCAAACGAGATTTGATTATTTCATTTAACCAAGAATGGTCATCTGGTTTATTAGTAATACAATGAATTAA

AAGTTCAATTTCAGATAAATTAAACCCTTCAGAAAGTAATTCTTCACGAATAGAAGCACGCACCGATGCA

-continued

TCCATTGATTTTATTTTAAAATCTTTTAGTTGCATTACTGAGTATTTCATTCAACTACCTCAATATCATA

AACTTTAAATGTTCCAAATGAATCGTGTAATTTTTCTTTTGAAATAGAAGTTATTTTATACTTTCCAATT

GGAATCATCCATTCTTGTTCACGCACAATCATCATTAAGTTATCAGTACGCTCTGAATCTAATCCATCAG

TATCTTCATACGTGTACTTAAACTCAGTATTAGGAGAAGAAAGTATAATATCGCTGATATGGTCAGAATA

ATTAAAAGCTTTATCAGTTTTTAAACGAAGTATTGTTTCAGTGAAATATTCAGCATAAGAAAAAGAACAC

GCTGTATGCAAACTAGTAGTAAATGAATCTACCCTGTTCGTTGAAAACACTTCTCCAACTTGTAAATCTT

TAATGAGTTCTTTTGTCGATTTTGATATACCACGATATAATTGATAAGGCGATTTAGTTAAATGCTTTTT

AATGATTTCATTTAAATGCTTATGAAGAGCTTCATTCTTTTTGGCTTCCATACATTGCCAAAGAACAGAC

TGCTCAAAGTCAGTAAATTTTTCACAGACCTTTTTATACATATCATATTGAAAATCAACGCTTTCAGCTT

TTATAGATAACTGTTCAACATCTGCAAGATTAATAATCATGATAGCCTCCGTATACTTCAGAAGCTATCA

TATCATCGTTAGAAAGGAAAGTAAACAACTTTTTGAATTATTTTGCCCAGGGAGCCCAAGGCGGAGGGTC

AAGATGGTATGAAGCTAGTTCTTCTAGAAGAGCATCTGGGGCTTCAATTCCATAATTCTGTAATACTATA

CGGTACTCTTTCTTATAATCACTAGAATCATTCTGGTTATTCGTAGAATGATTATCTTCTAACATCTCAA

ATAAATCCATATTAATTCCTAGCGATAAAAACCAAATTTACGATTAGTTTCAATGATCTTTCTTTCTTCT

TCGGACATTCTCCAGCGTAGTCCAACATCAAAATGAGCCCAGACCATCCTAACAAATGCATTTATATCTT

TAATATCTTCAATAATGAATGTTTTACTTTTAGAAGGTTGACTCGCTAATTTAACTTTATCGTCTTCAAA

CATGTCAAAAAGACCATATTCATGAGCTCTTTTATAGCCTTTAATAGTTAAAGCTTCAGAAGAAGAAAAT

GGTGAATCTGTATTCTGCAAAATATCTTCAGTATGCTTTATAATTAGAATAATATTTTCTGGATATTTTC

TTTCTTTTATATCTTTAATTAAAAAATCCGGATTTTCTGCTAAAGGAATAATTAATGAGCAATTTTTATC

AAGTGTATTTACTGATTTACCTTCTTTAGACATAAATTCTATTGAATATAATTTTGCTACTTCAATCATG

TGATTTCCTTTTGCCTACTAATGGACCGTCAGGAATTTTATTTTCCTGGATATATTTCTCATTTTCTTCC

ATCATTTTACTGCCAATTTTAAGAAGCAAATCCATTGCTTCATTTGCTTTTGCTTTAGCTTCTTCTAACG

TCATATCTTTGTTCATGATTTATCACCATAGATGTCTCTCATCAATTTAAGCGCTGAGCGTTCTAGTTTC

TTTTCTTTCTCAGCACTAATCATTGATTTCATCCATTCTTCTGATTCATTCTGCATTTCTTTATTTGCTT

GTTCAACCCAACCGTCATCAATATACATTGAGTTTGGTCTATTGAACCATTCAAGCATCTTCTTCAGAAC

TTTCATTCGTTTTACCTAAAACAATAGTAGGAGCATCGTCAAATTTATGAATTTTTAGCAAATTTGGATT

TAAATTATTCCATAAAGAGGTAATAAAATATGATAGCGCACTTTCGTCCGTAATTATAAATTTATTTCCT

TTATCTATTTTCCAATCATATATTGAATCATATGAATAGAAGGATAACGGTTTATTATTATAATATGCTT

CAGCAACATCAATATAGTTAGATTTAGTAAATGCTTGAATTGCCATAAATGGAGAATTTTGTACAGTTTC

AATAATTCCGATCTTTTTAAGTTTTATTTCAACATCTTCTGGAATTGGCATTGAAATAAAATCTTCTACT

AGATACATATTATTGTCATATCTTTTATCAATCATTACTGCTACAGTAATTGGAACATCCTTGACAAACG

CCATACTAATACTATTGATAGACATTTCAAACAAAATTGCTTCCATAATTTTCCTCAATCACAAGATGTA

GATGAACAACTAGAATCACAAGAACTTCCACATGAATCACCTGCCCATACATGAACAGGAACATTAGTAT

CATATGAATCAGAACTAGACTGTGTATTCTGTGTGTTAGATGATGTAGTAGGTGTTGACCAGCGCCAAGG

ATTTTTATAATATTCTTGGGCTTCTTCATAAGTCATAGTAACTGCTTCTACTGTTCCATCTCCCATATAA

ACATATTCAACTACAGTTAAAGGAAGGTAGTCATTTGAAATAGGAACTACACCTTCCCCAGGAGTTGTAG

AGAAAAAATCCGTAAAGAAACTTTTAAACCAATTAAAGATAAACATTACAAAAAGCCTCTTTTGAATTCG

ACTTGCTTCTCACCATAATCATATCGAATCTCTACATTAAATTCGACAGAACCATCTGCGTACATCATAA

ATGAATGCACAACAACTTCTGTAGACCATGGTTGTAGTTCATATTTCTTCATTACATGTCGTGAAATGAT

AATATCTAAATCTTCATTTGGTTTAATCCAACGATTTAACATAGTACTCTCCTCTATAAGATAATTCTAT

TATACCATACTCATTTTGGAAAGTAAACCATTTAAATGAAAAAAGGACTCCCGAAGGAGTCCTTGAGTTA

-continued

TTAACCAGTTACTTTCCACAAATCTTCATTTGCAGCAATCCATTCAGTACGTTGATTTTCTTCATATACT

GTAGAATATGCTGCTTTTTCTGAAGGGAATGTCTGGTAATGAGCGCCAGAAATTTTGTGAACGTCAGAAT

AAAGAGGGAAAGCTACAGAAATTTCCTTTCCTTCAATTTTCTTATTTCCATCTAATTTCTGCTCAAATGT

TTTGATATTAACATAACCGCGAGTACTAGCCATGTAATTCTCCTTTATTTAAATTACATGATTATTTATA

CATCTTCTTTTCTGAATAAGTAAATTAAATTCTTAAGAGCCGAACTTGTTACATCATATTTTCCTTTAAG

CGCCTTTACAACCGGGCCTGTTGCTGGTTTACCTAAAGAAACCCATAACTCGTGTATTTCGCTTTTAAGT

GGTTCATGCCAATGCGGTGCTTTTCTTTGCGCCCTTGAAGTTCCTTCTGAAATCTTTTTATTTCCGCCAT

TCGAATAAAACTTTTTCATTACTTCAGATTGCCGAGCTTTTCTTTCTGCCCTATTTTGGGCTATACGTTG

TGAATTCTTCATCCGAGTTTTTGTTTCAGGATTGTTTAATCTAAGTTTATGTTCTAATCGTTGTTGCTCA

GTCCATTTTCTTCCTTCTCCACCCTGACCACCAGGAGAAATATTAATGCAAGTATCTGGGTGTTTACGTT

TTAATGCAGATATTAGCTCACGTTCAACTTCATATGATTTTTCTCTAGAACCATGGCATTTTGACCATCG

TATTTTATAATTAAATCCATACTTACGATATATGTTCCATAGTATTTTACCTGAACCCGGATATTTATCA

TTATATGGATTTACAATAAATGATTCATGTTTCCCAGCGTACCAAAAGACGCCTTTCGGCGTCCTAACTT

TTACTATATATGTTCTATAAAATTTTTGTTTAATATCCATTATCTTGACGTTCAAAATTATGTTTGTTCT

TCAGATAATAAAGTTTAAAGATTTCTTCCGCATTCATTCCAAGGCCAACAAACATATTTAATACGAAATG

AAATATATCCACAAGCTCAAATTTAATTTCGAGCTGGTCTTCGGGGGACATTTCATCAATGCGTTTTTCT

TGCGCTTCAATATAACGTGCTTTCCATTTTTTCCATACAGCAGAAGCTTCTTTTTCACCACGTGACATTT

CACCAAGAGAAGTCAGAAGTTCGCGGAATTCATCATCAATACAGTCTTTTTGTTCACGCATCCAAGAAAC

AACATCACCGGCAGTTTCTAATTTATCTGGATGATAGCAGTATTCGCGGACATTAGCCAAACGAATCTGT

AAAAACCGCTGCATATCAAGCATAACTTGCAGCGGATCTTTTTCATCACCGAGAATATCCCAGTATTCAT

TTTGAGCTTTATCAACACCTTCGATCAAATGAGCACATTCATTAAAGTGAGCCATTAGTTTTCCTTTCAA

TTCATTAATAAGTTAAATAATTATATCATTTGAGTATGTAAGCAATTAATTAAAAATATATACTTCATCA

GTTCCATTCTTTTCTTTGGAATGATATATGTTAAAGACGTATTTTTTATTAAGATGCTTTACATTATATT

TTTTAGACCATTCTTTAAGAAGAGTGTTTTCCTTTCCGTGGTGTTCTAAAACATTCGACTGCCCAAATTT

TATTCCTCTATCATTTAAAGAATCTAAAAGATTTAAAAGGTCTTTTTCTTCATCTTCTGACCAAAATTTA

TTATAATCAGCAACTGTTATGAGATACGGAGGATCTACATATACAAAATCGCCGTCTAAAATTTTAACAT

CTTTAAAATGCAATGAACTAAAGATTATTTTATCACAATTTTGTTTAAAGTGATTATATTGTTTTTCACT

ATTTTTGTTTATAGTTCTTTTTCCAAACGGAGTAGTAAAATTTCCTTTATCGTTTATACGAATCATATTA

CTAAATCCGTGAAAATGAAGAACATAAAGTAAAAGAGGATCTCTAGTTTTATTATAATCTTCACGTAATT

TCAAAAACTCTTCTTTTGATGTTTTTGATAGTTTGTATTGCTTTATTACTTTTAAAACGTCATCCCATGA

TACATTAATAAGACGCTTATACATTTCAATAATTGGTTCTTGAATATCATTGGCCAATACAGGGCCATTA

ACATTCAAAGACACTGATAAACCTCCACAAAATAAATCCACGAATCTGTTATATTTTGGAAAGTGAGATT

TGAGTTCAGGTAATAATGATTGTTTATTACCTGTATACGCGATAGCTCCTAGCATTATATTCTCTCATTT

ATTGCAGCAAAAATGAATTATACAATTCTTCATCATATGTATTTGATAGTAATACTAACACGTTTTGCGA

TAAATATTAATTTAAAGGAGGATATATATGGTACAAAAATTAATGGCACTTGTTAATGCCATAAAAGGTA

ATAAGAAACGTATAGCTTTTACTATTTCTACTATGGTAGGAATTTTACTCTGGAACTTTATTTTATCACC

TGTTGCAATTGCACATGGTGTTAATATTCCAGTAGTTACTCTTGATACATTCGTAGATTTAGCATTTGCT

TTAGTTGGGTTAATTTAAATCTTAGCATATTTAGATAGCCGCATTTTAGCCATTAACCCCTGGGCAATAT

TATTTTTCATATATTCCATAATTTGTTCAGGGGTTGCACCTTCCTTTCTAATCATATCATTAACATCTTT

TGATTTCCAGGGAGATTTATCCCAAAACATAACCCTTTCTCCTGCATCAACTAATTTAGTCATTCGTTTA

-continued

ATAGTGTCAGGGTGACGAGGTTCATTATCTAAGACCCACACACGTCTATCTTTAAATGGAACAACTTCTA

GGTCTAATTGACCGCCCGTAATAGCTATACCATTTTCAATAAAAAGTGAATCTATAGGTCCTTCTAGAAC

ATATACATCACCATCTTTAACTCGTTCGACTCCATAGATTTTTGTTGCCTCAGGATAAGCTTCGATGGTG

ATATATTTTTGAGGAGCATCTTTCTTTAATGCACGTCCTTGAAAAGACTCAGCTTTTCCATTAGCATTAT

AAATTGGAATAACAAGACGAGGCTCAGAAATTTCCTTTTTGTATGTTCCCGGTGCTATGCTATTAACTAA

TTTAGGCCATTCGGTTGTAAACCAAAGATATTTCCATTTATCCTTTGGAATACAACGAGCTTTTACGTAT

TTTATAATTGGATGGTCTTCCGCCAGTTTATCTAATCTAACACATGACGGAAGAGATTTAATTATTTTCT

TCTCGGGTTGTTTAGGAAGTTCTTTAGGTTTTTCTATTGGACGACTTTTACCTTTTTCTTTTCTTATTTC

AAAGATATACTCACGATATAAATCGGGTTCAAACTCCTTTAAATATATTCCGATTGGTGCATGATAGTTA

CAGTTATAACAATGAATATTTCCTTCATTATTATCACCATAATACCATCCACGGGCTTTATTCTGGTCGG

TTTTTGAATCTCCACAAACAGGGCATCTAAACCGTAATTTAAAAGTTGAACTATTATTTACTTGTGTGAA

TTTAGGTAAATGAGCTAATGCACGGTATGCAAACTCATTATCAATCCAAGGTATTGATGACATTTTTACT

CTTCTTTTTCTTTAGATTCCTCTTTTTTCTTTTTAGGAATCTGTTCAGGACCTTTATTTACTACAGCGCC

TGATGTTGTTCCAATAGAGATATTTTCAGGATTACCACCTGAATCTCCAGCGACCATATCTTCTTTGATA

AATTCTTTAAATGTTTTCATATTAACCTCTATTCATAAAAGCATTAAAAATTTGGTCATCAATAGAAACA

TTTACTTTAGGCTGTTTTTCAGATGGCAATTCATATCCACATATTACAATTTTATGATCAATATCAAAAT

ACACAGAAGCAATATGATTAATGATATTTTCAGTAAAGTCTAAATCAACATCAATATCTTTTTGACCAAA

GCCCAAAGGATAAATAATGCGAGTAATTCGATTATCTTTAACAAAGATTCCACCGACATACTCTGTGCTG

CGTTTAAAGTCTACACGCCGACGAAATGAAAAATATTCAGGCTCTTTATGAGCTCGGCTCATAGGACACA

ACGAATAACTAGAATAAGAGATGTCAAATCCTACGCCTTCAATATGAACTAAATTGTCATGATTAAACCA

ATTATAATCATATGCCAAGTCCATTAGATTGTCATATGTGAAAAGCACCGGATTAACATCATTGGTCACA

AGCATATAATTAGCAACTGCTATAATTTCATTATTTTTAACGAATACAAACCGTGATTGATGCGAATGGC

CTGGACCTGCGTTTTCACGATTAATGATATAACACTGGGCACCTTTATATTTGTACGTGTCTTTACACTT

GTGCATTTGATAAAGCATTATTCACCTACCACTTCAGCGATGATATTTTTGTTATTAAAGTTTTTATCGC

AATACAGAACATAATTATACTGCATTACACCACCAGACTTAAGCTGTTTTTGCACTTCAGCTTTCATTTC

AGGACGATCACGCTTAACGATATTCATAATATCTGCTTCAATTTGAGTTTCAACCTCAGTCTGATCCGCA

GTCATAGACCATTCGCACAAATCTTTATCATAACCTGCCATAGCAGGCTGAGCAGCACAAGAAGCTAAAG

CAAAAATTGTAGCAAAGATGAATTTTTTCATGATAATCTCCTCAGTAGTTTATGTTTATATAGTATCTCA

ATTTCCAACAAAAGTAAACAGTTATTTTAAAATTTCTGCGTAATCACATGTTACAAACTGTTTCTCTAAC

TTGACGATTTTACGAAAGTATCTTTTGCATTGGCGAATCTGCCTCTTCGTAGGGCGAACAGCAAACTTAA

TAAATTCCACTCGACCAAATGGAGGGCTTTCTTCTGCTGGAATATCTAACACCAATTCCCACGTATCTGC

AATAAGTGCTTTGAATTGCGTATTTTTCCTGACGTTATACGGAGTAGGTTTAAATAAAACAATATGCATA

TTATCCTCGGCAATCCACTTCACATACTTTCTTGTCATCAATGAAAGCTTTAACTAATGCTTTATTAACT

TCAGCATATTGAGTAGTAGCCCATTGAACGTCATCTTTCATCATTGTGATTTCTTTAGTAAACATGCTTT

CATTCTTAAACCACCCCATAAAAACTACCTTTACCAATTCCATAACAATCTCCTCATTTAACCGACAAGA

CTACTATACCATAGTCTTGTCAGCTTGTAAACTAAAATTTAATTCATTCGCCAAAGCATCTAACTGAGC

TCGAGTCGATTCATTTCTTTGATAGCGATTCTGCTCAGCCTGAATCTGTTGTGAACCTGCTACTTCGTTC

ACTTCAGTTGGAGTAGAATCTTGTTCAATTTCTACCCATTTTTGATTTCCTTTTTGAACACCCATCAAAA

ACTTATTCCACTTATTCTTATCACCATATCGTGATTTGATTTGCTTAATGAGTTGTTGTTCAGCAGCTGC

TAGCTCCTCGGTTTCAATGACCGCAAGCATAAAATCGGCTGTTGCTGGAAGACCGGCAGATTCTGCAATA

TCGCTCATGTTAACATCGGAAGAGTCCCAAGCTTGTTTACCAACCTGTGCTGCAGTCCAAAGAACAGTTT

-continued

CGGTTTCAACAGCCAGAGCACGTAATTCCTCTGCAATAGCTTTAACAGTTGTGTAACTATTTTCTGAATA

AACTCTAATGCGGCAAGATTTACAAATACCTAGATAGTCGACAATAATGATTGTTGGAACAAAATTCTTC

TTGAGCTTCAATTCGTTTAAAAGTGATCGAAATGTATTAGCGTCTGCTCCACCAGTAGGATACTGTTTAA

CGATTAAACGACCAAGAGTAGATTTCTCACGCCATTTTTCCATTTTTCCTTTATACTCAGCGTAAGAAAT

ATGCCCATCATCAATGTCATCAAGAGAAACATCAAGCATATTAGCGTCAATACGTTTAGCACAGACTTCT

TCTGCCATTTCCATGGAAATGTAAAGAACATTATGTCCGAGCTGTAAATAATCTGCCGCTAATGAACACA

ATCCTAATGATTTACCAACGTTAACGCCAGCCATTAAAACGTTCAGTGTTCCAGTTTCAGCTCCGCCTTT

CGTAATTTTGTTCAGAATTCTGAGTTTAAATGGAACCTTACGAGCTTTATTCATATAAGATAGCCAACGT

GCTTCGTAGTCATCCATCCAATCATGACCAACGTAACTATCAAATGAAATTGATAATGCCTGGCGCATGA

TGTCAGGAATAGCACCAACATCCGGCATTTTCTTATTTCGTTTTTCCGGAGGAAGCTCAGCATTAGTTTG

AATTTCGATTATTTTAGACGTAGCATTAAACATCGCCCTTTGCTGAACATATTTTTCTGTTTCTTTTACT

AACCAGCTGTGGTCTTCCGGAGAATCAGCCAGTTTTGAAATAAGTGTTTTTACACCAGAATATTCTGTTT

CAGTAAATGAACTATTTTCTAATGCAACATTTAACGCATTAATAGATGGAACGCTATGGTACTCATTAAC

ATGAGATTTAATTAATTTGAATGTATTTTTAGCTGGACCACTTTCAAAATATTCTGAATCCATATATGGC

CAAACTTTTGAAAAATAAGCTTGATCAAATATGAGATGAGAAAGAATAATTTCTACCACACTTACTCCTT

AAAAGAATTTAAATTTTTTCTTTGACCTTTTATTAAATGCATCTTGCAGTTGCATTGTAATACATTTTTC

TACATGAGGAGCTAACTCAGCTTTTCTTTCTTGGTCAAGAACAGCAAAGTCCATTACAACCTTTCCATCA

ACCCAATCCAGTTTAGTTACATACACTATATGCGTAGAACCATCTTCTAGTTTAATGACAATCTCCTGGA

TAACATTTTCCATAGCAGATTTAATTATCTTAAGAGACTCATTAAAAAGACGTTCTTTTCTTTCTTCTTC

CCCCTCCGAAGAGGGGGATTCATCGATAATTTCTAGATCTAAATCTAAATCATCTTTATTCATTAAATTC

TTCCATATCACTTAGCTGTTCGAGGTCAGTTTCTAAATCAGCAGCTGATTTACTTTTACTTTCTGGAGAT

TTAAATTTTTCAACCTTTGAGTTAATCAATTCATCAACTTCAGCTTCAACAATTTCATTACTATCAATAG

CACCTAACTGATAAGCACGTTTAATAGCATCTCGGAATGGTTGATGCTTAAATAAAGGACCCCAGAATGT

AGTGCAGTTGGTATCTTTTGCACGCCAAGATTTTTCTTCGCGAATCATCTCGCCAGTTTCTTCGTCAAGA

AATTCACGAGCATACCAGCCATTTTTAGGTTTTACCACGAATCCTAATTCTAGAGCCATATCTAACAATC

CAGAATAAGGATCGATACCACCGTCAAATTTAACATCAATAAAGAATTTACTTTTTTCTTTAACGGTACG

AGATTTTTCTACATTTAGAACAAATTGATACCCCTGAAGATCAGAACCATCTTTAATCTGGCGTTTACCG

ATAATGAATACGGTATCAGCCGAATACATCGGTCCAGTACCACCTCCCATAACTGTTTTACTAAACATTT

CTTGTGTTTCGTATGTATGGTTAATAGCAATACATGGAATATTTTTAGTACTAAAATAGGGAGTTACGAT

ACGAAATAAGCTTTTCATTGTTTTAGCTCTAGTCATATCACTAACAACTTTTTCATTTAAAGCATCTTCA

GTTTCTTTCTTAGAAGCTAAGTTACCAAGTGAATCGATAAAAACGACTACCTTTTCGCCGCGTTCAATTG

CATCCAATTGATTAACCATGTCAATACGTAATTGCTCAAGTGATTGAACCGGAGTATGAATTACTCGTTC

TGGATCGACTCCCATAGACCGCAAATAAGCAGGAGTAATACCAAATTCACTATCATAAAACAAACATACT

GCATCAGGATATTGACGCATGTAAGATGACACCATTGTTAATCCAAAGTTTGATTTAAATGATTTTGATG

GACCTGCCAAAATTAACAGACCAGATTGCATACCACCAGTAATTTCACCAGAAAGTGCAATATTCATCAT

AGGAATTTTTGTTCGAACTACATCTTTTTCATTAAAGAATTTAGATGCTGTTAATTCTGCAGTCAATTTA

GAAGTAGAAGCTTTAATCAAACGAGATTTTAAATCAGACATATAATACCTTATAGTAGTGTTCTTGTTCC

ACGAAATACTTCGAGCATTCTTGCATAAGATTTATTTGGAAATCCAGCTTCAATTGCTAATTTTTTAAGC

TTAATAGCACCGGATTTTCCAGAGTTTTCCCATATTTCTTTAATCTTTTCAATGTTATCCCACATTATTG

GGTCACGTTTATGTGATGGTTTATTTCTATTATAACCATATGGATTATTAAGCAAAGCTTCTTTTCGTTT

-continued

TGCTTTAGTTTCTTCTGACTGCTTTTTGCCTAGCTGGGCTTTCCGGCAAACATCACTAAATCCAAGATGT

TTTGGTTTTCCTTTTTGAGCTTTTGAAATTTTTTCTTTGGTTTCTGATGAAACTCTATAACCAATTCTTC

TACCACCCTCTCCACCAATTTTTAAATTATAAGTCATAGGATCATTTACCACATCTATTGTTACTAATTC

TCTTTCAGCATCACGGGCTGATTTAAAATCTTTATAAAACCCAAGAATGCTTAAATTAAAATTTTTCTTA

CCATACTTTTTCTTGGCTTGTGCTAATAAAGTTCCTGATCCCATATAACCATCATTTAAATCATCGGTTG

AATGAGTTCCATAGTAAATTTTATTATTAACTAAATTAGTTATAACATAAGTATAATTATATTTCTTTTC

TTTATGTCTTTTCATGTCATTAATCAACTGCTATTCGATGAACTTCTCTCTTTTCTAATCAATATAACAA

AAGAAGTCCCAAAAAGCAAACAGACCTAAACCGATAATAAGCAATAAAGGTCCTAACATTTATTCCACCG

GTTAAAGATAAATAACTTTCTAATAATAGTTCATAATTTTTATAAATCAATAGCTTTTTTGAACGCATCT

TGCCATTCGGCTTTCTTTGCACGGGTTTTATTTAAAATATCATGTTGAATAGAAAGCATCTCTTTACGCA

AAACATCACTGTGTTTTAACTCATTGACTCTATCAATGAGTTCAGCACGATTATTTACATAAAAACGAGC

ATCATTAATAATTCGATGTTTGGTATCAAATTCTTCGTCAATTAGCATCACTGCATCAGATGCCATTGTT

TCCCAGACGCGTAAGGTAATAAAGTTGTCATTATAATTCTTGTCACCAATAATTAATGCAGCAATAGCTT

GACTATTCTTTTCAGATACCATGTTCATAGGAATTTTTCCAGTGAACACCGGAGCTTTGGTCCAAGGATA

TTTAGGATTTTTAAACTGTTTTTCTCGTGCATTGCCAAAAAACTCAATATTTAAACCGGTGTCAAATAAG

AATTCTACCATCTTGGATTCGCGTTGACCGGACCGAAATGAACCGCCATAAATAACATCCAAAGTTTTCT

TGGTAGGCTTAGATAATTGAAAATCGTTCATATGAATTTTATATTGTTCAATAGGAAAATATTCAAATTC

AATAACATTATCAACTTTCTTATGCGCAGCCTTAGCAATGTCTAAATTTATACCTTGGGAAATCACTTTA

ATTGGTGATTTAATTAATAGCTCTTCTTCAGTGTACAAATATGCCCATGGTCTATTTTTAACATTTGGCC

AAGACTGCGAAAACGGCAAACGTATATCTGTAAATAAATAATAAATTTTACTTTTGTATTTTGCCATAAA

TTTTTGCGCAGATAAAATTGCTAAATTAGGTTTACCGCCAAAAAAGTTAATAGAAGAATTAACAACTATC

AAACGGTCATAATCATTAACATCTACTTCATCAAAAGATTTAGTGTAAACACCATTTTTAAGAGAAATAA

TGTCGACATTAAGACCCATTTCAGAAATAACTTTAAAAAGATAAATAGTTTCAGAAGATGGAACAGTTTT

AAAATTAATAACATTATTACCCATATTAATTATAGCAATTTTCATATTATTCCTTTTATGTTAAACGATT

AAGCGTATTTTCCTACATAATCTTTTTTCGAAATATGTGTTTCGCCAGTTTTCCACCAATGATCAACCAA

ATAAAAATGACGAGAATACACATGTAGGCTTCCAACATTCCATATAATGGAACCTGCTTTATACTGGCGA

GTTGAATCACCTGCATTCAAATCAGATACTAATTTATCTAATACGTATTTTTGCCATGCATAATCATTAC

GGAATCCGAAGACCACGTCATTTGAGCGCATGTTAACAACCGCATTGATTTTCTTGTCACGAATCAGGTA

TTGTACTGTATTCGTGCACATGAAATCTGACATACCATCTTTATTATAGTCAAACTGCATAGATGGACGA

GTATAAATCATGATACCACGTCGAGAATCAGGATTTTGACCAAGTTCAGCTAAACACATGTCATACTGAG

CATAGTTATCTTCTGACCAGATAGCCCAACCATAATTCGAGTTAATTTCACCTTTAGAAGATGCTACTTG

TTGCCAAATCTTCGGTGTTTCACCCGGAATATCTTTAACGAACAAGCTTTTAGATTTATACCATTCAAGT

TCACGCTGAATGTATTCATCATTAAGAGCGCCAAAAATAAACGGTTCATCTGCTACAAATGATGCGCCAA

TAATTTCAATAGTTTTAACACCTGTTTTATCAACTACGAAATCTTTTTCTTTTAATGCAAGCCCCAAATG

AAGACGGATTTCTTCAACTGTCATAGAGTCACTAATCATTTAAACCTCAATTGATACATTCATATTTAAC

TTGTAACAGTAATAAACTCCAACCTAAAATAATAGTTGGAATCATAAGAGGAACCGTTACACTATAGTAT

ATACTTATTATAATCATCAAGATTAAAAGCAATGCTGCTATAATTTTGCTTTTCATTCCTTCTCTCTGAT

GATAATTACCTGATTTGGCTGCGCAGACTTTTTAGTTTCACCTGCAATTGACCAAATAAATGTAATAAAC

CAACCAATAATTGACCAGTTAAACAGTAAAGATGCGAAAAAGATTCCTACTGTCGATTTTGACCCACGCA

TCAAGGCGATAAACCATGGAAGCATGTATATAATAATAGCCAACACGCCTGAAACTAAAACCATAAAAAT

TGAACCTGCTACTAAAGTTTCCATGTTTTCCTCACTTAGGTCAAATTTTTTACACATGAATTATAAGAAT

-continued

TCACTACATACTCCATCGGAGCGTTTTTACCTGTACGCCACTGGTAATTATTAGCCCAATTTGCCCAAAG

CTCAGCGCAGTAGTTTTCAATTTTTTCTTCGCGTGTAATTACATCTGAATTACGATATGCTTGAGCAGAT

TCATCTGGACGAATAGCTTCGTCAAAATTCGCCTGCATTTGTTCTACTGTCTGTTTTGGAGCTTCTTTAT

AACACTTGACATTAGGATTATAAAATTTGCTTGAACAGTTTACAATTTTTCCTACATCAGACTGATTTAC

TACCGGTCCTTGAGCTACACAACCAGCAAGACCTAATGCAATAACCAAAATAGCGATTTTCATTTCATTC

TCCAAATCCGTATCAGTAGTTGATAGTTGTATAGTACCATGGAAGAACAGTCTTGTAAACAGTTTTGTGA

AAAAATTTTTAGGGAATCCAAAGGGTCCAGAATCATCTCTTTTTCATAAGTATAGATTTATATTACTTGT

ATGAAAAAGGGACCTGGAGGTCCTAGATTTATTCTATCAGCCAAACAGGAAGTCTAACGAAGCTTTTTCT

TCATAGTCCATGCCAGCCGATTCACACATACCCGCAAGCGGTTTAACAAACGATTTTTGGAACAAAGTTG

AGTGGTCAATCCAAGATAGCACATCAGAACGAATTTCTTTTGGAAGTTCTGTACCCGATGGCCAAGCAAT

GCACTTGTCACCAAATGGATTTCCTTCACGTAATGGAAGAACCATTACTTTATTTCCATCCAAAATTGGA

GCTACACCTAAACCGCTAACAGCTCGACGATAAGTTAGCACACCACGAATATGGAACGGGCATTTAAATC

CTGGCCAACCTTTATCATCATATTTCGCTATATCGTTCGCAGTTTTTACTTCAGCAATAACTTTATAGTC

AAGTTGACGATATTCTTTCTCGAAGTTCTTGTAGTATTCTTGGACAGACTCTTCACCTTCCTGAAGAATA

CGACGAATACTTTCTTCGAGAGCTTCTTGCACTGCTTTTGGTGTTGAACTCTGCTGAGTTTCCATACCCA

TGATTTTTAGATGCGGTTCAGCAAATCGCTTATCTTCCATATCATAAACGTTCAGAGCATAACGCTTTTT

CGCTTTCCAAAATCCACCAACGCCCTTTGAACCAAGCGGAGGGCAAGAAATAGCTTCACGGTCCATATGC

ATCAGATGCTCGCGGTTATTCATATAATCACATAACTCACGATATGCAACATCAATCATAGGTTCCATCT

TTTTCTTACCGAACTGATTCATGAATTCAACCAAATCGTTCTGCTCTTTGAATCGGTCAAGACCAACTTT

TTCAATAACTTTATCTACGCAAACATATACCGAATCAGTATCACCTGCTGCAATGAAATCTTCATCATTA

GTTCCGCATACTTTATTCAGATATTCATTAATTTTACGAGCAATCCACTGAATACCGACTTGGCCGAAAA

TTGTGATAGCAGTAGCATTTCGCAAATCATAGTAACGGAAATGAATATTACCAAGAGCACCATAAAGACT

GTTAATGAGAATTTTACGGTTCAGCTGATTTGTATTAGCAAGTGTAGCTGCTTTTTCACATTCTTCAATC

AGACTATTGAGAACAGATTCGGTGTAATTCGATAGTTCATTTAAGAAATCATCACTGAACTTAACATATC

GTTCAACTTCTGGTTTAGTTGAACAAGACCCTGCGCCTTTCATAATAATCTTTTTAATAGCTTCGGCATT

CATTTCTTCAGCGAACATTTTCTTTTTCCAGTCTTTACGCTGGAAAAATACTTTAGCGATTTCCTTTGGA

ATGATACCTTCTTGATGTTTATCATACATCCATCCATTCGGAGAACAAGAATATTCATCACTCGGTTTAG

GAGCTGTTCCTGCGATATATTCATGAATTGGATGAACTTTAAACTGACCACGAATAGTTTCAGGACTAAT

GTTAACCTGGCGAATAATGCTCGGATACAGAGACGTCAAGTCAAAACTCATAATGTATCGACGTGCAATT

GGTTTAGGTTCAAACACAAATGCACCCGGAAAACTCTGTTTAACGTGCGAACCTTGTTGAGGAATAACCT

TATGTTCACCTTTCAATGAGTTAAAAATAATAGCATCCCAAGTTTTAATAGGACTCATTACACCAGAAAA

AGGCATTTTAGCGTAATAAGACATACTTAAAACTAGATCGATAAACCCACGAATTTTATCGATTGCTTGA

ACTGATTCTACGTCAATGATGTTATAACTAATGTATCGTTGATGATTAGTCTCACGAAGTTTATTAATAG

GACCGTCGTATGGTAATTTACCTTTTTTGGTTTCATGTTGAGCAACTGATTCCAAAGAGAATGACGGCAA

ATTAGTAAAAGCGAATTTCTTGTACAAATCTAAATAATCAAGAATAGATACGCCATCAATAGAATAAATT

TCTTTGCTACCGTACATATTTTGAATTAGTTTAGATTTTACCCGACCGATTGGAGAGAAACGTTTCATAC

TACGTTCACCCAGAATCATTTTAACACGATTCATGATATACGGAACGTCAAACCCCTCAATATTCCAACC

AGTAAAAATAGCAGGTCGTTTCTGTTCCCAAAGATTGATATATTCCATGAGCATATCACGCTCATTATCG

AATGGCATATAAATTACTCGGTCAAGAATTTCTTGAGGAACTTCATCACCACCTTCACAGTCAAGCTTAG

CAGCTAACTTTGCATCCCATTTTGATACTGAACCGTACATTGAATTCAAAAGGTCGAAAACATAAAAACG

-continued

ATCGTCAATTGAATCGTAATGAGTGATAGCATCAATTTCATATTCTGCTTTCATTGGGTCAGGAAATTTA

TCACCAGTAACCTCAATGTCACAGTTAGCTACACGAACAAATTTTCGGTCATAAACAATTTCTGAACCAT

ATGTATCACTTATATAAGCGAGTTTAAAATCGTTCATACCGAGAGCTTCGAGACCGATGTCTTCCATTCG

CTTCATCCAATCTCGAGCATCTTTCATTGATGGAAATTTTTGAGGAGCGCAGTTTTTACCATAGATGTCT

TTGTATTTTGACTCTTCCTTACAATGCCTAAACATAGTTGGAAGATATTCTACTTCACGGGTACGTTCCT

TTCCATTTTCATCAATATAACGTTCAACAATGTTATTTCCGACTGTTTCAATAGAGATATAAAATTCTTT

CATAGATATTCCTTAGTTTATAGCCCGAGTTATTAGGCTCTTGATATATTATACTCCAAATAAGGGGCCG

AAGCCCCTTGCTTAATTACCAATCGTATATTTAGGAACGAGCTTCCATTCATGTTTTTGTTTAAAAGAAA

TAACTCGGAAGTTATTAGTTAAATCTTTCATAAAAGTTCTTTGACCAGGAACGATTTCAATTAGTCCCCA

ATCTTCTAATAGCCATGCAATCGAATCACGACGAACTTCATCTTCTTCTGTCATTTCAACTTGACGACCA

TCCATACGAAGCATTTCTTTAAAATGAACGATATAGTATAGTCCTTTTTTCTGAAGAATATGACAGGACT

GATATAGAACTTTATCTTTATTATTAGCAATTCCCATACGAGTCAAAGTTTCTTTTACTTTCAGAAAATC

TTCAGGTTTTTTAAGAGTAATTTCAATCATTTTACCATTCCAATGCTAGTTTTTTGAGTTGTTTCTGTTC

TTTTACGTTCTTAGTCACTTCTTTCAAAAAATCATCCGTGACTAAACCTTTTAGTTCTTTTAATACTAAA

GGAAGTTTTCCATTTTTAGTAAGAATTGATTTATAGTTAATTGCATCATTTGTATTAACTTGATACCGCT

TAGCAAGTAACTTAATAATCAATACTTCGGTGGAATCTTCAACCAGTTTTGCCCATTTACCATATCTTTT

ACCACGAGGAACTGCAGCCATTAGATAATTAAAATGAGCTTCATCACTTAAGCCTGATCCAATTAAATTC

ATAGCATATACAGCTGGCATACACTCTGGAAATTGTGATAATGCATTTTCAACCATGAATTTTGAATAAT

CTTTTTGAGCAATAGAGCATTTAGTTTTATTATTAATAGCTCCAATTATTTCAAAAAATTCATTTTCTGC

TTTTTCTTTAAAAGAATCAGCAGCGGATTGGACAGCTGTCCAATCTTTTGAATACCAAGCAACTTGATGC

TCGTTTAATTGAATATCATCTTTAAATAAGCTCATATCACTTCCACTGCATTTCGCATGCTAATTGAATG

AAAAGATAAGCTAAATGCAATTCAGTATTAGCTGCAATACCATGATACTGATTATTTTCGCCGACAATTT

CGTACATACGAATAATACTTTGTGGAGTTACACGTGAATAGATTTCTTCGGCAAGTTTACCCACGAACCA

CGAATAATCAGCCGCATATTTTGGTGCTAAAGCTCTGAGTTGTTTAACATCTTTATTTTTGAGAGACTCA

AGAACATCATCAATAGCACCACGATCGTTAGTAACCAGTGATAAAATACCAGCATCCAAAACACCTTTAG

ACGAATAACTATCGAGCTCGCCAATAGTTTTACGAAAATCAGGAAAATTCTTTTTAACCAAAGCTGCTAC

AACTTTCATATCAGCTATAGCAATTCCTTCATGCTTGCAGATTTCAGTCAATCGACGAATCATCTGCTTC

ATCATTTCAATTTTATCTTCATCAGTTGGTTGACCGAATGTAATAACTCGGCAGCGTGACTGAAGCGGTT

TAATAATACCATCAATATTATTAGCAGTAATAATAATACTACAGTTTGAACTATAAGCTTCCATAAAGGA

ACGAAGATGTCGCTGAGACTCTGCTAACCCTGAACGGTCAAATTCATCAATAACGATTACTTTTTGACGA

CCATCAAATGAAGCGGCGCTGGCAAAATTAGTCAAAGGACCACGAACGAAATCAATTTTACAATCTGACC

CATTCACAAACATCATATCAGCATTTACATCATGACATAATGCTTTTGCTACAGTTGTTTTACCTGTTCC

TGGAGAAGGAGAATGAAGAATAATATGTGGAATCTTACCTTTACTTGTAATAGATTTAAAGGTTTCTTTA

TCAAAAGCGGGAAGAATACATTCATCGATAGTAGATGGACGATATTTCTGTTCAAGAATGTGTTCTTTTT

CATTTACAGTAATCATAATTTCCTCATTCAAGTTTTAGTGTAAATTATAAAGGCCGAAGCCCTCTATTAA

AAATCGTGGGTAGAATCAGCTTCAAGAGCTACCACATAATTCGCGTGTTCACCTTCAAATTTAGCAGCAC

CTTGTTTACCTTTTGCCCAAAGCAGAAGTTTATAATTTCCTGGTTGCATTTTCATATTTGCCATATTGAT

AATGAAATTAAATGTATTTTCACCATCATAATCACCAAGAGTCAAAGAATATTTAACACGGGTCAGAGCA

GAATCTTCTACTTTATTAAAACCGTTAATTACGATTTTACCTTCTTTTACCGTGATAGCAATTGTATCAA

TTTGCAGACCACGAGATACACGCAACAGCTGTTGAAGGTCTTCAGCTTTAATTTCAGTAACAGCAGATGC

TACCGGGAATGGAATTGGTTTATTAGGAGCAACTACTGTACTCGGATCGGCTGCTGGCCAAAAAATTGTT

-continued

GAGCGGGCATCAGCAATTTTAATATTTCCATCTTCTGACTGGGAAATTTCTGCATCATCATTAACTAAAG

ACAGAATACCGAGAAAACCGTTCAAATCGTAAATTGCTACATCAAAATCAATAACGTCAGAAATATTTGC

TTCCGCATAAGTTGTACCATTAACTGCGCGAGTCATAATAAATTGACCGGATTTAAGCATAATACCAGAG

TTAATAGTAGCGAAATTTTTAAGCAGAGCAGTAGTATCTTTAGACAGTTTCATGTAATTTCCTTCAATTC

AAATGAGATTTAATTTTATAACTAATTTAATAAAGCAATTAACGATTAAAATCAGCCGCAATTGTTTCCG

CAACAATTTGAGCAGCAACAATTAGACGTTCATCTGCATTACCGCAATAATCATCTTCAAGGCGTTCACC

ACATGAAGTCATAATAAATTTAGCACCGGCGTTTAGGGATTCTGTAGTATGTTTGCGCATTAGTTCAATC

CATTTATTACTTACTTCACGATCGATAGCTTCATAATACGCATGACGAGCAGGTGCAGATTTAATTTTGT

TCTGAATAACTTCCATTGCGTTATCAGAAAGAGACAAAACCCATGCTCGACGAATTTTATTTTGGTTTTG

TGGATTTGATTCAGAACGCACGTGTTTTGGCTGAATATCTTTTACATCAACAGTATAATTCACAGTAATT

TTAGTCATAATACACCTTTAGTCATAATAATCAGTAACAGTCCAAGCTTCATTTCTATTGGACATTATTT

TTGTATATTCTGCTTTAAATGCATTCCTAAGCATAGATTCAGTAACTATATGCTCTTCATTAGAAAAATT

ATTTCTCAGAATATATCGTTTTATTTCAGGAATAGTTAATAGATGCTGTCCAGTTGAATATTCCATGTTT

TTCCTCCATAGAGATTATACTCTAATAAATTAAAGCATAATCTCTTATAAATTAAACCATTACAGTAAAT

CGACCAACTTTCTTCATTTGAAGATGCTGACCATATTCTTGCGGGTCATGGTCTTTATGCGAAATTATAA

AAACGTTAGTGTTTTTCATTGAATTTATAATATTAGCTACACCTTTAATACCTTCGGCATCAAATGACCC

ATCAAACACTTCATCAAGAATTAATGTACTAATACTAACACCAGATACGATAGAAGCAATATCACGCCAA

GTAAATAAAAGAGCAATATCGATTCGTGCCTTTTCACCTTCACTAAATGAAGCATAACTAAAATCTTCAC

GACCACGGGATTTAATTGTCTCATTAAATTCTTCATCTAATGTAAACACATAATCCGCTTCCATTATTTT

AAGATAATGGTTAATCTGCTTATTAAATAATGGAATGTACTTTTTAATAATAGCACCTTTAATACCAGAA

TCTTTGAGCATATCAGTCAAAATTCCTCGGTGGTATTTTTCCATTACTAAATTAGTTTTTGTCTTAACAA

TTTTATCAAGTTCTTCTTGAAGCAGTGCTATTTCATCAGCATGGTCAATAAACTCAGAAGATGCTTTTTC

TATAGCCGCTTTAACTTTTTTAGCTTTATCTACTGCTGCGATCAGAGATTGCTTTTTATTGCGAATATCA

TTTGCCAACGACTGCTGGGTTTTAATATTATCTCGGTATTCATCAACAAGAACTTTTAAATTATCACGAT

GTGTTGAAAGCTGTTCAAACGAATGTGTGCATTCAGAAACTTTATCTTTAATTTTAGAAACAACTTTATC

ACCGGAACTCAATTGTGACAAACAGGTTGGACATAATCCACCTTCGTGATACATATTAATGACTTTATTA

TACGAGTCAATTTTTGATTTAATTAAAAATGCTTCTTGACCGATTTTATTAAATGCATCAGTCGGGTCTT

CGTCCAAAACAATATTAACTAATCTTTCGTTAGCTTCTTCTATTTCCGATTTAGCGTTCTAGCTTCTTT

TGCCAAATCATCATACATATTTTGTAGACGAGTAAGGTTGTCACCCGTTAATTTTTTCTGGCGTTCAACA

TTATCATTATATATTTTAATTTGTTGGATAATACTATCTTTTTTAACATCAAGCACTTGGTTCTGCGAAT

TTAATTCACGTATTAGTGCTTTATTAAGCTTATCCATTTCAGCTAATGTTCCTACCTCAAGCAGGTCTTC

CACAAGCTTTCTTCGCGCAGGGGTCGACAAACCCATGAAAGGGGTATACCCTGCTGTACCAAGGACAACA

ATCTGCTTGAAACTGGCATATGACATTCCGATAAGCTGTTCAAATTCTGCTTGGAAATCTTTACTGCTGG

CAGATTCATTAAGACGTGTACCGTTAACGGTGATTTCGAAAACGTTTGGTTTTTGTCCTCTTTTGATATA

GTACTTTTTCTCATCATATTCCATCCACAGTTCAACTAAAAGTTCTTTCTTATTTGTGCTGTTTATTAAT

TGACCTTTCTTTACATCGCGAAATGGCTTACCAAAAAGCCCAAATGTGATGGCTTCTAGCATAGTAGACT

TACCACCGCCATTTCGTCCAGTAATAAGAGTTTTTTGAACCTTATCTAATTGAATGTCAATCCCATTTTG

ACCAACTGACATTATATTTTTATATTTTACTCTATTAAGTTTAAAATTCTTCACAAAAGATTCCTTTTAA

TGTATCTTTTAGACCATTCTATCATATCATCATAATCTAAAAAGTATTCATCAAATTCAGCCATGCAAAC

AACGCCTTGTGCTGTTTTTGATGTGATATAAATTATTCCAACATATCTAGAATCTTCTTCGGTATAATCA

-continued

ATATTTGCTATGAATTCATCATTAATGTCAAATGTCGAAAACTTCACAGTATGCATCCTTAATACAAGAT

ACAGCCATATCTCGTAATGATTTAGGTGTGTCATTATCTAAAATGTTGAAGTTAAAAGATACAGCCCAGT

CAGTGCAGACAGTAACCTTTTTAATACAATTATCTTCAACCTCTAACGGTTCAAACCAGTATTCAATAAT

TTCTTTATGACCAATATCATCTTTTACTTCACATTTAAAATGCTGACTCATCATAACATTTTTAAATTCA

TCAAAAGTCATTGTGTTGCCTCTACATATAGCTGATTTGCATATTGAATAAGTGCTTCACGGTCAGAATC

AGTGATGTCTGGAATTGCATTAATATACTCTTCCATTAATGTCTGAAGCGATTGAACTTCAACTTCTTCA

CTGTCATCTGACTCGACAGAGTTATCAATCTTTGACACAACTCGTAATGAATGCACAACTTTTTCTAGTT

CAGATTCGAACTTCGTCAGATTTTTGTCTACTTCAGTTACTATAACACGTACTGATAGATTTGTAAAATC

TTTATAGTCAATTTTTCCTTTAAATGGATAATGAATTCTACGATGCCAGGTAGTATTGTTTGGAATAAAT

TCCGTTCGTTCTGTTTCTGTATCAAACATCCAGAACCCACGAGGGTCATTCTCGTCACCTGCGGTTAGTG

TCCATGGTGTCCCAATATATCTGACGTTTGCAGCCTCAGAAATAGTATGGAAGTGACCAGACCACACTTC

TTTATAAGTCTTAAGGAAATCGGGTTCAAGACCATGAGATTTCATTCCTTTATAAAAATAAAATCCATTC

AGTTCCCAGTGACCAACACAAAAAGAAGCAGATGAAGTTTTGATATGCTCAAGAATTTCACCAGTATTTT

CTTCGCACATCCAAGGAATCAAATCAATCAAACACCCGTCAAAATCTACTGTAGTAGGCTTATCATACAC

TTTAACATTAGGATATTTAGCCAAAAGCTCAGTAGAAGCATTTGGATGCATTACATTTTTATAGTGGAGA

TCGTGATTTCCTACAATAGTGTGTAATGTAATTCCAGCATCATCAAGCGTTTGAACTATTTCACGGGCAA

ACTCCATAGTTTTATGTGTGATCGCTTTTCGCACATCAAAAATATCACCGTATTGAATCCAGGTAGTAAT

TCCATTTTTCTTAGAATATTCTATCGCTTGCTTAATTCCATCAATTTGAATACCGCGAATCCACTCATCA

TCAGCTTTAACGCCTAAATGCCAATCACCTAAATTTAAAATTTTCATATATCAAGAACCGTCATTGAAAT

GCAAAATAAAATTATTGAAATAAATCCATCTGGAGTGCTAAAGAACCCAATCCAACATGCTCTAGTGAAT

AGATAAAATGCAAGAAAAAGTATCACATATCCAAGAAATATCATTATATCAAACTCCGTATAAAGCTAAA

GGGCCGAAGCCCTTTATTTTGTAATAATGTCAAACTGTTCTTTAAAGCAGAAGCTTGAATCTTGATGCTG

ATACAAAAATTCATATGCTTTTTCTCGCTCACGGTCATAAAGAGCTCGGTCAGATGACAGTTCTTTAATA

CGTTCAAATGTTGATTCCATATCATTTTCATCAAACCAAATGATACCGCTATCATGCGAGGTCAAAGGAG

TATTATCAACACGGAATTTTAAATTTTCGCCAGTAGATTTCCAAAATACCGGAATTGTTCCACATGCACC

AAGCTCGAGATGAGTATATTCGAGTGAGCGTTGTAAGTATTTCTGGTTAAGTTTACTCAACTGATATCCA

AAGCCAGATTTACTCATTCGTTCAAGCATTTCACTATTAATATAACAATCTAGGATTTGTGCCGGTTGAT

TCGGCGCGAGATTCATTTTATCAATCTCACGATTACCGTAATATTCATACGGAATACCTTTTTCCTTAAT

TGCAATAAAAGCAGGGGAACGTTCCAGACCTTCCATTACAGTGGATTTACCAGCAGGTTTTAAGAATTTT

TCATGAAAATCAAACATCTGGTAAAAACCTTTCCATGTAGTCGTACGACCAATCCAACGGTTGATATTCA

TGTTAATTTCAGAAACATCTTTCCAATAAGTTGACCGAACCTTCACAATATCCATAGGAGGCTGAAAATT

ATATACTGTCGGTGCTTCTTCAATATCATCAAACAGAGAAACAGTTTCTGGATACCATTCTTTCATCAGA

ACTTTATTAAAATCACCATTATCAGAATGGCTAAAAATAACATCAGCTCGACGAACAGTTTCTTCTAATC

CCAAATTTCGACGCAAAGAAAGAACAGAATGATCATGCTGATAAACTACAACACGAATAGAAGGTTTAAT

ATTATCTAAAAGTTTTTTATAGTTATTAATCGTAGCTTCTTGAACGGAAGTAGCAGGAACAGAATTAATA

ATTAGAATATCACAATCATTTACTAGCTTAAGTGCTTTATCGTATTCTTTAGCTAAAATAACTGGAATTG

AAAATGATTTGTGGTCATGAGAACTTGTACGAGTAAATGATTTATCTTTAGCATAAACCAAAGTTACTTC

ATGACCATTTTTAATAAACCAATCACGTTGCTCGAGTGAGAATTTTGTTACACCACAACCTTCAAGACCT

CGAGCCATAAAAATGCAAATACGCATAGTTTTCCTCTTTTCATTTAATAAATCATGTAAATAATATTTTA

TTTTCTATAAAACGCTACGAATAGGCCCAAACATATCCATAAGCAATTTTGCTTTTTCCAGATATGCACT

TTTTAATATTAGACATGCATCCTTTAACGGATACAGCTGCGTCTTTAATTCTAGGAAATACTCGTAATAA

-continued

TTTTCCAGTAGTATCATATTGAAATACTGGCACATTTCTTTTCTGAGTTATCCCACGTTTAGATTTAGAC
ATTTTTTGTTTAGTTGCATTAGACATCCTAGAGGGCTTTCCTATGTTATCAGAATAATAATATTTCCATT
GAAATCCTCCAGCGGTTTTCCTTTTACCATCTACACATTGTTTAATTGAAGTTGAACAGCTATATGACAT
ATCTTCTGCAGCATCTGTAATACATCTATATTTGCGAATAAAATTTCCATTTAAATCATATTGATAAATT
GGTTTTCCAGCATTTCGTCTAGCGTTAGACATGTATTTTTTATTATCATCATCTTTCCAGAACTCTTTCA
TGCTTTCCGATATTGAAGAAGATACAGCTGTTTTAATCCATCCATACATTTTATTATTTAGTCTTGTTCC
GTCAGAACTATAACACATCATACGAATAGCTAAAGCCAATTTAGGAAGTCTATAAATTTTAAATAATAAT
AAATGCGCGGTAAAATGTTCTTCTGGTGTCAAAAGAACTAAATTAGTTTTATCATCTGTACCACCCATAC
ATCTAGGAATTATATGATGTGTTTCAGTATAGTATGTCAAAAGACTTTTATCATTGCCTCTGTTTAGTCC
TTTTTCGATCAGTAAATTATATATGTTTAAATAATTCATTTTAGTTTATTTTACCAAAAAATTTATAAAG
CAATATAGGAGCCGAAGCTCCTATCCACATAATACGCCATACAGAGGCTCGTTAGAACTTTTAAATTTTA
TGCGCTTATATGTTATAGTTCCTTCTGCTTTAGCTTTATCATGAGCCTCTTTAAAGCGTCTCATCATTTC
CTCTCTAGAGGAACGAATTTTATTATAATCTATTTCAGAAGTCGGATGTTCATCTTTCACAGTTGCCACC
ATTTTTTGACTTGATAAGAATCAACCCACACTTTCATATTAGGGTCTGCTCTTACAATAGGAGGATTAAC
TTCTTTGATTGAACTATCACGGTATTCTTTTTCAGAAATTTTCACGCAAAGATGACCATTCAAAGATTCA
GTAAATCCTGCATTAATTTTAAGACGCTTGAATTTTACGTGTGTAAGCATCAATCATATCCTCAATCTGC
GATCTAGTAGTCTTCCAAAGAATACTGATGAGTTCATCGTTATATGGCTGTTTTAGAATATCCCGACTTT
TCTTGATAGCATATTCGTATTGAGCAAAATTATTATTTTCAGCTGCGATCTGAGCGTGCTTATAAAGACG
ATTCAGTTCGCGTTTGTTTTTAGACAATAACTTATTTGCTTTTCTTTCTGCTTCAAGACGGTTCTTTTCT
TCAATAGAAGAAATAAGCTTTTCCACTTCATCATTAATTTCGGGTTTATCAGTCATATTATTTCTCTAAT
ATAAAATAAAAATCATCATCTGTTAAATGATACCGATAGTTTAATTCTACACCATTAGATTTAAAAGCGG
TATCATACGGATTTTCTGGATCAATATCAATGTCAAGAGCTAAAACTTCCCTGAGATACATTTTAAGTAA
ATAGGGAATAGCTTCAACTTCAGGTATTTCTTCCAAGAATCCGGAGAGGTTAATCGTTAGCCTCATATAA
AAAATCCAAACTAGGAGAATCATCTACAACACTTTTCTTTTCAGCCCCCGGTGTTCTATAGGTTGATTCT
TCGTAATGCGTCATTTTATCATAGATGTCTTGAATAAAAGTTTCATCTACTAACGCAACCATATCGTCGT
CACGGCTGTCATAGACATTGTGAACGAAGTAACTATATTTCTTTGCAACTTCCTTACGTTCTTTTTTAAT
ACGTTGGACGAATGCATTAAAACAAGCTTGAGTTATATACGCATGTGGGTTTTTATATTTCGTTTCATCA
AAATTGTGAAGCCCCTTAATAGAAGCTTCTATACCATCTGCAATCATTTCTTGTTTCCAAGACTGGGTGT
ATCCTGAAAAGTTGAAACGTTTAGATAAGCCTTCTGCAATAAGCATAATGGCTAATCCGATAGTATCATT
CTGACGAACTACTTTATTTGGGTCTTTATTATTTGCTAATTCTGTTTTCCAATCAATAATAGCTTGTAAA
AGCTCTTTATTGTTTACGTAATTATATTTAGGCTTAGTTTCTGACATTTTCACCTCTTAGCTCAATTCAT
AGATCTATTATATCATAATATTTGAAGACCTATCTTAAAGCATAGAGGATGAATCAATTTCAAGCACTTC
ATCAGATTAGCCGCTCCAAGAGCTGCATCTAGTGAATCAAATTGGTCAACATATTCAATTAATTCGCCGT
AATTAGCGTATAACCACCATTGGCTAAATTCATACTCAAGGATGAATCCATTTCCTTCAATTTGAGTTAA
ACCAATGCCATTTGTATTTACTTCATACCCAGCGAGACGTAAATCGTTAATAAGAGCTTCGTTCATAATT
ATACCTTAGTAATTTTCAGGTCTGCAAATTTTTTCTTGCGTTGATTTTTCATGCGACGAATAGTTTTATC
GGAAATTTCATGCTTTTGATAAGCTTTAGATTCTACACCAAAAGCTTTAACATCAAATTCTGACAAGATA
TATTGAACCAACAATTCACGGACAGTATTGCGTCCAATCTTCTGATCATTCTGTTTCATCGTTTGATGAA
GCTCTTTTTCCCATTTATCCAAAATTTGAGGAGTTACAATATCGCCTTTTTCTAGCAAAGAAACTACTTT
ATCATATGCGTAAGAATTGATGGCGTTTTTAATTTGAATAGTCATACATTATCCTCAATTACGTTAAAAT

-continued

TTTATTATCCAAAAAGGCCGAAGCCCTTAGGCTAAACTTTTTGGCACCCTTCCAGCCTTCGTACATCATT

GCGACTGACAATGACAAAGCTCCTTCACATGCTGCATACTTATTATTCCAGAACCAATTTAGAAAAACTT

CATCCTCAATACCGTTGTGTTTCATGTTCTGGAAAAATTTGGCGCGTTCTTCAGCAATTCGCTGCGATAA

TTTAGATTCAGGATTCATTTAAATTTCCCAATTGCCATTTTCATCAATAAATTTAATCCAGTCATTTACT

GACCACTTGGTCGTATCGCCTTTTGGAGTAACATTTAAAGTGTATAGCCCTTGCTTAAAAAGCATGCGTT

TGATATTCATATTTTCCTCAGCTGTAACGATAACACTCGTTTGATTTACGTTTAGCAACTCGTTGAGAAG

TATTATAATCAAAATCATCATCAATGTAAACTGATTTTTTCAACTTTCTTACTTCACCGCGTAATTGACG

ATTTAACTCATCTTTAACTTCTGAATCAATACCTTTCATTCTACGCCATTTATCTGAGCGAAAAATGTTT

TCAACCATATCTTTATGACTTACCCCATCAGGAGCTTTACGCTTTCCGAAATAGTCATAATCACGCACTT

TTAAGTCTTTACGACGATACGTTTTACCCATGGAGTTTAATTTCCTTAGCAACTGAACTAAATACAGCAC

GATCACAAATCATACGTTTATGTAACTTGAGTATAAGATAGTAAACATCAAAACCATTTACATAAGTAAC

ACGAACAACATTACCATTCACGAGATAATACTGTCCCTTTTTAATCTCTTTATCAACCACAACCATATCA

ATTCCTCAAAGGTAATTCATATGTTAATAATACCACGGTTTGAACTTGTTGTAAACAACTTTGTGAAAAA

TATTTTAGGGAATGATAAGAAAGGAACGATAGCTTAGAATGGTAATATACAGAATGTGAGAAAGAAAGGC

CCAGAGGGCCCGTCTTAATCTTCTATGATATCTCTATCATATCCAAGTGAAATGAGAGTTTCTTTGAAGT

GTTTAATGTTCTTTTGTCTAGAATCATTAATGAAAATGACTGGATAACGAATGTTAAGAGATGTGAATCC

AGCGCGTTTAGCAAGAGATACAATCAGCGGACGATCATACTCAATCTTACCATTATTTGTAAGAACTTTA

TAGAAAGTAAAAGGAGCATTGAGCTCCTTTAGAAGTTTTGTAACTGATTGACATCCAGGACAACGACCTA

CTTCATCTGGAATTCCATAGACTTCAATCTTATTTTGTTTCACAACTATTCCTTACTAAGAGCAGCATTC

AGCTTGTTAGTAATTTTATCCAGACGCTCATTGAATTCACTAGAAGATAAGCCCTTTTCTGGAGAAATCA

AACTAATCACGAAAAATATAGCAATAAAAGGAATAAGGAAAATAGCTCCAACTGCCATAAACAGAAAGAA

TGTTACAGTTGTAAGAAAATCAGCTAAACCTTTACGAAATTTATACATTTACATTTACCTTTAATTGATT

AACCAAGCATTGATAAGCACTAAACTATACTGCGAATAAAATTCTGGACCAAAATGAAAATCATATCATT

TATAGTATCCATAATGTAATTCAATTTAATCATGTTTCCACACCCCATCGGTATTTGACCAAAGTCGCTG

ATTATCTGATCCTCGCCACAGCTTTTTGGTCGGAAGATTTTTCTCATACTTCCCATCAATAATAACATCA

ACATATTTAAGCATTTCTAGTTGTTTAATATCTTCAAACTTATATCCTGTCCACAACCAGATATCTTTCT

CCGGAAATCTTGCTTTAACCCAAGAAACTAAATTTGAAATCTCTTCTCGGTTCTGTGGATAAAGTGGGTC

ACCGCCGGTTAAGGTAAGGCCTTGGATATACGATTTGCTTAAATGGGACGCAAGTTCTTTAACGGTATTC

ATAGTGAATAACTGTCCGTTACGAGCATTCCAAGTACTACGATTATAACAACCTTCGCATTTATGCAAAC

ATCCAGTGACGAAGAGAACGACCCTACATCCAGGGCCGTTAACGAAATCGCATGGATAAATTCTATCATA

ATTCATCTTTATATTTCCAAGTATATCCCTTATGAATAGATTGAATTCCTTTGCAACATTTATAAACAGC

AGAATGAAAAAATCCTGCATTTCTTATTTCAGTTGCTCCAGTTAGTTCTATTGTATTTCCGTCTGGTGAA

TAGCCAATAACCGTTTTGGTGTTAAAGCGATTTCTAGAACTATTTTTGATATGCTCTTTATGATTAGTAG

ACAAAGTTCTTCCTGTTAGCCCATCAGATATCCTTTTTCCAAAATCATCAGGAAGAGTTACTTTAGACCT

AGCTATGCTCATTAGCTTCTTAGTTTTATCGCTTCTTTTTGCGCCACGCTGATTTTCAAATTTCTTAGCT

TTTGCATACGCGTATTGTGAAGAAGTAACTTTTCTATGCTTACTATTACTCATTATCCAATATGCATCAT

ACATCTTTCCACCATATATTTTAGCCAATAAATGGTGAGCAGTATAGTGGGCCTTATAAGTTAAAAATAC

TAAGTTGTCTAAATCATCTGAACCACCCATACTTCTTGGAATTATATGATGAAGTTCATACCCGGCTTTA

GTTTGACGGGGCTTAGATGGGTGTTCAGCAGAATTAACTAGATTTGAATAGATTCTGTCATAATTCATTG

GTGCTTAACCCTATGCATGATTTCTTTATTTTTACCGAGATTAAATCCGCGTTCGTTCGGATTTCCCAAA

TAACCACATGTTCTTCTTATGGTATTCATCTTTTTAGGATCAGTTTCTCCACAAATAGAACAAACAAATC

-continued

CGTTTTCAGTAGGAGTCATTTCATGGGTACTTCCACATGTAAAACATTTATCTACTGGCATATTAACACC

AAAATAATCTAAATGCTGTGCAGCATAATCCCACACGGCCTCAAGACCTTTTAAGTTATTTTTCATATCA

GGAAGTTCAACATAAGAAATGTGACCACCTGTCGCAATGAAATGATATGGCGCTTCACGAGAAATCTTTT

CAAACGGAGTAATATTTTCTTCTACTGAAACATGGAAACTGTTAGTGTACCAGCCTTTATCGGTAACATC

TTTTACGCTTCCATATTTTTCTGTATCGAGTTTACAGAAGCGATAACACAGGTTTTCAGCAGGAGTCGAA

TATAAACTAAAAGCAAATCCGGTTCTTTCAGTCCACTGTTTAAGATGAGCATTCATTTTAGTTAAAATTT

CTCGTCCAATATCACGACCGACAAGAATATTCAATTCGTGAATACCAATGTATCCTAAAGACACTGAACT

TCTACCGTTTTTAAATAACTCAATTATGTCGTCATCAGGTTTAAGACGAACCCCGAATGCACCTTCTTGG

TAAAGAATAGGAGCAACAGTAGCTTTAACTCCTTTTAAGGAACTAATTCTACACATCAAAGCTTCAAAAC

ATAAATCCATTCGTTCATTAAATAGCTCAACAAATTTCTGTTCATTGAACTGTGTTCCAATATAAGAATC

TAACGCGATGCGAGGAAGATTCAGTGTTACAACACCAAGATTATTGCGTCCATCAAGAATTTCATTGCCA

GTCGAATCTTTCCATACGCTCAAGAAACTACGGCAACCCATCGGAGAAACAGGAACAGATGAACCAGTGA

TAGCTTTATTGTTCTTAGCTGAAATAATATCAGGATACATCCTTTTGCTTGCGCACTCTAGAGCAAGCTG

TTTAATATCATAGTTCGGATCGTCTTTATAAAGATTAACACCTTCTTCAACGAACATAACAAGCTTAGGG

AAAATAGGAGTTATCCCATCACGACCAAGACCTTTAATACGATTTTTCAGAATTGCTTTCTGAATCATTC

GTTCAGTCCAGTCAGTTCCCGTACCAAATGTAATTGTTACAAAAGGAGTCTGTCCGTTTGAACTGAATAA

CGTGTTCACTTCATCAATGTGTTCAGTAGAGTTCGCTACTTCTCTACCCGTTTATATGAAACAATGTAAT

TTGGATAATTGTCATCTAAACACAAATCTTTAATACGACTTGGGTGGAGTTTTAAATCTTTAGCAGCATC

CACAAATGATTTATAGATATTGTCATTTATTTTAACATATTCTGGGACGGGATGAATTGTTATTTTTATA

TCTATAACATTTGGATGATTACTAACCTGTTCTTCAGAGCATTTAAGAAATTTTGCAGCTGATTTAAAAC

TTCTAAATTTATTTCCGGATTTTAAAGCTATAGAAACAGTCTTTTTAGCCGTTCTACTACCAATATTATT

TTTAACATGAGCTTCACTTCTACTATTATTTTTATAATGCTCAATCAATTTCTCTCGTATCTTATCTTTA

TGTTTTAAAGATAAGATTTTACCTTTATGGGCATTACTAAGTTTTTGCTTATGTTCTTCTGAATCCGGAT

ATTTGTTAAATTTATATCCACCTATAGATTTATTAAGAATAAATTCGTTATTAAAATATTTCCTAATAAG

CATTTCTTCATGTTTAAGGGCCGATTCATAAGAATCAAAAACTTGAAGAATTATCCACTTAGCTTTATAA

TCTTTAAGCTTTTCTTTAACAAGCTTAGATGACGAATTGTATTCTTTCCAATTTGTATCTTTACCATATA

TAGTTTTGAATTTTTTAAAACCTATATAAAAAGACTTATCAGGAAATCTTACCATATAGGTAAATGCTAC

AGAATTGGCAATTTTTAAGCTTTTTCTTAATTTCCATTTCATCGTTTCACCTCGTATTCATATTTATACG

AGGATAAACAGCTGCATGTCACCATGCAGTTCAGACTATATCTTCAACTCTTAGAGTTGTCTGCCGTTTC

GGGTCGCTTGACCCTACTCCCTTACATTCATCAGGGATAGTCGTTGGGCATTTACAGCTACTGCTGATTT

AGCAACGGATTGTCTCAGTGAGAGTTTCCCGTTTTAGGCAGATTTTACATGAGCTTGACTTACGTTAACT

CATAAGCTTGGAATGCATCGTATACGTCTTTTTCTGTTTTAGATTGAGCATAATTCAACGCATCAGCGAT

TTGCCATTTTTCTGCATCCTCAATATGTTTTGCATAGGTGCGTTTAACATAAGGAGAAAGTACTTTATCT

ACATTCGCAAAAGTCGTTCCGCCGTATTGGTGAGAAGCAACTTGCGCAGTAATTTGTGCCATAATTGCAG

TAGCAACTCCAATTGATTTAGGAGTTTCAATCTGCGCATTACCAAGCTTAAATCCGTTTTCAAGCATTCC

TTTTAAATCTACTAAACAGCAATTAGTAAATGGAAGAGCAGGGGAATAATCAATATCATGCACGTGAATA

ATTCCGCTTTCATGCGCTTTCATAATAAAAGACGGGACCATATTTTTGGCAATGTGTTTAGACACAATAC

CAGCCATAAGGTCCCGTTGAGTTGGAAAAACACGAGAATCTTTATTAGCATTCTCGTTTAAAAGGTCTTT

ATTAGTTTTATGAATTAATCCTTCAATTTCTTTTTCAATTGTCATTTTAAACTCTTTCTAAGCTGCTTCT

TGAATGAAGCTATTAATTGTGTTTTGGTGTCAGATTCATTATATTCAAATCCTCTTTGAAGCATCTCGGC

-continued

CATCATTTCCTCTTTTCCTAAACGAGAAAATTCCTTTGATTTATCTCCAACAAAGTTAGGGTGAATATTA

TTTTGGGTGTAATCGGATTTTAAATAAGTAAGTAAATTTTCTAACCATTCAAGATAATCAACACCTTGTC

CCTTTAAGCCAGAACGATTAAATTTATGCTTCATTTGACCTTCTGCAGCATTGCATAGATTACAAAGCAA

TCCACGCACCTTTCCTGCTTTTGGTCCATTTAATTCATGGTCATGGTCGAGGTGATTAGCTTGAACATCA

GGATTTAGTTCTCGTTGGCAAATTAAGCATTTACCGTTTTGTGCATCATAAAATTTCTGTTTTTCTTCTT

TGTATAATTTGCCAGTCAATAACATAATAAACCCTTACCTTAAATAGATAAGGGTATTTATTATTTTCAA

GTATTGTAAAACATTTGATGCAATCGCTTATATTGCTGAATCATTCGGTCAGAAAAAGAAATTTGAGTTT

CAAGCCATTCAATGTACTCTGCGGCAGCTTGCATTAAATTTCCTTCATAGCCATCGTTATTTTCTTGTGC

AGCTAATTTAGCTAATGCGTATGAAATACGTTCACCTTGAAAATCGGCTTTAGGCTTCTGAACAACTTGA

TTAGTTCGCTCTACAACTTCTTCAATTTCGCCATTTTCTACTGATTCAGTATTCCACAAACACCAATACG

TAATTGGCTTATCGTAGATGTTAATAATCTTTCCATCAGAAAGTTCAATTTCAATAATTCCAGTGTCAGG

CTCTATATCATCTTCACATTCTTTTACAAGTTCACGAACTTTAAAGACAGTACCTGCACTAAGTTCCGGC

CAGTAATTACACAGCCCTGTATCAGCACGATTAATTCTAAACCATTTATCTACTGTAATCATGTCCCATC

TCCATATCAATTAAGTCATTTATCGTTGGTTCATTATACACCGTTTCTTCATCAGTGTAAACCGGTTCTT

CCGGCTCTGGCTCTACAGTTTCCCATCTAGCCGCCCACCAAGGTTTTATAGCGTAATCCATTCTCGTACT

GTCTGAGTTACTACACGTTCTCGAAGCTCAACCAGTTCAACAGTAGGAACTGCATAATACCAGTCAGAAT

GGTAAGAACCTGAGCGAGATTCATTTACAGCCACATGTACATTATGTTTTGGACTAAAATAAACACACTG

ACGATATTGGCATTTACCATCTTGCACCCAGTCTTCTATTTCGATAGGTTTAAGATAGTCGGAAAAATCG

AAATCATAGTTTTCCGAAAATGCATCATGGTCTTCAATGATTTCGCTCAGAACTGCATCAACATCTAATT

TATTTTCAATATTCATTTTTCACACCACCAACTGCTTACTTCAAAATCGGGTTCGCCATGTTCCCAGAAC

CAGGGGCCGATAGGAATCCACTTACCTTCATCGGTGACGTCATATTCTTCGGATTTAAGCCCAACGTATC

GCCATTCGACTTCATAAGCGGTACCACCGATTACAACTGTGTTCTCGCCATACGGGTTAGACACAACAAA

GTCTATACCTTCTGCTTTAGCTAACCAAATCATGTATTCATAGAGTTTATATTCCAGGTCGCCTTCTGTT

CCATCGCCTAGAAAAATAATTTGTTCATTTAATTCTATCATTTAAAGTATTCCCGCAATTGGTCAAATCC

ACCAATATGACTTCCATCAGGAGCAAATACCTGAGGCATTGTTAAGCCGATTTGAGTATCACGACCTAGT

TTAGTCAGAAGCTCAGCAATTTTCTCATCATCAAAAACACCTTTTTCCGGCATAATGTTGATAAATTCAA

ACGGCTGTTTCTTCACAGTCAAAAGACGTTTTGCATTATCGCAATACACACATTTATGAATGTTGCTATC

ATAACCATATACTTTAAACATATTATTCCTTAATTCCTAGTACTTGTTTAAAAGTCTCGTCGTAATCAAG

ACTTTGGCCCGTTTGTTCTTTATGCTTGTATATAATATCACTTACTTCTGATAGCATATTTTTATATGAA

CGAGTTAAAGCAGATTTAAGCACGCTGTATCTATCAGGAAATTTACCGTGTTCATTATAATAAGCTATTG

CTAATTCACGGACTGCCTTTTCAGCAGTCTCCATATATTCTTTACGCTTTGTCATTTTCTTCTCGGTCAA

ATCGGTGTTTACAATGGCGACATTTATAACGAAGATTATTAGTCTGCCAATGGACCAATTGCACCTGTTC

AGTTCCACATTCAGGGCAATTAGGAACGTTTTTAGAAGCCCTTTCGCGACGTTCAACCATGACCATTACA

GAATCCCAATTAACAGGAGGGCTATAATCATCACAACCATAAATCTTTCCACGCATTTCCAGATCGTCTT

CTTCACCAGCCATAATAATTTTAATTAGACTAGAATTACTTGAAGCTGCAATGTCTTCTAATAGACGCTT

TTTCATTTCAATACCTCAATAGCATTACGTAAACCATTTGCTTTGGCGGTTAAATCCTTAAGAACTTTAG

TATGCTCTTCAATCTGTTTTTCAACTTCAATCAAACGGGTACTGAGATATTCGCGTTCTTCTTTCATAGT

ATCATTCCCATGATTGGGCTTTGGCGTAGGTTTAAATTTATTAGGGTCCTTTAACTTAATAACAACTTTA

GTTTCAAACAGTGAAAGACCATAATTCGTATTATCATCAAAGGATTCAACTACGTCCATTTTAGACAATA

ACGTACGAAGTTTATAAGTCAAAGAACGAATCGTTTTATTATGTTTATTAGCTTCACATGGTTTCATATA

TGGAAGATTTTTATATATTTCATGCGGAGCACAAACAATAATTAACAATTCAAATGGTCCATTCTGAGAT

-continued

GATGGAATGAATTTAGCCGTAACCCAATCTTTTACATTTACATTAATAGTACGATCATCGCCATGACAAA

ACAGTCTACGAGAATGCTTAAAAAGCATATTCACATTATTATTAAATTCGTGTGAAAACTCACTGGCAAA

TTTTTCTTTACTATCTTTAGAAAACCATTCTTCTAAATAAGTTCTTTTCACGTCGTTAATAATATTAAAT

GTAACAACATTATCATTTGATACATTAGTCTCAATGTAGCTTGGATACATAAATTTTTTAACATTATTAA

CAGCTATCACAGAAGATAGTAATCGGGAACGTTTGAACCACTCGAGCAAAGAACCAAGAGAATGTGAATA

CGCATTTTGTGTATCTTTACAAATATGGTTTTCCCATCCAATATAGTCTAAAAAATCACGAAGAATATTA

TTGATTACTTCTCTATGTCCTTTCTGATAATCACGATGTTTAGTAATAAGACTGTCAAAATAATCAATAT

AATGTTTACGAGTTTTCATGTTCTTCTCACTTGGTTAATGATTTATACTCCGAGCCATCCTTGGCTTTAA

ATTTTACTTAATTAACTGCAAAGCTTGTTCTAGACGATCAAGACGATTAACGGATTCTTCCCAAATCTTT

TTAGCCTGCTCATATTCTTTCTGCGCTTTATTAGAAATTTCTAGAACTTCTTTATAAGCTTTTTCTAGTG

CAATAACTTCTGGACGAATTTCTATCGGTTCAGGTGAATCATCAAGACATTCCATTAGTTCCTCAAGGGT

AGTTTCTTCTTTAGGAGTATTCACAATTTCATCACATTTTTGTTGGTAAATTTCTTTACTAGTAGGTGAA

TAAGCACATTTCACTTCACGAAGGCTAATTACGAGTTTATATCCTTCCCAACCGCATATATTCTTAAAAG

GATATGTATGAATATTTTCTACTGTTTCCATACAAAGTAATGCGGTCTCTAATTGACGAGTTATAGTGCT

AGCAATTGAGAAAAATTTATTAATATTCTTTTGGTTAGTTTCTGGTGTAAAAAATCCATAATTCACAAAA

ATAGATACTTTATTTTTATCAAGTTCATATTCTTTTATGATAATCATATCAGAAGCCAAAGGATGAATTT

GACGATAATCGCCATAACATAATTTAGAAGCTGATTTTAGAATTTGCTTCTTGAAAAGTCTGAAATTACT

AATCCAACGACGAGTAAAAATATTCTCAGGGTCTTCTTTATTATTGAGATGATAAGAATTAACATCACCG

AACCAATTATATCCTACTACATCTTTAGTTCGTTTAATTTCTTTCCCAAAATTACCAAGAATATCCCGAT

TAACCAAATATGAAAGAAGACGAGACTCTTTAAAGGTTTTCTTGATAACATCTTTATCTACACGGCTAGA

AATTTTACGAATTTCATGAATAAATTTAGTAGAAGAAACAATACTTGCATCAACACTATTGAGCCACTGA

TTGATAATAGAAAGAACGCTATTTTGGCCAAACATCGGTATAGCTTTATCATCAATAACGCTATTGAATG

ATTTGATATATTCGTTACGAGTCATATTAATCTCCTCAGTAGAAAGTAAGAACATTATACCACATCCTTG

TGGCAAAGTAAACTAGTTCAGTGCATTTAGTGCATTGTTCAGTTTAGAACGTTGCTTTGTCAGATTTTGA

ACCCTTGACTGAGCTTGTTCTAACGCCTTTTCAGCTTCTAGCACTTCATTGGTCGCTTTAACTAATTCAG

CATCTACTGCCTTAAGAGACTTCTCAATCGCATCCGCGTGCCATTTTTCAACAGGTTTAAGACTTGGATT

TTCAACAGGAAGAAAATTCACTTTATTGAATTTCCATGCATCTTTATTACCTGAGCTATACATCCAAAAT

TTAGGATCGTTTGATAAGTAATTAGATAAATTTAAGTTATCTTGCACTTCTTGCTTTTTCTCTTGTGTGA

CTTCGTCCTTTCTCAAAAATTCATATTTAAATGAAACGATCATATCAAGTTCATATGATGTTGTATCTAA

CTTAAATCGTTCAAAACGAGGTAAAATCTTAGATTGAACAGCAGCAACAACATCCATATACTTAAATGCT

TCTGTCAACTGCGATTTAAGGCATTCGCAAATTGAAAGAGAATTTTTTGTATTAGGTTTAAAGCTAATTC

GTGCAGTTCTATTATTTTCTTTTAACGGTCTTACTTCCATCTGAAGAGTATAACCATCAAATTTCAGATT

CTTTAAGTTAATGTCAGAGCCTTTTAATCGACTAGCAGTAGACAAAATTTGCTTTAATTGTCTACGGAAC

AGAGCAATAAATCTCCATTCAATACGATAATGATTTGGATTGAAAAATCCAGATGATAAATCGACCTTAC

TTTGACCAACGCCTTGAACAAATAGAGGATTTTTATAATCAATAGTTTTACAGAAATCGGTGAGCTGTTC

ACGAGCAGTCATTTGAGTAATATACCCTGCTTTACTAAAATTACGCACCCATTCACTGCTATTCGTATAC

TTAAAGTGATGAATAACACGATTAACTTTATCAGGGTCTAAATTATTTTCACACAAAAATGTCATAACAT

CACGAGTATAGCTGGCATTACGAACCATATCTTCAATTTGAGAACGAGTTTTCATGGTGTTCCTTAAGAT

TTAAGTAAATCAACAATTTTAATTAACTTTTCACGCTCAGATTTAGCTTTACTACTCAATCCAGATAGTC

TGAAAATTTCATCATCATATTGTTGAATAGAAATATCAGCTCTTCAATTTGCTTATTAAAATAATCAATT

-continued

TGTTCAGAATGTTTTTCGTTACTACGAACTGGTACAGGTTTTGTAGGCAATTTAGTTGAACTGGATTCAT

TCGGGCGATAAATTAAAATGCAATTTGAACCAATCGGGCATTTAGCACCAGATGAATATTCTAACGTTCC

AGCTTCTTTTAAAACTTCAAAAGCTAAACAGAGATGATGCCCCATATTAACATAATCAGTAGAGCGAGCT

CTGATGTAATAATCATCTCCACGAGTGCTAAATTTAAAGCATTTAAGGTCTTCTGTATTATTAGTTTTAA

AAATCATTTGTTTATCTAGACCTTTAGCCAATCGAGCACCTAATGCTAATAATCGTCGTTGATTTTCCCA

CAAATCTGCGATCATTTGGTCAAATGATAATTTCGGCATTAGCCGACCATAAAGGTCATATCCTTTATTA

TAATTGCGAAGGATTTCACTCGCATTAATACGAGACAACGCTCCAATTTTATTAAGGGCTTTCATAATAC

GATTAGATAAACTCATTCCAGACCCGTTTGTTCGCTGTAAATGTTTTTCTAATCCAAATCCAATATCAAC

TTTAAATTTATCTAAAATTTCAGCATGAACATCTCTGTCAATAACATTCAAATCCAAAGTTGGGTTAAAT

CTATGAAAAAATTTATCTGGCTCTCCACGACGTAAAACAGTCCATTCATTCATCATTTTTTTATTAACTA

AAGATTTAATTACTGCGTTGACATTATTAATTACTACTGACATATTTTCCTCACTCAATTTTACCAATTA

CGCGGAATAAGATTGAACAGACTATATAAGTACCACATATAGATTGAACTAATGCCATTCCAAAGAACCA

AACAATATTATCAAACCATGTCTGTTTTACGTCGAAAGGACGTAAACTTACAGTAATATTATCACCTTTT

TCTATTGAAGAATACGTCTCTGGGGAAATATATTCACTAAATCTATAACCGTCTTTGAGTTCATATACAG

CAATAAACGATAAACTAGACCCCTTTCCTTGAGTTCCTGTAAGGGTATTAACTACAGTAACATCATAATC

TTTATAATGCATATAATCATTAATTGCGTAATAACCATATGCAATTACTATACATAAACAACATATCAAT

AAATTCAATCTTTTAATTATCAACTGTTTCATAATAATCTCAATTAAAAGGGCTTAGAACCATTATACCA

TCCTTGGTATAAAGCGGTTATGCGAGTACCGTATTTAACCGTTCTTCAAACTTCCGAAGAGTGTTCTGGC

GTTCAGCTCTTTGCTTTTTGTAAGTTTCAATACGCTCTGAAATGAGAGTGTATCGTTCATTTACTGATTC

TTTCATAAAATCAGGAATTTCTCGAGAAGCTTTAATCTCGTCAAATTTATCAATAACAGCTTGCTCTTCA

GCAATTAAGTTATCATACATCAAAATATCTTTCTTGATGAACTCAATATCTTCTTGAGTTACACGAGATA

ATTTAGATGCTTTATCCTTTTTGTACTGTTCGTTAGTATCACGAGACCAGTGTAATGTACGATTTTTATT

CGTATTCTTGTAAATTTCTACAATACCAATCTCATCGATAATAACGATCCAATTCCAACGGGATTTGTAA

ATTTGTCCTCCATTAACAGTGATTTCACCTCCGATTGAGATGTCATTAAAGAACTTGCTTTGTGCTTCTG

ATTTAAATTTACCATCGTTGTAATTTACCAGGTTGAAAATATCTTTAGCGTTCATTTTGTGTTCCTCCGT

AGTTGATAGTTGTATAGTACCACAGAGGAACGGTCTTGTAAACAACTAAAAGAAACTTCTTTCACAATTT

TTTCCACTGAACCAAGCGCTCACTGCTTTCTTAGTTTCAGGAGCAGTGTTATCCATAAACCATTCAAAGG

CAGCCTTTTTATGATTCTGGAGGGCTTCTCGGGCTTTAATCTGCTCACGGTCTATTAACACTAACATATG

AGCCTTTCTTGTCACCAGGGGCTTCTTATGATTTTTTGAATACTCCCAATCATTTGTCCATCGCATCGTT

GTTGCGAATTGAAATACAGCTTCTTTAATCTTAGTTTCGTAAATTTCACGAGCCTTTGAGTATAACATCA

TTACCTCCATTTACCAGTTTAATTCTAGTCATCTTTTTGATGGCAGTCCATATAATCTATTTCTGAACTG

CCTTTTTGTCTTAGAAGGCCTCTTATGAATTTATTTCAGAAGAGTAACCCGTAGCGATTTCTTCCCAACC

GTTTTTGTCGGTCATAATAAAGTCAGCAAGATAAAGTGCAGTACGCAGTGAAACATTACGTAAACGGTTA

ACATTGACTTTCATCCATGATAATGCTTTATAAGTTTCTTCATCAGAAAGACCACGCTTTTGCATCATGT

CGGTTGAAAGAATAACATCTTCAACCCTGACCATAATTTCTTCATTAGTGTGAACACCCAAATCCAAATA

AACTGAGCGGGACACTAATGCTTGTAAATGTGGAGCAAGTTTAGTACCACGGTCTAATTCGCGGTCAATG

TCAACGTTTGTGATAAAAACAATTGTTCCTTTAAATTCGAGCTCACGCTCAATGCCTTTTTCTTCTAAGT

AAGAAGATGCAGTGCTCCAGCAGACTTTACGGGTCTCTCCAGTGTCCAGAGCAGCTTTCAGAAGATTAAG

AATGTCCATATCAGAGAAAACATCCACATCATCAATCAAAAGGACAGAATTCTCTTCACGATTATTCCAA

AGCTGTTCATAAAGACCGATACCAGAGATTTTACCGTTAATGCTTTTATACTCAATGTATCCAATATCAT

TTGCTTTATTCAAAGCTTTATCTAAAGAATATGTTTTACCAATACCCGCCGCACCAGAGATAATTAATGA

-continued

ACGAATATTTCCGTTAATAATACCATTCGTCATCATTCCCATAACATTAAATCTTTTATTAATGCGGGTT

TTCATATCTTCATATGATTCTTTAACTTCTTCAACTTTTACACCATCATATGAAATGTCTGATTTGTAAA

CCCAAACACCGCGACGTTTACCGTCAATTTCAACAAAAACTTTACCATCTCCTTGTGCATCTACCGGAGC

ATTATCAGGGAACCATTCACCTAAGAGCTCAAAAGTTCCAGAGATTTCTTTACCGAAGTACATACCCTTA

TTGATAGTTACAGTTTTCATTTTATTCTCCAAATCCGTATCAGTTGATAGTTGTATAGTACCATAAAGCT

TTATGCTTGTAAACCGTTTTGTGAAAAAATTTTGAAATAAAAAAGGGAGCCCGAAGGCTCCCTATCATTT

ATAATAACTTCGATGGTTTTCAAGATAAACCCTCTCAAGGAAGTCATCCCAGAAACTCATGTCTACTTTT

TGCTGCATACCGTTCTTAGAAGCTTCAGTAGATGCTGCTTCTACTTGATCGACCACATCTTCCAAAAACT

CTTGAACGGTTTTAAATGGATGCTTACCCAACTTCACGTCGAGAATAAATGGAGCATCTTGGAGTGGATA

AACCAAGTCACCAGTTTTGTAAATTTCCAATAGTTGAAGTCCACCACGACAAGCATGGCTCAGAGCTTTC

CAGTCAATGCCTTCATTGGCTTCGGCCTTACGAGCACGTTCGCCGTATTCAGCATCTAATTTGTTCAGTG

ACTGCTTAAGCTCAATAAGAGAAAGCGTTGTCTGATATTTACGACCCAACACTGTGTAAAACGTTTGTGG

GCCTGTTTTCTCATGATTATGGAACACCCATTCACAGAATTCGTTTTCTGGAAGACGATGCTTAATATCT

TCAACTTTAGTACGACGCTGCTTAATGGAACCATCTTCTTGGTAATCAACCCATTGCTCAGGGATTTGAT

TAACTACTTTCAATACATCGCGTAATGCAGCCAAACGAGAACCCTTGACGCCGTATTTAGAAGCTTGCTT

GCGGACATATCCTAAATATGATTTCATGTTAGTCGTATAAAAACGAGAACGGTTGTCTTGAATAAACTTC

CAMACATCAGGCAAATCGGATTTAACCACTAGTTCAGGTGGAGTGTGAAGCATATCCAATGCTACAGGTT

CACCATCTGCTGCTAATTTAAAGAAATACTTAAGACTATACAATTCGTGGTCAATATTATCTTTAGTGTT

TTTAGATGATGTGTTGTTGGTATTTTTACTCATGTGCTCTTTGACGTTTCCAATAAGAATATCGCGAGCA

GGAGGAACAAAGATTTCTTTAAAATCTACATCAGATTCTGGAGTAGAAGTTCCATAAAGATGACTACCAA

AATAAGACTTAACTACAGTTTTCATTATTAGACCTTTCATAATCTTCATTAAATTGTACAATCAATCGAT

GATAATTAGATTTTGGATATCCTAATTTACTTATATAAGTTCCGAATGACCCACGTTTAGGTCTATTTAA

TTTAATCCATAACTTATAAAGTAAGTCATAGTCTTGCCAATGTTTACCAGTTCTTTGTCTAATTTTAGAT

GAATTTGATTGTTTCTTTTTAGCTTCAAAATTATTCAAAGATTTTTTGACTGCAGCAGAGTGTTTTTCTT

TAACTCCCGGTCGTTTAAAAGCAGCTTTCACCCCTTTAGATATTTTTTCTTTAACTTCCGGTTTGTTTTG

TGCTTCTAACTGGGATTCTGAAATTTTAGCCCTTATTTCAGGAAGACTTAATGTTATCGAACGTTTTTCT

CTGTATTCATTAGACTTCCACATTTCTTTCATTGTATTAGAATGTATTTTTGAAAATTTTTCTCTAACTA

ACTGATATCCTCTTGAAGTTAATTTGAGATTTCTTCCTAAAGAATCTTCTCCAAAATTATAAAATGACCA

CCATGCATAAATTAATCCAGGCGAATTGTAATGAATTTTAGCTAAAAGCCAATGGGCTATAAAATGCTCT

CTAGCTGTTAATAAAACTAGATTATCAGAATCATCATTACCACCAATACAAGATGGAATAATATGATGCT

TTTCCGTATAAAAATTTAATTTAGATTTATCTAATTTTCTGAGTTTTCCTTTCTTAATTAAATTATTATA

TACTTTAGTATAATTCATTGGTTCTTCGTCTCATTTAATTTTGCTTTGCATTTATAACACATGTCTGTTC

CACTTGAAATAAACATATTTCCTCACTTTGAAATCATAGTTGGAATAACAGAATCAAGATAAGTCTTTAG

TGCAATAGCTTCCTCTTTCTTTAATGTAATGATATGTGATCGAAAATCATCAATTTGACGAATAGATACT

ACATCTCCCTCTTCATAGCATTTTGAAACATTTAAAATAGTTTCATCATTCTGATTACAGGAGTTAGTAA

TAATAGCATTACATTTTTTAAACCATTTTAAATTATGTTTTCTTTTAGTAGAATCATAAAAATATTTAAT

GTTAGTTATAAAATTATCCCAATTATTAATTGATAAGCACATTGACTCGCTTTTAATATTAAATCCTGGG

CATGAAGAATAAAAATGAATTTTATGCTCATCATTAATGCTTACAATTTTATCAGTGTAAGCATATTCAA

TTTGGGTTAAACGAACAATTTCGCTAGGCGTAAAATATAACATGTCATCTTCTTGCGTCAAACGATACAT

GTTATTTACTTTTTCTATAGCCAATTCACCAAAAAGTGGACTAACTTCTAATACTAGTCGTTTCGCCTCG

-continued

CTCATCATTACATACTCCTCTGAATCATATTAATAATGTTATTCACCAGATTATAAGTAAACATTGGGTA

ATTATATTGAATCATCACATATATAACAAACAAAACTTTCATTCTCTTCTCCTTGGCAGTTGACAAGATT

ACTATACCATAATCTTGTCAACTTGTAAACCATTAAATGACGTTTTCGATAAAATTTTGAAGCTTTGTAT

GAGCATCAACCATGATTTTCATTTCTTCCTTGGAAAAGCTGTGCCTCTTTCCCGAGAAGAACATTCATAG

TCAGAAACTGCATTAGCATATTCTTCAATTAGCTTCATTAAAAACATCTGTTTTTCAGTTTTCATTATTC

CACCTAATCATTTCAAGATATTGAACTAACTTAGCTTTGGATTTATCCAAATCCCTTTTAGCTGCTTCTA

TACCGTCGTATGAATATCCTTCACAATGCTCAACTGCTAATTGATATGAATCTATTTCAATATCATGCGC

TAATTTAATGATTTTTTCAAACTGTTCGCGTGTTAGCATACTTAAACTCTCGTATTATGATCGATAATTT

CATCAAGAAACATATCTAACGCTTCTACAGCATTATTAACTTTAGCTTCAAATTCTTCAATACCTGATAA

GGCAAAGTTAATGCGTTCCTCATCTGCTTTACGAATTAAAGCTACCAATTCCTTAATTTTATCCGCTTGT

TCGATACTAATCATTATTCCACCACATATGAAAGAGAGAATATTGCACACGCCATGTGAGTTGCAACTTC

ATCACACATATTATAACGTTTCTTAAGAAGTTCTACAAGTTCTTCACTAGTAACTTCATCCATGTCGACG

AAAAAATCACCATTAATGATGACGTAGATATTTCCTTCTTGATTGAGTGCTTCAATTTTCATGATGTTCT

CCTCTTTATCCGATGGTTGTATAGTACCACAGCTCAAACGGAAAGTAAACCGGTAAAATGAAAAAAAGTC

TCCCGAAGGAGACTAATGTTATTCGAGGGAAAGAAGATACTTACTCTGGTAAAACATTCCAGTAATATCA

TCTATCGTGCTTTGGATGGCTGGAGGCATTTCTTTATAAATGCTGTTAGATTGGTCTAGTATGCGATCAA

TCATTTTAATTGTGTCGGTAGGAAGTTTACTGGCATCTGGAATTGAAGGCGTGTATTTTCGACCAGAATA

CCCCAAATATTGCTCACCAAATTTATCAATCAAATCTGGCAACTCGGAAAAAATAAAATCGTATGCTTTG

TGTCTAGCATAACTTTTAGTTTCAAAATGTGCAGAATGAAAATAAGCTTGTGCAGCCATTAATAAACCTA

AGTATTCATCTGCCTTTGAAGGTTTTCCACTTTGTGAAAAGTCGCTGAATTTCATTCAGTCTCCAATTTA

ATGTTCATAATTCTAGCGTATGATTGTGCCATCTCCGCGCCTCGCTCTATACATTCAAAATCAGAAGAGC

ACGGGTCATTTTTATAGGTCGTTCTCATAAAACTATAGAATTGTTCAGACGATTCTACGCTTTTATTTTC

AAAAAGCATATAAACGTGCCTAATACCAGATTCCATAAATTTATCAAAATGAGGATCGACATTCGCTTCA

ATCGATGGAGATAAAACAAATGACAATCCTAGCATGGCAAAAAGTGCTGTTGCTTTTAAGGCCATAAAGG

CCTCCTATCATTTTTGTCCTGTATTTACTTTGTGCCGATGCACGGCCTTAACTTTATCAAGGTATTTTTC

AAAATTTCGCAATCTAGTATAGTCTGCCGGAGATTGGTTGAGTGATACTTCTCGACGCAAAGCTGAAATG

ATATTTCCAACTTCCCTACGAATTTCATCTAATTGAAGAACAGTAAGATTGCGAAGTTGCTTTTCAGTTA

ATTGTAGCATATATACCCCTTTAGTTAGATAAACCTATTTATAACTTTTGCACTAACCGAGCTTTTTAGT

TAATTCATTCCAATGTTTTCTACACAAAGAAACATAAATTTCATCACCAATACAAATTTGATTACCTTCT

TTAACTGGTGTTCCATCTTCCATTAATCGAGCTGTCATAATCGCTTTTTTACCACAATGACAAACTGCTT

TTAGTTCAATAAGTTTATCTGCAATCGCTAAAAGTTCTTTAGAACCTTCAAATAATTTTCCAGCGAAATC

AGTCCTTAGCCCATAAGCCATAACAGGAACATTATATGTATCAACAATTCGGCTCAATTGATGCACCTGT

TCAGTTTTTAAAAACTGAGCTTCATCTACAAATACGCAATGAATATCTTTTTGTGCTTCAGCCCATTTAT

AGAACTCGAAAATATCCATATCATCTGTAATAATATTCGCTTCCTGCTTAATTCCAATGCGAGAAACGAC

TTCACAGACAGAATCGCGAGTATCAATAGCAGGCTTAAGAACTAATACACTCATTCCACGTTCTTTATAA

TTATGTGCAGCAATCAAAAGAGAAGCAGATTTTCCAGCATTCATTGCTGCATAAGTAAAAATTAAACTCG

CCATCTTAGTCCTTAGTTAAATTTTCTAAATATGTTTCTAAATCATTTTCAGCTTTATCGATAGATTTTA

CTAATTCGTAATATGTTTCGGCATCTCCATATTCAGAAGATATTTCAAAAGACAAATCCTTTTCTAAACT

AATAATTTCACCAACTAAAAATAATATTTCGTTCTTTTGTTCGCGAGTAATCATAAGGAATTTATATAAT

CAATGAGTTCTTGTTCTTTATTATCGAATTCTTTAGAAAGTTCTTCGTACTCGTTTGCGCTAAAAGGACC

GCATTCATTACAAACTTTTTCCAATTCACTATTTTTATCCATAACTTCGTGGATAAGAGAAAAGAGTGTG

-continued

TCTTTTTGTTCTTTGCTTAAACTCATAACCATGTCACCTTTAAGCAGTATTCTTCTACATGCTGTTTACG

ACCTTTCTTATCAATAAAGGTATATTCAACGAATGTTCCAATGTAGTCTTTATCTACATCATGTGGACTA

TTAATTGGACATTTAGTGCGACAAATGCGTTCCCATTGACGAATAATTACTGCCTTATTCTTTGGGTCAT

ATGGATGTGGATAATGTATATTCATAATAATGGTTCCCAATCAACAATCACAATTTCTAATTTAGAGGAA

TATGTATCTAAAATCCCCTCAATAATATCCCAGTTCCCTTTACCTATGCCTGCACCAATCCTAGGCATAT

AGATTGTAGGTTTAATCAGTTTATTTTCACCAAACTCATTTAATTCTAACATACAATTCATTAAAGCGGA

ATACTCAAAATTTGGCCCTGGTTGAAATTGAGTATAAAGATTGAAGCAGTAAGCTTTATGAGTCCTAAAG

TATTTTTCATAGACTGAGTAAGAACCGAGTTTAGTTACATCACCCCATTCAGTCTGTAATTTATCAGCTT

CCAAAATTTTAGGGAAAGCTTTGGTTAATTGACCCGCTACGCCTGAACCCATAGTATGAAAACAATTACA

TCCATGTGCAATATTTTTACCTTCAGCGAAAAGGGCGACAATATCGCCCTTGATATATTTTACAATCATC

TAGTACTCAATCCTCGATTATAAGAATCTACCAAACGGTCAACCATTGAATGACAAGCGGCTTTATCTTT

CTCCTCCGCAACTGAACATTCTAAGGTATTCCACTTTTTAGCATATCGTTTTAACAATGTATCGTTTTTG

TATCTGCTTGATTTATCTCTTTCTCCGTCTTTATATGCATATATTAATTTCTGTGCAAATTCAGCTTGGC

ATGCCTTATTTTTCCCACAATAATCTGCCGCAGTGCGGTTTACATATTCTCTAATTTCAGTATATGATGT

ATCTGCTGACGCAGAAGCAGAAAATGAAATTAATCCTATACATAAAACCAAAATTTTAGTCATTTACTAT

TTCCAAAAGTTTATTATTTTTAAGGTAATTAGCCTTTTCTAGGACTTCAGAAGCATATTTAGAACCTGCT

TTAACATTCCATCCCGAATTATAAGAGGATATTGCTTTTCTTATATCGCCCTTATGTATATTTAACCAAT

AAGAAAGTTCAATGTACGCCCAGGAAGCTGAATTGGATCGTTTATTCAACATTCTTTTTATTTCAGCATC

GGTCATATTATAACCAAGTTCCTTAACTCTTGCTCGCATAGTAGGCAAATAATTTTGGAACATTCCGTAG

GCGTGATGCTTTGGTTTAGATTTTAAATTAACTCCGCCAGAGCTTTCTTGCCATAAAATGGCAGCCATTA

TATGACCTAATCCGCTCTTGTGGATATTTTTGTGTGTTTTATATTTTCCATCCTTAGAAAATTGTTCCCC

GAATTGATACGCGTAACGCATGTTATCGAGTTGGACATTACTGAAAGTATGCTCGGAGCTATGTGCCATC

ATTGAAATGGCCAATAGACCAGCGAGTAGTGCTTTTCTCATGCTTACCTCATTGAGTTTTAATTACTGCT

TTAGAAGCCTTTCCTGGTAAACGACGACTGTTGATAATTGCCATCCTACATTGAAGTGACGGGTCTTTGA

ACTTCTCGTTAGGTTTACAAACTGTAAATCCAAGCCAAAGATTTCCATCTGTGATTTCTAAACGTCCAGG

ACGATATTCAACCCCATCAATAAAATCCTCGTCAATGTCAGGACGCGGAGGCATACTCAGGAATTCATTA

ACTTCTAAAACATGGTCTTTTATTTTATGGAATAATTCAAAAACGTATGTCTCATCAATCTCCCGTTGAA

TTGCGCGATCAAGAAGATGTTGAGAATATTTTAGATGAAACGATGAGACTCCTGCTGCTTTTGATGCCTC

ACGAATCTCATTGTTAATTTGACGAAACTCCGACTCAAAGTGACGACGAAGCTTATTTCGACGGATAAAA

ACTTCTGTATTGATAGTCATGTTATTCTCCTCTTAACTGATAGAAAAATTATACCACAGTCAAGAGGAAA

AGTAAACAGTTATTCTTTAAATCTAATCAATTTATTCATAGACTTTGAAACTTCGGCACGAACCTCATGT

AGATTTTTGAGCTGTTCAAGACGCTGCGTATAGTAAGCAATTTCATCTTCTTCGAGACAGTCCTGCGAAT

CTTCTTTAAGATAACGTGCATAGTCCTGGAAAGCGTTACGGACTACTTCCTGGAAGTCATCAAGACTTTG

AATTTTCTTAGGAGCAACAGATACACGACGAGGGGCAGTATAATACTCATAACCAAACCCTGCGCTTAAT

TGAGCCATTAGTATTTTTCCTCTGGTTGGAACACTGCACGACAAGCCCACATACTGGCTTCTTTGAGTTT

CGTTTTAGCAATAGTTAACTGATCGAGACTTTCAGCATAATTCTTCGCGAATTCACAGTCTTCGCAATTA

TCTAGTGCTTCCCAGAATTCATCATATAAAGCATCAAAGATAAGTCCTAAACGAACTTCAGCGTCTTTAA

TAGCATTTACTTTACCGATTTTCTCTTCAGTATGTGGTTTATAACCCTTAATATCTTCAATCATATTTGA

CTTCCTCACCAGTACATAATACGTATTCAACTAAACGAATAGGTTCATGAATGCCATAGCCTTGAACAGA

AATTTCTGTCGTAGGATAAATTCCATCAATATCACCCATATTCCACGCTTCATTAAATTGCTGTTCGCCT

-continued

GAGTTACTAAACCACTCGCGAAAGCATTTAGCACATCTTCAGAACCTTCAATAATTATCTTTGCCATTAC

AAACTTTCAGTAAAGGTACGAGCGATAACGTCGCGCTGCTGTTCCGGAGTCAGAGAGTTAAAGCGAACTG

CATAACCGGATACACGGATGGTCAGCTGCGGATATTTTTCCGGATGCTTAACTGCATCTTCCAGAGTTTC

ATGACGCAGAACGTTAACGTTCAGGTGTTGACCACCTTCAATTTTAACTGTAGGTTGTGGCTCAATTTCA

ATTTCACGGGCATGCAAACCATAGAAAATTTCTGGGTCTACAAAAGAGTCCTCTTTAAAGGTTTTAGAGA

CAATAATTCGTGCTTGAATACCATCTTCAAAATAAATAGTACCTTTATGTGTGCCTTCAAGAATTTGATA

TGCTTTCATATAAACCTCAATTAGAAAATAAATTTATCCAAGATTGTTCTTTAATTAAAAATGGCTCAGA

ATCATATGCCATTAAACTTTGCGTAATTAATCCTTTAAAAGGTCCATCAATAAATTCCATGGTAAAATAT

GGAATTTTATTCATTAGCCGTGCATTAGGAGCAGTGCACAAAACTCTGCATCCTTTGAATACGCCTTTTT

GTAATTTGTATTGCTTGGGATAAAATTCGCTCAAAATGTTATTTTTTGCCAAAATTTCAAAATGATTCAC

CAATTTATTTTTAATAGTTTTTGGCGAAAAATAAAGATATTCGAAAAGCTGAGTGTCTGTCATCATTGCA

TTCCGATTACGAAAAACTGTGGACGAGTAATACCACCAATGCAACATTTACTATTACAGCAGTAGTGTAC

GGTGTCAATATGGACACTATAAATCTTATCCATATCAGGAGATTTGACAGGCTCATCAATTATATACAAA

ATTCGCGAAAGCTTTAAACCTCTGAACTTGCTTCCTTTATTACCAATAAAACTGCGTACAGAATCAGTAA

ATAAACGAAAACGTATATCATCATTAGAATAACGCGAAAATTCCTTTTTGATGTTATTTGCAGAAATTTT

AGCATAAGCTGAAGTATTAGAAAGAACAATAACTGTTCCGCCATCATACAACCAATTAGCAGCAAAGTTA

GTCACAGCAATTGATTTACCGGATTGACGTCCACCATCTAGTCGAAGTGTACAATACTGTTTAAGTAAGT

CTTCAAATGGCGGGATATATTCGTTTTTACAAATTTCTTCTACTCTAGCATCAGAATGGTGTGTAAAAGC

ATTCATCAGGGATAGATAAGGACCAGTTAAAAATGTTCTCATTTCTTCTCTATAAGCTCTATAAGTTTGG

GCCATTCCGTGGCACATGAATTGTCCATTTCTGTATTTACCCATTACCGCGCTTGGGCTCGACCTTATTA

CAGGTTGGCGGGAATCCCTCATATAATCATGAGGTCCAGGTTGTTCCCTTATGCATAAATCGCCTTACCG

TAGTATTTGTACCAAGTAGGACGTTGTGCAATTTTTTCATCTAAACGAGCTTGTGATATAGCAATAGAAG

CTTCATGGGGAATATAATCACCACGGAATTCCTGAGGAATATCACTAATATCCTGGACTGTAGTATCCTT

GATATTAAAACCACGTTTTAAACATTCAGCTATAAGCTCAATTTGACGTTTACGTAAGAACTCGAGCTTA

TCGTAAAAGAATGTAACATGACCTGCGCCAAGGATAAAAGTAGGACTGATTTTAAAATCACGAACACGTT

TACCGTTAGCAACATGCTTACGAACTGCACCAAAAACACGCGGCAATTCACGATATTCAGCCATTAAGTG

TTGGTCAGCCAATTCAGATACTAAAGTAAGGTTGATACGAGTCATTTTAGTGTTCTCCTGTAGTTGATAG

GTCTATAGTATCATACCTACAGGAGATGTAAACTGTTATTTATCTTTAATTGCTTTAGCTGCTTCGATAG

CCGCTTGCTGAAGGTCATCCATAGACATGCCGAACTTAGAAGCAAAGTTATCAATTTTCTTTTCGACGGC

ATTCAAAGGCTTGGCCTGTTTACCTTCATTAGCGCCAGGAAGAGCGAGAATACGCTCTCTGTCAATATAA

AGGCTTACAAGTTTCTTACGGTCTTTATCGGGCAAATCATGAAATGAATGGGCCTTTTTATTTACAGCGG

CTTCTAATTTACCTGCGCCCACTCGCGCTTCGGCAATAAATTCTTGATATGTTTTCATATGTTTCCTTTA

AATGTAAATATTTTTATTATTCTATCCTAGAATTGTGATAATATATTCACAATTCTAGGAGTTGTAAACT

GCTTTTATTTAAGCGTCCCAAGTATAAGCTTTATTAAGAATTACCACGGGCTGCATTAGCAACGGCGTAA

GCGTACTGAATATTAGCGTCTTTAAACTTACCTTTAGAGGTATCTATTTCTGCCTTAAAGCCGCCTTTAG

TCATAACATCGGCAAATTCTTTACGGAAAGCCATTGCATCAAGACCTTTCCATGATGATTTATGCTTGGC

AAATTCAAGACCTGCGAAGTTGACAGCTTTAGCCAATTTATTATCAATGACCCATTTACCGGCTTTAGGC

ACAAACTTCGGGCCTTTCTGTTTAGAGAACAGTTTTAAATTCCAGCGGCGAAGGTCTGCATCAGCTTTAA

CAAATTCTGAGTCTAAGTTACTAGCAACAACATCTTCAATATGAGCAAATTTAAGTCCGTCAACTTCAAT

ATTTAAATCGGTACGCCAGCGAAGTCCTTCCCAAGCGAAGGCTTTAAAGTCGGAAGCCTTTGTAGCTAAG

TACCGTTCAATAGGAGCTGTTTTAGGGTCAAAGCCGTTTCCTGATCGGTAGGTCCACTCATCTTTGTTAA

-continued
TGCCTTTGGCCTTTACTACAGAAGCTTCGGCAATAAATTCTTGATATGTTTTCATATGTTTCCTTTAAAT
ATTTTAATTAGTAATTGTCTATTCAAGTAATTGTGAATATACTATCACAATTCCAAGAGAAAGTAAACAG
CTTTATAGATTTTTATACGCGTCCCAAGTGCCAGTTCTAAACGTTGTAATGACTCGTTTTGCGCGATTAG
GTGTTTGATTATACCATATACTTTTAGCTAAGTTAACTGCTGCTTCATCCCAGCGTTTTTGTTGAAGCAT
ACGTAAAGAGTTAGTAAATCCTGCCACACCGGTTTCTCCCATTTGGAAAACCATATTAATCAATGCACAG
CGACGAACCGCATCAAGAGAATCATAAACCGGTTTTAATTTAGCATTTCTCAGAATTCCGCGAACAGCAG
CATCAACATCCTGATTAAAGAGTTTTTCAGCCTCATCTTTTGTAATTACACCATTGCAATTACGCCCAAT
AGCTTTATCTAATTCAGATTTAGCAGCATTAAGTGATGGACTTTTTGTAAGCAAATGACCGATGCCAATA
GTGTAATAGCCTTCTGTGTCTTTATAGATTTTAAGTCTAAGACGTTCATCTATACGTAACATTTCAAATA
TATTCATAATACCTCCTAAGTATTTATAGAAGGTATTTATAAAATTAAAAGAGGTTGTTCATTATTCGGT
AAAGTGAAGGACCCATCACATATTGCCACTGAGTACGAGGAATAAGAGCAAAAGCGTCCATCTCTGGAAT
CATAACGCCATCTTTATTTTCAAAATAAGACTCGCAACGGCAATTTCTGAACATCTCATGCTCTACTGGA
ATCGTGTAATAAAATAACTGTAGGTCTTTATTACTAGAATATTTAAATACACCTAGGTCTTCTAGAAGGT
CTGGATTATAATTGCTAAAACCAGTCTCTTCTAAACATTCTCTTCGTGCTGCATCTAATGCGCTTAAATC
AGAATTTTCTACACGGCCCTTTGGAATATCCCAACGATGTGCCATCATTCCAGTCTTACGAGAACCAGTA
ACCCGACCCATAAATAAATCTTTATCTTCTGTCATAAAGATAATACCAGCTGATAATGTTTTCATTTTAA
TTTCCTGCATTCAGTGATAAAGTTATTTAAATTTTGAGCATATTTCTTTTCATCAAAAATCTTTTGCTGT
CTGCGTAACCGCCATGGCATTTCAATGAACATACGCCATATCCCTAGATAATACCGCTGCTGTAAAAATA
TTAACAAGTATAGTTAAAAGAATCCAATCGCCTATTCTGTCCATTGGATTTTTATAAAAAAGTAAAATAC
GAATGATGATATAGGAAGACTAATGATATACCACAGAAGAACCTTCTTATCTGTGAACCAATCAGCATTC
GTTAACTTAGCGCGACCATTTTGAATACACACGAATTTATCATCTGTTACAGTAAATGGCTTAGCTGCTT
GATATCCCATTCTAAACTCCCTAATTAATCGTTTCTTTGTATCTTCGGAACAACCATTCCAATCAACTCT
ATCAACTGGAATGCCATCATCCCCATCATCTAAATCATACCAGCGAGTTTTTAAAATCATTTAATTTTCC
TGCAATCAATCACAAACTCTTTCATTGATTCATTTTCAATATAAGACATGTAGCTATTATATTCTTTTAA
TTGTATTTTGTAATCCTTTTTTCTTTGCCAATTTATTTTAAAATTATCATAATGAAAATATAAAATGATA
CCAAAGAATGAAAACAATGAAATAATTTTAGTATAACAAAGCTCGCTCCAAACTTCTATTATATCTACTG
TACCACTGATTTTTAAAATAAAACAGTCAATTAATAGTCCAATAAGACTACCTGTAAGAGCTGCAGCCAA
CGCCACAGCAAAAATTAAAAATGACTCAGAAAACGAATATTTGACTTTATTTAGCTTTGGCTTTTGCATC
GTGATTCCTTAACAAATTTCATAATTTCATTAAATTCATACTCAGCAAGTTTAAGCTGGTGTTCCTTTTT
AATCTTTTTGCACTGGGCTTTCCAATCACGTACGCGTTTACGATAATGTCTTCCTTGATACCAGTATCCT
ATCCAATTTACGGGTACTAATAAAAATGGAACTACCAATGGAAGAGTTAGCATTAACATAATTATTACGC
CAGAATCAATATCAGTCATAACATCTAAAACACCTCCAATAATCAATAGAATTACAAATGATATAGCTAT
CACAGGACCTATTAATACATCAGTAGAAATTATCTGGCGCTTTAATTCATACTTCAAAGGTTTACTTGGA
AGGTATAGTGATGGCTTTGACATATTCTCTACATTCCTTAACAAATTTTTCTAGTAATAAATCACTTTCA
AAATTAGGATTTTCCACTAATTTATCAAAAAGATCATCAACAATATTCAAGATATTTCTTTTACTAAGAA
TACGTTTATTTTCATGCTTCGTTTCAGAATCAACTATAAGAGTAAAGAAATATTTCTTTCCCTGAAATTT
TACCGTAGTATCAATATAAAATAAATTTGACTTTTGTAAATTACGTTTAAACCATGCGTCACTTAAACTA
TAAACACCGAGATAATCAAAATCGTCGTTTAAATAACAAACTGACCATTCAGGAGAAATGAAATCAGTAA
ATTCAACATCAAAATCACATGTCAATGAATGAATTGATTCAATACTGTTAATAAGTATTCCAGGACGTAT
TAAAGACTTTTTACCTCTGGAAAATCTTCCAGAAAGACTTTCATCAGTTTCATATGAAGAACCCCAATAA -continued

TAATTACGTCCTTTTGCCATATGTTTAAGAGCATTTAGTAATTGGTCTGGAACATCAACGTGTCTTTGGA

ACTCTTCAAACATTGAATTGAAATCACTTTGCATTTTCATTCCTATTTACTCCAAGTAATAGGGGCCGAA

GCCCCTTATCATTATTTCAGAGAATTAATATATTCCTGAACATCGGCAGAGGTAGTTTCAACCCCAGAAA

TATTACCATTAAAGGTTTCAACTCGAGCAAGAGTATCTTCAATATCAACCTTAGTCAGTGCTGCAATTTC

AACTACATCATCAGCAGTACTAATTCCAAGGGCATTTGCTGCACGAGTTTCACGGATATATTCCAATTTA

ACTGCAAGTTCTTGGCGAGCATCATCTAACTCAACTACTTTCTTGGCGATTTCAATTCGCATTTCAGCAT

AACCATCAGCTTTAGTAGTCAGCTGTTCAGCTGTTCGACGATATAGCAAGCCGAGTTTAGCATGCATTGT

TACATCTTGACCTTCGGAAAGAAGCTTGCGAATTTCACGCTCTTTTGATTCGGCCTGTTTATTCTTTTCA

ACAATAAGTTCACGAATACGTTTTTCTTCATTAATAGATTTAACAGAAGCAGTTTTTAGGTCTTTAATTT

TATCAAGTAGTTTTGCTGCTGCAGCAGTATACTGTTCTTCAACAGATAGATTTTTAGCCATTGCAGAACC

AAGTTTAGTGCGAATAAACTCAACAATTTTCTTCAGTGTGTTCATAGTATTTCCTTAGGTTGGTATAATT

AGATAATATAATATCACGTTTCTAATAGATTGTAAACTTATTCTTCGTCTAGCTCGTCGATAAAGGCGTT

GATGGCCTCGATAATGGCATCATTGATAGCCAATAAAATAAAATCATCGTCAGTACCTTTAGAAGATTCT

AAAGCATTGATATATGCTTGGTTGACGAGTTCCCAAGCCTTTTTAAAATAAGGAGCTTCATCATCAGGAC

AAATATCCCGCACGCCTTCAAAGATACGTTTGGCATAATCTAACACCCATTGTACAGGCATGTTTTGAGA

ACGTTCGTTAAACTCTTTAAAGTCCTTAGATTCAAAAAGCTCTTCAGGATAATTATTTCTATTACAAAAA

GCTTTACTAAAGTTACGTTTCATAATGTTTTCCTCATTTGTATAGGCTCATAATATCTCAATCATSAGCC

TATGTAAACTTATTTCATATTATTGAAATATTCTTCTGCGATTTCGTCGTTATCATGGTAAACTTTAGAA

GACAGTTTAACATAACTTTCAGCAGTGAACATGTTAATCACAACCTTTACAGTATACCACTGACCGTCTT

CATTACCCATTACTGCGTAAGTTTCAAACATCGGATGGTCAGGACCGATAACTTTAATATCATTCACCGT

ACGACCGAAATCTTCTGAAACACATTTCATAAAGAAGTTGAAAAGTTCACCGTAATTATCCATTTTATTC

TCCAAGTTATTTTCTGTATCAGTAGTTGATAGTTGTATAGTACCATGGAAGAACAAGGATGTAAACAGTT

TTGTGAAAAAATTTTTAAAAAGTTTTAGGGAATTCTAGGGCGGAGAGGGGCAATTAAAAGATAGGATAAT

ATATTATAAAGGGTATAAACTAAATGATGCCTAGAGAGGTCTGGAAAGGCTTAGATACCAAAAAGCCCCA

ACCTTTCGGTCGGGGCTAACCGTTGCGGCAACCTTGTCGGGGTTCCACCTGCCAAGGCAAGTGTTTGTAC

GAAACGCCGGGATTCGAACCCGGTTATTAAGTAGTTGACGCTACTCAATATTTTTAAAAGGCCATATCTC

AACCATATCCGAACGTTCCGTCAAAAACGCTACTCGGCTTACGGCAAAGATATTTCCTCGAATCGATAAT

TTGGTGCGCCGTTTCTGCTGTGATGTAAGAGGGCATCAATAAACGCAAAGATTATTAACGCAATTCCTTA

CTCAGGGAACCATCAGTCCGACGACTTACCGGTAGCGACCCGGTTTCTCATTTGGTATCCCGCCCTGGGA

TCGAACCAGGACCGCAAACTTAGAAGGATCGTATGCTATCCATTACACCAGCGGGACGTAATTTAAAATT

TCATTTTTCGACCTTTAAACCATCCTTCTGGAATTGGGTCAGTTTTCTTAATACGTTTAGAAACTTTTTC

ATCTAATGAATGAATCCACATCATACCGAATTGGGAATTCTTTTCACCTTTCTGGTGATTATTTTTGGCG

TGAGATTCTTTCATTTTATTAATAGTTTCAGGAGTATGATGCTTATTTAGAAATCTGCTATTATTTAAAA

ATTTTTCCCTGTATTCAGGAGTTGACCACAAACGTTTAAATACATTTGAACCAATTTTACGATATTTTTC

TTGAAGTAAAATATCATTTTCAAAACGTGACTTAAACGATTTAGCTCCTTTTAAGCTAGCATCTTTCTTC

TGGTTTAGCATTCCAGGAATATTTACATGATCCCATCCACCTTCACCGCCAAGTTTTAAATTATACACAT

CTGGTCTATTTAAAAACTCTTCTGTGACAATATTTTTCTCGGCTTCAAGCATAGATTCTTTATCGTCAAA

ATACTCTAATATTTCTTTAGAAAAATTTTCTATACCATATTTATCTTGGGCTCTTTTTAATAATTTACCA

GAACCCATATATCCATCATCTAAATTTTCGGTAGAATGCACACCAATATAAATTTTATTATTAATTTTAT

TTGTTATTTTATAAGTGTAATAGAACATAAATATCTCCTATTTCTAAGAGTATTTATGTTCTCAAAATAT

GACCCAGACCAGATTTGAACTGGTAACCTTTCCCTTATGAGGGGACTGCTGCTAACCATTGAGCTACAGG

-continued

GCCTTGGTGCTGATTGACGGAATCGAACCGCCGACATCCTCATTACAAGTGAGGTGCTCTACCTACTGAG

CTAAATCAGCAAAATTACGGAGGCGATAGGATTTGAACCTATGAGTCGCCGGAGCGACTGCCGGTTTTCA

AGACCGGTGCATTAAACCACTCTGCCACGCCTCCAGTCTCCATACAAGGATTTGAACCTTGGACCTCCTG

ATCCCAAATCAGGCGCTCTACCAAACTGAGCTACACGGAGTAAATTAAATTGGAGCGGATAATGAGAATC

GAACTCACATCATCAGATTGGAAGTCTGAGGTAATACCATTATACGATATCCGCAAATTTGGTGCGAGAA

GTGGGACTCGAACCCACAAGGAAATCATTCCGCAGCATTTTAAGTGCTGTGCCTTTACCAATTTGACCAT

TCTCGCGCTGGGAATAAAGGACTCGAACCTTTGCATCTAGCAGTCAAAGTGCTATGCCTTACCAACTTGG

CTAATTCCCAATTATTAACAAAGGCTCTCTAACAAGAACCCTTGATGATAGAGGGTATTAATCAGTGCGG

TATGAGTTAATAATAACAAATAATTCTTAAAGCATATTTACCATTTATGATGATACGTATTTACGATACA

TTCAAGACCCAAAGGATTCTTGAAAATATCATATTCAAGAGGACCTTTTTCTGTTTCAATAAAGAAATCA

AAATTTACTGTATTAAATTTACGGTCTTCCTTTACTAATTTAACTTGAGAAGATGAACGATCAATGTAAA

CCTTTTCAACTTCAAAACACGTTAAAATGCCATAATCATCAATCAAGGCTTTAGCTGCTTCTTGATCATA

TTTATATCCATTTTCAACGGATGATACTTTCGCATAAAGAATCATCATCAACCTCTATCAACAATAGCAT

GAGTATGGGCATTTACGATTTGCCACCAGTCGAAACGATTGGAACCATAATCTGGTTTATTTTCATTTTC

TTTAATGATATCACGCAGTTTATCTTCTGTTTCAGCATACGCAATTAAATCATCATATCCACCACAAGGA

TAATAATTATCACCTGCGAATAAAAGAAAATTTACCTTAGATGGATTTACGTAATAATGGTCTTTAGGAT

ATTTAGTTCCTCTCCAATCAGTTACTTCAACATAACGGTAAGAAAATCCATTTTTACTTTCAATCCAACT

CCACGCTTCAAAAGGAGTATTAAAAACTTTATCAGGTATTAAATTACCTTCAAAATGAGAAGGATTTGCA

TAATCCCCGGCATAAACATAATATTCGTTAATACTCATTTATTCACCTTTAGAAATTTTATCCATAACGA

TAGCAATTAAACCAATTAAAAATGCTACTACAAGTGAAAACACATTTTCTGCTGTAGTTAATAATCCGCA

TATAAATCCAACAAACATTGAAAAACTAAAAGCAGAAGCAGAAATTGCAATAGCAACATTTCGAATTAAT

TCACAGCGTTTCATTTTATTCTCCTCAGTAGTTGATAGGGTAATAGTATCACAGCTAAAACCCTATGTAA

ACAACTTTGTGAAATATTTATTACAAAAGATTTTTAGCAATAATCTTGAGATGTGCCGCAGAAATGTGTT

TAGCTTTAAACAACGCAGTTTCTTCAGCAGGAGAGATAACGATTGTAGCACCATCCTTTTTAGCAGACCA

CCCATCACCTAGGTAAACAGTACCTTTGATTTCTTCGCCATCAACCAGACTAATCATTGGTTTACCTTCT

CGTCCTTTATTTGCTTTAATAACTTCAGAAGTAAGAGTAGCTTCGGTAATGGTAGAAACCGGGGTAGTTG

TAGAAGTAAATTCTTTAAATGTTTTCATTTTTATTTTCCTAATTAATTTTGATGAGGTAATAGTATCACT

ACCTCATCAGTATGTAAACAACTTTGTGAAATTATTTTAAATCATCTGCCCAATCGAGTTTAAGAGGCTC

TTTGTATTCACGATCTAATACGACCGGAATTTGTACATCACCGCTAAATGATAAGGGCCCAACATTATAA

GACAATGTTATATGCGGTGTGTAATCATCAAAATCATGTGTAGCACCTAGTGCCCGCGCATACATGTGTC

GACAGCGCAGATATTCAGAATCTAGCACAAGTACAAGAGTCGATCCATCTTGTGTTTTCCATACTTCTAA

ATGTCCAGAAGAAGCTACTTCAAAACTTCCACTCGATGGAACATATGGAACATTTACTCTTGAATAACAT

ATAGTCGAATGAATTTTTTCTCTAGGAACTGGATTAGGAACACGTAAAGAGCGCTGAAGTTCTTCCAGCG

CATCAAGTGTTAATTCTGAAAACTTAGCTGCTACATAAAGACCCGTTGAAAAGTCTTTAAATTCCATCAT

TCTTCATCTTTTGCTTCATCTGCAGATTCAGCAGTAAGATTTTTGACAGCTTCAACGATTTCTTCAACTT

TGATAGTATCGCCAGTGATACCTACTGCACGAGCAATTTCAGCCAAAGTTCCTTGCAGAATTTTGGATTC

TTCCATCAGACGAGCAGCTTGATCCTGCGTATCAAGAATGCGAGATTTCAGAGTTACGATTTCAGCAGAC

AGTTTTTGTTCAACAGTTTGTTCAGACATTATAGTACCTTTAGTGTATTTTTAATTTTAGAAAAAAGTTC

TTCAAGAGAACCATCGTTTGTAATTACTAAATCGCCATCACGAATTGGCAATCCAGCTTCTGTAATATGT

GTATCATTGGATTTTTGACCAGGACGAACTACATGAATTACTGTAGCACCCATCGCCCTAGCCGCATCCA

-continued

TTTCATGATCTTGACGGGTATCAGGAACGATATAATAATCATAACCTGAGTTAAATTTATCAAGATAATC

TAAAGCAAATAATTTTACCCAGTACATGCGGTCGAAGTTATTAACAATCAAATCCGTACCTAGGGCTTGC

ATCAGACGACGGACTGACCATTGATCTTCAATATTATTTATAACGTCAGTAATCTTATTAAATGCTACGA

AATTAACTGATTCTTTTCCTTCGTCATCAAAAACAAACACACCTTTAATTGGGCTTTTACCATTAAGATA

ACAAAATGCTTGTTCCATAATCGTGATTACTTCTAATTTAGTCAGATTTAAATTAGTCTCACGATCATAG

TCAATTCCTTCAAACTCTTTACGAGTTAAGCAAGGATAGTCAGTGTTTGCTGCAAATACTCCCCATGCAT

AAGCCAATGCATCCTTAATAGGACCAGCAAGTTGGTATTTAACTGCAGAATAATTGCTCATGATAAAATC

AGCAGTAGTATCTTTTCCACTACGCTTTACACCGCTTAAAAAGATTAGTTTCATGTGTTTCTCCTCAAAT

TTAATTAAGATTATAACACACAAAACTGAAGCATTAAACTTCTGCTATAATTTTACCATCTTTTTCTACT

TGAAAATAGGTGTAAGGAATTGTTGCAGTACATACTAAAGCCGGGTCTGAATCTTCCGTGTAGCTAAATT

CTACTTCAGATAGGTCAGAAACCCAAGGCTTATAAAAATTTATTGACATCACGATTTCAGTTTTGCTATT

ATCTAAGATGTAAAGCGTAATGTACTCAGGACCTGTTTTTTGGGCAGTATTTTCACCTGTAAGATAGTTG

CTAGTTCCTAGCATCCATTCATACATTCCTATCCACGACTTAAGTTCTTCATCAACTATAAATCTCACAA

TGAGTGGATCATACTCAAATGTAACACCTGGACGTTGTGCTCGGCCCAGTCCAAACGGCCCAGTCACGGT

ATCAGTAACAGGTATTCTAATTCCTGGAATAGGAACTGACTGAGCATTTAAAGTAAAAGCAGATGTAGTA

TTACTATGTGGTATTGATACTACAAAGTTAGTTGTATTTGCTTGGTTAAAAATTTGTTGCAGAGCTTGCG

ACATATATTCCTCATAATGCTTTATAACTGTTGGTGGTATAATGGGTCTAAGTCCCTTCCATTCAATTCC

ATTTAGAACAAACAACAGAAAAGAATGGAAGATAATAGAATTAGATATTTGACCAGACTTTGTTTGCAGA

GAAACGTTTTCCTTTTGAAACGAACTGCTGAAGTGGCATCAACACAACGTTCGCCCAGTCTTTCGGGGCG

ATTTCAACAAGGCTACCCATAATATTACCAGGTATATATGCCTTAATCATTTGGTCTGCACCCCTAAATC

CTTTCACTTGACTCCAATCAATTTTTAATTTCGTTTTATTAGTAATAGTAGGTGTATTTGCATATTGCTT

TAAAAGCTCTTCTAGGAATTGCTGACGAGCTTTAGGTGGAATATAGTGCAAGTTTAATCCGTACATTAAA

TTATGCTTACCTAAACCAAGGTAAATTATCAAAGGAAATTTATCCCAGTAAGGAAGAGTTTCCTTGTGTT

TAGCATCATAAGCAAAAGCATATATTCGTCCCGGCTGCGGGCGAACAACTTTATGTCCTTTTACTTGCTT

AATAGTTTCAGCAAACCACTTTCTGGTTTTATTATTAATTGCTGCGCCTTCATTACGAATTTTATCACGC

AATGTTTGTCTGAATGAATTTATCATAAGCAGTTGTCTTTCTTGCTTATTGAGTTTATTCATTGGTTTTG

ATTCAAGTTTTTGAATCTTTTCAGCCGTTTTAATTCCTGAAGCATATTTTGACATTGCTGAAGTAAACGT

AGAGTATTTGATTCCTCTTTCTTCAGCAAATTGCTTTCCTGTCATTCCTTTTGCTTTGGCCTTTTTATAT

TCAAGACCTATCTGAATCCATTTCTTTTCGTTTAATGATTGCTTAACCTTTGGAACTTGGGGAGTGCTTT

CATTAATTATTTGAAAAATAGCCATTATGCCCCCTTAAAGCCAAGAGCTCGTAATCCATCTTCTGTTAGA

ATTCTAAATTTTATTCCACGCTTTTCAGCTAAAGATTGTGCTGCTTTCCATTTGTCAGTGTTCACAGACC

AGGTATAAATTTCATTCATAAATCTTTTCTTCGCTGCGGTCGTTAGATGTGCTGGTTTAACTGGTGGTTG

TGTTTCTTTTTTAGGTTTTATTTCAATAAAAAATTCTTGTCCAGAAGAATCTTTCATCCAAATATCCATG

AAGTATCTACGTTTTTTCCCTTCTGCATTACAAAAATAAGGAATTACTGCTGTTTCACTACCCCATGCAA

TAATTTCTGGATTTTTATCTAACCATTCAAAAAAGAATTTTTCCCAATTTGATCTATACGTAATTTTTTT

AGGGTCACCTCTATACTTTGATATATTTTTAGGAACCCATTTTCCAGAATATGCCATTGGATTCTCCTTA

TAAATAGATAATATATTTATAAACAGGAGGGCCCATGCTCTTTACATTTTTTGATCCGATTGAATATGCG

GCCAAAACGGTGAATAAAAACGCGCCGACTATTCCTATGACAGATATTTTTAGAAACTATAAAGACTATT

TTAAACGCGCTCTTGCGGGATACCGCTTACGTACTTATTATATTAAAGGTTCACCACGCCCGGAAGAATT

AGCAAATGCTATATATGGAAATCCACAGCTGTATTGGGTTTTATTGATGTGTAATGATAATTATGACCCG

TATTATGGATGGATTACTTCGCAAGAAGCTGCTTATCAAGCATCTATACAAAAATACAAAAACGTAGGTG

-continued

GAGACCAAATAGTATATCATGTGAATGAGAACGGTGAAAAATTTTATAATTTAATATCATACGATGATAA
TCCATATGTTTGGTATGATAAAGGCGATAAAGCTAGAAAATATCCTCAATATGAAGGAGCGCTTGCTGCG
GTCGATACGTATGAAGCTGCTGTTCTTGAAAATGAAAAACTTCGTCAAATAAAAATAATAGCAAAATCAG
ACATCAATTCATTTATGAACGACCTTATACGTATAATGGAGAAATCTTATGGAAATGATAAGTAATAACC
TTAATTGGTTTGTCGGTGTTGTTGAAGATAGAATGGACCCATTAAAATTAGGTCGTGTTCGTGTTCGTGT
GGTTGGTCTGCATCCACCTCAAAGAGCACAAGGTGATGTAATGGGTATTCCAACTGAAAAATTACCATGG
ATGTCAGTTATTCAACCTATAACTTCTGCAGCAATGTCTGGAATTGGAGGTTCTGTTACTGGACCAGTAG
AAGGAACTAGAGTTTATGGTCATTTTTTAGACAAATGGAAAACTAATGGAATTGTCCTTGGCACGTATGG
TGGAATAGTTCGCGAAAAACCGAATAGACTTGAAGGATTTTCTGACCCAACTGGGCAGTATCCTAGACGT
TTAGGAAATGATACTAACGTACTAAACCAAGGTGGAGAAGTAGGATATGATTCGTCTTCTAACGTTATCC
AAGATAGTAACTTAGACACCGCAATAAATCCCGATGATAGACCGCTATCAGAGATTCCGACCGATGATAA
TCCAAATATGTCAATGGCTGAAATGCTTCGCCGTGATGAAGGATTAAGATTAAAAGTTTATTGGGATACC
GAAGGATATCCGACAATTGGTATTGGTCATCTTATCATGAAGCAGCCAGTTCGTGATATGGCTCAAATTA
ATAAAGTTTTATCAAAACAAGTTGGTCGTGAAATTACAGGAAATCCAGGTTCTATTACAATGGAAGAGGC
GACGACTTTATTTGAGCGTGATTTGGCTGATATGCAACGGGACATTAAATCACATTCTAAAGTAGGACCA
GTCTGGCAAGCTGTCAACCGTTCTCGTCAAATGGCGTTAGAAAATATGGCATTTCAGATGGGTGTTGGTG
GTGTAGCTAAATTTAACACAATGTTAACTGCTATGTTAGCAGGAGATTGGGAAAAAGCGTATAAAGCCGG
TCGTGATTCATTGTGGTATCAACAAACAAAAGGCCGTGCATCCCGTGTTACCATGATTATTCTTACGGGG
AATTTGGAATCATATGGTGTTGAAGTGAAAACCCCAGCTAGGTCTCTATCAGCAATGGCTGCTACTGTAG
CTAAATCTTCTGACCCTGCTGACCCTCCTATTCCAAATGACTCGAGAATTTTATTCAAAGAACCAGTTTC
TTCATATAAAGGTGAATATCCTTATGTGCATACAATGGAAACTGAAAGCGGACATATTCAGGAATTTGAT
GATACCCCTGGGCAAGAACGATATAGATTAGTTCATCCAACTGGAACTTATGAAGAAGTATCACCATCAG
GAAGAAGAACAAGAAAAACTGTTGATAATTTGTATGATATAACCAATGCTGATGGTAATTTTTTGGTAGC
CGGTGATAAAAAGACTAACGTCGGTGGTTCAGAAATTTATTATAACATGGATAATCGTTTACATCAAATC
GATGGAAGCAATACAATATTTGTACGTGGAGACGAAACGAAAACTGTTGAAGGTAATGGAACTATCCTAG
TTAAAGGTAATGTTACTATTATAGTTGAAGGTAATGCTGACATTACAGTTAAAGGAGATGCTACCACTTT
AGTTGAAGGAAATCAAACTAACACAGTAAATGGAAATCTTTCTTGGAAAGTTGCCGGGACAGTTGATTGG
GATGTCGGTGGTGATTGGACAGAAAAAATGGCATCTATGAGTTCTATTTCATCTGGTCAATACACAATTG
ATGGATCGAGGATTGACATTGGCTAATATACTTCCAATGAGCGCTGATTTAGGAGAATCCATGGAAGGTT
CTTCTATCGACGTCACCTTTACCGCTCAATTAGAAACAGGTGAAACGTTAGTATCTATAAATATAACTAG
TTACGAAGAAACTCCTGGGGTTTTAGTAGAAGAAAATCGCTTATATGGAACATATGAATCTGTATTTGGT
TTCGGAAATGACGCGTTGAAATATCGTTTAGGCGATGAATTTAAAACTGCTGCTTCATGGGAAGAACTTC
CTACTGATTCTGATACTCAGTTGTATTTGTGGAAAGCTCCTCAAAACCTCCAGAAGACATTCACTTACGA
AGTAACATTAATATATGACTACCAAGAACAAAGTGAATCTGGGGGTTCTGGCAGTAATTCTAGGTCATCT
TCTGATACTACTGAACCGACAGATCCTCCTGCTCCAGTAAGAAAAACTCTAGTTAAAAATTATACTAAAA
CTATAGTTGGAAATTGGAGTCGTTGGGCTAATAAACTGAGAAAATATGCCTATGCAAGACCATAAATATT
TTTATTTGTATTCAATAACTAATAAAACAACAGAAAAAATTTATGTAGGCGTCCACAAAACTTCAAATTT
GGATGATGGGTATATGGGTTCTGGCGTTGCCATTAAAAATGCCATTAAAAAATATGGCATAGATAATTTT
TATAAGCATATTATAAAATTCTTTGAATCTGAAAAAGCTATGTATGACGCAGAGGCAGAAATAGTCACAG
AGGAATTTGTTAAATCTAAGAAAACTTATAATATGAAACTAGGCGGTATCGGTGGCTTCCCAAAACATAA

-continued

CACAGCGGGTGCTAAAAATGGATTTTACGGTAAATCTCATTCGCGTGAAACTAGATTGAAAATTAGCATT

AAATCGTCTAGAAAAAGAGGGCCTAGAGGGCTAGAGGTAAAACTCTGAAGATGTGTGGCGCCAATAACCC

AAGGTATGGCAAAATAGCCCCTAATGCTAAATCTGTTATTATCAACGGCGTTTTATATAAAAGTATTAAA

ATCGCAGCTAAAGCTCTTAATATAAATTATAGTACCTTAAAGGGGCGAGTTAAAGCGGGGTATTATAAAT

GTCAGGATTAAGTTATGATAAGTGTGTTACTGCTGGCCATGAAGCGTGGCCTCCAACAGTTGTGAATGCT

ACACAAAGTAAAGTATTCACTGGAGGAATTGCTGTTCTCGTAGCAGGCGATCCAATTACAGAACATACAG

AAATTAAAAAGCCGTATGAAACACATGGCGGAGTGACACAACCTAGAACTTCTAAGGTATATGTCACTGG

AAAGAAAGCTGTTCAAATGGCTGATCCAATATCATGCGGTGATACTGTGGCTCAGGCATCATCTAAAGTA

TTCATTAAATAGGATTTAAAATGGCAAATACCCCTGTAAATTATCAATTAACAAGAACAGCAAATGCTAT

TCCCGAGATATTCGTCGGGGGTACATTTGCTGAAATAAAACAAAACCTCATTGAATGGCTTAATGGCCAA

AATGAATTTTTGGATTATGATTTTGAAGGCTCAAGATTAAACGTTCTGTGTGACCTTTTAGCTTATAATA

CATTATACATTCAGCAGTTTGGTAATGCTGCTGTGTATGAAAGCTTTATGCGTACTGCTAACTTACGAAG

TTCAGTTGTTCAAGCTGCACAAGATAACGGATATTTACCTACTTCAAAATCCGCTGCGCAGACCGAAATT

ATGTTAACATGCACTGACGCATTGAATAGGAATTACATTACTATTCCTCGCGGAACTCGCTTTTTAGCAT

ATGCAAAAGATACTTCTGTTAATCCATATAACTTCGTTTCTAGGGAAGACGTTATTGCTATTCGTGATAA

AAATAACCAATATTTTCCGCGTTTAAAATTGGCCCAGGGACGTATAGTAAGAACTGAAATCATTTATGAT

AAATTAACACCTATTATCATTTATGATAAAAATATTGATAGAAACCAGGTTAAATTATACGTTGATGGAG

CGGAATGGATTAACTGGACGAGAAAGTCAATGGTTCATGCTGGTTCAACATCAACGATTTACTATATGCG

TGAAACTATTGATGGAAACACTGAATTCTATTTTGGTGAAGGTGAAATTTCTGTTAATGCTTCTGAAGGA

GCTTTGACCGCTAATTATATCGGAGGTCTTAAACCTACTCAGAACTCTACGATTGTTATTGAGTACATTA

GTACTAATGGTGCTGACGCGAACGGAGCAGTCGGATTTTCATACGCAGATACATTAACAAATATAACTGT

CATCAATATTAATGAAAATCCAAACGATGATCCAGATTTTGTTGGGGCAGATGGAGGCGGTGATCCAGAA

GATATTGAGCGTATTCGCGAATTGGGTACTATTAAACGCGAAACCCAACAACGATGCGTAACTGCGACTG

ACTATGATACATTCGTTTCAGAGAGATTTGGTTCTATTATTCAAGCTGTTCAGACTTTCACTGATTCTAC

TAAACCTGGGTATGCATTTATTGCTGCTAAACCTAAATCAGGATTGTATTTAACTACCGTACAGCGTGAA

GATATTAAAAATTATCTCAAAGACTATAATTTAGCTCCTATTACGCCATCAATTATTTCTCCTAATTATC

TTTTTATTAAGACTAATTTAAAAGTCACATATGCTTTAAATAAACTGCAAGAATCCGAACAGTGGCTTGA

AGGTCAAATAATTGATAAAATAGATCGCTATTATACCGAAGATGTAGAAATTTTTAACTCGTCTTTCGCT

AAATCTAAGATGTTGACATATGTAGATGATGCAGATCATTCTGTCATTGGTTCATCAGCGACTATTCAAA

TGGTTCGTGAAGTACAAAACTTCTATAAAACGCCTGAAGCGGGTATTAAATACAATAATCAAATAAAAGA

TCGTTCTATGGAATCTAATACGTTTTCATTTAATTCTGGACGAAAGGTTGTAAATCCTGATACTGGTTTA

GAAGAAGATGTATTATATGACGTTCGTATAGTATCAACAGACCGAGATTCTAAAGGAATTGGTAAAGTTA

TTATTGGTCCATTTGCTTCTGGCGATGTTACAGAAAATGAAAACATTCAGCCGTATACAGGCAACGATTT

TAACAAATTAGCAAATTCTGATGGACGCGACAAATACTATGTTATCGGTGAAATAAATTATCCAGCTGAT

GTGATTTATTGGAATATCGCTAAAATTAATTTAACATCTGAAAAATTTGAAGTTCAGACCATTGAATTAT

ATTCTGACCCAACCGATGATGTTATCTTTACTCGCGATGGTTCACTGATTGTATTTGAAAATGACTTACG

TCCACAATACTTAACTATCGATTTGGAGCCTATATCACAATGACAGTAAAAGCACCTTCAGTCACTAGTC

TCAGAATTTCCAAGTTATCCGCAAATCAGGTGCAAGTACGCTGGGATGACGTTGGTGCTAATTTCTACTA

TTTTGTAGAAATCGCTGAGACAAAAACAAACTCGGGGGAAAATCTCCCGAGTAATCAATATCGTTGGATT

AATTTAGGATATACAGCAAATAATAGTTTCTTTTTTGATGATGCTGATCCATTAACAACATACATTATTA

GAGTAGCCACAGCTGCGCAAGATTTTGAGCAGTCTGATTGGATTTATACCGAAGAGTTTGAAACTTTTGC

-continued

TACAAATGCTTATACATTTCAAAACATGATTGAAATGCAATTAGCCAATAAATTCATTCAGGAAAAATTT

ACTCTTAATAATTCTGATTATGTTAATTTTAATAATGATACTATAATGGCTGCATTGATGAATGAATCAT

TCCAATTCAGCCCATCGTATGTTGATGTTTCATCAATAAGTAATTTTATTATTGGTGAAAATGAGTATCA

TGAAATACAAGGTTCTATTCAGCAAGTATGTAAGGATATTAACCGAGTTTATTTGATGGAATCAGAAGGA

ATTCTATATCTTTTTGAGCGCTATCAACCTGTAGTTAAAGTATCCAATGATAAAGGACAAACCTGGAAAG

CTGTAAAGCTCTTCAATGACCGTGTAGGATATCCTTTATCTAAGACAGTATATTACCAATCTGCGAACAC

AACATACGTTCTAGGATACGACAAGATTTTCTATGGCCGCAAATCTACTGATGTTAGATGGTCAGCCGAT

GATGTCAGATTTAGTTCTCAGGATATAACATTTGCTAAACTTGGCGACCAATTACATCTAGGATTTGATG

TAGAAATTTTTGCCACTTACGCGACTTTACCAGCGAATGTATACCGCATTGCAGAAGCTATTACTTGCAC

CGATGATTACATTTACGTTGTCGCCAGAGACAAAGTTAGATACATAAAAACGAGTAATGCACTTATAGAT

TTTGATCCATTATCTCCAACATATTCGGAAAGACTTTTTGAACCTGATACCATGACTATAACCGGAAATC

CTAAAGCAGTATGCTATAAAATGGATTCTATCTGTGATAAAGTTTTTGCTCTTATTATTGGTGAAGTTGA

AACATTAAATGCTAATCCTAGAACATCAAAAATAATTGATTCCGCTGATAAAGGAATATATGTTTTAAAT

CATGACGAAAAAACATGGAAAAGAGTTTTTGGTAATACCGAAGAAGAAAGAAGACGTATTCAACCCGGAT

ATGCGAATATGTCAACTGACGGTAAATTAGTTTCTCTGTCTTCGAGTAATTTTAAATTTTTAAGTGATAA

TGTTGTTAATGACCCTGAAACTGCAGCAAAATATCAGTTAATTGGCGCTGTTAAATATGAATTTCCTCGT

GAATGGTTAGCTGATAAGCATTATCATATGATGGCATTTATAGCGGATGAAACATCTGATTGGGAGACTT

TTACTCCTCAACCAATGAAATACTACGCAGAACCATTCTTTAACTGGTCTAAAAAATCTAACACACGTTG

TTGGATAAACAACTCTGATAGAGCTGTGGTAGTTTATGCTGATTTAAAATACACTAAAGTTATAGAAAAT

ATTCCGGAAACATCACCAGATAGATTAGTTCATGAATACTGGGATGATGGTGATTGCACTATAGTAATGC

CAAATGTCAAATTCACTGGATTTAAAAAATACGCATCAGGAATGCTTTTCTATAAAGCCTCCGGTGAAAT

AATTTCTTACTATGATTTTAACTATCGTGTGAGAGATACAGTAGAAATTATTTGGAAGCCAACTGAAGTA

TTTTTAAAAGCATTTTTACAAAACCAAGAGCATGAGACTCCTTGGTCACCAGAAGAAGAGCGTGGATTAG

CTGACCCTGATTTAAGACCATTAATTGGCACAATGATGCCTGATTCTTATTTGTTACAGGATTCGAATTT

TGAGGCATTTTGCGAAGCATATATTCAGTATCTTTCTGATGGATATGGAACTCAATACAATAATTTACGA

AATTTAATTCGTAACCAATATCCACGAGAAGAGCACGCATGGGAATATTTGTGGTCAGAGATATATAAAA

GAAACATTTATTTAAATGCTGATAAACGCGATGCTGTTGCGAGATTCTTTGAATCACGTAGCTATGATTT

TTATTCTACTAAAGGAATTGAAGCATCATACAAGTTTCTTTTTAAAGTTCTTTATAATGAAGAAGTTGAA

ATTGAAATTGAATCTGGGGCTGGTACTGAATATGATATAATCGTTCAATCTGATTCTTTGACTGAAGATT

TAGTAGGACAAACGATTTATACGGCAACAGGAAGATGTAATGTTACTTATATAGAAAGAAGCTATTCTAA

TGGTAAATTGCAATGGACCGTAACTATTCATAATCTTTTGGGACGATTAATTGCTGGTCAAGAAGTTAAA

GCAGAAAGACTCCCTAGTTTTGAAGGCGAAATTATTCGTGGGGTTAAAGGAAAGGATTTGCTTCAAAACA

ATATAGACTATATTAATAGAAGTAGATCATACTATGTAATGAAAATTAAATCCAATTTACCTTCTTCCCG

CTGGAAATCTGACGTTATTCGTTTTGTTCATCCAGTAGGATTTGGATTTATAGCAATTACCCTTTTAACA

ATGTTTATTAATGTTGGTTTAACTCTTAAACATACAGAGACTATAATTAATAAATACAAAAACTATAAAT

GGGATTCTGGATTGCCTACTGAATATGCCGACAGAATAGCTAAATTAACTCCAACCGGTGAAATTGAGCA

TGATTCAGTAACAGGCGAAGCAATTTATGAGCCTGGCCCAATGGCTGGTGTAAAATATCCTCTTCCTGAT

GACTATAATGCTGAAAATAATAATTCAATATTTCAAGGTCAATTGCCGTCTGAACGACGTAAATTAATGA

GTCCTTTATTTGATGCATCTGGAACAACATTTGCGCAATTTAGAGATTTAGTTAATAAACGTCTAAAAGA

TAATATAGGAAATCCAAGAGACCCTGAAAATCCAACACAGGTTAAAATAGATGAATGATTCAAGTGTTAT

-continued

CTATCGTGCGATAGTTACTTCAAAATTTAGAACAGAAAAAATGTTGAATTTTTATAATTCAATTGGAAGT

GGTCCGGATAAAAACACTATCTTTATCACATTTGGAAGATCAGAACCGTGGTCATCAAATGAAAATGAGG

TGGGCTTTGCCCCACCTTATCCAACCGATTCTGTATTAGGCGTAACTGACATGTGGACGCATATGATGGG

AACAGTAAAAGTTCTTCCATCAATGCTTGATGCTGTTATTCCTCGCAGAGATTGGGGAGATACTAGATAT

CCGGATCCATACACATTTAGAATTAACGATATTGTAGTGTGTAACTCAGCTCCTTACAACGCTACTGAAT

CAGGCGCTGGTTGGTTAGTGTATCGTTGTTTAGATGTTCCTGATACCGGAATGTGTTCAATAGCATCTTT

AACTGATAAAGATGAATGCCTTAAGTTAGGTGGAAAATGGACTCCTTCTGCTAGGTCAATGACTCCGCCT

GAAGGTCGAGGAGATGCTGAAGGAACAATTGAACCCGGAGACGGGTATGTGTGGGAATATCTATTTGAGA

TTCCGCCTGATGTATCTATAAATAGATGCACGAATGAATATATCGTGGTTCCTTGGCCTGAGGAATTAAA

AGAAGACCCGACTAGATGGGGATATGAAGATAATCTCACTTGGCAACAAGATGATTTTGGATTAATTTAC

CGTGTTAAGGCAAATACTATCCGTTTTAAAGCATATTTAGATTCAGTTTATTTTCCTGAAGCTGCATTAC

CAGGAAATAAAGGATTTAGACAAATATCAATAATCACGAATCCTCTTGAAGCTAAAGCTCATCCAAATGA

CCCAAACGTTAAAGCTGAAAAGGATTATTATGACCCAGAAGATTTAATGAGGCATTCGGGTGAAATGATT

TATATGGAAAATAGGCCACCTATTATTATGGCAATGGATCAAACAGAAGAAATCAATATTCTGTTTACAT

TTTAAATTAAGGGAGCCCATGGGCTCCCTTTTTCTTTATAAATACTATAAACTCATAAGGAAACCGCTAT

GTTCATTCAAGAACCAAAGAAATTGATTGATACCGGCGAAATTGGTAACGCTTCTACTGGTGATATCTTA

TTCGACGGTGGTAATAAAATTAATAGTGATTTTAACGCAATTTATAATGCGTTTGGCGATCAGCGTAAAA

TGGCAGTAGCAAATGGCACTGGAGCAGATGGTCAAATTATCCATGCTACTGGATATTATCAAAAACACTC

TATTACAGAGTACGCAACTCCAGTGAAAGTTGGCACTAGACATGATATTGATACCTCTACTGTAGGTGTT

AAAGTTATCATTGAAAGAGGCGAACTCGGCGATTGTGTTGAATTCATTAACTCTAATGGATCAATATCAG

TTACTAATCCTTTGACAATTCAAGCTATTGATTCAATTAAAGGTGTTTCAGGTAATTTAGTAGTAACTAG

CCCATATAGTAAAGTTACTTTACGCTGTATTTCATCTGATAATTCTACGTCGGTTTGGAATTATTCTATT

GAAAGTATGTTTGGACAAAAGGAATCACCAGCTGAAGGTACATGGAATATTTCTACATCTGGATCAGTTG

ACATTCCATTATTTCATCGTACTGAATACAATATGGCTAAATTGCTAGTTACGTGCCAATCGGTAGATGG

AAGAAAAATTAAAACAGCAGAAATAAATATTCTTGTGGATACTGTTAATTCAGAGGTAATTTCTTCTGAA

TATGCTGTCATGCGAGTTGGGAATGAAACCGAAGAAGACGAAATCGCTAATATTGCATTTAGTATTAAAG

AAAATTATGTAACGGCGACTATAAGTTCTTCAACTGTCGGTATGAGAGCAGCAGTTAAAGTTATCGCTAC

GCAGAAAATCGGGGTGGCTCAATAATGAAACAAAATATTAATATCGGTAATGTTGTAGATGATGGTACCG

GTGACTACCTGCGTAAAGGTGGTATAAAAATAAATGAAAACTTTGATGAGCTTTATTATGAACTCGGTGA

TGGTGATGTTCCATATTCAGCCGGTGCCTGGAAAACTTATAATGCTTCATCAGGACAAACATTAACAGCA

GAATGGGGAAAATCATACGCTATTAATACATCTTCTGGAAGAGTGACTATAAATCTTCCAAAGGGTACAG

TTAATGATTACAACAAGGTAATTAGAGCTAGAGACGTATTTGCTACATGGAACGTCAACCCAGTTACACT

AGTAGCTGCTTCCGGCGATACGATTAAAGGGTCTGCAGTACCAGTTGAAATTAATGTTCGATTCAGCGAT

TTAGAACTAGTGTATTGTGCCCCAGGACGTTGGGAATATGTCAAAAATAAACAAATTGACAAAATTACCA

GTTCAGACATTAGTAATGTAGCTCGCAAAGAATTTTTAGTTGAAGTTCAAGGACAAACAGACTTTTTAGA

TGTTTTCCGTGGAACTAGTTATAATGTAAATAACATCAGAGTAAAACATCGTGGTAACGAATTGTATTAC

GGCGATGTGTTTAGCGAAAACAGCGATTTTGGCTCTCCAGGCGAAAATGAAGGAGAACTGGTTCCTCTTG

ATGGATTTAACATTCGATTAAGACAGCCTTGTAATATTGGTGACACTGTTCAAATTGAAACATTTATGGA

TGGTGTATCACAGTGGAGAAGTTCATATACAAGACGTCAAATTAGATTGTTAGATTCAAAATTAACGTCA

AAAACTTCTTTAGAAGGAAGCATTTACGTTACTGATTTATCAACAATGAAATCAATTCCATTTTCTGCTT

TTGGATTAATTCCAGGAGAACCTATTAATCCTAACTCTCTTGAGGTTCGTTTTAACGGGATTTTACAGGA

-continued

ATTGGCTGGCACAGTTGGAATGCCATTATTTCATTGTGTTGGTGCCGATTCAGACGATGAAGTAGAATGC

TCTGTTTTAGGTGGAACTTGGGAACAATCTCATACCGATTATTCAGTTGAAACTGATGAAAACGGCATAC

CAGAAATTTTACATTTCGATAGCGTATTTGAGCATGGTGACATTATCAATATCACCTGGTTTAATAATGA

TTTGGGTACATTATTAACAAAAGATGAGATTATTGATGAAACTGATAATCTCTATGTATCGCAAGGACCT

GGAGTAGATATTTCTGGTGATGTAAATTTAACAGACTTCGATAAAATTGGTTGGCCAAATGTAGAAGCAG

TTCAATCTTATCAACGCGCATTTAATGCTGTTTCAAATATCTTTGATACGATTTATCCTATTGGAACTAT

ATATGAAAACGCTGTTAATCCAAATAACCCTGTTACATATATGGGATTCGGCTCATGGAAATTATTTGGG

CAAGGAAAAGTTTTAGTTGGATGGAATGAAGATATTTCGGACCCTAACTTTGCTCTAAATAACAACGATT

TAGATTCGGGTGGAAATCCTTCACATACCGCAGGTGGAACAGGTGGTTCTACTTCTGTTACATTGGAAAA

TGCTAATCTTCCTGCAACTGAAACAGATGAAGAAGTTCTAATAGTTGATGAAAATGGATCAGTCATTGTT

GGTGGGTGTCAATACGATCCAGATGAATCCGGTCCAATTTACACTAAATACCGTGAAGCTAAAGCATCTA

CTAACTCTACTCACACTCCGCCAACATCAATAACTAACATTCAACCATATATTACAGTTTATCGTTGGAT

AAGGATTGCATAATGAGTTTACTTAATAATAAAGCGGGAGTTATTTCCCGCTTAGCCGATTTTCTTGGTT

TTAGACCTAAAACTGGCGACATTGATGTAATGAATCGTCAATCAGTCGGGTCAGTGACAATATCTCAATT

AGCGAAAGGATTTTATGAACCAAACATAGAATCAGCTATTAATGACGTTCATAATTTTTCTATAAAAGAC

GTTGGCACAATTATTACTAATAAAACTGGTGTTTCTCCTGAGGGTGTTTCTCAAACTGATTATTGGGCAT

TTTCTGGAACTGTAACAGACGATTCTCTTCCTCCGGGTTCTCCTATTACGGTATTAGTATTTGGTCTTCC

AGTTTCAGCAACAACTGGAATGACGGCAATTGAGTTTGTTGCAAAAGTTCGCGTTGCACTACAAGAAGCT

ATTGCGTCATTTACTGCTATCAATTCATATAAAGACCATCCAACTGATGGTAGTAAATTAGAAGTTACTT

ATTTAGATAATCAAAAACATGTATTAAGCACATATTCTACATATGGAATAACTATTTCCCAAGAAATTAT

ATCTGAGTCTAAGCCTGGCTATGGTACATGGAATTTATTGGGCGCACAAACTGTAACTTTAGATAATCAG

CAGACTCCTACAGTATTTTATCATTTTGAGAGAACAGCATGAGTAATAATACATATCAACACGTTTCTAA

TGAATCTCGTTATGTAAAATTTGATCCTACCGATACGAATTTTCCACCGGAGATTACTGATGTTCACGCT

GCTATAGCAGCCATTTCTCCTGCTGGAGTAAATGGAGTTCCTGATGCATCGTCAACAACAAAGGGAATTC

TATTTATTCCCACTGAACAGGAAGTTATAGATGGAACTAATAATACCAAAGCAGTTACACCAGCAACGTT

GGCAACAAGATTATCTTATCCAAATGCAACTGAAACTGTTTACGGATTAACAAGATATTCAACCAATGAT

GAAGCCATTGCCGGAGTTAATAATGAATCTTCTATAACTCCAGCTAAATTTACTGTCGCCCTTAATAATG

CGTTTGAAACGCGAGTTTCAACTGAATCCTCAAATGGTGTTATTAAAATTTCATCTCTACCGCAAGCATT

AGCTGGTGCAGATGATACTACTGCAATGACTCCATTAAAAACACAGCAGTTAGCTATTAAATTAATTGCG

CAAATTGCTCCTTCTGAAACCACAGCTACCGAATCGGACCAAGGTGTTGTTCAATTAGCAACAGTAGCGC

AGGTTCGTCAGGGAACTTTAAGAGAAGGCTATGCAATTTCTCCTTATACGTTTATGAATTCATCTTCTAC

TGAAGAATATAAAGGCGTAATTAAATTAGGAACACAATCAGAAGTTAACTCGAATAATGCTTCTGTTGCG

GTTACTGGCGCAACTCTTAATGGTCGTGGTTCTACGACGTCAATGAGAGGCGTAGTTAAATTAACTACAA

CCGCCGGTTCACAGAGTGGAGGCGATGCTTCATCAGCCTTAGCTTGGAATGCTGACGTTATCCAGCAAAG

AGGTGGTCAAATTATCTATGGAACACTCCGCATTGAAGACACATTTACAATAGCTAATGGTGGAGCAAAT

ATTACGGGTACCGTCAGAATGACTGGCGGTTATATTCAAGGTAACCGCATCGTAACACAAAATGAAATTG

ATAGAACTATTCCTGTCGGAGCTATTATGATGTGGGCCGCTGATAGTCTTCCTAGTGATGCTTGGCGCTT

CTGCCATGGTGGAACTGTTTCAGCGTCAGATTGTCCATTATATGCTTCTAGAATTGGAACAAGATATGGC

GGAAACCCATCAAATCCTGGATTGCCTGACATGCGTGGTCTTTTTGTTCGTGGTTCTGGTCGTGGTTCTC

ACTTAACAAATCCAAATGTTAATGGTAATGACCAATTTGGTAAACCTAGATTAGGTGTAGGTTGTACCGG

-continued

TGGATATGTTGGTGAAGTACAGATACAACAGATGTCTTATCATAAACATGCTGGTGGATTTGGTGAGCAT

GATGATCTGGGGGCATTCGGTAATACCCGTAGATCAAATTTTGTTGGTACACGTAAAGGACTTGACTGGG

ATAACCGTTCATACTTCACCAATGACGGATATGAAATTGACCCAGAATCACAACGAAATTCCAAATATAC

ATTAAATCGTCCTGAATTAATTGGAAATGAAACACGTCCATGGAACATTTCTTTAAACTACATAATTAAG

GTAAAAGAATGACAGATATTGTACTGAATGACTTACCATTCGTTGACGGCCCTCCTGCAGAGGGCCAGAG

CCGCATTTCCTGGATTAAAAACGGCGAAGAAATATTAGGAGCTGACACACAGTATGGAAGTGAAGGCTCA

ATGAATAGACCTACGGTTTCTGTACTAAGAAATGTTGAAGTTCTTGATAAAAACATTGGAATACTTAAAA

CATCTTTAGAAACCGCAAATAGTGATATTAAAACAATTCAGGGCATCTTAGATGTATCTGGTGATATTGA

AGCTTTGGCCCAAATAGGTATCAATAAAAAGGATATTTCTGACCTCAAAACGCTAACCAGTGAACACACA

GAAATATTAAATGGAACTAATAATACGGTTGACAGTATTCTTGCCGATATTGGTCCATTTAACGCCGAGG

CCAACTCTGTATACAGAACGATCAGAAATGATTTACTGTGGATAAAGCGTGAACTTGGACAATACACTGG

TCAAGATATTAATGGTCTTCCTGTTGTAGGAAATCCTAGTAGTGGAATGAAGCATCGCATTATTAATAAT

ACTGATGTCATCACTTCGCAGGGAATACGTTTAAGCGAATTAGAAACAAAATTTATTGAATCTGATGTAG

GTTCTTTGACCATTGAAGTTGGTAATCTTCGTGAAGAGCTTGGACCGAAACCACCATCATTTTCACAGAA

CGTTTATAGTCGTTTAAATGAAATTGACACTAAACAGACAACAGTTGAGTCTGACATTAGTGCTATTAAG

ACCTCAATAGGATATCCAGGAAATAATTCGATTATCACGAGTGTTAATACAAACACTGATAATATTGCAT

CTATTAATTTAGAGCTAAATCAAAGTGGAGGTATTAAACAGCGTTTAACCGTTATTGAAACTTCCATTGG

TTCAGATGATATTCCTTCGAGTATTAAAGGTCAAATCAAAGATAATACAACTTCAATCGAATCTCTAAAT

GGAATCGTCGGTGAAAACACTTCATCTGGCTTAAGAGCGAATGTTTCATGGTTAAACCAAATTGTTGGAA

CTGATTCTAGCGGTGGACAACCTTCTCCTCCTGGGTCTCTTTTAAACCGAGTTTCTACAATTGAAACTTC

TGTTTCAGGCTTGAATAACGCTGTTCAAAACCTACAAGTAGAGATTGGTAATAACAGCGCAGGAATTAAA

GGGCAAGTTGTAGCGTTAAATACTTTAGTAAATGGAACTAATCCAAACGGTTCAACTGTTGAAGAGCGCG

GATTAACCAATTCAATAAAAGCTAACGAAACTAACATTGCATCAGTTACACAAGAAGTGAATACAGCTAA

AGGCAATATATCTTCTTTACAAGGTGATGTTCAAGCTCTCCAAGAAGCCGGTTATATTCCTGAAGCTCCA

AGAGATGGGCAAGCTTACGTTCGTAAAGATGGCGAATGGGTATTCCTTTCTACCTTTTTATCACCAGCAT

AACATGGGGCCGCAAGGCCCCAAAGGATTTTAAATGTCAGGATATAATCCTCAGAATCCAAAGGAACTCA

AAGATGTCATTCTAAGACGTTTAGGGGCTCCAATTATTAATGTTGAGTTAACACCCGATCAAATTTACGA

TTGTATCCAGCGTGCCCTAGAATTATACGGTGAATACCATTTTGATGGACTCAATAAAGGTTTTCATGTT

TTTTATGTAGGGGATGATGAAGAAAGGTACAAGACCGGAGTCTTCGATTTAAGAGGTTCTAACGTATTTG

CAGTAACCCGCATTTTACGCACAAATATTGGGTCAATAACATCTATGGATGGAAACGCTACATATCCGTG

GTTTACTGACTTTCTTTTAGGAATGGCTGGTATTAATGGCGGAATGGGAACGTCTTGTAATAGATTTTAT

GGACCAAATGCCTTTGGAGCTGATTTAGGATATTTTACCCAGCTTACCAGTTATATGGGAATGATGCAAG

ATATGCTCTCTCCTATTCCAGACTTTTGGTTTAATTCAGCAAATGAACAGCTCAAAGTCATGGGAAACTT

CCAAAAATATGATTTAATTATCGTAGAAAGCTGGACTAAATCATACATTGATACAAACAAAATGGTTGGA

AATACAGTAGGATATGGAACAGTCGGTCCACAAGATAGCTGGTCATTATCTGAACGATATAATAACCCAG

ACCACAATTTAGTAGGTCGTGTTGTCGGCCAAGATCCGAATGTTAAACAGGGTGCTTATAATAATCGTTG

GGTGAAAGACTATGCAACAGCTTTAGCTAAAGAATTGAACGGTCAAATTTTAGCACGCCACCAAGGTATG

ATGCTTCCGGGCGGTGTTACAATTGATGGGCAGCGCTTAATAGAAGAAGCCAGATTAGAAAAAGAAGCAC

TGCGCGAAGAATTATACTTACTTGATCCTCCATTTGGAATTTTGGTAGGTTAATATGGCTACTTATGATA

AAAATCTTTTTGCTAAATTGGAAAACCGCACAGGTTATTCTCAGACCAATGAAACTGAAATATTAAATCC

TTATGTAAATTTCAATCATTATAAAAACAGCCAAATATTAGCTGATGTATTAGTAGCTGAAAGCATTCAA

-continued

ATGCGAGGTGTAGAATGCTATTATGTTCCAAGAGAGTATGTTTCCCCTGATTTGATATTCGGCGAAGACT

TAAAAAATAAATTTACTAAAGCTTGGAAATTTGCTGCATATTTAAATTCATTTGAAGGATATGAAGGAGC

TAAATCGTTCTTTAGTAACTTTGGTATGCAAGTACAAGACGAAGTGACTTTATCTATTAACCCAAATTTA

TTTAAGCATCAAGTTAACGGAAAAGAACCCAAGGAAGGTGATTTGATATATTTTCCTATGGATAACAGCT

TATTTGAAATTAACTGGGTTGAACCATATGATCCATTTTATCAATTAGGCCAAAACGCTATTCGTAAAAT

TACGGCAGGTAAATTCATTTATTCTGGAGAAGAAATTAATCCAGTTCTACAGAAAAATGAAGGAATTAAC

ATTCCAGAATTTAGTGAATTAGAATTAAATGCTGTTCGCAATCTTAACGGTATTCATGACATTAATATTG

ATCAGTATGCTGAAGTAGATCAAATTAATTCTGAAGCTAAAGAATACGTTGAACCTTATGTTGTTGTCAA

TAACAGAGGCAAATCTTTCGAATCTAGCCCATTTGACAATGATTTCATGGATTAATAAATATTATAAACT

AATTAAAGCCCGGATTAGGAGAAGTCATGTTTGGTTATTTTTATAATTCGTCTTTTAGACGATATGCTAC

CTTGATGGGCGATTTGTTTTCAAATATCCAAATCAAACGTCAGTTAGAATCTGGTGATAAGTTTATACGT

GTTCCTATTACGTATGCATCAAAGGAACACTTTATGATGAAATTGAATAAATGGACATCAATAAATTCAC

AAGAAGATGTAGCTAAAGTTGAAACTATTCTACCTCGTATAAATTTACATTTAGTTGATTTTAGCTATAA

TGCTCCATTTAAAACAAACATTTTAAATCAGAATTTACTGCAAAAAGGTGCAACTTCTGTAGTATCGCAG

TATAATCCATCTCCTATTAAAATGATTTATGAATTGAGTATCTTTACTCGCTATGAAGATGATATGTTTC

AAATAGTTGAACAGATTCTTCCATATTTTCAACCTCATTTTAATACAACTATGTACGAGCAGTTTGGAAA

TGATATTCCATTTAAAAGGGATATTAAAATTGTACTGATGTCTGCTGCTATAGACGAAGCTATAGATGGG

GATAATTTATCTCGTCGTAGAATTGAATGGTCATTAACATTTGAAGTAAATGGATGGATGTATCCTCCAG

TAGATGATGCAGAAGGATTAATTCGTACTACTTATACAGATTTTCACGCCAATACAAGAGATTTGCCTGA

CGGCGAAGGTGTTTTTGAATCTGTCGATAGCGAAGTTGTTCCTCGAGATATTGACCCAGAAGACTGGGAT

GGAACAGTAAAACAAACTTTCACTAGTAATGTAAATAGACCAACACCGCCAGAACCTCCTGGCCCAAGAA

CATAGAGGTTATTATGGAAGGTCTTGATATAAACAAACTTTTAGATATTTCTGACCTCCCCGGAATTGAC

GGGGAGGAAATCAAAGTGTATGAACCTCTGCAATTAGTAGAAGTTAAAAGCAATCCACAAAACCGTACTC

CAGACTTAGAAGATGATTATGGAGTAGTTCGTCGAAATATGCATTTTCAGCAACAAATGCTAATGGACGC

TGCCAAGATTTTTCTTGAGACAGCAAAGAATGCTGATTCTCCTCGTCACATGGAAGTATTTGCAACTCTT

ATGGGGCAAATGACTACGACGAACAGAGAAATACTGAAGCTTCATAAAGATATGAAAGACATTACATCTG

AGCAGGTTGGCACCAAAGGCGCTGTTCCTACAGGTCAAATGAATATTCAGAATGCGACAGTATTCATGGG

TTCACCAACAGAATTAATGGACGAAATTGGTGATGCTTACGAGGCTCAAGAAGCTCGTGAGAAGGTGATA

AATGGAACAACCGATTAATGTATTAAATGATTTCCATCCGTTAAATGAAGCTGGAAAAATTTTAATAAAA

CACCCAAGCTTAGCGGAAAGAAAAGATGAAGATGGAATTCATTGGATAAAATCTCAGTGGGATGGAAAAT

GGTATCCTGAAAAATTCAGTGATTACCTTCGTCTACACAAAATAGTAAAAATTCCAAACAACTCTGATAA

GCCTGAATTATTTCAAACTTATAAAGATAAGAATAATAAAAGATCTCGGTATATGGGTCTTCCTAACTTG

AAACGAGCTAATATTAAAACACAATGGACTCGTGAAATGGTTGAGGAATGGAAAAAATGCCGAGATGATA

TTGTTTATTTTGCAGAAACATACTGTGCCATTACTCATATTGACTATGGTGTCATAAAGGTTCAATTACG

TGACTATCAGCGTGATATGCTCAAAATAATGTCATCTAAACGTATGACTGTTTGTAATCTATCGCGCCAG

CTCGGTAAAACCACCGTAGTAGCTATTTTCCTTGCACACTTTGTATGTTTTAACAAAGATAAAGCTGTAG

GTATTCTTGCACACAAAGGCTCAATGTCTGCGGAAGTTTTAGACCGTACTAAGCAAGCAATTGAACTGCT

TCCTGACTTTTTACAACCAGGAATTGTTGAATGGAATAAGGGTTCAATTGAACTAGATAATGGTTCTTCA

ATTGGCGCTTATGCTTCCTCTCCTGACGCAGTTCGTGGTAACTCGTTCGCAATGATTTACATTGACGAAT

GTGCGTTTATTCCAAACTTCCATGATTCCTGGCTTGCTATTCAACCAGTAATTTCATCTGGTCGTCGTTC

-continued

GAAAATTATTATTACTACGACTCCTAATGGATTAAATCATTTTTATGATATTTGGACTGCTGCTGTCGAA

GGTAAATCTGGATTTGAACCATATACTGCTATTTGGAATTCAGTTAAAGAACGTCTTTATAACGATGAAG

ATATTTTTGACGATGGATGGCAATGGAGCATACAAACCATTAATGGTTCTTCATTAGCTCAATTCCGTCA

AGAACATACTGCAGCGTTTGAAGGGACTTCTGGTACATTAATTTCAGGAATGAAATTAGCTGTTATGGAT

TTTATTGAAGTAACACCAGATGATCATGGTTTTCACCAATTTAAAAAACCTGAACCAGATAGAAAATATA

TTGCAACTCTAGATTGCTCAGAAGGTCGTGGGCAAGATTACCACGCTTTGCATATTATTGATGTTACTGA

TGATGTGTGGGAACAGGTTGGTGTTTTGCATTCAAACACTATTTCTCATTTAATTCTACCTGACATCGTT

ATGCGTTATTTAGTAGAATACAATGAATGCCCAGTTTATATTGAATTAAATAGTACTGGTGTGTCAGTTG

CAAAATCGCTTTATATGGATTTAGAATACGAAGGTGTTATCTGCGATTCATATACTGATTTAGGAATGAA

ACAAACTAAACGCACGAAAGCAGTAGGATGTTCCACGCTAAAAGACCTTATTGAAAAAGATAAGCTTATT

ATTCATCACCGAGCGACTATTCAAGAATTTAGAACGTTTAGTGAAAAAGGCGTGTCTTGGGCGGCTGAAG

AAGGTTATCATGACGATTTAGTAATGTCTTTAGTGATTTTTGGATGGTTATCAACGCAGTCAAAATTTAT

TGATTATGCGGATAAAGATGACATGCGATTAGCATCTGAAGTATTTTCAAAAGAGCTTCAGGATATGAGC

GACGACTACGCGCCAGTTATATTTGTGGATTCGGTTCATTCTGCTGAGTATGTTCCAGTATCTCATGGTA

TGTCAATGGTATAAATATATTAAAGCATATTAAAGAGGATTAAAAATGACTTTATTATCTCCGGGCATTG

AGCTCAAAGAAACTACGGTTCAAAGCACCGTAGTTAATAACTCTACTGGTACAGCAGCTTTGGCCGGTAA

ATTCCAGTGGGGTCCTGCTTTTCAGATTAAACAGGTTACAAATGAAGTAGATTTAGTTAATACTTTTGGT

CAACCAACCGCTGAAACTGCTGACTATTTTATGTCTGCGATGAATTTCTTGCAGTACGGAAATGACTTAC

GAGTAGTTCGTGCTGTTGATAGAGATACCGCTAAAAACTCATCGCCAATTGCTGGTAATATTGATTACAC

AATTTCTACCCCAGGTAGTAACTATGCGGTTGGAGATAAAATCACGGTCAAATATGTTTCAGATGATATT

GAAACTGAAGGTAAAATTACTGAAGTAGACGCAGATGGAAAAATTAAGAAAATTAATATTCCTACTGGCA

AAAATTACGCTAAAGCGAAAGAAGTCGGTGAATATCCAACACTAGGTTCTAACTGGACTGCGGAAATTTC

TTCATCTTCCTCTGGTTTAGCTGCAGTAATAACTCTTGGAAAAATTATTACTGATTCTGGTATTTTATTA

GCTGAAATTGAAAATGCTGAAGCTGCTATGACAGCGGTTGACTTTCAAGCAAATCTTAAAAAATATGGAA

TTCCAGGAGTAGTAGCGCTTTATCCAGGCGAATTAGGCGATAAAATTGAAATTGAAATCGTATCTAAAGC

TGACTATGCAAAAGGAGCTTCTGCATTACTCCCAATTTATCCAGGTGGTGGTACTCGTGCATCTACTGCT

AAAGCAGTGTTTGGATATGGACCGCAAACTGATTCACAGTACGCTATTATAGTTCGTCGTAATGATGCTA

TTGTTCAAAGCGTTGTTCTTTCAACTAAGCGTGGTGAAAAAGATATTTACGATAGTAACATCTATATCGA

TGACTTTTTCGCAAAAGGTGGTTCAGAATATATTTTTGCAACTGCACAAAACTGGCCAGAAGGCTTCTCT

GGAATTTTAACTCTGTCTGGTGGATTATCATCAAATGCTGAAGTAACAGCAGGAGATTTGATGGAAGCTT

GGGACTTCTTTGCTGACCGTGAATCTGTTGACGTTCAACTGTTTATTGCAGGTTCTTGTGCCGGTGAATC

TTTAGAAACAGCATCTACTGTCCAAAAACACGTCGTTTCAATTGGGGATGCTCGCCAAGATTGCTTAGTA

TTGTGCTCTCCTCCGCGTGAAACTGTAGTTGGAATTCCTGTAACCCGTGCTGTTGATAACCTAGTCAATT

GGAGAACTGCGGCAGGTTCATACACTGATAATAACTTTAATATCAGTTCAACCTATGCAGCAATTGATGG

TAACCATAAGTATCAGTATGACAAATATAATGATGTGAATCGTTGGGTTCCATTAGCAGCTGATATTGCT

GGTTTATGCGCAAGAACTGATAACGTATCTCAGACTTGGATGTCTCCAGCTGGTTATAATCGTGGTCAGA

TTCTTAACGTTATTAAACTTGCTATTGAAACTCGCCAGGCTCAGCGCGACCGTTTATACCAAGAAGCTAT

CAACCCGGTAACCGGTACAGGTGGTGATGGTTACGTATTGTATGGTGATAAAACAGCTACTTCTGTTCCT

TCTCCATTTGATCGTATTAACGTTCGTCGTCTGTTTAATATGTTGAAAACGAATATCGGACGTAGTTCAA

AATATCGTTTGTTCGAATTAAACAACGCGTTTACTCGTTCATCATTCCGCACAGAAACTGCCCAGTACTT

ACAAGGGAATAAAGCTCTCGGTGGAATTTATGAATATCGTGTAGTTTGCGATACAACAAATAACACTCCG

-continued

TCAGTAATTGATAGAAATGAGTTTGTTGCAACATTCTACATCCAACCGGCTAGAAGCATTAACTACATTA

CCTTAAACTTCGTAGCAACTGCTACTGGTGCAGATTTCGATGAGTTAACTGGTCTTGCTGGTTAATACGG

TGCATTCTAAAGGCCTGTTTCGGCAGGCCATATAAATACACTATATCCTTAATTCTTTAATTCTATATGC

CCTAGGTTAAACATAGGGATATAAATACTACAGAGGCTAATATGTTTGTAGATGATGTAACACGAGCGTT

TGAATCTGGTGATTTTGCTCGACCTAACTTATTCCAAGTAGAAATTTCTTATCTTGGACAAAATTTTACG

TTCCAATGTAAAGCTACTGCTCTACCAGCTGGTATTGTAGAAAAAATTCCAGTCGGATTTATGAACCGTA

AAATTAACGTAGCAGGCGATCGTACATTCGATGACTGGACTGTTACAGTAATGAACGATGAAGCTCATGA

TGCTCGTCAGAAGTTCGTTGATTGGCAAAGCATTGCTGCGGGGCAAGGAAACGAAATTACTGGTGGAAAA

CCTGCAGAGTATAAAAAGAGCGCTATCGTTCGTCAATATGCTCGTGACGCTAAAACAGTAACAAAAGAAA

TTGAAATTAAAGGTCTGTGGCCTACTAACGTGGGTGAACTTCAATTAGATTGGGATTCAAACAATGAAAT

CCAAACTTTTGAAGTAACTCTTGCTCTCGATTATTGGGAATAAAATGAATGGGGAGAAATCCCCATCCTG

CTTAAAGCAGAGAAGTCCATTATAAATATAACTATAATTCCCATTTGGAGAATACAATGAAATTTAATGT

ATTAAGTTTGTTTGCTCCATGGGCTAAAATGGACGAACGAAATTTTAAAGACCAAGAAAAAGAAGATCTT

GTTTCCATTACAGCCCCAAAGCTTGATGATGGAGCAAGAGAATTTGAAGTAAGCTCGAATGAAGCTGCTT

CTCCTTATAATGCTGCATTCCAAACAATTTTTGGTTCATATGAACCAGGAATGAAAACTACTCGTGAGCT

TATTGATACATATCGTAATCTCATGAATAACTATGAAGTAGATAATGCAGTTTCAGAAATCGTTTCAGAT

GCTATCGTCTATGAAGATGATACTGAAGTCGTAGCGTTAAATTTGGATAAATCTAAATTTAGCCCAAAAA

TTAAAAATATGATGTTAGATGAATTTAGTGATGTATTAAATCATCTATCGTTTCAACGAAAAGGTTCTGA

TCATTTTAGACGTTGGTATGTTGATTCAAGAATTTTCTTTCATAAAATCATTGATCCAAAACGTCCAAAA

GAAGGCATAAAAGAATTACGTAGATTAGACCCTCGCCAAGTTCAGTATGTTCGTGAAATTATAACAGAAA

CTGAAGCTGGCACAAAAATAGTTAAAGGTTACAAAGAATATTTTATATATGATACTGCCCATGAGTCATA

TGCATGTGATGGTAGAATGTATGAAGCTGGCACAAAAATAAAAATTCCTAAAGCTGCCGTCGTTTATGCC

CATTCTGGATTAGTCGATTGTTGCGGTAAAAATATCATCGGGTATTTGCATCGTGCTGTTAAACCTGCTA

ACCAATTAAAATTATTAGAAGATGCTGTAGTCATTTATCGCATTACTCGTGCTCCTGACCGTCGTGTTTG

GTATGTAGACACAGGTAATATGCCTGCTCGTAAAGCTGCTGAGCACATGCAACATGTTATGAACACGATG

AAAAACCGTGTAGTATATGATGCATCAACAGGTAAAATAAAAAATCAACAGCATAATATGTCTATGACCG

AAGACTATTGGTTGCAGCGCCGTGATGGTAAAGCTGTGACAGAAGTTGATACTCTTCCTGGTGCTGATAA

TACTGGCAATATGGAAGATATTCGTTGGTTTAGACAAGCTCTTTATATGGCATTACGTGTTCCTCTTTCA

CGCATTCCGCAAGACCAACAAGGCGGTGTGATGTTTGATTCTGGAACTAGCATTACACGTGATGAATTAA

CGTTTGCTAAATTTATTCGTGAGTTACAGCACAAGTTTGAAGAAGTTTTCCTAGATCCGCTTAAAACAAA

TCTTTTGCTTAAAGGTATAATCACAGAAGATGAGTGGAATGATGAAATAAATAATATTAAGATAGAATTT

CATCGGGATAGCTACTTTGCTGAGCTCAAAGAAGCAGAAATTTTGGAACGAAGAATTAATATGCTAACCA

TGGCAGAACCATTTATTGGTAAATATATTTCTCACAGAACTGCTATGAAAGACATTTTGCAGATGACTGA

TGAAGAAATAGAACAAGAAGCCAAGCAAATTGAAGAAGAGTCTAAAGAGGCTCGTTTCCAAGACCCCGAC

CAAGAACAAGAGGATTTTTAATGGAAGGTTTAATTGAAGCTATTAAATCAAACGACCTCGTAGCCGCTCG

TAAATTATTTGCTGAAGCCATGGCTGCAAGAACGATTGATTTAATTAAAGAAGAAAAAATCGCTATCGCT

CGCAATTTCTTAATCGAAGGTGAAGAACCTGAAGACGAGGATGAAGATGAAGATGACGAAGATAGTGATG

ATAAAGACGACAAAAAAGACGAAGACTCTGACGAAGACGAGGATGATGAATAATGCTTCTGATCCCTGAA

ACTCATGAATTAGTTCTCGAGAATGTCGAAGCACTTATTCCTGAAGCACAGGGTCGCTTTGACGAATTGT

CTTCTGCTTTAAATAAAGACGATATAAATACAATTGTCGAGAATATGCTTGATGATGAAACTGATTTAGC

-continued

GGTTGCATTAGCTTCTATTAATGAAAATATGCCGTTAAATGAATTCATCGTTAAACATGTTTCTGCCCGT

GGTGAAATTACTCGCACTAAAGACCGCAAAACGCGTGAACGAAATGCATTTCAAACCACTGGGCTGTCTA

AAGCAAAACGTAGACAAATTGCTCGTAAAGCTACCAAAACGAAGATTGCCAATCCAGCAGGTCAATCTCG

TGCTCAGCGTAAGCGTAAAAAAGCTCTTAAACGCCGTAAAGCATTAGGATTAAGCTAATGAATGAACCCC

AATTACTAATTGAAACTTGGGGTCAACCTGGCGAAATTATTGATGGCGTACCAATGCTTGAATCTCATGA

TGGAAAAGACTTAGGTTTAAAACCGGGTTTATACATCGAAGGAATATTCATGCAAGCGGAAGTCGTCAAT

AGAAATAAACGTCTTTATCCAAAACGTATATTAGAAAAAGCGGTAAAAGACTATATTAATGAGCAAGTTT

TAACTAAACAAGCTCTCGGAGAATTAAATCATCCTCCACGCGCTAATGTTGACCCGATGCAAGCCGCTAT

CATTATAGAAGATATGTGGTGGAAAGGAAATGACGTATACGGACGAGCTCGTGTTATTGAAGGTGACCAT

GGTCCTGGAGATAAATTAGCAGCTAATATTCGTGCCGGATGGATTCCAGGAGTTTCTTCTCGTGGATTAG

GTTCATTGACTGACACAAATGAAGGTTATCGTATCGTAAACGAAGGATTCAAATTAACTGTAGGTGTTGA

TGCAGTATGGGGTCCAAGTGCTCCAGATGCATGGGTAACTCCTAAGGAAATTACCGAATCACAGACGGCG

GAAGCCGATACAAGTGCCGATGACGCCTATATGGCTCTCGCAGAGGCCATGAAAAAAGCGTTATAAATAT

TATTATCTAAACAACAGGACTACAAAATGCTTAAAGAACAACTGATTGCCGAAGCGCAGAAAATTGATGC

TTCCGTTGCTCTTGATAGTATTTTCGAATCAGTTAATATTTCTCCGGAAGCAAAAGAAACTTTCGGCACT

GTATTCGAAGCTACCGTCAAGCAGCACGCCGTTAAATTAGCTGAATCTCATATCGCTAAAATTGCTGAAA

AAGCAGAAGAAGAAGTAGAAAAAAATAAAGAAGAAGCCGAAGAAAAAGCTGAGAAGAAAATCGCTGAGCA

AGCTTCTAAATTCATTGACCATCTTGCAAAAGAATGGCTCGCTGAAAATAAATTAGCAGTTGATAAAGGC

ATCAAAGCCGAACTGTTTGAATCCATGCTTGGTGGATTAAAAGAGCTCTTTGTTGAACACAACGTTGTTG

TTCCAGAAGAATCAGTTGATGTTGTAGCTGAAATGGAAGAAGAGCTGCAAGAACATAAAGAAGAATCGCC

TCGTCTGTTCGAAGAACTGAATATGCGCGACGCATATATCAATTATGTGCAGCGTGAAGTGGCATTGAGC

GAAAGTACTAAAGATCTGACTGAGTCTCAAAAAGAAAAAGTCTCTGCTCTGGTCGAAGGTATGGATTATT

CAGATGCATTCTCAAGTAAATTGAGTGCAATCGTAGAAATGGTGAAGAAATCTAATAAAGATGAAAGCAC

TATTACTGAGAGTATAAATACTCCTGATACTGAAGCAGCCGGACTGAATTTCGTCACTGAAGCTGTAGAA

GATAAAGCTGCACAGGGTGCAGAAGATATTGTAAGTGTATATGCGAAAGTCGCATCTCGTTTCTAATTTT

AAAGGTTAACACAAATGACTATCAAAACTAAAGCTGAACTTTTGAACAAATGGAAGCCATTACTGGAAGG

TGAAGGTTTACCGGAAATTGCTAATAGCAAACAAGCGATTATCGCTAAAATCTTTGAAAACCAGGAAAAA

GATTTCCAGACAGCTCCGGAATATAAAGACGAAAAAATTGCTCAGGCATTCGGTTCTTTCTTAACAGAAG

CTGAAATCGGTGGTGACCACGGTTACAATGCTACCAACATCGCTGCAGGTCAGACTTCTGGCGCAGTAAC

TCAGATTGGCCCAGCTGTTATGGGTATGGTACGTCGTGCTATTCCTAACCTGATTGCTTTCGATATTTGT

GGTGTTCAGCCGATGAACAGCCCGACTGGCCAGGTATTCGCACTGCGCGCAGTATATGGTAAAGACCCAG

TGGCTGCCGGTGCTAAAGAAGCATTCCACCCAATGTATGGTCCAGATGCAATGTTCTCTGGTCAGGGTGC

TGCTAAGAAATTCCCAGCTCTGGCTGCTAGCACACAAACCACAGTAGGTGATATCTATACTCACTTCTTC

CAGGAAACTGGTACTGTATATCTGCAAGCTTCTGTTCAAGTAACAATCGATGCTGGTGCGACTGATGCTG

CTAAATTAGATGCTGAAATTAAGAAACAAATGGAAGCTGGTGCACTGGTAGAAATCGCTGAAGGTATGGC

TACTTCTATCGCTGAACTCCAGGAAGGTTTCAATGGTTCTACCGATAACCCATGGAATGAAATGGGCTTC

CGTATCGATAAGCAAGTTATCGAAGCTAAATCTCGTCAGCTGAAAGCTGCTTACTCTATTGAATTAGCAC

AAGACCTCCGCGCTGTTCACGGTATGGATGCTGATGCTGAACTGTCTGGTATTCTGGCTACAGAAATTAT

GCTGGAAATCAACCGTGAAGTTGTTGATTGGATTAACTACTCAGCTCAGGTTGGTAAATCTGGTATGACC

CTGACTCCGGGTTCTAAAGCTGGTGTATTTGACTTCCAGGACCCAATTGATATTCGTGGTGCTCGCTGGG

CGGGTGAATCCTTTAAAGCTCTGTTGTTCCAGATTGACAAAGAAGCAGTTGAAATTGCTCGTCAGACCGG

-continued

TCGTGGTGAAGGTAACTTCATTATCGCTTCCCGTAACGTAGTTAACGTTTTGGCTTCAGTTGATACCGGC

ATTTCTTATGCTGCACAGGGTCTGGCTACCGGCTTTAGCACTGATACTACCAAGTCAGTATTTGCTGGTG

TTCTGGGTGGTAAATACCGCGTATATATCGACCAGTATGCTAAACAGGATTATTTCACTGTAGGTTATAA

AGGTCCGAACGAAATGGATGCTGGTATTTACTATGCTCCATATGTAGCTCTGACTCCGCTGCGTGGTTCC

GATCCGAAGAACTTCCAACCGGTAATGGGATTCAAAACTCGTTACGGTATCGGTATCAACCCATTTGCAG

AATCCGCTGCTCAGGCTCCGGCTTCTCGCATCCAGAGCGGTATGCCTTCTATTCTGAATAGCCTTGGTAA

AAACGCTTACTTTAGACGTGTATATGTTAAAGGTATCTAATCTCTAACGATAGAAACACAATTTTAGGGA

ACCTTCGGGTTCCCTTTTTTCTATTTTATACGATAGCAATCAGGCATATCATCCGCATTTATCCAATTGC

GAATAGTTTTAGGACTAACTTTAAAATGCTCCGCTGCGTAATCAGGATTATCAAATTTAACGCCCTTTAT

ACATATTGGAATAAATTTTTTAATACCACCAAGTTTTTCAGAAATAGCTTTACGATGTGAAATCGATATA

GGTTTGTTTTTTCGTGGATGAACATGTGTTTTATAATATTCATTGCGCCCTTTAACTCGCTTCGCAATAG

TTTCATCAGATTGCTTAACGCCTGTTTTTGCCTTTGATATTTTTCGTTTAGCTTCCACAGTCATTCCTTC

TTTTGTTCGTATTGATAACATATTACGATATGAAGGATCTTGCAAATGAACTATAACTGGATTTCCTCTG

CCACCAATAGCAGCATTATAGGTATCAGTTCTCATAACGAATTCCTCATTAACTAGTAAAGCTTCCATTT

TATACATCTCCTCAGATGAGGAGAAAGAATAAAGAATTTCTTTTTTAAAGTTATGAATACCATATTTTTT

GATGGATTTTTTGATGTTTACGCCAGAACCCATATAACCATCGTTTTCGTCAAGAGTAGCATGAGCTCCG

ATGTAAATTTTTCCATTGATGATATTAGTAATTTGATATATTAAATATTTCATTTTAAACATCACTCCGT

TTGTATATGATTATAATATCATATTACTTTGGTCTTGTAAATAACTTTATAAATAGTATTATATTTCAAC

AAGGAAAATACAATGGCTAAAATCAACGAACTTCTGCGCGAATCAACCACAACGAATAGCAACTCAATCG

GTCGCCCAAATCTCGTTGCTTTGACTCGCGCTACCACTAAATTAATATATTCTGACATTGTAGCAACGCA

AAGAACTAATCAACCTGTTGCTGCTTTTTATGGTATCAAATACCTTAACCCAGACAACGAATTTACATTT

AAAACTGGTGCTACTTACGCTGGCGAAGCTGGATATGTAGACCGAGAACAAATCACAGAATTAACAGAAG

AGTCTAAATTAACTCTCAATAAAGGCGATTTATTCAAATATAATAATATCGTTTATAAAGTATTAGAAGA

TACTCCATTTGCTACTATCGAAGAAAGTGATTTAGAATTAGCTCTTCAGATTGCAATCGTTCTTTTAAAG

GTTCGTCTATTTTCTGACGCAGCGTCAACAAGCAAATTTGAAAGCTCTGATAGTGAAATTGCGGATGCTA

GATTCCAGATTAATAAATGGCAAACTGCAGTTAAATCTCGTAAACTTAAAACTGGCATCACAGTTGAATT

AGCGCAAGATTTAGAAGCAAATGGATTCGATGCTCCTAATTTCTTGGAAGATTTGCTTGCAACTGAAATG

GCAGATGAAATCAATAAAGACATTCTGCAGTCTTTGATTACAGTGTCAAAACGCTATAAAGTTACAGGAA

TTACTGATAGTGGATTCATCGATTTGAGTTATGCATCTGCTCCTGAAGCTGGTCGTTCATTATACCGAAT

GGTATGTGAAATGGTTTCGCATATCCAAAAAGAATCAACTTATACAGCAACGTTCTGTGTTGCTTCAGCT

CGTGCCGCTGCGATTCTTGCTGCATCAGGCTGGTTAAAACATAAACCAGAAGATGACAAATATCTTTCAC

AAAATGCCTACGGGTTCTTAGCTAATGGTTTACCGCTTTATTGCGATACTAACAGCCCATTAGATTATGT

AATCGTTGGCGTAGTAGAAAATATCGGTGAAAAAGAAATTGTTGGATCAATTTTCTATGCTCCGTATACA

GAAGGTCTCGACTTAGATGACCCTGAACATGTAGGTGCATTTAAAGTTGTTGTTGATCCAGAAAGCTTAC

AACCATCTATCGGTTTATTAGTTAGATATGCTTTATCAGCAAATCCTTATACTGTAGCAAAAGATGAAAA

AGAAGCAAGAATAATTGACGGTGGAGACATGGATAAAATGGCAGGTCGTTCAGATTTGTCTGTTTTATTA

GGTGTTAAGCTACCAAAAATTATCATTGATGAATAAAACAAAGGGACCTTTCGGTCCCTTTTTATTTAAC

TTACCAACTCAATCCAAGCTGGACGAAGTACATCTTGTACCATTTTAACTAATTCCTTTTTAATCAAAGA

AGGATTATCTGCTTGAGTTAGAGTAATACCTTCACGAGAAGTTTCTTCCAAAATATCTTGAACAGTTAGC

CCCATCACCTTTCCAAAATCCTTTGGACCAATTTCGCCAATTTTAGAAATAACGTTATTTACGCGGTTCA

-continued

GTGTAACGTAACAAGCTAAAATTCCCACCAATTTGTTATCAGCTTCTGATAGCTCAACTTTAGCTTTAAT

AGGCTTATCAGACTTTTTCTTTTCACTAAATTTAGAGTTCTTGCATTTAATCGCTACACGATTTCCATTA

CGAAGCCAAGAAGGATAACAAGGTTTCAATACATATCCTTCAGCAGTAAATACTTCGCCTTTTGCTTCGG

CATTCCAAACGCATTTATTTGCATCAACTAATCCAGCATGGTCTACTGTAAAATTATAATCTTGGACGAC

AGAATCTAAATCATTTGGCAATTTAATAAGCTCTTCAAATTTACCGCGACCTAAAAGTGGAGCCATTTTA

AATTTAAATGTATTACAGAATGATTCCATCATATAATCATCTACATAAGTCACATCACCGCTTTCTGTAG

TAACAATAATGTCAAATACATAAAAATCTTTATCACAATAATCAACATTCTTCTGAATGCCAGGTCCAGC

GAATTCGCCAAAGACTTGATAAGATACAACCGCTGAGGTTTCCATAATATCTTGTACAGCTTTAATGGAA

TCAGCATAATTCTTCAAAATAATTTCATACCCAAAGAAATCTTCAGCAGGAAGAATCGGTCCAGTGCGTT

TAGCGCAAGTCACTTTATCACGCTCAATAATCAATGAGAAATTTGTGCCGTGAATCTTTTCACGAGCTAC

CCACTCCCCACCAGTCAATCCCAAGCTATAAAGTTTTTCAATAAATTTAGAGTTGTAATGATTTTCAAGA

CTGCTATACTTTTTAAACATAATTAATCCTCAAAATGTAATTTCTAACCAATCACCATCACGCTGATCAC

TATTGACTTTAAAGCTGAATCCTTCTTTTCTCAGCCAATCACCAATTTCTTCTGTAATCAATTTATCACG

AGCAATACAATAATAATTAAAATGTGTTTTACCTTGTTCAGCTGCTTTATTAGCAAGTTCTGAAAAATCT

TTAATAAAACACTCTAGCTTAAACTGTTTACTTTTTAATGCTTTTTCGCGTAATTGATTAGCAAAAGATT

CATTTTCATAAAGATCATACTGTTCCATTTTTCACCTTTTTATTGATATGTCTTTTTCTATAGACAACTT

TTTCTCGAGCCCATAATACAGCCACTTCTTTTGCCTGTAAGTTTAATTCACGAGCAATTTCAATGAATGA

CTTTCCAGACTCATGAAGAGTAAACACCACAACCTCAGTTCTCATAATCAATCTCATGTTATCGAGTTGG

TGCCATTATATACATCATTTTCTGATTGTGTTTTGTGTGCTTTCAAAATGAAGAAAGGGGCCGAAGCCCC

TTATGATTATGGATAGGTATAGATGATACCAGTTTCTAAAGCAGTTTTATGAATGATGTATCCATTACGC

GATTCTTGGACATCAACTTCTGGATAGTCTTTCATCATCTTCTGGAGAGTGTAACGATGCAGGTAATATT

TACTATCTGGGTCGTCAGTTTTCCAATCTTTACCTTCTTCGGTCATTTTTTGGATTTCATCCATAACCCA

CCAACCGCACCAGATGTAAGCTGAGCTACGGTGTGGAAGAGGATGAACATAAGGTAATTCACCTTCTGGT

TCTGGAGCAACTTTAGCCGTGACTGTTACATTACCAGTTTTGGTAACGGTTACAGGGTTATAATCTGCAG

CAGTAACAGTTGCAGTAACTTCAATAGTTTGACTTCCAACAGATGAGGTATCGACAGTATATACGTTAGT

TGACCCTTCTACAGGAGAAGAATCTTTCTTCCATGAGTAAGTAATTTGTGCTTCTTCTGGAGCACCCGTA

ACATTAGCCGTAAATGTAGCCGAAGCATCTTGCTGAACATTAATAGAAGGAGGAGTCAATGTAACCTGTG

GATTCATTGTCTTCTTATTAACCGTTAATGATACTTCATTAGAAGTAACGCTTAGTGCATCATAATCTGT

CGCGGTTACTTGGGCTACGCATTTAATTCTTTTTACTCCACTTGTAGTTGGAGTATAGCTAAATGTAGAG

TTAGTTTCTCCACCAACTTGTGAATCATCTACATACCACTGATACGTAGCAGATGCTCCATCAGGTTGAG

AAGCTAAGGCAGCAGTAAATTGAACTGGGGTTCCAATCACTCCAGCCGCAGGACTAGCAGGAGTTACGGC

TAAGGTAGTCGTCTGTGTCTTATTTTTAACTGTGATAGTTGTTGTCGCTTCAGCCGTTTCCGGGCCTCCT

TCAGAAAGTGTATTTGTTGCAACTACTTTAATAGTCTTTTGACCGGCAGGTCCTTTTAGTACATAACTAA

AAGTTGCTTCAGCTCCATCTTGTGGAACATTATCTACGCTCCAAGCATATGTAATAGTTCCGCCTCCAGT

TTGACCACTGGGTGTAGCAGTAAACTGCTTAGTTTCATCAATAACCCCTGTAGGTGTTTTAGGAGTTATA

TCAACTGTAAAAGTCATAAGTTATCCTTATTTTAATGTTACGAAAGAAGAGTTGCGTGTTTCACGAATTA

AAACTGATCCATCGCGATTAATGTAATAAATTAAGCTAAATAAAGTTTGGTGTGCTGACGCATGTTCAAA

ACTAGTTGGGTGAGATTTCCAATCAGGAGTTTCAGCAATCCATTGATAAATCCACCAAGGAACAGTACAG

AATCCTAGATTTTTTCCAATCAGTTGAAGATTCGGACTAAAGTTTTCCGGAAGAGTAAATACAGACGGCT

TTTCAGATTCAATAATCTCAGCTACAGCCTGTTCGAATTTTTCTTCAACAAAAGGAGTATCTTCAATCAA

AACATCGGTATTTTCAGGAATTTTATCCGTTTCTACTACTTCAATTTTAATGTCAGATTTAATCGGAGAA

-continued

TCAATCAGAAGTGCTGCTTCTGGATTGACTTCTTCATCGTCATATTTTAATCCCTCTGCGGCATCAGCAG

CATCAATTAAGTCTTTAATAGATAACCCATCAGTCTCTGGCATAGGTTCACTAGCGAGCTTCTGGAGGGC

TTCTTCAATATCAACAACGATATTATCAAAAGATTTATTCTTTTTGACCTTTATACCAAACTGTTCAGCA

TATTCAGCTAATTTAGCTTTAGCTTCTTTGTTATCATCAAGAGCCTTCAGCTCTGCAATATAATCTTTAT

CTATCATAATATTTCCTCAGTATAAATATAGATATATTTATTACTCGGAAAATAGTATGTACCACTTTGT

ATATGAAACAACAAATCTAATAAATGGTAAAAAGTATATAGGAAAGCACTCTACTGATGACTTGAATGAT

GGTTACCTTGGTTCCGGTAAGGCAATTCAGCAGGCTATAAAGAAATATGGTGAAAACAATTTCTCTAGAA

CAATACTAAAAGAGTTTAAAACTTCCGAAGAAGCGTACATGTATGAAGAAGAAATTATAACTCCTGAACT

AATAAAAAGCAAAAATTATTATAATATGAAACCTGGTGGAATTGGTGGAATTGTTATGACTACAGATGTT

ATAGCAAAGATGAAAGAATCTTCCGCTAAAAGATTTGAAAACTCACCGGGCACGGTATTAGGTAAAACTT

GTTATACTAATGGAACTAAAAATATTTTTATTAAACCTGGAGAACTTGTTCCAGAAGGATTTGTAAAAGG

GATGGTTCATCCTAATAGAAAGTCCAGAAAAGGATGTAAAGTCAAACCGACTACCACAGGAACTTTTTGG

GTCAATAATGGCGCAATAAATAAATTAATACAACCAGACGGTATTATTCCCGACGGATTTATTAAAGGTC

GTCTCATGAAAAGAGATTCTAAAGGCAAATTTAGTAAGGCATAATTATGGATATTAAAGTACATTTTCAC

GACTTCAGTCATGTACGCATCGATTGTGAAGAGAGCACGTTCCACGAATTAAGAGATTTCTTTTCGTTTG

AGGCCGATGGATATAGATTTAATCCTCGCTTCAGATATGGCAACTGGGATGGACGAATCCGTCTTTTAGA

TTATAATCGTCTTCTTCCATTCGGCTTAGTCGGGCAAATTAAAAAAATTCTGTGATAATTTTGGCTATAAA

GCCTGGATTGACCCACAAATTAACGAAAAAGAAGAATTATCAAGAAAAGATTTTGATGAATGGCTTTCTA

AATTAGAAATCTATTCAGGAAATAAAAGAATTGAACCGCACTGGTATCAAAAAGATGCAGTGTTCGAAGG

ATTAGTTAATCGTCGTAGAATTCTTAATCTTCCAACATCTGCAGGTAAATCTTTAATTCAAGCTTTGCTT

GCGCGATATTATTTGGAAAATTATGAAGGTAAAATTCTTATCATTGTTCCAACAACTGCTCTGACAACTC

AGATGGCTGATGACTTCGTCGACTATCGTTTATTCAGCCATGCAATGATAAAGAAAATTGGTGGCGGAGC

ATCAAAAGATGATAAATATAAAAATGATGCACCAGTCGTTGTTGGTACATGGCAAACTGTAGTAAAACAA

CCGAAAGAATGGTTCTCACAGTTTGGAATGATGATGAATGATGAATGCCATCTTGCTACAGGAAAAAGTA

TTTCATCTATCATATCAGGTTTAAATAACTGCATGTTCAAATTCGGTTTGTCTGGTTCATTACGTGATGG

CAAAGCCAATATCATGCAGTATGTTGGAATGTTTGGTGAAATATTTAAACCAGTAACGACTTCTAAATTA

ATGGAAGATGGACAAGTAACTGAGCTAAAAATTAATAGTATTTTTCTTCGCTATCCCGATGAGTTCACTA

CTAAATTAAAGGGAAAAACTTACCAAGAAGAAATAAAAATTATTACTGGGCTTAGTAAAAGAAATAAATG

GATCGCTAAATTAGCTATTAAGCTTGCGCAAAAAGATGAAAACGCTTTTGTCATGTTTAAACATGTATCG

CATGGTAAAGCTATTTTCGATTTAATTAAAAATGAATACGATAAAGTTTATTACGTATCAGGGGAAGTTG

ATACCGAAACCCGCAATATAATGAAAACCTTAGCTGAAAATGGTAAAGGAATAATTATAGTAGCTAGTTA

TGGTGTATTTTCTACTGGTATTTCAGTTAAAAATCTGCATCACGTTGTTTTAGCGCACGGTGTTAAATCA

AAAATCATTGTATTACAAACAATCGGTCGTGTATTACGTAAGCATGGTTCTAAGACAATAGCAACAGTCT

GGGACCTCATAGATAGCGCAGGCGTCAAGCCAAAATCTGCTAATACGAAAAAGAAATATGTTCATTTGAA

CTATCTTTTAAAACACGGCATTGATCGTATTCAGCGCTACGCAGATGAAAAATTTAATTACGTAATGAAA

ACAGTTAATTTAATAAGCTTCGGCCCTTTGGAGAAAAAGATGTTACTAGAATTTAAACAATTTCTTTATG

AAGCTTCTATTGATGAATTTATGGGTAAAATTGCCTCTTGTCAAACATTAGAAGGTTTAGAAGAACTTGA

AGCTTATTATAAGAAAAGAGTCAAAGAAACTGAATTAAAAGATACTGATGACATCTCTGTGAGAGATGCT

TTGGCAGGAAAAAGAGCTGAATTAGAAGATTCAGACGATGAAGTAGAAGAAAGCTTTTAAATTAAAAAAG

GCCCAACCAAAAAGGAAGGGCCAAAACTATAGACTAAAGGTCACACTATAGCAAAAGTTGTGTTTCATTT

-continued

AATTGTTCTTCCGAACTTTCTGAAACTGGTAGTTCTTTAATGTAATTATAGCAAGGCCCAGGATGTACAG

GACCTTTGTCTGTTTCAACAACCAATGCAGAATCGATTGGAGTTTTACAGACAACACAAATCTTATCTGA

CATGATTGTCTCCTCTGAATTATATCTATTTATACAACTCTCATATGCATATCAATGCCCATATCTTTAG

AATAAAAATATTCATCAAGATATCCGGCAAATTTTCCTTTAATATAAAGGACATCTTCACCACACGGGTG

GTCGGCCAGGATACGAATATCCTGACGCTTAAGATTATGCTTTTTCATTAAGAATTGAATTTCCGTTTCA

AATTCTTCTTCATAATTAAAAGCATCATCAATGCTATATCTCATTATTTTCCAGCCTCAAATGCTCGCAT

GTCTTGAATATGCTTAATAGCAAATCCACGTGATTTAATAGCATCAAGAGCTCCGCTACAGAAATCTAAT

AAAATCCCCCAATACTGCAACGAGGTATCAACCTTTAAAACATCCTTATCCGCTGATAGAACTGTCTTCA

TTTCTGATTTCTCGTAACGATCCATACTAAATTCATCACCATCTCCTCGTCCCGAGTAGTAGTCTAATCT

AGCTTTAAGAGCAACTTTTTCTGTGCTTCAATTCTAAGCATTTCCTTTTTAATACTTGAATGCTTATTA

AGCCATTTACTATATAACATCACATTATTAGCTGCTTCATACTGTAATTTAGTCGAATCTATAAACACAT

CTTTCTTCAATTCTTCTTGAAGATCTTCTAATCTCATATTGTTCTCTATTCAATTGTTATTGGTTGTTAT

TGGATGGACTTAGATTCATTATACCACGTTTTAACGTGAAGCATTATACTCTATTACTGGAAGCCAGCTG

CAGTTTTATCTGCTCAATATCATCAGGATTATCGATGACCGAAAAGCGTATTTCTACTATCAGAGTATAA

TCGTCATAAACGGGTATCACATTAACTGCTAATTTATCAATACGTGGCTCATAGTTTCTTACTGCGCTTT

CGATATTGCGTTCAACCGTGTCAGCAGTAAGAGGAGTCATATTTTCAAAAAGCTGGTCTGATAAATCACA

TCCAAATTCAGGGTCAAACGGTCTTGAACCTTTTCTTGTTGTAATAATTCCCAAAAGACTGTTTTTAATT

GACCTTAATCCAAGCGATCTGGAAACGTCTTTGTTCCAATCCATTTTCATTTCCGGGTCAATATCAGAAT

AAAGCTTATTAATATTTGCCATTATAGTAACTCAAAGAACTCTTTGAGGCCTCTTATTACGTGAGCATGG

GTTTTTCCACACTCTGGACACTTAATTGGAACAGCCAAATAAACGGTAGGCTTTAAAAGCATATCTTTTA

TAGCTACAATATCTGACTCTGTGATGATAGAATATAAATCTTCTAGTTCCTTTTCATTTAAGTCTTCAAC

TGGAATGCTTTCCCCGTTAGCATGAATCGTTTCTATACATGATACTATCATGTGGGCTATATTTTTATCA

TCAAAAATTTTAGGGTATCGGAATTTAATTTTAATGTCACCTAGTGTATACCAGAGGTCTTCTGGTGCAT

CTATTTGTGTATGTAATAGATTTATATGGGTTGGTATTTCAGTTCCACAGGTGCACTTCCAGGAGTTTTC

GTGATTAACTTCACCGAGAGAATGTGCCCATAAATGAATCAACAATAGTTCTGATTCTTGGCGGTTTAAA

TCTTTTGCATTTGTGCAGTCTTTGATTAGCTTTTTAACAATTACTTCTACGGAACCATTATTTTTGGCAG

TAATAAGTTCTAGATATTCTTTAAGCGTGAATGCGCGACAATTGATTATTTTAGAACCAACTCTCACATC

AAATTTGTATTCATACATATTTAGCTCCTTTATTTATCATATTTATAAATAGAATAAAAGGAGCATCTAT

GGCAAACATTATTCGTTGTAAATTACCAGATGGTGTTCATCGTTTTAAACCATTTACGGTAGAAGATTAT

CGAGATTTTTTGTTAGTTCGAAACGATATAGAACATCGGTCACCACAAGAACAAAAGCAAATAATTACTG

ATTTAATTGATGATTATTTTGGAGACTATCCGAAGACTTGGCAACCATTTATATTTTTGCAGGTATTTGT

AGGGTCAATAGGTAAAACTAAAAGTACGGTCACATTTATATGTCCAAAATGTAAAAAAGAAAAGACAGTT

CCATTTGAAATATATCAAAAAGAATTAAAGGACCTTGTTTTTGATGTAGCTAATGTTAAAATTAAATTAA

AGTTTCCTTCTGAGTTTTATGAAAATAAAGCAAAGATGATTACTGAAAATATTCATTCTGTTCAAGTAGA

TGAAATATGGTATGATTGGAAGGAAATTAGCGAGTCCAGTCAAATAGAACTAGTTGACGCCATCGAGATA

GAAACATTAGAAAAAATTCTCGATGCAATGAATCCTATTAATTTAACTCTACACATGTCATGCTGTAATA

AGTACATTAAAAAATACACTGATATAGTAGACGTGTTTAAGCTATTAGTTAACCCAGATGAGATATTTAC

TTTTTATCAAATTAATCACACACTCGTAAAAAGTAATTATAGCTTAAATTCAATAAGTAAAATGATTCCT

GCCGAGCGCGGATTCGTATTAAAACTGATTGAGAAGGATAAACAATAATGAGTATGTTGCAACGCCCCGG

ATATCCAAATCTCAGCGTTAAATTATTTGATAGCTACGACGCTTGGAGTAATAATAGATTTGTTGAATTA

GCTGCTACTATTACCACATTAACTATGCGGGATTCTCTTTATGGCCGAAATGAAGGAATGCTGCAGTTTT

-continued

ATGATTCTAAAAACATCCATACAAAAATGGATGGAAATGAAATAATTCAGATTTCTGTAGCTAATGCAAA

TGATATTAATAATGTTAAAACACGAATTTATGGATGTAAGCATTTTTCCGTGTCAGTAGATTCAAAAGGT

GATAACATCATTGCTATTGAATTGGGAACTATTCATTCTATAGAAAATCTTAAATTTGGTAGACCATTTT

TCCCTGATGCAGGTGAATCTATAAAAGAAATGCTTGGTGTCATTTATCAGGATCGCACATTATTAACTCC

AGCAATAAATGCTATAAATGCTTATGTTCCTGATATTCCATGGACTAGCACATTTGAAAACTATTTGTCA

TATGTAAGAGAAGTTGCTCTAGCTGTAGGAAGCGACAAATTTGTATTTGTATGGCAAGACATCATGGGCG

TTAACATGATGGACTATGATATGATGATAAATCAAGAACCATATCCAATGATTGTCGGTGAGCCATCTTT

AATAGGTCAATTCATCCAAGAATTAAAATATCCATTAGCATATGATTTCGTTTGGTTGACTAAATCGAAT

CCTCACAAACGTGACCCAATGAAAAACGCTACTATCTATGCGCATTCATTTTTAGATTCTTCAATACCAA

TGATTACTACAGGAAAGGGTGAAAACTCTATTGTGGTGTCAAGGTCAGGTGCTTATTCTGAAATGACTTA

TAGGAATGGATATGAAGAAGCTATTCGTCTTCAAACTATGGCACAATATGACGGCTATGCTAAATGTTCT

ACTATCGGTAATTTTAACTTGACTCCTGGTGTTAAAATTATTTTTAATGATAGTAAAAACCAATTTAAAA

CAGAATTTTACGTTGATGAAGTTATCCATGAATTATCCAATAATAATTCAGTAACTCATCTATATATGTT

CACTAATGCAACGAAACTGGAAACAATAGACCCAGTTAAGGTTAAAAATGAATTTAAATCTGATACTACC

ACTGAAGAAAGTAGTTCTTCCAATAAGCAATAAAGAAGTTTCTATTCCTAAAATGGGTCTTAAACATTAT

AACATTTTAAAAGATGTTAAAGGTCCTGATGAAAATTTAAAACTTCTCATTGATTCTATTTGTCCGAATT

TATCACCGGCAGAAGTTGATTTCGTTTCTATTCATTTATTGGAATTTAATGGAAAGATTAAATCTCGTAA

AGAAATAGATGGTTATACTTATGACATTAATGATGTTTATGTATGCCAAAGATTGGAATTTCAATACCAA

GGAAATACATTTTATTTTAGACCTCCTGGAAAAATTTGAACAATTTTTAACGGTGAGCGATATGTTATCTA

AATGCTTACTTAGGGTCAACGATGAAGTTAAAGAAATTAATTTTCTTGAGATGCCAGCATTCGTTTTAAA

ATGGGCAAATGATATTTTTACAACTTTAGCAATTCCTGGCCCTAATGGTCCAATAACTGGAATTGGCAAT

ATTATTGGATTATTTGAATGAAAAAGCCACAAGAAATGCAAACGATGCGTAGAAAAGTTATTTCAGATAA

TAAACCAACACAGGAAGCGGCTAAATCCGCTTCTAATACTTTATCTGGGCTTAATGACATATCTACGAAA

TTGGATGATGCTCAAGCTGCTTCTGAATTAATAGCTCAAACTGTCGAAGAAAAATCGAATGAAATAATTG

GAGCAATTGACAATGTAGAAAGCGCAGTGAGTGATACATCTGCCGGTTCTGAGTTAATTGCTGAAACTGT

CGAAATTGGCAACAATATTAATAAAGAAATCGGTGAATCGCTCGGAAGCAAATTAGATAAATTAACAAGT

TTACTAGAGCAAAAAATCCAGACAGCTGGAATTCAACAGACTGGAACTAGTTTAGCTACGGTTGAAAGCG

CTATTCCTGTTAAAGTCGTTGAGGATGATACTGCTGAATCTGTGGGTCCTTTATTACCAGCTCCTGAAGC

AGTTAATAATGATCCTGACGCTGATTTTTTCCCTACCCCTCAGCCAGTTGAGCCAAAGCAAGAATCACCA

GAAGAAAAACAGAAAAAAGAAGCATTTAACTTAAAATTATCTCAAGCTTTAGATAAATTAACGAAGACTG

TTGATTTTGGATTTAAAAAATCCATTTCAATTACTGATAAAATATCAAGCATGCTATTTAAGTACACCGT

CAGTGCTGCTATTGAAGCTGCTAAAATGACTGCAATGATATTGGCTGTTGTTGTTGGAATAGACCTTTTG

ATGATTCACTTTAAATACTGGTCAGATAAATTTTCAAAAGCCTGGGATTTGTTTAGTACAGACTTTACCA

AATTCTCTAGCGAAACCGGAACTTGGGGTCCTTTATTACAGAGCATCTTTGATTCTATTGATAAAATTAA

ACAACTTTGGGAAGCGGGAGATTGGGGTGGATTGACAGTAGCTATTGTTGAAGGGCTTGGAAAGGTTCTT

TTTAATTTAGGTGAACTTATTCAATTAGGTATGGCTAAATTATCTGCAGCAATTCTTCGAGTCATTCCTG

GTATGAAGGATACTGCTGATGAAGTAGAAGGAAGAGCATTAGAAAATTTCCAAAATTCTACTGGAGCATC

TCTCAATAAAGAAGACCAAGAAAAAGTAGCAAATTATCAAGATAAACGAATGAATGGAGACCTTGGCCCA

ATAGCAGAAGGACTAGACAAAATCTCTAACTGGAAAACTCGTGCATCTAACTGGATTCGTGGTGTAGATA

ATAAAGAAGCGCTGACTACCGACGAAGAGCGTGCGGCAGAAGAAGAAAAATTAAAGCAACTTTCACCGGA

-continued

AGAAAGAAAAAATGCTTTAATGAAGGCTAATGAAGCTCGTGCTGCGATGATTCGTTTTGAAAAATATGCC

GATTCAGCTGATATGAGTAAAGACTCAACGGTTAAATCAGTTGAAGCTGCCTATGAAGACCTTAAAAAAC

GGATGGATGACCCGGATTTAAATAATTCACCGGCAGTTAAAAAAGAACTTGCTGCTAGATTTTCTAAAAT

TGATGCTACTTATCAAGAGCTCAAGAAAAATCAGCCTAATGCCAAACCTGAAACTTCTGCTAAATCACCA

GAAGCGAAACAAGTCCAGGTGATTGAAAAGAACAAAGCACAGCAAGCTCCTGTTCAACAAGCATCTCCTT

CGATCAATAATACTAATAATGTTATTAAGAAAAATACTGTCGTTCATAATATGACACCTGTAACGAGCAC

GACTGCTCCTGGTGTATTTGATGCGACTGGAGTTAATTAAGGAATAATATGGCAATTGTTAAAGAAATAA

CTGCTGATTTAATTAAAAAGTCCGGTGAGAAAATTTCAGCCGGACAGAGTACTAAATCAGAAGTAGGAAC

TAAAACATACACAGCCCAGTTTCCAACTGGGCGTGCTAGTGGTAATGACACTACAGAGGACTTCCAGGTA

ACAGATCTATATAAGAATGGATTATTATTTACTGCATACAATATGTCATCTAGGGATTCTGGAAGTCTTA

GATCGATGAGATCTAACTACTCTTCTTCATCTTCGAGTATTTTACGTACAGCTAGAAACACTATTAGTAG

TACAGTATCAAAACTATCAAATGGATTAATATCAAATAATAATTCAGGAACAATAAGTAAATCTCCTATC

GCAAACATTCTTTTACCGAGATCTAAATCTGATGTTGATACATCATCACATAGATTTAATGATGTTCAAG

AAAGCCTTATCAGTAGAGGCGGAGGTACTGCTACTGGTGTGCTAAGTAATATTGCTTCAACCGCAGTATT

TGGGGCACTGGAAAGTATAACACAAGGTATAATGGCTGATAATAATGAACAGATTTATACGACAGCCAGA

AGTATGTATGGTGGTGCTGAAAATAGAACTAAAGTGTTTACATGGGATTTGACTCCACGTTCAACAGAAG

ATTTAATGGCTATTATTAATATCTATCAATATTTTAACTATTTTTCTTATGGTGAAACGGGTAAATCTCA

ATATGCTGCTGAAATAAAGGGGTATTTAGATGATTGGTATCGTTCTACGTTAATTGAACCTTTATCTCCG

GAAGACGCAGCTAAAAATAAAACACTATTTGAGAAAATGACATCGAGTTTAACTAACGTTCTAGTAGTTT

CAAACCCGACAGTTTGGATGGTGAAAAACTTTGGCGCAACATCTAAGTTTGATGGAAAAACGGAAATATT

TGGTCCATGTCAAATACAGAGCATTAGATTTGATAAAACACCTAATGGTAACTTTAACGGATTAGCTATT

GCTCCAAACCTCCCTAGTACATTTACTCTCGAGATTACTATGAGAGAAATTATCACGTTAAACCGTGCTT

CTTTATATGCGGGGACTTTTTAATGTATTCTTTAGAGGAATTTAATAATCAAGCAATAAACGCAGATTTC

CAACGTAATAATATGTTTAGCTGCGTTTTTGCGACAACTCCATCAACTAAAAGCTCTTCGTTGATAAGTT

CAATTAGCAACTTTTCTTATAATAACTTGGGCCTAAATTCAGATTGGTTAGGATTAACTCAAGGTGATAT

TAATCAGGGAATTACCACGCTAATTACAGCTGGCACACAAAAACTGATAAGAAAATCAGGAGTCAGTAAA

TATCTTATTGGTGCCATGAGTCAACGTACAGTTCAAAGTTTATTAGGCTCATTTACAGTTGGTACATATT

TAATTGACTTCTTTAACATGGCATATAACTCATCTGGATTGATGATATACTCTGTAAAAATGCCAGAGAA

TAGATTATCCTATGAAACTGACTGGAACTATAATTCTCCTAATATTCGTATAACCGGAAGAGAATTAGAC

CCTTTGGTTATTTCATTTAGAATGGATTCAGAAGCTTGTAACTATCGTGCAATGCAAGACTGGGTTAACT

CCGTTCAAGACCCAGTAACTGGACTGCGTGCTTTGCCACAAGATGTCGAGGCAGATATTCAGGTTAATCT

TCATTCTCGCAATGGATTACCTCATACTGCGGTGATGTTCACGATGCATTCAATATCAGTGAGCGCTCCT

GAGTTATCATATGATGGAGATAACCAAATAACTACATTTGATGTTACTTTTGCGTACAGAGTGATGCAGG

CTGGAGCAGTTGATAGGCAACGTGCGCTTGAATGGCTTGAATCTGCTGCTATAAATGGTATTCAAAGCGT

TCTCGGAAATAGTGGAGGTGTTACTGGACTATCTAATTCGCTTTCACGACTTAGTAGATTAGGGGGAACT

GCAGGAAGCATTTCAAACATTAATACTATGACAGGAATTGTCAATTCGCAGAGTAAAATATTAGGAGCAA

TATAACAATGGGGACCGAAAGGTCCATATTTTTATTTACGGAATGAAATGAAAGCAGCAACTGAAGCAAC

TAAACTGTCTTCAATATAAACTTCAATTTTTACAGGAGCTTCTGACTCAAATTTACCTGTTACTACACCC

TGAAAAATACTTTCAGTCTGTTCTGGCTTTGAAAAATTTTCAGAAGGAAAAATTCCGAACTTTTTATCTG

TTCCAAAAATTTTGATAAATTCATCGTAAACCGCTTCGTTAAAAGCATTATCAGCAGGAATAACGCCTTC

AACTACAAGTTCTTGACCTAAAAAGCGTAAAGAAGATTTCATTTTGTGTTCCTCATGTTATGTTAGTAAG

-continued

ACTACTATAACACAACACGAGGGACTTGTAAACTACATTTTGAACTTTTTAGTACGCGTAATAGGCATGC

GTCGATTTTATACTGTTTCATTGTTTGAAGAGCAGTATCAAAAACAGCATTAATGACACCAATTGGATTT

CCACCCAAGTTTTTAAGCTTAACTAATGATAGTTTCTCATTAACACCTATCATTACGATATGCATCATTT

TATCGCCTGGTTTAACGTTTTATTTGTATCACCGCCAGAGGTGTATGTACAAAATCTAAATCCAGGAAGT

ACACTTTCTTCACCGGCTTGAATAGCAAAAATTTGTGGTATTTTATGCTTAGGATTTAATGTAACAACCG

GCGCCGAAGCGCCGTCAAATAATTCTGTAATAAGTTCCATGATTTATCCTTGAACGAACTTGTAAGGCAT

GTTTGCAATATCTATGCAAGACGCAATAATTCCAAGAGATGATTCTACTTTCTGTTTAACATTTGATGAA

ACAAATGATGCAAAGTCAACTCTATCTTCTATATCACCTGTCATTGTAACCAATTCACCAGTTTCCATTA

AATGGTCTCCGTCATAGATTACCGATTCGGTGAGTTCTTCTGTGGTCATAACTTCAGCTTGAATAAGCTT

GTTGTTAGTTTTAACTGTTCCATCATTGTAAGATGCATCGGTTATTTTATTAACTTTGACCATTAATCCA

CGTGGCAAAATGACTTCCATTTCATTTGAAGGCGCTAAACTTCCACCGGGTAAAACAACATTGACCTTAT

CAGCCCCAGTAATAACCCATCCAATTCCAACTAAATTATCGCTAGAATTTACAAGTCCTTCATCAGTTTT

ATCAATAGAAACGCTTAAACGCTTTTCGTCTGGTAAAACACCTATAGATGAATCAGTCATCCAAGTACCA

AAAATATTTGGATATAATGATGTTGACACAAAGTTTCTAAAATAAAAAACTCGATTTTTTACCATTGCTT

CGTATATTGAAGGTAACATTCGTTGTGAACGATACAAAGTAATACCTTTTGGTAATCGTTCACCATTTTT

AAAGGCTGAATCTAAATTATCAATAGCTTTTTCTATGTCAGATGCTGTCAAAATACTTGTACGCTCATCT

GGATTATATAATCCCAAAAGAGCATTATTTATGTCTACATATCCTGAACCTACGTATTCACGAATTCCGC

GTTTTTGCGCTGGTGTGTATTTAGATGAATCTTTATTTTCGACTATAGGATGTAATGACCATCCAGCGGT

AAGAGCATATCCACGTAATTCTCTTCGAATAATCTTTGTTTTTATTGCATTCCAAGAATTTTGTACTAAC

TCATTTGCAGCATCTTGGTTTAAATGCGAATGTTTGTTAATATTTCTTTCAAACCAAGCACCCTTATATT

TTTCTAAAGTATCATCGACGATAGAAGCAATAGTTTCTAAGGTTTTTATTGAAGTAATAGATTCTTTTCG

TAATCTTTCTAAAGCTTTATTTTTTATTTCTGCGTTAATAATGGATTCTTTATCTTCAGGAATTATAGAA

GCTTCTCTGAATGCCATCCCAGCTGTAACACTGCTAAGAGCATTCTCTAGTGCAAATCCTGAAGTAGAAA

TTACCGTTAATTCATTAGAATCAGAAATTAAAGGCGCGTCCGCTGGTTTATTTAATTCGGCCGCTGAAGC

CTCAAATTTTTGAAACATTGGTGTTTCAAATCTAGAAGATTCCAATGACTGACTTTGCGCAATTGCTCTA

CGGGAAATTTTAACTTTAACGATTACAGCTTGGTCAGAACGTTTATCATTTTCTTGCGCAATAGATGCTG

CAATTGCCTCATTTTTAGTTACTTGAGCCCCAGTATCTTTATTGATATAAACATCACCGACCTTCGATTC

AACTTTAGTAAAGAGCTCGGTACTAATTTCCGGAACTCCTGGAATGTCTTCTAGTGATACATTTTTGCGA

TGTATAAGAATATATGCATACTTTTTATCGTAATCCCAGAGTTCCTTAAGAAGGACGTATCTACCACCTG

AACGACTACGGATAAGTCTATCAGCAATAACTTGAATTTGTCGAGCTTGGCCAGCAGTTTTAGACTTAAG

AATACGGAGCATACAGGCATCAATTTTATACTGGCGCATTGTTTGCATTGCAACAGTAAAAACTGAATTG

ATATAATTAATTGGGCTTGGACCAAGACCTTTTAATTTAGCAATTGAACCTTTAGCAGTTAATGTAAAAG

GAACAATATGCATCATTTTTATCGCCCATCTTTAAATCACGATTAGTATCACCTCCAGATGTATAGGTACA

TAAACGAAAGCCTGGTTGTTCAATTGCATCATCAACATGAACTGAAAAAATTTGCGGTATTTTCTTCTTT

GGATATAAGTTTGTAATTGGAAGAGTAGTATCTTCGTCAAATAATTCTGTAATAAGTTCCATCATATCCT

CTCTAGTGTTTATTCTATTCTATTTATAAAATTAAAGGCCCGAAGGCCTTTAATAATCTATTGGTAAGAG

AGTACGATATATTTCAAACTTTGGACCTTTTTCATAAGCATCAAATGTTTCTGTGAATTTATTATAAGCA

TATGCATCTATAAATTCAATCATGATTTGTGATACAGAAGTAGAAACATCTCCACCTTCTTTTTGAGCCA

CGACAATTGTTTCTAAGTAAGCTTTCATAGACCAGTTACCTCATGAAAATCACCAAATACATCTTCGAAT

GTATTAGCTTTAGTTTTATCTTCACGTAAACGAATCGCAATCGGAAGAAATAATTTAACGTAATCAGTGC

-continued

GGCCATCAGATTTTAACCAACCGTTGCATTCGCACTCTAGAATTTTTCCAATATAATAATTTTGGTTTTC

CATAATGCGAGTACGGTCAAGTTCATGCGATTTTACACCGGCTTTATCTTTTAAGCCTGAACCAGCATTT

ACCTTAATTTTTCCACACTCTGACTCAAGAATAAATCCACCCGCTTTAGTAGGGTCTTTACGGTGAGGAT

AAATTCCTACAATTTTTAAATCAACATCAATTACTTCTTTAAATTTATAAAGATTTTTTGAACGAGCATT

TTCCCATAATCCATCGATATTTTTGAGAATAATACCTTCAAGACCTTGGTCAATATACTTTTTATAAATT

ACCTTAGCTTCATCTAGGTTATTTACTACCTGGTTTTCAATTAAAATTACTTTATCATATCCAGATGTCA

TTTGTTCTAGTTTAGAAAAACGTACATCATATTTCAAACGAAATGCAGGAAGACTGTATATTTCTACCAA

CGGGACATAATCCCAGACCTGAAACTTCATGCATTGTGCTTCTTTTTCAGAAATGGTTCCCTTTAAAGAT

TTATTGGCGATTCCATTAGAAGCAGTACGTGATTCAGCTACTTCGGCGAATTCTTTAGCTTTACTGTTTT

CAGGATAAGCATCAAAAAGAAAATCTAGGCCTTCTGGCTCCTTTTTAACTTGCTCATGGTATACCAATTC

GCCATCAATCAACACACCTTCTGGATGAATCTGGCGGGCTTCAGCGGTCATTTTAATTAACTCTTCCTTA

AGAAGATCTAATCCTAGATATTCATTACCAGCTCGTGATAAAAGACGAACATCATCTAATTCATCACCTC

TAACTTCAGCAAAACACCGAGCTCCATCAGCTTTTAACTGAGCAAAGGCTGGAAATTTGATATTCTTATT

AATGCCTTTTTCATCATAAGAACTTGCGAGCATTTGAGGTTGTTCAGGAATTAAACCTGGCCAAACTTTG

TTTGCAATAGATACTGAAGCACCACATTCAAGGTCTCGCATCATCACTCGACGCAAAACTTCAACATCAT

CTTTTTTACCATCGGTGATATATCCAGTTAATTCCTCAATTGCTGCATTTCCAGTCAATTTCCGAGTAGC

TAATGTGAATTCAATGAAGTCAAGCATATCGGTAAGAGTCAACATTCCAAAACTCTGGGTAGCAATACCA

GGTTTAGGCCATTTCTTGATATAATACTGTAACCCACGAGAATAAGTCAGACGATATACTCGTTTAAGCA

ATTCATTATCTTTATTCTTTTCAAGAATTGCTTGCTTCTGTTTAGTTGAACCAATAGATGCTATTTCGTT

CAGAATTTTAAGAATCATTGTTCATCCTTTAGAGTTTGGTTTACAGCTCTATTATAAATCAATTCATCAT

TAAGCTCAGTCAAAGACCTGTGGTACGTGGTTCTAACTTTATTTCCTTGCATCCAGTGCTTGATATAAAT

GAAACCTTGCTCTACACATTTTTTAAAAATTCGTTCGTCTTTTTGAGCTCGGAATTCTGGATTGCATCTA

AAAAATTGATTTACGTGACCGTAATCACGTGTAGTATTACCTTCATTTTCATAAATAGTGTGAACAACAA

ACATTAGAATGCTCCTTGGAAAATATTATCACCACAAGTAGGTCTATTATACAAATACTCTATACCGCCG

GGCTTAATATAGTTCCATGTCTGAAACGGATGCGTCTGATATGGATGATATGGATTATAAGGATTAAATC

CAGGAGTTCTCCAGGTAGTGTTCCAAGGAAAAGAATCGTTTTTAATCATCTTTTCAATTACATCTTTTAT

AGCTTTTTCACTATCAAAACTTTCTTTATTTTCCTTTGGTGAAAAAAGCTTATTCTCTACATCGTTCCAT

GTATAAACTCGCTGAGCAGTTTTTGGAATATTGTCACGCTCTCCTCGAGCCATCCAATACACAGGAACAC

GTAATATTTCACTCGCGTGATCGCAGTGGTGAGCGAGATCGTCAATATAACAAATTACGTTATATTTCTC

TTTTGCTTTTTTGAACAACTCTTCTTTTGAAGAATCATGACTACACATCAGTACTTCTGAGAAAGCACCA

GGAAAAAGAGCATTCAAATTAAATTGACGATTTAATAGAGCGTCAATAGAATCACCCAATGCTGTAACAG

CAACAAAATTATAATCTTCTTTTAATTTGTTAATTACACACAGAGCATCTTTATATGGAGACAAGTAACG

AATAAAATCCGAACGATTGTATTTTTCAATTAACTTGACGCCAAGTTCTTCATCACAGTTAAAGAGTTTA

CCAGGAGAAATAAATTTCTCATCTTGGATCATTTTTAAAATATGTTCTAACGGAAGATTATATTTCTGAG

CAAAATAAGGAAGGCCTGATTGCCAGCTTAAACATACTCCATCAATATCAGTTAAAATAGTAGGCTTCAT

AGAGAGTCTCTTAATAGGTTTAACACATCAATAAATTCAGCTTCGGTTAGTATTGTATCATCTTTTGTTA

GACCACTAGCAATGCTGTGCTTCAAAACTTTTCCTTTCGAGGCTTGTAATGCATCACGAAAGCCCTTGTT

TTGAATCGCTGCTTCAAAATATGCATTTGTGTATAATTCTTTCCACGCCGGGGAGTATCTTGAAAACGGA

ACTCCAAGCCAAAAGAGGGTCCCACGGTCCTGAGCTCTAGCATAAGACCTTCCAGCTTGTTGGGCGGCAA

GCCCGGATAACCCAAATATACGACGTTGTTGTTCAACATTTTTCACCTTACACCCTTGGAGGAATCCTTC

AAGACCTCCAAATTGAATACCATCCATAACGAAAGGCCATTGGGCGAAATTACTTAATGCACATGATGGC

-continued

CACCTAAAATTGCTTCTAATCTCTAACTCAGACATTTTCAATGCTTATAATTTCAACATCAGCCCAATGA

CCATAGCAAGGAAGACGAAATTCAACTGGCCAGTTAGGGTCCCTTTCTAATATAATAGACTCAACTTGTG

GTTCTTCGTGTTCATCAGTATACGGATTTTTATCTGTTACTTTATATGTGACCTTAATGTACTGAATTCC

AAAAATCTTATTAATTATATTCATACTAATTCCTTTAATCCGTAGATAGGAGATAATTCATCACCCATAC

GAAGGTCTTCATTTCCATCTACCCAGGAAACAATATAAGCCTCTTTTATTTGAATACCACTCCATTTAAA

TGGAGGTAGAACCTTAGAAATTAATCCAGGTATACCAACTCCCTTTAATTCAACAGTTTGACCTAAAAAG

AATTTCATTAGAACCTCATCTGAAAACCGTGCGATTTAACATTACCGCCGCCAATATCAGAAATGTTAAT

TTCACGCGCAATTGAAGGGTCAATGTCAATTTCACGATTGAGTTTAGTGATAGCTAAAGTATCACGCCCA

TTTACAGTACGGAACTCTAAAGGACAAACCACATCAACGTAGTTTTTAATCGATTCGCTAGTAAGTTGCA

AATGTGCAGGAAGGTCTTTAGGTGCCTTTGAGAAAACCACTTCACAGAAATTTTTGCGGGTATCAAAATA

AGTAGTCATAAACATAATATTTTCCTCAGTAAGGGGCTGAAGCCCCTCATTTTATTTTAAATATCAAATT

CATTAAGAACTACATCAAAGATTGCTTCAAGATGCTCAGGTTTAGCTCTGTTACTCAGAATATGACGAAT

CCAAGTTTTAACTAAGAGTTTACGATTAGCACCATTCCAGCAAGGATGAGTCCCTAAATCGCGTTGGCGG

AAATCATCATCCAGAGCGATTTTGAAGTTGGAACCTTTCATCGTGATTGAAACCGTGATACCGTTTTCAA

ATCGCATATAAACGTAGTTAGGAGTCATATACTGTTCAATTTCGCATACTGATCCATTTTGATGTTTCCA

GAGGCAAATAGTATCAATAGAACCTGCAATACCATTAGAAACATATTTACGTTCAAAGTTAATGTAGTTC

ATTTTTATTCTCCGAGATGTTTAATTGCGGTACAGGTATATAATATCATATCCTGTACCAAAGTAAACAA

TTATTTTACTACTTTCCAATGCTGCATGTCAAGTTTACCAACTTTTTTCATCTTCTCAATTAAGCGTTCT

GCACGTTGGCGAGCTGTAACATAATGCCATTCGCCTAATTCATTTTGTTCAATTTTTCCAACGATTACTG

TATTCAATTCATAAATCCAACCAGTAAAGAAATTATGAACTTGAATTGTAAAGGTGAAATCTGTTCCCAT

ACCTTCTGTTGTTTCTACTTCAATAATATCACCTTCAACTGCCATTAAGAACCACATAGTTTCATCATAT

TTACCATTGAAGCATTTAGTTTTAACTGCAGCGTTCAGATTAATCGTTTTCATTTTATTCTCCTTTGTTT

GTGTAAGATAATACTATCACAAAGGAACTATACTGTAAACAACTTTGTGCAATCTTTGGAAAATAAAAAA

GGACTCCCGAAGGAGTCCTCAACTTATGCTTTCTGCTTACCAAAACGAGAAGCATCATCTCGAAGAACCG

CACGTGCTCGGCGCATGATCTTCTCAACAGTTTGATTGATACGAGAGTTCGACCCACGCTTGTAGCCAGC

GCGTTTAGAATCACCAACTTTCTTTTCAACTGCTTTCTTTGCTTTAGCTTGTTTTGCCATTATAAATTCT

CTTTTAAATGAAAATGCAGGACTTATTGGCATTGCCTGCGCAAGCCCTCAAGGGGAACATAGGTTTTTGG

ATATTTAACGACCAGGATAACCATAAACCCGTCATCATTCACATTCAAGAGGTACACCGTAAAACTGTCG

GGGTCTTAAAACTATAATGATTCGCAAATCATTAATCAGACAGTTCGACGGCTCCTCGATTTAGCTCACA

CTAAGGCAGTGAATCTCCAATAAATTACTTCAGTGTTACCACAAAGTGACGAACTGCTTTTCGTGCAGCA

GAAGCCAGAGGCTTAGCATATTTAAGTTCATCTTTTTCCTGAAGCTCAGCAGCTAATGCAGTTTGAGCAG

GATTCAGATGTTTGAAATAACGCAGGATTTCAAGAGCTTCGGCTTCAACATCAATAGATGCGCCATAGTT

TTCGTGACCATTATTCCATGCGTTTCGTTGCAGTTCAAGAGCGTGTTGTAATTGTTTAATCATTTAAAAA

TTCTCGTTAGAGATTAAAACTCGGTAGTCACGTTCTTCTGAATTTCATCTTCTTTCGACAGATCTCTCAG

TTGTAGACTACCACATAGAATTGTTCGGTTAACTTATTATTCCGACACCCAATTCATATTATTATTTATA

TCACTTATAAAGACACGGAATAGCTTTATAGTGACAGGTAACGAATTTTTGTTTAATTTCTTTTGGCTGC

TTAAGACCCAGAGCTACAAAAGGATGCGGAACATTTCGAATTTGACCAACTGGAAGAGAAGTCAAATCAC

CAACTTCGCAGAAACCTTCAGGAACATCAGGACCGACAGAGTGAACTACACACAGTTCAGGAACTTCACC

TTGAACACGTTTACCGATAATAAGTCCTGATTCTGTAACTTCTTCATCACCGGCTTGTGCAGGTTCAGAA

ACTAAAATAACATATTCACCGACAGCACGAATTGGTAGCTGTTGTACTTCAGACATCGTTTTTCCTTTTT

-continued

GTTAACAGATGAATTAATAATAACAAATAGTTCTTAAAGCATTTATTTACCAATAAATTGAAGCAAATGC

TCAACTTTCATACCATTAACGGAAATCAATTTGTCAATAGAAAAACCTCGCCACGCACCAAGCTCAACAT

CAAATACTGGAATCATGTCAGTAGATTCTTTCCGAGTAGATTCAGTCAATTTGCCAGTTTGCATGGTTGG

CATAAAGTCTGCATCACGAGTACCTTTCATAGTACGAATAGTACCATCAGACTTTTCAAAAACTACGTTT

GAAACACCCATGGACAATTTAGTTTTCAAAATTTCACGAATTGCTACTTTCTGCTCAGTTGTCAGTTTCA

TTTATTTACCTATTACAGTTTTAATATGAGTTGTTCCACGTTCTTTAAGGGTGGAAAGTAATTTTTGGCA

TTTTTCTAAATCAGATTTCCAACTATATGGTCTATCAATACAAACCCAATTTGTCTTATAATACTGTTTC

CATTTAGAGAAAAAATATTTCTTATACTCTACAGCAAATGAGATGTTCTCGTTAGAATAAGAACTAATTG

CTGTGAGTTTTACCAAACGAAATTTCATTATTCACCACAGAATTCGTTGATATTTTCCCAGTTTAACTTA

TTCAAGTTTTTCTTAGGAACATTAAACACTTCAATACCTGCATTTCGCAGAATATCATCCCAACCGGGTT

TATTTTTGTCGTATGTTTCACAATAAACCAGCTTTTTAATACCAGATTGAGCTATCGCTTTTGCGCAATC

TGGACAAGGAGAAAGTGTTACATACATAGTAGCACCTTCAATAGAAGAACCATTTCGTGCAGCAAACAAA

ATTGCATTTAGTTCAGCATGAATTTCATTTTTAGATGACCATTCCGAGTGAGCACTACGATGTTCTTTCG

CCAAAACAAAACGATCAGTTGAACCAAATGATACGCATTCAGGCTTATGACCTTGAATGATAGCATGTTT

AGGCTTATTCAACAACCATCCTTGCTCAGCAGCATAATCACAACAGTTCACACCCCCTGCGGGTGAACCA

TTATACCCAGTAGAAATAATACGTCCATTCTTTTCAATTACTGCTCCTACCTTCCAGGAGCAACATTTTG

ATTCCTGCGATACTAAATATGCAATTTGAAGTACTGTACTCGCTTTCATTTCATAATCACCAGATAAGCA

GATTTAGCAGTTTCAACACGATAAATTTCGTGACGAAGTTTAGTTATACTTTTAATAACAGAACTAATTA

TATTCTGCCCATCTTTAAAGCGGTTTTTCTTATCAATAAAAACTGCGCCAGTCATCTTTTTGTGAAGCTC

AACTGGATACTTCGTCACAATAATAGCATCATACACAGAAGGATGAATACTATTCACCAGAGTATCATTC

ATTAAAGTTATTCTAATGAACTGTGCTGTTTCAGAATCAAGCGCTCTATGATCGCCAGTATCATTTTCAA

GACAATTATCAATTATATCAGTTAAATTCATCATAGTACGCCATACACCCTTTGTGCTTCAACTAATCCA

TCAAAATCCAGTTTAAGATGCGATATTTGATCGCCATCACCTGGATTCACAATTACTAATACTGAACGAG

GAGTTTCGGTAATAACACGAACCGATGTTTCAGGAAATCGTTCAGAAACCTTATTTACTAATTCCTGCGC

AAATAGTTTAACTTTTTCTTGGAATTCCTTTAACAGTAATCGGTTTTTCACTTAGCAACATTTTGTTTTC

CTCATTTGTTTTGGTAGAGCTATAATATCACAACTCTACCGTAAAGTAAACCATTAAATCGCTTTGAATT

CCGCAGTTTGAGATTCAAAGCGAATATCGCCTTTGATAACAAGCTCAGCATCAAGACCAAATACGACAAT

GATATGCGCGGAACCTGGATACAGTGTAATGGCAATAGAATCCACCTGGTCTGGAAGCAAAGTGTTCAAT

ACATGAGTCACTTGAGCATGGATTCGAAGCTCAGCTGCGTTATCAAGTTTTTCAAACATATTATTAGCGA

TAATTTGGCTAAACACTACTTCTACGATTTTAGAGTAAGTCGGAAACATATTTACCTCACATAATTTTCT

TCAAGCCAATCAATAACATCCAACGCATTATCAAAAGTTGAACCATCTACTCTGTCTTCTGTTTCATAAT

CAAGAACATCTAGGCCTACTCTTCCGTCAACAATAGGCCATAGACAAAATAGATATTTCTTTTCTTTTTC

AATTTTATCACAAAGACGATAAATCTTTTCTAGGTTATTCATAAGTTTTCCATGGTAAAGGCAGTTTAGT

TTTCTTTACTACTAGTTCAACATCGGGATTCTTTTCTCTTAATTTAAGACATTCCTCCCATGCTCTATTT

TCACTAGTAAATACACAAAATTGCCCATTACTAGTACCAACTAAACCGCTATTTACAATAACAATAGCCC

AAGTTTCATGGTGCCAAGCCATTAAAAATCTCCCGAAGCGACTTGCCAGCATTCAACACCGATACGACGC

CACATTTCAACTACTTGAGTTCGGTCATCAATAGCTAATTTCACGTCAAAATGCGGTGCAATGTGTTTCC

AGAAAATTTCTTCTTTAACTACATCGTCTTTACGGGTATCGCCTTGTTCGCGCTGACATTGCATAACTAA

TGGAACGCCAGCAATGTCCTCAACCCATTTACGGGTCATACGATAATATTTCGTTGGGTCTTCTTTAGTT

CCACTTTCACGACCTGAAACGACTACGATTTGATAACCCATAAGAGCATACATCTTAGACAGTTCAACAA

CCATAGGATTGATAACATCGGTATCGCATTTTTCAAGGTCATAAGGACCACGACCATTCATTTTAGCTAG

-continued

TGTACCATCAACATCAAAAATAACTGCTTTTGGTTTACCAGGAGTCCCATTATATACTGGAAGACCGAGA

TACTCTCGCATGCTTTTATACATTGAACGTAAAACATCAATTGGTACTGCTTTAGTTCCGCGTTTTGAGT

TACGTTTAACCAATTCAGTCCAAGGAACATCAAACACTTTATGTTCAACTTTCCAGCCGTATTCTTTGGC

AAAAGTTTCCCATGCTAGGCGACGTTCAGGATTCAGGTTAGTATCTGAAATGATTACTCCCTTAACAGAA

TCGCCACCGTACAGAATACTTTTAGCTGTATCAAACTGCATACCAGTTACGATACCTTCTTTCTTTTTGG

TATACTTGTACTCATCGCGTTCTTCATGCGCCATAATAGATTGGCGATAGTCATCACGATTGATATTATA

AAACCCGGGATTCTTAGCAATAAATTCACGAGCCCAAGTACTCTTACCAGAACCAGGACAGCCAATAGTC

AAAATAATCTTTTTCATTTATTTTTTCTCAACTAATGATTGAATATAATCATGTAGGTCTTTAGATGCTT

TACCCCACTTATTTTGATATTCATTTTTGAGATTAGCACGTGATTGAGCTAATAAAACATCATTAGTTGG

AGGTAAAGATTCTAACCGCTGAATCTGGCGTCCATAAATCATTGCAGCCATCTCGGATTCATAAATCAAT

CCTTTGAGATGTTCAAATTGATGCCATGAAATCATTTACATTTATCCTCTTTTAGCTCTTGACGATAATA

ACATATCATAGTTTTCTGGTCATGTACATATCGTTTTACATCATTAAGCCAAATACGAAATTCCTGAGAA

TCTTCAAATGGCATACCGACCCAGGCTTTACCATCAATAACTTTAACTTGCCAAGATAGTTTAGCTTCAT

CATATGACTTTATTTGCACAGGCCAATTAGGATGAACTGTTTCTTTCTTTACTTCTAGAGGCTTTGTCGA

ACAACCAACTAGAAGACCAATAGATAATATTACTGCTGATAGTTTAATCATTTAGAAAGGTCCTGGATGT

CTTCTGCGAACTTGTTGAAGGAGTTGTTGATTTGTTTTTCAACCAATCCTGGCTTATGAGCCACCACATC

CGCCTTCTTTGCATCTTTGCGCAGTTTTTCATTTTCACGCTCAATAGCAGCAATTGCCTCACGATTTTTA

TTATTCATCGCATCAATATAATTATACTGAATTCGCAAATTATTTAATGCTAAGGCGTTTTCATTGGCCG

TTTTTGTAATTTCAGTAACTGATGTTTCTAATCTTTCTACCTTATGTTTTAAAATAATAGATGTTCCGCC

AAATGCTATTACAAGTAATAGCAATCCAGCTGTAAAATTACTTACATGCATAAAGTTTTAATAACCTCTA

CAATATCGTCTTGAGAAAGACCGTTAATTAAAATATGATGTTCAGCTGGAGATTTAGAAATTTTAAAGCA

TGCCTCAACATCTTCTGCCATATCCGATGCACTACGATTTGGATTACTAATACCAAGGCGATGTTTTCCC

GTCAAAGGATTAACGATGATATAGCATTTGCAGCTATTGATATGAACATTGGGTTGAGTCTGATTAATGA

ACACTTCACAATCATACTTAGCAAGTTGATTTTCTAAAAAGACTTTCATCTCTTCAACCGCATCAGGAAG

CATATCACGGGCTTGCTCAAGACGACGATTTCGATATTCTTTAATGGTCGTTTTCCGCTTGACTTGCTTA

GCTAAATCTTTCTTAAGACCAGTGATATATCCAACTCGACGATTTCCTTTGAATACAGAAATCCCATCTG

TAGTATCACCGTATGCTTCAACGACCATTTCAGTAGTAATAAGTTGTAAATCCATCATAAAGTCCTCATG

TTATGTCAGTAAGACTACTATAACACAACACGAGGGACTTGTAAACAACTTAGTATCCTTCTGGGATAAA

TTTTTTATAATTTTTCAAAAAATTCTGTTCGATTTCACACATGACCTTTTCTTGACTATCGTACCCCTGG

TATAAGCTCATGATGATACCGAACAGGTGATCCATTCCAGCACCTTTAGCAACACCTTGTGCTTCCATTG

CATAAGTCTTTCTATCCTTACCGCAATGCTTATTATGACAGTCAAGAACTAAAAACAGAGCTCGGTCTAA

GTACTTCAGATAAGTCGTTTCAAATGCTTCAATTTTTCTGTATGAATATTCATCGTCAGCATACATTGCT

TTAAGATCATCTGATGCACCATCAATAATAGTCTTAAACAATTTTTCTGGATTATCTAATGAACTTTTTG

TACTATGAAGAGACACGTACCAGTCAGACTTAATTTTAAAATGAGAACCATCTTTCATCACAGCAACATA

GCCTTCGATGTTTTCTGCATTTTTAGCTTCTTCTATCCATTTAGGGCTATCGATTTCGTATCGTTCAACT

AGATACGGACGAAGAGTAGCATCTTTATAAATATCATCGTATGAAATGTATTCACCCGTTTCGTTTTCAC

GAACATTCAGTAAAATAATTTTCATCTCTTGATAAGCAAGAACGATTCTATTCGTCGGGGCAACGAATTC

GAAGTTAGCAGTAAATCCATCTTCAGCTAATTCTTTAAGTCTATCACGCAACCGATGGTGATTAATATTC

ATCAAAATTCCATTAGCCATTAAAGCCTGCTCAGATTTGATTGAACCCCTTTGATTTGAACAGAATTTCAT

CACCGTCTAAATAAGTTGATACCAAAGACCCGTCTTCTTTTGTTAGAATATAATCAACATCGTTTAAATC

-continued

GATATTCATCGTGAACGGATTTTCATTCAAGTTAAAAAACTTTTCCATAGGACGAGAAGCAATTCTTACT

GGTTTTTCTCCATCCATTTCAAACATAATTCCACGACATTCTAGTGCATCTGGAAGTAACCAATCAGAAT

AAGATGCATAATTATATGAGAAAATTCTGTAAGTTCTTCCAGATGCACTTACATCATCTGAGTAAAAAA

CTTACGCTGCGAATCCTTACATAGTTCCATTAAATTGTTAAAAAGTTCTTGCATTGTGTATCCTCTTTTG

TGTTTTGAATATAGTACCACACTCCATGTGGAAGCATCATTTTTTCTTGTGTTGAATATTCCAAGGCGGG

TTAAACAGTTTAATGAATAGAGGCTCCTCTAAGTCAATCGTTGCGATTGTCATTGTACCTAACTCATTTG

TCATAGAAAGATTAAAACATTGGCGGGCGTAAAATTCAACTTTGCTTCCTTCCTTTAGCGCAGAATGAAT

TAATGCAGATTTAGTAGAATCAGACGTTTTGTCTTTGCGGTTAATAGCAGTTCTATAATAGTTTATTCTT

TTACGTAAATTTTTAGTTTTTCCAATATAAACAAGCTCATCATTTATAGCAATAGCATAAATTACGTTAT

ACTTGTTTGGAATAGATAATTGTTTTATACTTCCATTGTCGTCTAATTCTAGCTCAGTATATTTAATAAA

TGAATATTCTGTTGCAATTTCTTTCATAATAAAATGGGCCTTGCGGCCCACTCCTTAAAAGTATTTTTTA

AAACTCATCATAACTTTATCATCAACATCATTATCAATCTGTGCAACAAGGTAAGATGACAGTTCTACTT

CTTGCGGCGCGGATTGAACATTATCAGAATTAAGATATTCACGAATCCAAGGATATGGATGTTTAACCGG

AGCATCGGTAATTGGGCATGGAAGACCGCACTGTTTCATACGAGATACAGTTAAGTAATCAATAAAGCTC

CACATGCTATTTGTATTTAATCCAGGAACATCACCATCTTTAAATAAATGAACTGCCCAGTCTTTTTCCT

GGCGGTTAACTTCCATGAAAATATCAACTGCTTCTTGTTCACACTCTTGGGCAATTTTAACCCATTCATC

ACCATCAGTACCGGATTGAAGTTGACGAATAATATATTGGGTGCCTTTAAGGTGAAGCTGTTCATCACGT

GCAATGAACTTCATAATCTTGGCATTACCTTCCATGATTTCCATGTTCTTATGGAAGTTAAAGGTACCGT

ATGTTCGATTGAGCTCGCTAATTCTCAACCCGTTCTCTTATGAACTGCTGCATGTTACCATGCAGTCCAG

ACTATATCACAATCCCGGAGGGATTCTCCCCATTTCGAGTCGCTTGACCCTACGTCCGAAGACTAGTCGT

TGAACCTTGTTTTGCAATTGTCGCCGTGCCATCGTTTATATGTTGATGGTGATAAATCTTTCTTATCACA

ATATGGACAATTCAATTGAATTCTATTTGGATTTAATTTACATCTGTCATTATGTTTTAGATAAAATCCA

GGACCTTTACCAATGTGACCACAGAAATCACATGTGATTTCTTTTTGTGCAGGATGGGTCCCGTTCTTAA

CCATTTCTAATGTTTTTGCTGATGTTCTTTTCTTATGTTCTTCCATCAGAATCTTTAGGTATAGGTCCGT

TAGCATCTATCCAAATTTTTCTATAGTTCAATTGTGCATCCTCTTAAAAGTATAATCATATTTATATTAT

ACTAATTAAAGGTGCAAGCAAAACCTTGGCTGCTAGTTTTCCATAAAGGACTTTCCAGCAATTAAAGGAG

TTTTCGATAAACGTTACCGTTTAAAGGCGCATTTTACGCAAAAGATACATAAAAACGAATAGCTTCTAAG

GCATTAATAACGTGCAAACAGAGGTAAAGAGATTTCATCAGATCTCGTTTAGCTCTTTGCTCAACGTCTT

TATCAGCTAGAATTAGACCTTGGTCTTTATAATATTCAACCATGTCTTTAGCATTTTCCCATTCACGGGT

TTTAACCAAGACATCATCGTAATATCGCCCAATGGACTCAGCACGTTTCATAATAGCTTCATCTAATACA

ATCTCATCAAACACCTTCGATGGATCAGTATAAAGATTTCGCATGATATGAGTATATGAACGACTGTGAA

TAGTTTCACTAAAAGTCCATGTAGCAACCCATGTATCAAGGCTTGGGTCTGAAATTAATGACATAAGTAC

AGCAGATGGCGCACGACCCTGAATGCTATCCAAAAGTGATTGATACTTCAGGTTGTTAGTAAAAATATTT

TGCTGATACTGAGGAAGCTTATTAAATTGCGCAGCATCCATCATTAAGTTTACTTCTTCAGGACGCCAAA

AAAAACTGATCTGCCGCTCAATGAGTTCTTCAAATACTCGATGTCGTTGAATATCATATCGAGCTAAACC

TAATCCAGAACCAAAGAACATCGGTTCATTCAAAACATCAACTGGATTTGTATTAAAAACTGTACTCATT

TAGAATCCTTAAATTTACATTTATCATAATGCCATCTTAAAGCATTGCCTTTATTAACTTTCTTACCACA

GTGCGGGCAAGGTGGATACTCTGCTCCTTGTTTAGTTCTCAAAGAAATCAAATCACGGGTTTCTTTAGTA

TGAGGAACATCTCTTGTCGGAGAAATTGTACCATACATCGGATTAAGCACGCCGACTTTAGCAGCAGCTA

TATTCTTTTTAGCTTCTTCAGTTTTAGGCTTTCTCATCTTTTTCTTAGGTTTCTTCGCTTTTAGCCCTTC

CTTTGGTTGCCGCCGATATTTTGTGTTTGGTTTCTTCTGTTAAACGCAGACCTGTTTTCGCTTTTTGACA

-continued

TTTTCAGTCTCGTTTCTTCAGAAATGACCGTACCTTTGCGAAATTGCGAATTTAACTTCTTTGCATGGGC
ATATATTTTAGAATGAACTTTATAATGACGTTTCTTAGTTCCTTTCATATTGCACATCATGAAAAATGCG
AATATAACAGATTTTACCGGATAAATCTTTGATAAAATAGCATGCGCTATAAAATGCTCTCTAGCTGTTA
ATTCAACTAAATTTTCTTTATCATCAGAACCTCCCATGCATCTAGGGATTATATGATGTGTCTCTTTATA
TTCGGATAAAGGTTCCCGAGCCTGAGCTCGGGAAATTAGGTCGTTATAGATTTTTTGATAATTCATTACA
ATTTACACGCTGCACAATCATCGGCTTTAGGAGTTTCTATTTCATAATCATCAGTACCAGAACCATCACG
GGTATTATGATAATAGAAATTTTTAATGCCATAATACCATCCGTATAGCATGTCATCAATCATTATTGAC
ATTGGAACCTTTCCTTTTGGAAAAATCTGCGGGTCATAATATGTATTCGCTGAAGCTGATTGACATACCC
ATTTCAGCATAATAGCTACCTGCGTAAGATAAGGTTTATTACCTTTCTTAGCTAATTTCCATGTATAATC
ATAGAGGTCTATGTTATGCTCAATATTGGGCACGACTTGATTAAAGGAACCCTCTTTTGATTCTTTAACA
CTTACCGGTCCACGTGGAGGCTCGTAGCCGTTTGTACTGTTAGAAACTTGGGAAGATGACTCACATGGCA
TAAGTGCTGATAATGTGCTATTACGGATGCCAAATAGCTTAAGGTCTTCCCGCAGCGCCGACCAGTCACA
AACGTATTTTGGAGCTGCGATTTGGTCAATCTTTTTATTGTACCAGTCGATAGGTAATTCGCCTCGAGAC
CAACGAGTGTCTGAATAATATTCCGAAGGTCCTTTTTCTTTGGCGAGCTTAATGGATGCTTTAATGAGTC
CATACTGTAATCTCTCAAATAGTTCATGTGTTAAATCGTTAGCATCTTCATAAGAAGCAAAGTTACTTGC
CAGCCAAGCTGCATAGTTGGTAACACCTACACCGAGGTTACGACGCTTTTTAGCTTTTTCTGCTTCAGGA
ACCGGATATCCTTGGTAATCCAACAGATTATCAAGAGCACGAACTTGAACTTCTGCCAATTCATTAATTT
TATCTTGGTCTTGCCAGTCAAAATTATCTAATACGAATGCAGAGAGAGTACACAATCCAATTTCAGCATC
AGGGCTATTCACATCATTTGTTGGAATAGCAATTTCACAGCACAAGTTACTCTGACGAATAGGTGCCTTT
TCACGAATAAACGGAGTATAGTTATTCGTATTATCAATGAACTGCACATAAATCCTTGCTGTTCCTGAAC
GTTCAGTCATGAGCAATTCAAATAGTTCACGGGCTTTAATACGCTTTTTACGAATATTAGGGTCTTTTTC
TGCTGCTTCGTATAATTCACGGAAACGGTCTTGGTCTTTAAAATAAGAATAATAAAGCTCGCCACCCATT
TCATGCGGACTGAACAAAGTAATGTAATCGTTTTTTCCAAAACGTTCCATCATCAAATCATTCAGTTGAA
CACCATAATCCATATGACGAATGCGGTTTTCTTCTACGCCTTTGTTATTTTTCAAAACGAGAAGATTTTC
AACTTCCAAATGCCAAATAGGATAATAAGCAGTAGCAGCGCCGCCACGAATTCCACCCTGTGAACATGAT
TTAACTGCAGTCTGAAAATGTTTCCAAAAAGGAATAACACCAGTATGGCGTACTTCACCCATGCCAATCT
TAGAACCTTCGGCACGAATCATACCAACGTTAATACCAATTCCAGCGCGTTTAGAGATATATTCAACAAT
TGAAGCAGAAGCCTTATTGATAGACTTCAATGAATCTCCTGCCTCAATAACAACACATGAACTAAACTGT
CGAGTCGGAGTACGACAACCAGCCATAATAGGAGTTGGCAATGAAATCTGTCGAGTTGATACTGCTTCAT
AAAAACGGATAACATGTTTTAATCTATCAACAGGTTCATCTTGATGCAGTGCCATTCCAATAGTCATAAA
TGCAAACTGTGGAGTTTCATAAATTTGACCAGTGGTTTTATCTTTAACTAGATATTTTTCTTTTAATTGC
ATTGCCCCGGAATAAGTAAATTCCATATCCCGTTCGTGCTTAATTTTTGATTCTAAAAATGTAATTTCTT
CTGCTGAATATTTTGACAATAATTCAGGGTCGTATTTACCTGCATTTACACAATAAGAAATATGGTCAAT
AAATGAACGTGGTTCATACTGCCCATAAACATGCTTACGAAGAGCAAACATTAAACAGCGTGCAGCTACA
TATTGATAATCAGGTTCTTCAACCGAAATAGAATTCGCAGCAGCCTTAATGACAATAGTCTGAATATCAT
CAGTTGTCATTCCATCACGGAGATAAGATTTAATATTTTCATATAATTCATAAGGATCTACTGATGTTCC
TTCAGCTGCCCAAGATAAAACTTTAATAATTTTTTGTGGGTCAAAGCTCTGAGAAACACCACTACTTTTG
ATAACATTAATTAATTGCATAAGTCCTCAACTTGAAAATCGTCTTTAAACAATCGGTTAACTATATGAGC
TATTATATCACCATGACACGGCTTTGGTTTACATGTGCATCCTAGCCTCATTCCACGTAAAGGCTCTAAA
TGTGCTTTAGTTATTTCTCCGGATTTAATTCGACGTATAAAATCTTTTTTGAATAATTCAATGGCAGCCT

-continued

CCCGGCTGCCAGCATCTTTACCGACGTAATTTCCCCAAAATGTACCGCGGTGAATATTAACATCAAAGTC

GGATTTATATTTATTCACTACCCGGCATAGACGGCCCACGCTGGAATAATTCGTCATATTGTTTTTCCGT

TAAAACAGTAATATCGTAGTAACAGTCAGAAGAAGTTTTAACTGTGGAAATTTTATTATCAAAATACTCA

CGAGTCATTTTATGAGTATAGTATTTTTTACCATAAATGGTAATAGGCTGTTCTGGTCCTGGAACTTCTA

ACTCGCTTGGGTTAGGAAGTGTAAAAAGAACTACACCAGAAGTATCTTTAAATCGTAAAATCATATATCC

TCGCAATAATAAAATTACACCGCCATCTTTCCTTTAATAGGAGGGTGTGATACATAGTTGTTAAGAACGA

AATCTTTAGGCCTAAGTTTAAGAACATATTTTAATTGTTCTTTAGTAGAAAGATATCGGAATTTATAAGG

TAGACCACTTATTACCAGCTCACAAAGCTCTTTAGGTTCACGCCTCAAAATTTCTTTACATTGTTCTACG

TGATTCATATAGATATGAGTATTACCACCAGAAAATATCAAATCCCCTGGAATAAGATTACACATCTTAG

CTACAATATGAACTAACGTAGCATATGACGCAATATTAAACGGTAGCATTATGTTCAGATAAGGTCGTTA

ATCTTACCCCGGAATTATATCCAGCTGCATGTCACCATGCAGAGCAGACTATATCTCCAACTTGTTAAAG

CAAGTTGTCTATCGTTTCGAGTCACTTGACCCTACTCCCCAAAGGGATAGTCGTTAGGCATTTATGTAGA

ACCAATTCCATTTATCAGATTTTACACGATAAGTAACTAATCCAGACGAAATTTTAAAATGTCTAGCTGC

ATCTGCTGCACAATCAAAAATAACCCCATCACATGAAATCTTTTTAATATTACTAGGCTTTTTACCTTTC

ATCTTTTCTGATATTTTAGATTTAGTTATGTCTGAATGCTTATGATTAAAGAATGAATTATTTTCACCTG

AACGATTTCTGCATTTACTACAAGTATAAGCAGAAGTTTGTATGCGAACACCGCACTTACAAAACTTATG

GGTTTCTGGATTCCAACGCCCGTTTTTACTTCCGGGTTTACTGTAAAGAGCTTTCCGACCATCAGGTCCA

AGTTTAAGCATCTTAGCTTTAACAGTTTCAGAACGTTTCTTAATAATTTCTTCTTTTAATGGATGCGTAG

AACATGTATCACCAAACGTTGCATCAGCAATATTGTATCCATTAATTTTAGAATTAAGCTCTTTAATCCA

AAAATTTTCTCGTTCAATAATCAAATCTTTCTCATATGGAATTTCTTCCAAAATAGAACATTCAAACACA

TTACCATGTTTGTTAAAAGACCTCTGAAGTTTTATAGAAGAATGGCATCCTTTTTCTAAATCTTTAAAAT

GCCTCTTCCATCTCTTTTCAAAATCTTTAGCACTTCCTACATATACTTTATTGTTTAAAGTATTTTTAAT

CTGATAAATTCCGCTTTTCATAAATACCTCTTTAAATATAGAAGTATTTATTAAAGGGCAAGTCCTACAA

TTTAGCACGGGATTGTCTACTAGAGAGGTTCCCCGTTTAGATAGATTACAAGTATAAGTCACCTTATACT

CAGGCCTCAATTAACCCAAGAAAACATCTACTGAGCGTTGATACCACTGCAAATCCAAATAGCCATTACG

CACATTAAACTGATAGAACATATGACAAGGCGGTAATGCCATATATTTAAGTTCAGCTGGATTCCATGCA

GAAACAATTTGACGCCTATCATTTGGCAGTTTTTTAATACGATCAATAACTTCTATAATTTGGTCTACAC

CACCAAAATCACGCCACTGTTTTCCATAAATTGGACCAAGTTCACCGCTATGGTATCCTAAATCTTTTGC

TTGATTTTCGTAATTTTCATCCCAGACTGTTTTGCCTTGGATTAACGAATCGTGTTGAATTAATCGTAAA

TCATTGACATTTGTGCTTCCTGATAAAAACCATATTAGCTCAGCAATGCAAGCTTTCCAGGCGAGCTTCT

TAGTTGTTACCGCAGGAAAACCTTTAGTTAAATCCCAGCGTAATTTAGATCCGAACAGAGCAATTGTTCC

TGTGCCTGTACGATCATCGGTTTCATAACCATTTTCAAAAATGTCTTTAATTAAATCTTGGTATTGTTTC

ATTTATATACTGATTCCGTAAGGGTTGTTACTTCATCTATTTTATACCAATGCGTTTCAACCATTTCACG

CTTGCTTATATCATCAAGAAAACTTGCGTCTAATTGAACTGTTGAATTAACACGATGCCTTTTAACGATG

CGAGAAACAACTACTTCATCTGCATAAGGTAATGCAGCATATAACAGAGCAGGCCCGCCAATTACACTTA

CTTTAGAATTCTGATCAAGCATAGTTTCGAATGGTGCATTAGGGCTTGACACTTGAATTTCGCCGCCAGA

AATGTAAGTTATATATTGCTCCCAAGTAATATAGAAATGTGCTAAATCGCCGTCTTTAGTTACAGGATAA

TCACGCGCAAGGTCACACACCACAATATGGCTACGACCAGGAAGTAATGTAGGCAATGACTGGAACGTTT

TAGCACCCATAATCATAATTGTGCCTTCAGTACGAGCTTTAAAATTCTGGAGGTCCTTTTTAACTCGTCC

CCATGGTAAACCATCACCTAAACCGAATGCTAATTCATTAAAGCCGTCGACCGTTTTAGTTGGAGAATAA

CGGAATACCAATTTAATCATTACGTAAATCCTATTTTAATTGAAAACGAATGCTTACTTGGATAATTTCA

-continued

ATGACATACATAATATTTTCCTCAAACAGACTTTTTCACAATTTTCCAATCAGCTTTAAACTGCTCGACG

TCAGAATGGTAAATCCAAAATCCTGCGCTTTCTCCGTCTTCATAAAGAGGACATCCATCGCATTCATCTT

CCCATCCCATATCACGTAAAAGATGTTCAGCTTTTTCAACAAGTTCAGAATCTTTACCGATGATATTAAA

ATACCATTTACCTCTAACTTCTGAATCTTTGATGCTCTGGCGTTGTAATCTCATTTTATTCTCCTTAGCA

AGCTTTAATCAAAAGATATAAACAGACCAACATAACTGCTGCCATAATATAAGGTGCGAACATTTTCTTT

TCTCCATTAGTTTTGATAGGGTAATAGTATCACACTACTACCCTGATGTAAACTACTTTTTGAAAGTTTT

TCGCAAAAGTTCAATGATTTCATCTACATTGTTTTCGTCAACAATGCAGTGAATTTTTGTTACGCCAGAA

ACCTTGTCTTTGACTTCATCTTCTTCAGAAGTCGGTTCTTTATATTCGCGGAAACAATAAAACTCTTCTT

CACTAAGTTCAAAATAATCATCACCCATACCATCATCATTATAGATTTCACCATTAGCACAAATGATTTC

GGTTACATAATCAAAGCCATCTAAACTTGATATTGATTTAACTTCAAACCAACCGCCATTTTCTTGAATG

ATGCCGACCATACTAGCATTTGATGAACTAATATCAATGAAAGATTTAATACGATGTGGATTTAACTCGT

ATTTTTTGCCGATTTCCATTTTGATTTTCCTCATTTTAATAGGGGCTTGATAGCCCCTTGATAATTATTG

TTCAATCAGTCCCATGTAAAATTCTGCGTCTTCAGAATCCATGCCATCACAATATTCATTAGCCATAAAG

CGGGTGAGGTCTTCAAGAGGACCTTCAATAACGATTTGAATACTCCAAAACTTAGAATCTTGCACGCTTG

TGATACTAAGTTCAGGATAACGATTACGAATAATCTCTTCAATATATTCAAAATCAACGATGTCAATATC

AACTTTAGCCATATTATTTTCCTCTTTAATTATTAGCAGTATTGCCGATAGTTGTATAGTACCATAAAGC

TTTATGCTTGTAAACCGTTTTGTGAAAAAATTTTTAAAATAAAAAAGGGGACCTCTAGGGTCCCCAATTA

ATTAGTAATATAATCTATTAAAGGTCATTCAAAAGGTCATCCAGGTCCGTGTCATCAGCACTAGATGAAC

TACCAGAGCTTGAGCTCATAAAATCATCTTCAGTTTTTGTATTGAAGTCATCAACATTGAATGCATCCAA

ATCATCAGCCACTTTATCAGCTTTCTTAGCAGCAGTTGCAGCAGCACCGCCCATCACAGCAGTTCCCATA

ACTTGACCGAATTTAGTATTAAGTTCTTCAAACGATTTGAATTTATCTTTAGAAGTCATTTCAGAAAGGT

CAACCATTTGTTCGAACAGTTCTTTCTGGAAAGATTCATCGTCAATGTTTGGAATCGCAGATTGATTCAG

GAATTTAGATTCATCGTAGTTACTAAATCCAGAAACTTGTTTAACTTTCAGTACAAAGTTAGCACCTTCC

CACGGACAAGTTACATCAACTGGAGTTTCACCCATTTCAACATCAACCGCAATCATTGCATTGATTTTAT

CCCAGATTTTCTTACCAAAGCGGTATTTAAATACTTTACCTTCGTTTTCTGGAGCAGCTGGGTCTTTTAC

TACAAGAATGTTAGCCCAGTAAGAAGTTTTACGTTTAACAAGACTGTACTCTTTATTGTCAGTGTTGTAT

AGATCATTTTTACTGATGTATTGACATACTGGGCAAGAATCGTAATCACCATGGGTAGATGAACATGTTT

CAATATACCATTTACCATTTTTCTTGAAACCGTGATTTACAAGAATTGCGAATGGTGCTTGTTCATCATT

TTTAGACGGAAGAAAACGAATTACTGCTTGACCGTTACCCGCATTATCGAGTTTCAGTTTCCACTCGCCT

TTATCTTCAGAAGAAAAACCTTTATTGCCATTCAGTTTAGCCATTTGTGCAGCGAGTTCAGCAGTAGATT

TACGTTTAAACATTTTTATTTCCTTTTTAATTTAATTTAATTAACAGTTGGTGCTATGACACTTTACCTC

ATAGCTGGCATAATTCGCAATACTCTGGGTCTTCGAGAGGTATCCAACCTGAGTTGAAATACTTTACCAT

CGATTTAGCAGTTGTATCAGTTATATTTATATTACCTTTAACTCTTCGCCATCCAGGAGTTTTACCGTAC

AGATTAGAGGATAATAATAACACATAATTCTCGTAAGCAATATGAGATAATTTCCAAGACTCTATATTAG

CTCGTGATGTTTTCCAAGGTCTAAAATCGTCACGGTTCATATAATTAGCCAATCTCATATGCTCTCTAAC

TTCCGGGTCTTTGGCTGGATGAGTTTCACCACTCACACCAAATCCACCACCAGCATATACCAGATTAAAA

TAGTCTGGATTATCTCTGGCATTTACTTCAAGTTGGTATTTTCGTTCTGCTTCAATAACATCCAAGTCAT

CATCAATTTGAATTATTTTAACGCTCGGTTTTTGAAGCATTAGCGCATTCAAAAATCTTTTTTGTTTACA

TGAGCTCCAGTATTCCTTTCCGGAAGAGTCATATATTATTCCGTTCTCAAATGAGCAATTTAATTTACTA

CCGATATAGTAGTATGGCGGAGTCTTATTTTTGACACGGTCTTCAAATGTAAACCAATATACTATATTCA

-continued

TATCAATACTTGCAAGATTTCACAGTTTCAATGAAAACATTTTTAGCTTTCTGTGAATCAATATTTAAAA

TTTTTCTATAAGCCTTTAACTTTATAGAATAATTATTCCAGACTAAATTATCAGTCTGTTCATCATGTTT

ATCAATTATATTTAAAAACGAATCAAGCAAGATAAACGTCTCAAACGAAATTATGTTCGATTGCAGAAGT

TTAAAAATATAACTTGATTGAACTTTTGGATTATACTCAAAAATTTCTTTAAAAGCAGAAACTTCAACTT

TTTTACTAAAATAATAAATGTTGCGAATATCTTCTTCAAACTTAAATTTAATTTGCTTTAAGCGTCCGAT

ATATTCACGATAAAACACAAGTGCATCAGCGTCAGAGATGTCACCAATCCAAGCATCTTGGTTAGCAACC

AAATTGCTTATAAAGATTAAAGCAAGTTCCTTTAATTTATATTTTTCTGATAACTTCTGGAAAAAATACT

TATCCCTTCGCTTTTGATAAGCGGCATCAGACACCCGCATGCACCAATTATACTTAATTACATCATACTT

TCCATTCATATGTTGTTTTATCATTAAGTATAATTTATAAACTGATTTACCATCAATGTATCTTTCACCA

CCAGCAGGCATGCGGAGTTTAATCATAGTAGAAAATCTAATGTATTAGTTTTTTCACAACGAACAACAGA

AGGACGTAAAAGATTTTCGTCAATAGCTTCTGACTGAATTTTTTCAATTATACCCGAAGGAATAAATTTA

GCAAATTGAGTTTCAGGAATAGAATTTTCTTCTAAGAATGCTGTTGTAGCTTCAAGATAACTCATTCCAA

ACTCTTCTACCATTTTTTCAATAATAAATCCATTTTCTTGGCGGTCAAGAAGCTTTGCTATTTCATCCTT

TTCTTTCTTAATTGAAAGTTCTTTTTCTGAAAGACCGGTCTCATCGACCGGACGAATATCATTTAGAGAA

AACTGTGTCATAAAGTTCAACTACCTCTTCAGTTTCAGCTTCAAACACATCACGGTTATCTTTATGATAC

AAAGCTAATAGACGATTAAACATCTTACCATCAACGCCAAGTTCATCTTTAGCACGAATTCGAATATCTT

TAATCAGTTCATTATAACCGGAAATTTTCAGTTTATGATCAGATGCTTCTTTAATAAATTTAGCCAAGTC

TTCGCCATGGATAGCTTCATCAAATTCAACCATTTCTTTTTTAGCCATTATTCACCTCAAAATTCATTAA

TGCTATTAGTTAATTTAGAAAGACCCGCTTTTACAAAATATGAATAAATTTTGCCACGCGGTGGTAATTT

ATATGAATTATAGTAATTCACAATGTTTGAAGCAATATTATCAGGAATATAATCAAAATCAATTAGAACT

AAATTTTCTTTATAACGATTATATTCAGATTCAGTGAGAAGCACCTTAGCTTGCTCACGGTCATTAGCAA

TAGCTTCAACGATTGAAGTTTTCATTGAAGGAGTTCGTTCACCTTCAACTCTGGTAAACCAAAAGTCAGA

TCGTACTTTAACTGAAGCAACGTTATCCTTTTTGTCGCCTTTAAGGATTTTAGTCATACAGTCAATTTCA

GCAGAACCGCTTTTAATTTTAACCCATTTCTTATGCATCGGAGACCATTGCTTAACATTTGGATATTTGT

GAAGCTGAGTAAAGTCACCATCTGACGAAATGATTAAAATCTTATGTCCTTCTAAAGAGAACTTTTTAAC

AAGAACAGCAATGTGGTCATCTGCTTCATACTTATCAATATCCATAACAATGTATGGCATATAAGCTTTC

AATTCATCTATAACTTTATGGCTGGATTCAAAATAACCTTCCCAGTCCCAAGTAGATTCTTCTCGTGCTT

TTCCACGGTTTTTCTTATAATAATAAGCGAAATCACGACGCCAATATCCAGATTTCGCGTTATCAATACA

CAGTACAATTTTAGTGTATCCAAGCGTTTTTGCTTTTTTGACATTAAACTTAATTGAGTTCAATATCAAA

TGACGAACCATTGATAAATTAATTTTTTCTTTATCTGGGAAGTTTACCAAAGCAGTTGAAAGCGCAATTT

GACTAAAGTCAATTAAGCAGATTCCTTCTTTGTAATCTTCATCCAACATCATTTCTAAATCCATATGAAC

CTCGTTCAATTAGTGAGATTTCTATTATATACCATCCAAATCTTAAAGTAAACAAGTATAAATACTTATT

ATTGAAAACACAATAGGAGCCCGGGAGAATGGCCGAGATTAAAAGAGAATTCAGAGCAGAAGATGGTCTG

GACGCAGGTGGTGATAAAAATAATCAACGTAGCTTTAGCTGATCGTACCGTAGGAACTGACGGTGTTAACG

TTGATTACTTAATTCAAGAAAACACAGTTCAACAGTATGATCCAACTCGTGGATATTTAAAAGATTTTGT

AATCATTTATGATAACCGCTTTTGGGCTGCTATAAATGATATTCCAAAACCAGCAGGAGCTTTTAATAGC

GGACGCTGGAGAGCATTACGTACCGATGCTAACTGGATTACGGTTTCATCTGGTTCATATCAATTAAAAT

CTGGTGAAGCAATTTCGGTTAACACCGCAGCTGGAAATGACATCACGTTTACTTTACCATCTTCTCCAAT

TGATGGTGATACTATCGTTCTCCAAGATATTGGAGGAAAACCTGGAGTTAACCAAGTTTTAATTGTAGCT

CCAGTACAAAGTATTGTAAACTTTAGAGGTGAACAGGTACGTTCAGTACTAATGACTCATCCAAAGTCAC

AGCTAGTTTTAATTTTTAGTAATCGTCTGTGGCAAATGTATGTTGCTGATTATAGTAGAGAAGCTATAGT

-continued

TGTAACACCAGCGAATACTTATCAAGCGCAATCCAACGATTTTATCGTACGTAGATTTACTTCTGCTGCA

CCAATTAATGTCAAACTTCCAAGATTTGCTAATCATGGCGATATTATTAATTTCGTCGATTTAGATAAAC

TAAATCCGCTTTATCATACAATTGTTACTACATACGATGAAACGACTTCAGTACAAGAAGTTGGAACTCA

TTCCATTGAAGGCCGTACATCGATTGACGGTTTCTTGATGTTTGATGATAATGAGAAATTATGGAGACTG

TTTGACGGGGATAGTAAAGCGCGTTTACGTATCATAACGACTAATTCAAACATTCGTCCAAATGAAGAAG

TTATGGTATTTGGTGCGAATAACGGAACAACTCAAACAATTGAGCTTAAGCTTCCAACTAATATTTCTGT

TGGTGATACTGTTAAAATTTCCATGAATTACATGAGAAAAGGACAAACAGTTAAAATCAAAGCTGCTGAT

GAAGATAAAATTGCTTCTTCAGTTCAATTGCTGCAATTCCCAAAACGCTCAGAATATCCACCTGAAGCTG

AATGGGTTACAGTTCAAGAATTAGTTTTTAACGATGAAACTAATTATGTTCCAGTTTTGGAGCTTGCTTA

CATAGAAGATTCTGATGGAAAATATTGGGTTGTACAGCAAAACGTTCCAACTGTAGAAAGAGTAGATTCT

TTAAATGATTCTACTAGAGCAAGATTAGGCGTAATTGCTTTAGCTACACAAGCTCAAGCTAATGTCGATT

TAGAAAATTCTCCACAAAAAGAATTAGCAATTACTCCAGAAACGTTAGCTAATCGTACTGCTACAGAAAC

TCGCAGAGGTATTGCAAGAATAGCAACTACTGCTCAAGTGAATCAGAACACCACATTCTCTTTTGCTGAT

GATATTATCATCACTCCTAAAAAGCTGAATGAAAGAACTGCTACAGAAACTCGTAGAGGTGTCGCAGAAA

TTGCTACGCAGCAAGAAACTAATGCAGGAACCGATGATACTACAATCATCACTCCTAAAAAGCTTCAAGC

TCGTCAAGGTTCTGAATCATTATCTGGTATTGTAACCTTTGTATCTACTGCAGGTGCTACTCCAGCTTCT

AGCCGTGAATTAAATGGTACGAATGTTTATAATAAAAACACTGATAATTTAGTTGTTTCACCTAAAGCTT

TGGATCAGTATAAAGCTACTCCAACACAGCAAGGTGCAGTAATTTTAGCAGTTGAAAGTGAAGTAATTGC

TGGACAAAGTCAGCAAGGATGGGCAAATGCTGTTGTAACGCCAGAAACGTTACATAAAAAGACATCAACT

GATGGAAGAATTGGTTTAATTGAAATTGCTACGCAAAGTGAAGTTAATACAGGAACTGATTATACTCGTG

CAGTCACTCCTAAAACTTTAAATGACCGTAGAGCAACTGAAAGTTTAAGTGGTATAGCTGAAATTGCTAC

ACAAGTTGAATTCGACGCAGGCGTCGACGATACTCGTATCTCTACACCATTAAAAATTAAAACCAGATTT

AATAGTACTGATCGTACTTCTGTTGTTGCTCTATCTGGATTAGTTGAATCAGGAACTCTCTGGGACCATT

ATACACTTAATATTCTTGAAGCAAATGAGACACAACGTGGTACACTTCGTGTAGCTACGCAGGTCGAAGC

TGCTGCGGGAACATTAGATAATGTTTTAATAACTCCTAAAAAGCTTTTAGGTACTAAATCTACTGAAGCG

CAAGAGGGTGTTATTAAAGTTGCAACTCAGTCTGAAACTGTGACTGGAACGTCAGCAAATACTGCTGTAT

CTCCAAAAAATTTAAAATGGATTGCGCAGAGTGAACCTACTTGGGCAGCTACTACTGCAATAAGAGGTTT

TGTTAAAACTTCATCTGGTTCAATTACATTCGTTGGTAATGATACAGTCGGTTCTACCCAAGATTTAGAA

CTGTATGAGAAAAATAGCTATGCGGTATCACCATATGAATTAAACCGTGTATTAGCAAATTATTTGCCAC

TAAAAGCAAAAGCTGCTGATACAAATTTATTGGATGGTCTAGATTCATCTCAGTTCATTCGTAGGGATAT

TGCACAGACGGTTAATGGTTCACTAACCTTAACCCAACAAACGAATCTGAGTGCCCCTCTTGTATCATCT

AGTACTGGTGAATTTGGTGGTTCATTGGCCGCTAATAGAACATTTACCATCCGTAATACAGGAGCCCCGA

CTAGTATCGTTTTCGAAAAAGGTCCTGCATCCGGGGCAAATCCTGCACAGTCAATGAGTATTCGTGTATG

GGGTAACCAATTTGGCGGCGGTAGTGATACGACCCGTTCGACAGTGTTTGAAGTTGGCGATGACACATCT

CATCACTTTTATTCTCAACGTAATAAAGACGGTAATATAGCGTTTAACATTAATGGTACTGTAATGCCAA

TAAACATTAATGCTTCCGGTTTGATGAATGTGAATGGCACTGCAACATTCGGTCGTTCAGTTACAGCCAA

TGGTGAATTCATCAGCAAGTCTGCAAATGCTTTTAGAGCAATAAACGGTGATTACGGATTCTTTATTCGT

AATGATGCCTCTAATACCTATTTTTTGCTCACTGCAGCCGGTGATCAGACTGGTGGTTTTAATGGATTAC

GCCCATTATTAATTAATAATCAATCCGGTCAGATTACAATTGGTGAAGGCTTAATCATTGCCAAAGGTGT

TACTATAAATTCAGGCGGTTTAACTGTTAACTCGAGAATTCGTTCTCAGGGTACTAAAACATCTGATTTA

-continued

TATACCCGTGCGCCAACATCTGATACTGTAGGATTCTGGTCAATCGATATTAATGATTCAGCCACTTATA

ACCAGTTCCCGGGTTATTTTAAAATGGTTGAAAAAACTAATGAAGTGACTGGGCTTCCATACTTAGAACG

TGGCGAAGAAGTTAAATCTCCTGGTACACTGACTCAGTTTGGTAACACACTTGATTCGCTTTACCAAGAT

TGGATTACTTATCCAACGACGCCAGAAGCGCGTACCACTCGCTGGACACGTACATGGCAGAAAACCAAAA

ACTCTTGGTCAAGTTTTGTTCAGGTATTTGACGGAGGTAACCCTCCTCAACCATCTGATATCGGTGCTTT

ACCATCTGATAATGCTACAATGGGGAATCTTACTATTCGTGATTTCTTGCGAATTGGTAATGTTCGCATT

GTTCCTGACCCAGTGAATAAAACGGTTAAATTTGAATGGGTTGAATAAGAGGTATTATGGAAAAATTTAT

GGCCGAGTTTGGACAAGGATATGTCCAAACGCCATTTTTATCGGAAAGTAATTCAGTAAGATATAAAATA

AGTATAGCGGGTTCTTGCCCGCTTTCTACAGCAGGACCATCATATGTTAAATTTCAGGATAATCCTGTAG

GAAGTCAAACATTTAGCGCAGGCCTCCATTTAAGAGTTTTTGACCCTTCCACCGGAGCATTAGTTGATAG

TAAGTCATATGCCTTTTCGACTTCAAATGATACTACATCAGCTGCTTTTGTTAGTTTCATGAATTCTTTG

ACGAATAATCGAATTGTTGCTATATTAACTAGTGGAAAGGTTAATTTTCCTCCTGAAGTAGTATCTTGGT

TAAGAACCGCCGGAACGTCTGCCTTTCCATCTGATTCTATATTGTCAAGATTTGACGTATCATATGCTGC

TTTTTATACTTCTTCTAAAAGAGCTATCGCATTAGAGCATGTTAAACTGAGTAATAGAAAAAGCACAGAT

GATTATCAAACTATTTTAGATGTTGTATTTGACAGTTTAGAAGATGTAGGGGCTACCGGGTTTCCAAGAG

GAACGTATGAAAGTGTTGAGCAATTCATGTCGGCAGTTGGTGGAACTAATGACGAAATTGCGAGATTGCC

AACTTCAGCTGCTATAAGTAAATTATCTGATTATAATTTAATTCCTGGAGATGTTCTTTATCTTAAAGCT

CAGTTATATGCTGATGCTGATTTACTTGCTCTTGGAACTACAAATATATCTATCCGTTTTTATAATGCAT

CTAACGGATATATTTCTTCAACACAAGCTGAATTTACTGGGCAAGCTGGGTCATGGGAATTAAAGGAAGA

TTATGTAGTTGTTCCAGAAAACGCAGTAGGATTTACGATATACGCACAGAGAACTGCACAAGCTGGCCAA

GGTGGCATGAGAAATTTAAGCTTTTCTGAAGTATCAAGAAATGGCGGCATTTCGAAACCTGCTGAATTTG

GCGTCAATGGTATTCGTGTTAATTATATCTGCGAATCCGCTTCACCCCCGGATATAATGGTACTTCCTAC

GCAAGCATCGTCTAAAACTGGTAAAGTGTTTGGGCAAGAATTTAGAGAAGTTTAAATTGAGGGACCCTTC

GGGTTCCCTTTTTCTTTATAAATACTATTCAAATAAAGGGGCATACAATGGCTGATTTAAAAGTAGGTTC

AACAACTGGAGGCTCTGTCATTTGGCATCAAGGAAATTTTCCATTGAATCCAGCCGGTGACGATGTACTC

TATAAATCATTTAAAATATATTCAGAATATAACAAACCACAAGCTGCTGATAACGATTTCGTTTCTAAAG

CTAATGGTGGTACTTATGCATCAAAGGTAACATTTAACGCTGGCATTCAAGTCCCATATGCTCCAAACAT

CATGAGCCCATGCGGGATTTATGGGGGTAACGGTGATGGTGCTACTTTTGATAAAGCAAATATCGATATT

GTTTCATGGTATGGCGTAGGATTTAAATCGTCATTTGGTTCAACAGGCCGAACTGTTGTAATTAATACAC

GCAATGGTGATATTAACACAAAAGGTGTTGTGTCGGCAGCTGGTCAAGTAAGAAGTGGTGCGGCTGCTCC

TATAGCAGCGAATGACCTTACTAGAAAGGACTATGTTGATGGAGCAATAAATACTGTTACTGCAAATGCA

AACTCTAGGGTGCTACGGTCTGGTGACACCATGACAGGTAATTTAACAGCGCCAAACTTTTTCTCGCAGA

ATCCTGCATCTCAACCCTCACACGTTCCACGATTTGACCAAATCGTAATTAAGGATTCTGTTCAAGATTT

CGGCTATTATTAAGAGGACTTATGGCTACTTTAAAACAAATACAATTTAAAAGAAGCAAAATCGCAGGAA

CACGTCCTGCTGCTTCAGTATTAGCCGAAGGTGAATTGGCTATAAACTTAAAAGATAGAACAATTTTTAC

TAAAGATGATTCAGGAAATATCATCGATCTAGGTTTTGCTAAAGGCGGGCAAGTTGATGGCAACGTTACT

ATTAACGGACTTTTGAGATTAAATGGCGATTATGTACAAACAGGTGGAATGACTGTAAACGGACCCATTG

GTTCTACTGATGGCGTCACTGGAAAAATTTTCAGATCTACACAGGGTTCATTTTATGCAAGAGCAACAAA

CGATACTTCAAATGCCCATTTATGGTTTGAAAATGCCGATGGCACTGAACGTGGCGTTATATATGCTCGC

CCTCAAACTACAACTGACGGTGAAATACGCCTTAGGGTTAGACAAGGAACAGGAAGCACTGCCAACAGTG

AATTCTATTTCCGCTCTATAAATGGAGGCGAATTTCAGGCTAACCGTATTTTAGCATCAGATTCGTTAGT

-continued

AACAAAACGCATTGCGGTTGATACCGTTATTCATGATGCCAAAGCATTTGGACAATATGATTCTCACTCT

TTGGTTAATTATGTTTATCCTGGAACCGGTGAAACAAATGGTGTAAACTATCTTCGTAAAGTTCGCGCTA

AGTCCGGTGGTACAATTTATCATGAAATTGTTACTGCACAAACAGGCCTGGCTGATGAAGTTTCTTGGTG

GTCTGGTGATACACCAGTATTTAAACTATACGGTATTCGTGACGATGGCAGAATGATTATCCGTAATAGC

CTTGCATTAGGTACATTCACTACAAATTTCCCGTCTAGTGATTATGGCAACGTCGGTGTAATGGGCGATA

AGTATCTTGTTCTCGGCGACACTGTAACTGGCTTGTCATACAAAAAAACTGGTGTATTTGATCTAGTTGG

CGGTGGATATTCTGTTGCTTCTATTACTCCTGACAGTTTCCGTAGTACTCGTAAAGGTATATTTGGTCGT

TCTGAGGACCAAGGCGCAACTTGGATAATGCCTGGTACAAATGCTGCTCTCTTGTCTGTTCAAACACAAG

CTGATAATAACAATGCTGGAGACGGACAAACCCATATCGGGTACAATGCTGGCGGTAAAATGAACCACTA

TTTCCGTGGTACAGGTCAGATGAATATCAATACCCAACAAGGTATGGAAATTAACCCGGGTATTTTGAAA

TTGGTAACTGGCTCTAATAATGTACAATTTTACGCTGACGGAACTATTTCTTCCATTCAACCTATTAAAT

TAGATAACGAGATATTTTTAACTAAATCTAATAATACTGCGGGTCTTAAATTTGGAGCTCCTAGCCAAGT

TGATGGCACAAGGACTATCCAATGGAACGGTGGTACTCGCGAAGGACAGAATAAAAACTATGTGATTATT

AAAGCATGGGGTAACTCATTTAATGCCACTGGTGATAGATCTCGCGAAACGGTTTTCCAAGTATCAGATA

GTCAAGGATATTATTTTTATGCTCATCGTAAAGCTCCAACCGGCGACGAAACTATTGGACGTATTGAAGC

TCAATTTGCTGGGGATGTTTATGCTAAAGGTATTATTGCCAACGGAAATTTTAGAGTTGTTGGGTCAAGC

GCTTTAGCCGGCAATGTTACTATGTCTAACGGTTTGTTTGTCCAAGGTGGTTCTTCTATTACTGGACAAG

TTAAAATTGGCGGAACAGCAAACGCACTGAGAATTTGGAACGCTGAATATGGTGCTATTTTCCGTCGTTC

GGAAAGTAACTTTTATATTATTCCAACCAATCAAAATGAAGGAGAAAGTGGAGACATTCACAGCTCTTTG

AGACCTGTGAGAATAGGATTAAACGATGGCATGGTTGGGTTAGGAAGAGATTCTTTTATAGTAGATCAAA

ATAATGCTTTAACTACGATAAACAGTAACTCTCGCATTAATGCCAACTTTAGAATGCAATTGGGGCAGTC

GGCATACATTGATGCAGAATGTACTGATGCTGTTCGCCCGGCGGGTGCAGGTTCATTTGCTTCCCAGAAT

AATGAAGACGTCCGTGCGCCGTTCTATATGAATATTGATAGAACTGATGCTAGTGCATATGTTCCTATTT

TGAAACAACGTTATGTTCAAGGCAATGGCTGCTATTCATTAGGGACTTTAATTAATAATGGTAATTTCCG

AGTTCATTACCATGGCGGCGGAGATAACGGTTCTACAGGTCCACAGACTGCTGATTTTGGATGGGAATTT

ATTAAAAACGGTGATTTTATTTCACCTCGCGATTTAATAGCAGGCAAAGTCAGATTTGATAGAACTGGTA

ATATCACTGGTGGTTCTGGTAATTTTGCTAACTTAAACAGTACAATTGAATCACTTAAAACTGATATCAT

GTCGAGTTACCCAATTGGTGCTCCGATTCCTTGGCCGAGTGATTCAGTTCCTGCTGGATTTGCTTTGATG

GAAGGTCAGACCTTTGATAAGTCCGCATATCCAAAGTTAGCTGTTGCATATCCTAGCGGTGTTATTCCAG

ATATGCGCGGGCAAACTATCAAGGGTAAACCAAGTGGTCGTGCTGTTTTGAGCGCTGAGGCAGATGGTGT

TAAGGCTCATAGCCATAGTGCATCGGCTTCAAGTACTGACTTAGGTACTAAAACCACATCAAGCTTTGAC

TATGGTACGAAGGGAACTAACAGTACGGGTGGACACACTCACTCTGGTAGTGGTTCTACTAGCACAAATG

GTGAGCACAGCCACTACATCGAGGCATGGAATGGTACTGGTGTAGGTGGTAATAAGATGTCATCATATGC

CATATCATACAGGGCGGGTGGGAGTAACACTAATGCAGCAGGGAACCACAGTCACACTTTCTCTTTTGGG

ACTAGCAGTGCTGGCGACCATTCCCACTCTGTAGGTATTGGTGCTCATACCCACACGGTAGCAATTGGAT

CACATGGTCATACTATCACTGTAAATAGTACAGGTAATACAGAAAACACGGTTAAAAACATTGCTTTTAA

CTATATCGTTCGTTTAGCATAAGGAGAGGGGCTTCGGCCCTTCTAAATATGAAAATATATCATTATTATT

TTGACACTAAAGAATTTTACAAAGAAGAAAATTACAAACCGGTTAAAGGCCTCGGTCTTCCTGCTCATTC

AACAATTAAAAAACCTTTAGAACCTAAAGAAGGATACGCGGTTGTATTTGATGAACGTACTCAGGATTGG

ATTTATGAAGAAGACCATCGCGGAAAACGCGCATGGACTTTTAATAAAGAAGAAATTTTTATAAGTGACA

-continued

TTGGAAGCCCGGTTGGTATAACTTTCGATGAGCCCGGCGAATTTGATATATGGACTGATGACGGTTGGAA

AGAAGACGAAACATATAAGCGAGTTTTAATTCGTAATAGAAAAATTGAAGAATTATATAAAGAGTTCCAA

GTTTTAAATAATATGATTGAAGCTTCTGTCGCCAATAAAAAGGAAAAATTCTATTATAAAAACCTTAAGC

GGTTCTTTGCTCTTTTAGAAAAGCATGAGCATTTAGGTGGTGAATTCCCTTCATGGCCTGAAAAAGAACA

GAAGCCTTGGTATAAGCGTTTATTCAAGCATTACGTATAAATATCTTAAAGGAGGGTCTATGGCAGCAC

CTAGAATATCATTTTCGCCCTCTGATATTCTATTTGGTGTTCTAGATCGCTTGTTCAAAGATAACGCTAC

CGGGAAGGTTCTTGCTTCCCGGGTAGCTGTCGTAATTCTTTTGTTTATAATGGCGATTGTTTGGTATAGG

GGAGATAGTTTCTTTGAGTACTATAAGCAATCAAAGTATGAAACATACAGTGAAATTATTGAAAAGGAAA

GAACTGCACGCTTTGAATCTGTCGCCCTGGAACAACTCCAGATAGTTCATATATCATCTGAGGCAGACTT

TAGTGCGGTGTATTCTTTCCGCCCTAAAAACTTAAACTATTTTGTTGATATTATAGCATACGAAGGAAAA

TTACCTTCAACAATAAGTGAAAAATCACTTGGAGGATATCCTGTTGATAAAACTATGGATGAATATACAG

TTCATTTAAATGGACGTCATTATTATTCCAACTCAAAATTTGCTTTTTTACCAACTAAAAAGCCTACTCC

CGAAATAAACTACATGTACAGTTGTCCATATTTTAATTTGGATAATATCTATGCTGGAACGATAACCATG

TACTGGTATAGAAATGATCATATAAGTAATGACCGCCTTGAATCAATATGTGCTCAGGCGGCCAGAATAT

TAGGAAGGGCTAAATAATTATTTGTTCGTATACATCTCTAGATATCGATATACACCCTCAAAACCCTCGT

TGAATTCGTCGATGAGGGTTTTCTTATCTTCTTGAGTTAATTCAGAAACAATTTTACGGAATGAATTTTG

ATTTAACTTTCTACCTTCATGCGTTACTCCAATCTCATTTAGAAATGCAATAAAATTAGCACGATTCTCA

ACAATATCTTCTCTGGAAAATTTAATCAAAATAGATGCAACAGTAATAATTTCACGAACTGTATCAATGT

TTTTATTCATTAACTATACCACTCAATTAGTTGACTTTGTTATAATATCATCAGACGCTTGATTTGTAAA

CTGGTCTGTGTAATTTTCTTCAAAAATTTTTTCTACGAATTCCTTGAACGATTCACGTTCCTGAGCTACA

TTATGCTCGATTACCTTTTCAAGATTATGACTCATTCGAAATAATCTTCAATTTCATAATCATGGACATA

AATCATTATAGTTTTAATACATCATCAATATTTTTTCCTGGAGCTGGAATTACGTAAAAATACCCTGCT

TTTGAGAGGTCTTTATAAGTTCCAATCAAGAAATCATTATTCTCAAGATGTAACTCTTCAACTAATTCAT

TGACAATTGAATGGTATAGGTTTGGCAGAAACTTATATAGCTTTTCTAGAATATCAATTTTGAATGTATA

TTGAACCACGGACTGAGAATCAATAATCATAGACCTTCCCCTTATGTTTCTGTTTGCGATTAGATTCTTT

AAACGCTTTCTTCTTATCCTTATGAACAGAAGCTTTATTAAAATTATGCTTTGCGACTAAATTGTTCATA

GTGCTGAATTACCTCTCTTAAACATTTGCATGTGAATGAAAACTTTTTAGCTACACCACATTCAAATATA

TGTTCTCTTAAATCGCGTGTATCGGTATATCCCATCTCAACAATAAAATGCCGTATTAGATTTTTATCTT

TATCGTTTAGAGAATTAAAATAATCAGATTTTGAATTAATTTCCCTGGCCAAATTGAATCACCTTCAGTT

GACGTTTTAACTCTTTTATCATCTCTTCGTTCATCGCAATATAAAGATCGCGTAGAGCAGGTTTTAGCAT

TCCATTTACTGGAGAACTAAATGGACATACATAATCTTTTCCTACGAGCTTTTTAGTGAATTCCATATCA

CAGAACTGAAATCCCGGCTCATTGGTATAAATTCCCCAATTAGTTGACATCATTTTATTGGCATATTCCA

GTGCCTGGATTTGATTCATAATTCCATCAATTTGAAACTTTTTAATATTCATTAGTAAAGGTCCTCAGAG

TAAAGTTCTTTTTCACTACCACGTTCAATACTTACTTGTCCAGCGTAAGTTGCAATAATCATTGCTTCTT

CACGTGTCCAATAATTACTATATTGGTCAATAAACCCTTGGTCATCATCACAAACTTGCTGAGTAACTAA

TTGAGGTTTAACTACATCTAAAACTTCTGCCATATCTTTAGAATAATGACGAGCACCTGGAATAATAAGA

GTTCGTCCATCTTTTAATTTAAAACGGTTGGCTGCGCAAACAATTCGTCGTTGATACTTTTGGTTTTCAT

CCCAGTACGCAGTCTGCCAACAGATTTCAGGAACTTCTTTCAGAATATCTTCTTCTGTGCATTTATAACC

ATGCGCTTTAAATTTTTCAACAAGACTTTCTGGAGTTTCACGAGATAAAGGAACATTCAGCATTTTTAAA

CGATTGATAAATGGGTTCATTTAAACCATCCTTTAATACGCTGCCACAAAGTTTTCTGTTGAGCTTTGTT

GACGCCAATTGAGCGAATAACCGGTTGAGATTCCTGGAATTCTTTATAATCAGCAAGGTAAATTTCGTAA

-continued

GCTGCATCCGTAAATGAACTTATCGCTGCCATAAAATTATTGCGAATACCTACTGGAGCATCTTTACTTT

CACGAATGATCATGTATTTACCAGTCTTAATCTTTACGATAGTTCCAAGATAAGCTCCATGGTACCAAAT

ATCCCAACCCTCTTGAGTAGGTTCTGCGCAACGACGAAGTTCATTGACAATTTCTAACTTGTTTATTATT

TATTCCTCACAGTTCAGATGCTACAGTGATTACAGCTTCAATGTTTTCTGCCGAGCGTTTAATGTCAAGA

TACACATTACCGTTTTTAGCGATTTTACATGACATTCCGATGTCAGTAAATTTCTGAATATGATGTTCCA

TCATTTTGTATCCAAAAATTCGCATATTTCCATTGTTATTAATTTCAAAATTACGAATTCCGTTAGTGCG

TTTTTCTAAAATAGCAAGATAATTACTACGATAAATTTCAACCTTTTTAAGAACAAATCCATTTTTATCT

AAAAGTTTTAACATGAGGTCTTTATCTTCTTCCATATCGGAAGTAATCTCGCGAGCTTTACGAGTTGCTC

GTTTTTTCAGCAGTTCCGGAGCATTTTCCTGTGCATATAAAGTTGCTGCATTTGAAATAATATCCTGAGC

TTCACCAGTAATGATTAATCCATCACCAGATTTCTCCACCAGGCCTTTTTTAATCAATACCCCAATATTA

CTATTAACTACTGCGTTACCTAAATCTGGATGCACCTCACGAACTTCTGCAGCTGTAATGAAATCTTTCT

TAGCAATGGTAATTAAAATCGTAGCAGTTTTTTCATTCAGAACATCGTTAGAAGCTTTGATGATGTAAGT

TACTTTAGACATTTTCTAATCTCCGTAATTCTGTATCAGTAGTTGATAGTTGTATAGTACCACAGTATGC

TTTGGTTGTAAACCGTTTTGTGAAAAAATTTTTAAAATAAAAAAGGGAGAGCCTCGGCTCTCCCTAAAAT

TACTGCATGACTGTGATAACTGTCATGATAACACGTTGAATTCCGAACGCAAGAAGACCTCCTGCTACGG

CTGGAACAACGCCTAAACCCGCCAGTAAAATGCTACCAGATACTAATGCAGCGCTTGTAATACCAATGAA

TGGACTCATTTGATTTCCTCTAAATCTTTGGTGTATTCAGTAACTACATCAGTAGTTTTCCAATATTCGT

TTTCTTCTTTTTTAGCTTTAGCTTCTTCAGCAAGTTTCTTTGCTTCATCGGAAGTCATATGAAAAATATT

CATTCCAACTAGTTTATCAACATAAGAAGAATACATATCGATTTTCGAAAGTTCTTCGGTCAGTTCTTTA

CGAGTTTTACCCTGTACAACAATTTCACCTGAAATTACTTTCTTAATGAAATGTGCTTTGGCAAAGGCTA

AACGAAAAGCTGACTCAGTTTCTTTAATTTTGTTATCAATTCGTTTTTGGACATAAGTTTTACGAACTTC

AACAAAGTCTTTAATTAAATCAACTACGTTATCGTAAACTTGCAGCTTTCCTTTCTCATTAATAACCGTA

ATATTCTGGGAACGACGCTCAATCAGTCCGAAGTCTTTCATAATTTTTGCATGGCGTTCTTCTTCGTTAT

CGCTCAAAGAATATTCTTTGCGGAATTTAACTTTGAAGCCAAAACCATGCTCACCACAAGCATCATCCCA

TGTAATGAAGCCTTTATTTTCAAGTGGGTCTAAGATTTTACTCACATAAGTTTCACGATCATACTTATAC

GGAATCTCAGTGATATGCATTTGAGTTCGTGAAGTAAACTTATATGTTCCACGAATTTCATATTGCCCAT

CAATTTCAACGACTTCACCACGAAATTCTGGGAATTCTACTTTCGGTTTAGTTACTTTCTTTCCTTGAAG

AGCTTGCAGTACAGCTTTCTTGACAGAAGAAACACTATGAGGAAGAATGTAAGTTGCATAACCAGTTGCA

ATACCGGAAACGCCATTAAGAAGAACAGTAGGAATAATAGGCAAATAGAAAGCAGGCGGAATGTGTTCTT

TATCTTGATGTACCGGAGCATATTCAGTATCTTTATATACGTTATAGAAATTTTTACTTACACGAGCAAA

AATATAACGACTTGCCGCTGCCTTTTGGACAGTACGAGAACCAAAGTTTCCTTGACCATCTAACAGAGGA

AAGTTATTATTCCAAGTATTAGCCATCAAAGCACCTGCGTCTTGTGCAGAGTTTTCACCATGATGATATC

CAAGGTCCGCTACACCACCTGCAATAGAAGCGAGTTTGTGAAACTTATCTTTATTTCCTCGTGCCAAATC

AAGAGCTCGAGCAATAACAAATCGTTGAACTGGCTTAAATCCATCAATCATATTTGGGATAGCACGATTT

TCAACCGTGTACATAGCATAAGCCAATGCTTCATTATCAATGATACTTTTTAAATCGCGATTATTCAGTT

GCATAAATTTACCATACTAGTGAATGTAGTGCCATAATAACATCAGAAATGAAAAGCACGACTTGAATTA

ATCCGAACATTACTCCGTAATATAGTGCTACCAATAAAGCAGCAAGGGCTAATGAATAGCCCAAGATTTT

CTTAATCATTAGATAACAACACAAATGTTAAATATGCACACATACCCTGGGCTAAAGCTTGTGAAAACAC

ACTGCTAGCATCGATACAGATAGTTAAAACACATGCTACTATCCAACAAATAAATGAAATAACTCCTAAT

AATTTTGCAATATTCATATTTTCCTCACTGGCGTCCGAAGACGCCTTTAGTTTTAAGATTGTTACGATAG

-continued

AACTGCATCACGTGTTCGTTATGGAAATTACTCATTAATATGCCTGTAAAACAAATTTAAAGTTATCAGC

CAACATACGGTTCATTTCTTCGAGTGTTTGATACTCAGAATGATGATTACGAGTAAACGCCAAAGCTAGC

TGACCTTTTCCAAATCCCGTCGTTAGAGGTTTCATCTTAGAAGCAGGCAGATAAAACACTGTGTATGGAA

CATTGTTATTTGCAATAGTACGCGCAAGTTGAGACCGGCGTTGACGAATATGACTTAAAACCGCACTGAA

TCCTTGCTTAGAACGCTGATTACCTACATAAAATCGTGCAGATACGCATGGATTACTAAATGGACCACCG

AGTTTACTCACTAAAAAGTAAAATCCAGGTTTAGATAAAATATCTTTATGCGGAGTTCCTAAAAACCATT

CACCACCCTTGATTGTACCAATAACAGTAGCGCCTGCATCATTCAGATCAGTAACAGTCATATATTTCAT

ATTAATTTCCTCTAAATTATTTTCTACTCCAAGGCCGCATGAATACACACGGCCATTAAATTACTCGTCG

CAGTCGACGCTCAATTCCCAAAACTCTTCTACAGTATAAGTTTCAGTATCATTTTCAATACAGAAACGTT

CATTACTATTATTTGCTAAAGTAGCATTAACTGTCATTTTTTCGCTAGTGCTCTTAAGAGGTGAAATACG

AATTAACTGATCACCGTTATCTAAACAAAAAATTTCACCAACTTTTACATCTTTAAAACTTTTCATAATT

CACCTCAAGGAGTATAAAATCCAAATGCAGTTGTTGACCATCCCATCCAATATGGAAAATTTACACCAAT

GTAAAACATAAGAATATAAAACCAACCGCTCAGCAAATTCATCATTTTACACCATTCCAAATTGTTTCAA

CCACGGATTTTAAACCATTTTGATGAATATCCATTCCTACTACCGCCATCAAATAAATTCCAACTACAAC

TGAACCTAAGGCAAAAATCAGCATGAAAATGAATAAAGCCGGAAAAATATTATCGAAAAACCATTCAATA

AATGTAAAAGCACTGCGTTTACGTTCATATTTTCCTCACATAAATCCAAAGTAAACGTTTAATACATCAA

TCATTAAAACGATTGGGAATATACTCAAAACTATTAGTATTATAACTACATTCCATATAGCTTTAATAAT

CTTTTTCATTTTCTGTTCCTCCATAGTTGATAGGGTAATAGTACCACGGAAGAACAGTCTTGTAAACAAC

TTTTTTAAAAATATTCGTAATAAATGTGAATACCAACTACTACCGCTGAAACCTGTGCAACCCACCACGC

ACAAGCAATAAGTACAGAATTCAAAATTTTCATAATAACCTCATTACAAAAGTAAATGTTAAACAAATTA

CTGGAATACTAATTAACCAAACAAAACACCACCATAATGAACTCATAGTTCAATCTCAGCGATTTTCATT

TTATTCTCCAAATCCGTATCAGTAGTTGATAGTTGTATAGTACCACGGTCCTTGTGGTATGTAAACTGTT

TTGTGAAATTTTTTAAATGGAAAGATACCATCCGTTGTAGTTGCTTTTTCTTACAACTTTACGAAGGTCT

TCTCTGTCACCGATGAACTTCGGAGTGTACTGGATGACACCTGGATGAATTTCTTTAGTGTTGAATATAA

TTATACAGTCAGCGACTTGATGATTTAGAATGGGCCCTAGATTTATTCCAGAACCATATGGATACTCTCC

GCTGCATCCCGTTGTTACCGAAATCCAACGTGAGTCAGTTTGATGTGTCTTAACTTCTACACGAAGCCCG

CAGTATTTTGGATGAGCCAATACATCCCATGCATATGTGTACGGATCATCGACATCCTCTTGGCCTTTAT

TGACATATCCACTCAACCAATCTGCCACAAAAAACTCTGCGTACACAGCGATACGGCATCTTTCGATAAC

TTCTGCCTTATCTTGATTTGGGTTTTGTTTTAAAGAGTATCTTGCAGTATCAGCAATTTTGACCTTCATT

TCACAGGTCAAGTCACTGTTCGATAGGGTAAATGTCGGAATCTGAAATAGTCTCTGTAACCCAGGATTCG

TTTTCTGCATTTAAACTTTCCTTTATGTCGGAATCACCGATATTCATATAAATCATAATTTCTCTTAAAA

CAAAAGGCCGAAGCCCTTTATTTTACTTGAATTGTGCAATTCTTTTCTCTAGACATTCAGCATAAGATTT

CATTGAGATGAACTGCGAAAGTAGCAGTTCTTGCTCAACTGCGCTAACTGTTAGAAACTTTGCGCTTTCT

AAAAATTTGCTCAGTGCATTAATTTTGAGCATTAATTGATCGTATTCTTCTTTTACTCGTGCTTGATAAG

CTAACATAATTTTCCTTAGTTAAGGGCCGAAGCCTTATTTAAATTGTTCAGTAACGTCTTCAACTACTTC

ATATTGGCAGGTACGCATTTTAGCATCGTTGTAATCAATCGGAATTGATACTACATCGCGAGGATGAACT

TTAACTTTTACAACTCGGCTGGTTGAACTACCAAAGTGACGAATATAAGATTTAGAACACACATGCAAAC

CACGAGAACAAGTTTGTGTATCATCGTCATTCACACGAGTACGTGGCATTTTAACTACTTTACCCGGACT

GTTATCAAAGGTGTTTGAGTGACAGTCAAAGTAATTGCTGCGAACTACTTTCCAAGCATAGAAGTAACCA

TCTTCTGTAATTTCAATATCGTTTGCTACCAAGAAATCAAAGAGTCGAGATACCGCTTTTTGGCTTGGGT

TTTCCAACAGATTTTCCAAGAACGGAAAATAAAATTCAAAGTTTTCGCCTTTTTCCATCGAGTCAAGAAT

-continued

ACGATCAACCAAACCAGACCGCAATTCAATATTTTGATAGAACAAGCTTCCACCTTCAATTCGAACATCG

CCGGAAATATATTTTTCAACAGCACGACGAACATTAATTTTTTGTGCCGCTTCTTCCAACTTATCCGCTA

CAAGCAGATTAAGAATTTCCTGGAAGTTTGAATGAGTATTAGGAGTTGCGTTATAAGTTACGCCATCAAC

AGTAATTGAAATGAATTTTTTAGATGCATTCCAAATAATGTCAGATTTAGCAACTGGAGCAATAACTGCA

TCGCTATTAACTTTAACTGTAATATCACCGCTAATAGTAACTTTAGGGCGTTTAGCTTCTTCAGCATTTT

TCAAAACACGACGGATTGTGTCAACCGATACACCTTGCCAATCAGCCAATTCCTGTTGGGTGTAATTACC

ACTTGAATACAGTTTAACAATTTCAGCTTGTTCGTTTTTGGTCAGGCATTTAATATTGTACAT

Spacer targeting *E coli* fimH
(SEQ ID NO: 6)
CGAATGACCAGGCATTTACCGACCAGCCCATC

Spacer targeting *E coli* bolA
(SEQ ID NO: 7)
AGTGGGAAGGGTTGCAGGACACCGTCTTTGCC

Spacer targeting *E coli* rpoH
(SEQ ID NO: 8)
CCGATGTTACCTTCCTGAATCAAATCCGCCTG

Spacer targeting *E coli* IptA
(SEQ ID NO: 9)
TGATTGACGGCTACGGTAAACCGGCAACGTTC

Spacer targeting *E coli* murA
(SEQ ID NO: 10)
GCTGTTAACGTACGTACCGCGCCGCATCCGGC

---

The invention claimed is:

1. A composition comprising a plurality of transduction particles, wherein (a) each transduction particle comprises a nucleic acid encoding a Cas nuclease and a nucleic acid encoding a crRNA or guide RNA that is operable with the Cas nuclease for targeting the genomes of *Escherichia coli* (*E. coli*) cells, wherein (i) each transduction particle is a phage and the nucleic acid encoding the Cas nuclease is integrated into the genome of the phage, or (ii) each transduction particle is a phage capsid and the nucleic acid encoding the Cas nuclease is a phagemid contained in the phage capsid, (b) the *E. coli* cells are cells of *E. coli* phylogroup B2; and (c) wherein the plurality of transduction particles comprises a first type of transduction particle and a second type of transduction particle, wherein the first type of transduction particle comprises a first adhesion moiety that is capable of recognizing and binding to LPS displayed on the surface of phylogroup B2 *E. coli* cells, and the second type of transduction particle comprises a second adhesion moiety that is capable of recognizing and binding to Tsx displayed on the surface of phylogroup B2 *E. coli* cells.

2. The composition of claim 1, wherein the *E. coli* cells comprise an *E. coli* strain selected from the group consisting of ST131 and ST1193.

3. The composition of claim 1, wherein the *E. coli* cells comprise a plurality of different phylogroup B2 strains of *E. coli*.

4. The composition of claim 1, wherein the B2 *E. coli* cells comprise a strain of *E. coli* that causes sepsis, septicaemia or diarrhoea in humans.

5. The composition of claim 1, wherein each particle comprises a phage capsid containing the nucleic acid.

6. A composition comprising a plurality of transduction particles, wherein (a) each transduction particle comprises a nucleotide sequence (N1) encoding a Cas nuclease for targeting the genomes of *E. coli* cells and a nucleic acid encoding a crRNA or guide RNA that is operable with the Cas nuclease for targeting the genomes of *E. coli* cells, (b) the *E. coli* cells are cells of *E. coli* phylogroup B2; and (c) each transduction particle comprises an adhesion moiety that is capable of recognizing and binding to a cognate moiety selected from the group consisting of a LPS, LamB and Tsx displayed on the surface of phylogroup B2 *E. coli* cells, wherein each transduction particle is a synthetic T-even phage comprising an insertion of N1 into the genome of the phage, wherein the insertion is between the pin (protease inhibitor) gene and the iPII (internal protein) gene.

7. The composition of claim 1, wherein the nuclease is a Type I, II, III, IV, V or VI Cas nuclease.

8. The composition of claim 1, wherein the composition comprises at least $1\times10^7$ PFU of the transduction particles.

9. The composition of claim 1, wherein the *E. coli* cells comprise a strain or at least one strain that is an antibiotic-resistant or MDR (multidrug resistant) strain; and/or wherein the *E. coli* cells comprise a strain or at least one strain that is a B2-I strain.

10. The composition of claim 9, wherein the antibiotic-resistant strain is resistant to fluoroquinolone, carbapenem or vancomycin; and/or wherein the *E. coli* are a beta-lactamase (ESBL)-producing *E coli*.

11. The composition of claim 1, wherein each transduction particle is a lytic phage.

12. The composition of claim 3, wherein the plurality of different phylogroup B2 strains of *E. coli* comprises *E. coli* ST131 and ST1193 cells.

13. The composition of claim 5, wherein the phage capsid comprises capsid proteins of a T-even or lambda phage.

14. The composition of claim 1, wherein the crRNA or guide RNA is operable with the Cas nuclease for targeting the genome of an *E. coli* strain selected from the group consisting of ST131 and ST1193.

15. The composition of claim 1, wherein the plurality of transduction particles comprises a third type of transduction particle, wherein the third type of transduction particle comprises a third adhesion moiety that is capable of recognizing and binding to LamB.

16. The composition of claim 1, wherein each transduction particle is a synthetic T-even phage.

17. The composition of claim 1, wherein the Cas nuclease is a Type I Cas nuclease.

18. The composition of claim 6, wherein each transduction particle comprises a nucleic acid encoding a crRNA or guide RNA that is operable with the Cas nuclease for targeting the genomes of *E. coli* cells.

19. The composition of claim 6, wherein the plurality of transduction particles comprises a first type of transduction particle and a second type of transduction particle, wherein the first type of transduction particle comprises a first adhesion moiety that is capable of recognizing and binding to LPS displayed on the B2 *E. coli* cells, and the second type of transduction particle comprises a second adhesion moiety that is capable of recognizing and binding to Tsx.

20. The composition of claim 6, wherein the nuclease is a Type I Cas nuclease.

21. The composition of claim 20, wherein the plurality of transduction particles comprises a third type of transduction particle, wherein the third type of transduction particle comprises a third adhesion moiety that is capable of recognizing and binding to LamB.

22. The composition of claim 1, wherein the crRNA or guide RNA targets a chromosomal sequence of the *E. coli* cells.

23. The composition of claim 22, wherein the plurality of transduction particles comprises a third type of transduction particle, wherein the third type of transduction particle comprises a third adhesion moiety that is capable of recognizing and binding to LamB.

24. The composition of claim 22, wherein the nuclease is an endogenous nuclease of the cells and is not encoded by the nucleic acid comprised by the transduction particles.

* * * * *

SEQUENCE LISTING

```
Sequence total quantity: 10
SEQ ID NO: 1            moltype = AA  length = 446
FEATURE                 Location/Qualifiers
source                  1..446
                        mol_type = protein
                        organism = Escherichia coli
SEQUENCE: 1
MMITLRKLPL AVAVAAGVMS AQAMAVDFHG YARSGIGWTG SGGEQQCFQT TGAQSKYRLG  60
NECETYAELK LGQEVWKEGD KSFYFDTNVA YSVAQQNDWE ATDPAFREAN VQGKNLIEWL  120
PGSTIWAGKR FYQRHDVHMI DFYYWDISGP GAGLENIDVG FGKLSLAATR SSEAGGSSSF  180
ASNNIYDYTN ETANDVFDVR LAQMEINPGG TLELGVDYGR ANLRDNYRLV DGASKDGWLF  240
TAEHTQSVLK GFNKFVVQYA TDSMTSQGKG LSQGSGVAFD NEKFAYNINN NGHMLRILDH  300
GAISMGDNWD MMYVGMYQDI NWDNDNGTKW WTVGIRPMYK WTPIMSTVME IGYDNVESQR  360
TGDKNNQYKI TLAQQWQAGD SIWSRPAIRV FATYAKWDEK WGYDYNGDSK VNPNYGKAVP  420
ADFNGGSFGR GDSDEWTFGA QMEIWW                                     446

SEQ ID NO: 2            moltype = AA  length = 294
FEATURE                 Location/Qualifiers
source                  1..294
                        mol_type = protein
                        organism = Escherichia coli
SEQUENCE: 2
MKKTLLAAGA VLALSSSFTV NAAENDKPQY LSDWWHQSVN VVGSYHTRFG PQIRNDTYLE  60
YEAFAKKDWF DFYGYADAPV FFGGNSDAKG IWNHGSPLFM EIEPRFSIDK LTNTDLSFGP  120
FKEWYFANNY IYDMGRNKDG RQSTWYMGLG TDIDTGLPMS LSMNVYAKYQ WQNYGAANEN  180
EWDGYRFKIK YFVPITDLWG GQLSYIGFTN FDWGSDLGDD SGNAINGIKT RTNNSIASSH  240
ILALNYDHWH YSVVARYWHD GGQWNDDAEL NFGNGNFNVR STGWGGYLVV GYNF        294

SEQ ID NO: 3            moltype = DNA  length = 1341
FEATURE                 Location/Qualifiers
source                  1..1341
                        mol_type = other DNA
                        organism = synthetic construct
SEQUENCE: 3
atgatgatta ctctgcgcaa acttcctctg gcggttgccg tcgcagcggg cgtaatgtct  60
gctcaggcaa tggctgttga tttccacggc tatgcacgtt ccggtattgg ctggacaggt  120
agcggcggtg aacaacagtg tttccagact accggtgctc aaagtaaata ccgtcttggc  180
aacgaatgtg aaacttatgc tgaattaaaa ttgggtcagg aagtgtggaa agagggcgat  240
aagagcttct atttcgacac taacgtggcc tattccgtcg cgcaacagaa tgactgggaa  300
gctaccgatc cggccttccg tgaagcaaac gtgcagggta aaaacctgat cgaatggctg  360
```

```
ccaggttcca ccatctgggc aggtaagcgc ttctaccaac gtcatgacgt tcatatgatc  420
gacttctact actgggatat ttctggtcct ggtgccggtc tggaaaacat cgatgttggc  480
ttcggtaaac tctctctggc agcaacccgc tcctctgaag ctggtggttc ttcctctttt  540
gccagcaaca atatttatga ctataccaac gaaaccgcga acgacgtttt cgatgtgcgt  600
ttagcgcaga tggaaatcaa cccgggcggc acattagaac tgggtgtcga ctacggtcgt  660
gccaacctgc gtgataacta tcgtctggtt gatggcgcat cgaaagacgg ctggttattc  720
actgctgaac atactcagag tgtcctgaag ggctttaaca agtttgttgt tcagtacgct  780
actgactcga tgacctcgca gggtaaaggt ctgtcgcagg gttctggcgt cgcgtttgat  840
aacgaaaaat ttgcctacaa tatcaacaac aacggtcaca tgctgcgtat cctcgaccac  900
ggtgcgatct ccatgggcga caactgggac atgatgtacg tgggtatgta ccaggatatc  960
aactgggata acgacaacgg caccaagtgg tggaccgttg gtattcgccc gatgtacaag  1020
tggacgccaa tcatgagcac cgtgatggaa atcggctacg acaacgtcga atcccagcgc  1080
accggcgaca agaacaatca gtacaaaatt accctcgcac aacaatggca ggctggcgac  1140
agcatctggt cacgcccggc tattcgtgtc ttcgcaacct acgccaagtg ggatgagaaa  1200
tggggttatg actacaacgg cgatagcaag gttaacccga actacggcaa agccgttcct  1260
gctgatttca acggcggcag cttcggtcgt ggcgacagcg acgagtggac cttcggtgcc  1320
cagatggaaa tctggtggta a                                           1341

SEQ ID NO: 4           moltype = DNA  length = 885
FEATURE                Location/Qualifiers
source                 1..885
                       mol_type = other DNA
                       organism = synthetic construct
SEQUENCE: 4
atgaaaaaaa cattactggc agccggtgcg gtactggcgc tctcttcgtc ttttactgtc  60
aacgcagctg aaaacgacaa accgcagtat ctttccgact ggtggcacca gagcgttaac  120
gttgtcggaa gctatcacac ccgtttcgga ccgcagatcc gcaacgatac ctaccttgag  180
tacgaagcat tcgctaaaaa agactggttc gacttctatg gttatgcgga tgcgccggta  240
ttcttcggcg gtaactccga tgcaaaaggt atctggaacc acggttctcc gctgtttatg  300
gaaatcgaac cacgtttctc catcgacaag ctgaccaata ctgaccttag cttcggtccg  360
ttcaaagagt ggtacttcgc gaacaactac atttacgaca tgggtcgtaa taaagatggt  420
cgccagagca cctggtacat gggtctgggt accgatatcg acactggcct gccgatgagc  480
ctgtccatga acgtctatgc gaaataccag tggcagaact atggcgcagc gaacgaaaac  540
gagtgggacg gttaccgttt caaaattaaa tactttgtgc cgattaccga tctgtggggc  600
ggtcagctga gctacatcgg cttcaccaac ttcgactggg gttccgattt aggggatgac  660
agcggtaacg caatcaacgg tattaagacc cgtactaata actctatcgc ttccagccat  720
attctggctc tgaactacga tcactggcac tactctgtcg tagctcgtta ctggcacgac  780
ggtggtcagt ggaacgacga tgcagaactg aacttcggca acggcaactt caacgttcgc  840
tctaccggct ggggtggtta cctggtagta ggttacaact tctga                  885

SEQ ID NO: 5           moltype = DNA  length = 168903
FEATURE                Location/Qualifiers
source                 1..168903
                       mol_type = genomic DNA
                       organism = T4 phage
SEQUENCE: 5
aattttcctt attaggccgc aagggccttc atagttttag cgatttggga aacttcatca  60
tcacttaaag agttgcgata accgatgaag tcggaaacaa tacggaattt cttggtaaac  120
tcagcaacca ttttatcact gttttttgaa gcattatttg ataatacatc aaaaagatta  180
gttactgtcc aaatgtcatg accgatggta tcttttccac cattaaaata tacaccctgt  240
aatgaactaa ccatattagc gagtcgtgta tattcttcag aaacttcatc tatactgaag  300
tacttcatca taaaatctaa ctcaggatac ttgataattt tatcaatata tcgtttagct  360
gaacttgaat aacctacata cttatcataa tctacatcat caaaagcatc tacatataaa  420
tcacgcaaag cttcaaaaat acattggcac tgaccgagtt cttttacctt tttctgtaaa  480
agcggacgaa taacataaaa ttcattaatg ccaataagat tagccatacg aatcaaaata  540
ttcatagatg gatgacaaag agatgtagta ccatccatag agaaaatatc agaacgatgc  600
atatacgcta cataaccagt aatttcatct gcttctgatg tgaggcgtaa ataattcctc  660
ttttcccagc gcccgtcttt aatttcaaac ttaaacgctg tagcagcttt aggacgagga  720
gctttacttt taactacctt tggaatataa ctttttacta aagcttcaat ttctgacaaa  780
taatgaatgt taacttcatc actttcaaac atcgccataa tatcaggaag caaatcaatc  840
tgcgattcta cttctggatt aataaacaga agacgttcgt tatgatgaat attcaaagtg  900
ttattaaatt cactatcatc taacgcacgt gctaatccac ggacaatatt aacacgattt  960
ttaatattat caataacgat attaattttt gttgtattaa taccaaacag acgataactt  1020
gatgcaacgg ctgaagtttc atgactttgc ttaatgcgct tcagtcgagg gtcaagattt  1080
acttcataca caactcccgc gttgcataac ttactgtcag gttcaaacat gctctgcatc  1140
tttttatatg acagattttt agtcgtgaat ttgactgaat tactaatcat ataatctcga  1200
gcagaatacc ccatcttcat caattcacga tatgtgtgac gaggagatgt agattcttta  1260
aatcgtttta catcttcatt aaatgctttc tcactgagtt ctttaactcg ttcaataata  1320
tttttacgag tgcgatcatc cagtgaaaga gcctcgcgag atggagcaat atcaagtgaa  1380
cccattggaa acttaatgta attcacttca ttgcgaatgc ttagccagtt acggtctcta  1440
ataacaccat cgataggata aacaatacca ccgtagatag catataatcc accacgatca  1500
ggccagtatc tttctggatt tacaccgtaa tagtcatcaa aatccggaaa ataatcaatt  1560
tcgcggtcaa gaccattaat gatagccaaa tctttgaacg gtcgcatgat ataagaaact  1620
tcataagcaa agtttctaaa gtctttttct tcaactggaa ctacgatttc aataccagtt  1680
ttatcatctg gacccatttc ttttacgaat gtaggtttaa tctgtggacc atcaccatcc  1740
atgtaagcta cataaccacg aatttcacct ttatgatacg aagtaatact aaacgtatca  1800
gtataactaa acggagattt agaacctaaa ccaaatccgc caataaagtc attagattca  1860
gctttagatg aactgaagta tgaattatac aacccaggag aattatcatc accttgaata  1920
tcaaaatcac tcatacccgg accaaaatct cgacaaacaa atcgtgggtc taaacgtcca  1980
```

```
ggaacttgta tgataaattt ttcaggattt ccattaagtg catgagcatc aatcatgtta  2040
gtaatcaatt cacggactac tgcgcgaatc ttgtttgtat acaaatcaga tgacagaatt  2100
ttaaatactt taggagatgc tgtgatgcta aatgcttttg atttagaacc attaccaaga  2160
attgtttctt tttcagtggt gataatcata atttcctcat taattcatat tacgcttaat  2220
aacttcagca acttctagta gttcatcttt agttgcggtg tcggattgaa ttttatctct  2280
aatatcttta aagcgggttt taaattcttc ggcttctccc atatcgaaaa agcgttgaat  2340
gattctatat tctcgatgaa ctgctttatc aaaaagttct aaatttactt tatatgattt  2400
catttcaata tcctcatttg cccaattaat tataccacat ccttgtggta aagtaaacta  2460
ctggctcatc cattctttac gaaggtcagc attatctccc atgagcattt caaaaagctc  2520
tttccagttc tcaggaagtt taacaacatc atatactggg ttttgaatca tctcacgata  2580
ttcagatttt tccaaagagc caagtccctt aatataacgg atgctatgtt taggtagagc  2640
atctttggca ctctcatatt cagcgactgt ataaaaccat tcttgttttt taccgacctg  2700
agcgatgatt acaggagttt tgacaaagcg aattcgtcct tgctcaaaca attctggcca  2760
attactaaaa aatccgagca gagaaggata aatagaacct aatccaataa tctcttaatt  2820
atgaggtatt tctatagata gcccgaaggc tatccatcgt gatctgcgtc tgtcataata  2880
gcgacattcg catagttcat tgaagaggat ttaatagaac gacgaacatt gttctgcaat  2940
ttatattttt tcatatcaac gctagaagaa tcaattttta caaatttcat tatacacctc  3000
atagaacttt tcatcaggaa tccaaccgcg tttaaattca ttaaatgctc ggccgaataa  3060
ttttgaattc acagttatat tattaactga tttccattta gcaactcccg ttcgtttata  3120
atgatcgggg tcatatttcg tgacgtacca ttcatataaa tttggtatta attttacagc  3180
ctctggattt gtcgctgatt tattatacca tggtttcgct ttttcaagtt cagctgcttt  3240
tgcagtagca gcaacagtat ttccaacacc aactaatttt tcagttttaa tgcgtggatc  3300
attaacatga agacgaaaaa cttcgccctt ttcattttta aagcatgtca tgcctttaat  3360
tccaggaagc ttaacacctt tattaacacc gcatcattcc tttgggttaa atgatccttt  3420
aattaataag gcgcatttac ccgatttaac tacttctcat tcaacaactt tatctttcat  3480
aacgtttttt gaccattcag atactgctct ttgatggcta aattctagca atttcactat  3540
aatttgcact agaacgtaaa ctatttttca gtgtttcaac attctattca tcgcatatgc  3600
catttcacga ttacgatgaa ttttatatag tagaaaatag tgctaaaaag tgttcacgaa  3660
aagtcatgtt tcaccaaatt ttcgttatca tcagaacctc ccattgatct tggaaggata  3720
tgatgaattt cacccttaaa tttagaaacg cgggttttac cccgcactat taagtcatta  3780
tagattttt cgtaattcac ctactgttat ccatttacca ttaatctgta cttcatcatt  3840
ttcatttacg ataattgtat cgccatttag ctcgaaagta aaccactcgc catcttcttt  3900
ttcttcaaac gctttttcac cgagaactag accagtgatt gcgcaaatat caaatagttc  3960
tttgttttta agcatatctg cataagacat accccaactg ttgagaactt taccacgcaa  4020
tggataacca ccgtgaagtt ctttatcacg aacatcaata agatatccga tagccgaatc  4080
accctcagtc aagaaaagag tagtatcagc atctttaccg caaagattcg ctttgatatg  4140
tttatgaacc ttagctttag aagccttttt agctgcttta gtttctgctg ctttttctgc  4200
cgccaattta cgagccaaag cagcttcaat aatcggcatt agaattgctt cattatttag  4260
aatatcacgt gaaatctttt tagcatcaag ttgaatatga ctacgaattt cgccaaatgg  4320
agaagtcaaa cgctctttag tttgacgaat caatcgcatg tttttcatat cacgaacaaa  4380
cataacgata gtcaaacatt ctttgacacg tgctttagtc acatcaattt tgaacttacg  4440
tttgatttgt ggaataaggt cttcacaaat atcatccata gcgcagtcaa tgtgatggcc  4500
accattctta gtatgaatgt tattgacgta tgttaattga cgaaaaccat ccggtgaacg  4560
accaaccgca atagaacaat tttcttgctc ttgaacaata gcatgttcat catactgccg  4620
tgcatatttc ttaaaattgc cctgaacctt tttaccatta aaggtaaatt gaatatcagg  4680
ataaactaca gcaagtgtct ggagacgatc cagtgtaatg tcaagataaa cttgggacag  4740
ctcattagtt tcaaatgaca taaaatcagg aatgaaagta acacgagttc ctttccattt  4800
tccaggaata tcttcccatg atttattttc catgccattt gaacaacgaa ctacaatatt  4860
attttgaccg tcgccagttt caccgacaaa catcacagaa aaaatgtttg tcaaactaga  4920
accaacaccg ttcataccgc cggtgacgcg ttctttatca tcaccaaagt taccacctgc  4980
ttttggaata gtccatgcgg caacaggacc aggaatttct tcaccggtag gtgttttaac  5040
catcgcttgt ggaataccgc gaccgttatc ttcaactgtt acttgattgt ttttaatagt  5100
aacattaatt ttattcgcga atttaaactt agtacgaata ccttcatcta ctgagttatc  5160
gataatttca tcaataagct taacaagacc aggtacatac tgaacacttt cccatttacc  5220
aaacataaag cgctcatgcg tttcattagc agaagagcca atgtacatgc cactacgctt  5280
tttgatatgt tcaatatcgc tcagaatttt aatttcattc ttaatcatca cttatcctcg  5340
tttggtttcg ggaatattat actccggtaa tcataaagct aaaggcccga aggcctttta  5400
tttaaaacga atagttgaat ccttaaagaa cagcccagaa catactgttc cttctacttt  5460
ctgcccggta ggtccaatag cacgaaatcc agtatgctgg aaatcatttt cagagcaacc  5520
gaaccaatta tatccagtga tttcaatatt agtaaaacca cttgaagaca aaactttggt  5580
tgcattaatc agcatcagta ctattaatta aagacactgc taatactaat gctgcaattg  5640
aacgactaat atatttcata actacccttt aagcaagtcg taaaatccat tattcccatg  5700
cttaggaagc ggaaactaac cgaacagcca gccgatgaca atcaggacat acaccagtat  5760
ctcttccaga aattttcttg attttttcgt attcttttgc acagtctttg gattgacatt  5820
tataatcata aagcggcata attattcctt aaagtaagct ttcaacatct gatataaaga  5880
ccacgcctga tcattatttt caatagtaac tttcatgact gggaattctg tgaaatcttc  5940
tatttgttct tgctctttct cttcctgctc ttgctcttca accgcctgat atggattttc  6000
cacttcatca aagaacccag cttcgttagt agagagccag ataaagtttt cgtcaaggat  6060
atcaccgccg gcacaacgtt tgagtacacc tatggatgtc ataattttag taggacgccc  6120
aagataatca gcatctaaaa ttttaaaagg ctccatacct aaacgtcgtg catagattcc  6180
gttatcagta tggtctttaa taaaattttc ttgagcttgt ttattttttaa attgatacca  6240
tttattaact tcaaatttaa tagccattaa taaatttcct tccagtaagt tgtgccgtct  6300
tcagtaattt cacgaaatac accataaatt ggctgtttat caccgacttt ctcatacaca  6360
taaacagaag tcaagtgagt aaacttgcta gtatgttcct tttgaactac taccaaattt  6420
ggatcaaata atacatcttc aaattcatca ttagtgcaat tctgaacaat tttacgtttc  6480
attacaattt cctcattaat tgaacagtgg agcgatacgt ttcagaagag tatcaacacc  6540
tttagcgaat tttccatttt attctccaag ttgttttctg tatcagtagt tgatattgat  6600
atagtaccat aatcaactac tgatgtatat agttttatga aaaatttaaa ctttatgcat  6660
agagagcatt gctatagtgt ttaatccaac tttcaggaat gactttgtat gttcctaaaa  6720
```

```
ataccacgtt gtacaactta acaccatctt ctacccattg atcggtaatg tatccacaca  6780
tagcgcgagt ataaacaacc cttccatcat ctttaataaa gttaaattca caaggagcaa  6840
tgaacttgat agcctgaccg agtttccact taaagtctac acctacatgc gaagtatcaa  6900
tcgtttcaat tcctttagca ggaacagctt ttaaaaacgc agactcaaga aatttcgcac  6960
gaacatagcc aaactggggt ttagactttc catctttagg aatgatacgc acttttactt  7020
cagaatcttc atctttaaca ccatgcttaa gctgaatgct tacaacttcg accaattttc  7080
ctgctgcttt agaacgggat ttatcagata cacgagctaa ttcaccaata ttaataatca  7140
tagttatctc tcacttgtta aaaagatttt atactccacg ggaccattat actctggtcc  7200
caagagtttg taaactatta attcaaaata gctaccactg cactacgagg aactacggag  7260
tactctccag catgaactac gttcagaagt tcaacgccat cttccaatcc attggtcagt  7320
tacccaacca ccaatcggat tcgcaaatgg acgacgaatg taaactgcct tacacaacaa  7380
atcagtcggg tcttcaggtt tttcaatttc tgtcaataga ttaaaatctt cttcatagat  7440
gatgaatgat gatacccttc cataatagtt tctaatttcc atgtacactg taccaatgag  7500
aattccacta ttaacactaa tgacagtaaa aggatatccg ccagttgtac caagaagttc  7560
ccaaaatttg ctatcagtcg tattcgacat tgtctgaaaa tcaatttcag atggtttttt  7620
catttgatac gcagtattaa ttttaatcat aattttctct ttagtttaag gtaataaagc  7680
cttttagttc ggcataggat ttacggaaca ttacttgatg cccgccaatg ataacttggt  7740
catctggtac ttcgtataca gcaagataaa atcctttcga agctaattct tcacgctctt  7800
ctcgtgtgaa ccatttcatc atatcatatt cgctagcaaa agcaaaatga taaagagcta  7860
caaaccatcc gggaatatga tattctactc caacataatc tttcttgaac ttagtattaa  7920
ttacgatatt agcattttta actaatagtt tgtcttcgtg cggcacagga attcttttat  7980
tatcattact atgatgcata aaattaggtc tgtcataacc tacatgtaat aaccactctt  8040
cactccatga atctattata cttctatacg gcgttatttg aacacaaaga tctcggcgta  8100
ttgttatagc gtcttcataa ttaagaatac taaacgatga ttcaacacga taaattttca  8160
ttttattatc ctcagtagct atggtgttat agtaccacaa ctaaccgagg aagtaaacaa  8220
ctttttatcg ttttgttgga agagatagag gatcgcattc ttcctctgat ggagcatctt  8280
caagacccat agcatatcgc aaagcatact tcatcatcag gatgtctttc gcacagtcat  8340
gaatagaatc atgtgcaacg aatccatcta aagttccctt tggaagagga cacgttgtca  8400
tatcacgaac aagcagaagt gcttcaattc tagtacgaat atcacgctga ttccaaaatt  8460
tacaaggttc taacttaaat gtatcaagct cattctcgga aacgccgtta agacgttgaa  8520
tatcgcgaat aagatcgact aaaattggaa aatcaaacga cattccacgg caccagcctt  8580
gagatttcca aggatcgata ttatgtgcat tgatgtaatc attaaatttt gcaataccgt  8640
cgatagtgct tacatcttca tcggatggtg caatattttt tcgagcttca ggagattgat  8700
tcttccacca ttcgatagta cttttagtaa aaagacggtg tcctttttgg ctttttaaat  8760
caaatttgat tttaatgcca cgtgaaacta attcatcgaa tgtttcaact acttctggat  8820
tagggtcaaa agcaattaca gccaaatcaa taaccgctgc tttttcacca cttcccattg  8880
tttcaaaatc tataataaaa tcaaacatta aattttcctc gctaaatcac gaatttgacc  8940
tacagtatag tcttgaatat aaactttatt aataggctca tcaataaatt ttgccataga  9000
ttcaatatct ttttgtattt cttcaagact gtatactatc tttgaagctt tttcgcgaat  9060
agtgatattt tcaggacccg gattttcttg aatgacaact ttaacatttg tcataagaga  9120
tttaaactgg taccaactta attcaatcat taataatcgc ctcataaaga tagctaattt  9180
cgcctaaaac ataatcattg attgtaacag ttttaacttc accgcaaaag aattctaacg  9240
caattaaatc tcgttcaatt tcttctaatt gaagcatcaa cttactagat tcaattttta  9300
cagtttcacg atttttgcta taagctattt cataaatttc gcttacttta tcttgaagaa  9360
gataaaactg atctttagtt atttccacga atagcttcct caaatttaat catacataaa  9420
acacatcata acgaccacgg gtgacaccaa cataaagaag ttgttgagct aattcaacat  9480
ctgcataatg aatacaaggc gtataaatga aagcacggtc tacagacata ccctgcgctt  9540
tatggaatgt tgatgcagga agtgctttca ctttactaaa ctgtgattta gcatcccaaa  9600
aatcactcca cggagctttt ccgcctttgt tccaattttt ataagtttct gctgttttag  9660
ctaaaaatag gttaaactta tacaattctt cgtcagatga aattatttta atcttttcac  9720
gataatattc atcatcgcca taagtttcta ctgttaaatc ccaatgacga attagatatt  9780
ctccaggaac accacgggct ttaacaaacg ttgatgtata ctctgcttct ataatacgaa  9840
ctaattgtcc gttattaaaa ataatttctg acacaggctt tccatcaatt ttatatgttt  9900
taaataatgg ttcctgcatt acaataattt caccgacaat aaaatcttta tcagtttcaa  9960
aaatcttttt acgaataatg ctatttaact tgtcaacaga tttattcgta aatgccatta  10020
cgcgattttc aaacaaatca tctagtgatt tgacgattga aaaataattt accataaaat  10080
cgcgtaaagc ggtatcacca gtaaatccac gtactccatg cccgtcaaca actttatcat  10140
aattccactt accgttgcga acgtcagtag ctacatcaat aataggagca ttactgcgtt  10200
taacttcagt gagttcacac tgataaaaat ctttatgtgt aaagaatgga ctgatataag  10260
cagtattttc tcctggttca acaggtctga tttgcttatt atcccctatt ccaattatag  10320
tacaccaagg tggaatagtt gaaagcagaa ttttaaatag ctttctatca tacattgaca  10380
cttcgtcgca gattaatact ctgcatttgg ctaaatcagg tacttctttt tgttcaaaaa  10440
gaacattttc ttcatatgtt actgggttaa ttttaagaat actatgaata gtactcgctt  10500
ctttccctga tagttttgaa agaatctttt tagctgcatg tgtaggagct gctaaaataa  10560
taccagttcc acccgtagat attaaagctt caatgatgaa cttagtaaga gtagtcttac  10620
cggtaccagc aggtccatta atagttacat gatgtttctt ttctttaata gccttcataa  10680
caatgttaaa ggcatttttc tggccttcgg tcaaatcatc aaatgtcatc gtaaattccc  10740
tgcaattggt atactaacaa tacgcccagt atctaaaatt cgctgatata atctttgcgt  10800
gtctacgtca ggcttaacat gtttaacttc tattttatta aaccaaaatt tacgtggagt  10860
ctcaactaat cttggaattc ccttacctaa agctaatcga tactgctctt taagagtggt  10920
aaatacttta tcagcaatct tccattcaaa aaatacagca ggacgatgtt catcaagcgg  10980
aactggcgct gtaaatccgt ctttgtctcg gtaaactatc gcatatacat aaaccatatt  11040
atcctcggat aagtttaaaa attgaacaat ttagcggata tcctcttttc agtttaagtt  11100
tatcaataaa agacaaattt tgataccgct ctacaccttg aataatttta tcacacatat  11160
catattgcat ttctgcttct gacaactttt tcacaatttt ccaatccgag cctttaagaa  11220
gaacgttcaa tttaacaact tcagcgcctt ctgctatgcg agaaccatca atacgtgctt  11280
taagtgctat aattctcagc ttaatgtcag aggtctgttt tgatttagaa agctgagaaa  11340
tgtgttcaat tcgatttcca cgttttttct gtatagcttt aatttgatta taagtctttt  11400
tgattttagc ccatttcttt tcatctaaat ttagtttatg aactttttttc gcagatgaac  11460
```

```
gaccaattcg caaagcaaat aaatcacgct tttcaatcaa ctcttctaaa gtataatcag  11520
aacgaaatgt attatacttt ttctttactg caataacatt ccctttaatg tatccaacgt  11580
tattatcaaa acgttctaat gataatttct ctccttcaat acgattatca aaaggttctc  11640
ccgagtaagc acaaactttt tgatctaaaa tgttcttaat gtaattgaag tctaagttaa  11700
aatctttaga acgtcttttt gcagatgcct gagtatgctc taaacgacgt ttaattttac  11760
gaatttggtt attagacagc ttcatatttt tctcacatct tacggacggt taactactta  11820
tactataaca tttttacttt aacttgtaaa caactttatg aaaaatgctt taaaactttc  11880
atggtataat gaatctaagt ccttccatta tagattaaat ccttcaaaat caagagtata  11940
gatagtgtat gttgaacact ttttatactc atatctatct gcaattctaa atacacttcc  12000
agctggtatc attacttctt gttcatctga aactaattcc atattacgat aacgatgact  12060
atccggaaac ttaaagtttg gattgtattc tttacagcgt agagctttta tagcatactc  12120
ctggaaattg aataccatag gagctttgaa ttcaaaaata acttgtgtgt tatactctaa  12180
accagaagca aaatgtagag ctatattttt atcatatgaa gctgatacga ctttatcaaa  12240
tgtaataata tcaattcctt gatttaatac ttgtttagtc tcagctggaa cacctctcca  12300
aagaggttta tcgtttggaa ccaaacgaga tttgattatt tcatttaacc aagaatggtc  12360
atctggttta ttagtaatac aatgaattaa aagttcaatt tcagataaat taaacccttc  12420
agaaagtaat tcttcacgaa tagaagcacg caccgatgca tccattgatt ttattttaaa  12480
atcttttagt tgcattactg agtatttcat tcaactacct caatatcata aactttaaat  12540
gttccaaatg aatcgtgtaa tttttctttt gaaatagaag ttatttttata ctttccaatt  12600
ggaatcatcc attcttgttc acgcacaatc atcattaagt tatcagtacg ctctgaatct  12660
aatccatcag tatcttcata cgtgtactta aactcagtat taggagaaga aagtataata  12720
tcgctgatat ggtcagaata attaaaagct ttatcagttt ttaaacgaag tattgtttca  12780
gtgaaatatt cagcataaga aaaagaacac gctgtatgca aactagtagt aaatgaatct  12840
accctgttcg ttgaaaacac ttctccaact tgtaaatctt taatgagttc ttttgtcgat  12900
tttgatatac cacgatataa ttgataaggc gatttagtta aatgcttttt aatgatttca  12960
tttaaatgct tatgaagagc ttcattcttt ttggcttcca tacattgcca aagaacagac  13020
tgctcaaagt cagtaaattt ttcacagacc tttttataca tatcatattg aaaatcaacg  13080
ctttcagctt ttatagataa ctgttcaaca tctgcaagat taataatcat gatagcctcc  13140
gtatacttca gaagctatca tatcatcgtt agaaaggaaa gtaaacaact ttttgaatta  13200
ttttgcccag ggagcccaag gcggagggtc aagatggtat gaagctagtt cttctagaag  13260
agcatctggg gcttcaattc cataattctg taatactata cggtactctt tcttataatc  13320
actagaatca ttctggttat tcgtagaatg attatcttct aacatctcaa ataaatccat  13380
attaattcct agcgataaaa accaaattta cgattagttt caatgatctt tctttcttct  13440
tcggacattc tccagcgtag tccaacatca aaatgagccc agaccatcct aacaaatgca  13500
tttatatctt taatatcttc aataatgaat gttttacttt tagaaggttg actcgctaat  13560
ttaactttat cgtcttcaaa catgtcaaaa agaccatatt catgagctct tttatagcct  13620
ttaatagtta aagcttcaga agaagaaaat ggtgaatctg tattctgcaa aatatcttca  13680
gtatgcttta taattagaat aatattttct ggatattttc tttcttttat atctttaatt  13740
aaaaaatccg gattttctgc taaaggaata attaatgagc aatttttatc aagtgtattt  13800
actgatttac cttctttaga cataaattct attgaatata attttgctac ttcaatcatg  13860
tgatttcctt ttgcctacta atggaccgtc aggaatttta ttttcctgga tatatttctc  13920
attttcttcc atcattttac tgccaatttt aagaagcaaa tccattgctt catttgcttt  13980
tgctttagct tcttctaacg tcatatcttt gttcatgatt tatcaccata gatgtctctc  14040
atcaatttaa gcgctgagcg ttctagtttc ttttctttct cagcactaat cattgatttc  14100
atccattctt ctgattcatt ctgcatttct ttatttgctt gttcaaccca accgtcatca  14160
atatacattg agtttggtct attgaaccat tcaagcatct tcttcagaac tttcattcgt  14220
tttacctaaa acaatagtag gagcatcgtc aaatttatga atttttagca aatttggatt  14280
taaattattc cataaagagg taataaaata tgatagcgca ctttcgtccg taattataaa  14340
tttatttcct ttatctattt tccaatcata tattgaatca tatgaataga aggataacgg  14400
tttattatta taatatgctt cagcaacatc aatatagtta gatttagtaa atgcttgaat  14460
tgccataaat ggagaatttt gtacagtttc aataattccg atctttttaa gttttatttc  14520
aacatcttct ggaattggca ttgaaataaa atcttctact agatacatat tattgtcata  14580
tcttttatca atcattactg ctacagtaat tggaacatcc ttgacaaacg ccatactaat  14640
actattgata gacatttcaa acaaaattgc ttccataatt ttcctcaatc acaagatgta  14700
gatgaacaac tagaatcaca agaacttcca catgaatcac ctgcccatac atgaacagga  14760
acattagtat catatgaatc agaactagac tgtgtattct gtgtgttaga tgatgtagta  14820
ggtgttgacc agcgccaagg atttttataa tattcttggg cttcttcata agtcatagta  14880
actgcttcta ctgttccatc tcccatataa acatattcaa ctacagttaa aggaaggtag  14940
tcatttgaaa taggaactac accttcccca ggagttgtag agaaaaaatc cgtaaagaaa  15000
cttttaaacc aattaaagat aaacattaca aaaagcctct tttgaattcg acttgcttct  15060
caccataatc atatcgaatc tctacattaa attcgacaga accatctgcg tacatcataa  15120
atgaatgcac aacaacttct gtagaccatg gttgtagttc atatttcttc attacatgtc  15180
gtgaaatgat aatatctaaa tcttcatttg gtttaatcca acgatttaac atagtactct  15240
cctctataag ataattctat tataccatac tcattttgga aagtaaacca tttaaatgaa  15300
aaaaggactc ccgaaggagt ccttgagtta ttaaccagtt actttccaca aatcttcatt  15360
tgcagcaatc cattcagtac gttgattttc ttcatatact gtagaatatg ctgctttttc  15420
tgaagggaat gtctggtaat gagcgccaga aattttgtga acgtcagaat aaagagggaa  15480
agctacagaa atttcctttc cttcaatttt cttatttcca tctaatttct gctcaaatgt  15540
tttgatatta acataaccgc gagtactagc catgtaattc tcctttattt aaattacatg  15600
attatttata catcttcttt tctgaataag taaattaaat tcttaagagc cgaacttgtt  15660
acatcatatt ttcctttaag cgcctttaca accgggcctg ttgctggttt acctaaagaa  15720
acccataact cgtgtatttc gcttttaagt ggttcatgcc aatgcggtgc ttttctttgc  15780
gcccttgaag ttccttctga aatcttttta tttccgccat tcgaataaaa ctttttcatt  15840
acttcagatt gccgagcttt tctttctgcc ctattttggg ctatacgttg tgaattcttc  15900
atccgagttt ttgtttcagg attgtttaat ctaagtttat gttctaatcg ttgttgctca  15960
gtccattttc ttccttctcc accctgacca ccaggagaaa tattaatgca agtatctggg  16020
tgtttacgtt ttaatgcaga tattagctca cgttcaactt catatgattt ttctctagaa  16080
ccatggcatt ttgaccatcg tattttataa ttaaatccat acttacgata tatgttccat  16140
agtattttac ctgaacccgg atatttatca ttatatggat ttacaataaa tgattcatgt  16200
```

```
ttcccagcgt accaaaagac gcctttcggc gtcctaactt ttactatata tgttctataa  16260
aatttttgtt taatatccat tatcttgacg ttcaaaatta tgtttgttct tcagataata  16320
aagtttaaag atttcttccg cattcattcc aaggccaaca aacatattta atacgaaatg  16380
aaatatatcc acaagctcaa atttaatttc gagctggtct tcgggggaca tttcatcaat  16440
gcgtttttct tgcgcttcaa tataacgtgc tttccatttt ttccatacag cagaagcttc  16500
tttttcacca cgtgacattt caccaagaga agtcagaagt tcgcggaatt catcatcaat  16560
acagtctttt tgttcacgca tccaagaaac aacatcaccg gcagtttcta atttatctgg  16620
atgatagcag tattcgcgga cattagccaa acgaatctgt aaaaaccgct gcatatcaag  16680
cataacttgc agcggatctt tttcatcacc gagaatatcc cagtattcat tttgagcttt  16740
atcaacacct tcgatcaaat gagcacattc attaaagtga gccattagtt ttcctttcaa  16800
ttcattaata agttaaataa ttatatcatt tgagtatgta agcaattaat taaaaatata  16860
tacttcatca gttccattct tttctttgga atgatatatg ttaaagacgt attttttatt  16920
aagatgcttt acattatatt ttttagacca ttctttaaga agagtgtttt cctttccgtg  16980
gtgttctaaa acattcgact gcccaaattt tattcctcta tcatttaaag aatctaaaag  17040
atttaaaagg tctttttctt catcttctga ccaaaattta ttataatcag caactgttat  17100
gagatacgga ggatctacat atacaaaatc gccgtctaaa attttaacat ctttaaaatg  17160
caatgaacta aagattattt tatcacaatt ttgtttaaag tgattatatt gtttttcact  17220
atttttgttt atagttcttt ttccaaacgg agtagtaaaa tttcctttat cgtttatacg  17280
aatcatatta ctaaatccgt gaaaatgaag aacataaagt aaaagaggat ctctagtttt  17340
attataatct tcacgtaatt tcaaaaactc ttcttttgat gtttttgata gtttgtattg  17400
ctttattact tttaaaacgt catcccatga tacattaata agacgcttat acatttcaat  17460
aattggttct tgaatatcat tggccaatac agggccatta acattcaaag acactgataa  17520
acctccacaa aataaatcca cgaatctgtt atattttgga aagtgagatt tgagttcagg  17580
taataatgat tgtttattac ctgtatacgc gatagctcct agcattatat tctctcattt  17640
attgcagcaa aaatgaatta tacaattctt catcatatgt atttgatagt aatactaaca  17700
cgttttgcga taaatattaa tttaaaggag gatatatatg gtacaaaaat taatggcact  17760
tgttaatgcc ataaaaggta ataagaaacg tatagctttt actatttcta ctatggtagg  17820
aattttactc tggaacttta ttttatcacc tgttgcaatt gcacatggtg ttaatattcc  17880
agtagttact cttgatacat tcgtagattt agcatttgct ttagttgggt taatttaaat  17940
cttagcatat ttagatagcc gcattttagc cattaacccc tgggcaatat tatttttcat  18000
atattccata atttgttcag gggttgcacc ttcctttcta atcatatcat taacatcttt  18060
tgatttccag ggagatttat cccaaaacat aaccctttct cctgcatcaa ctaatttagt  18120
cattcgttta atagtgtcag ggtgacgagg ttcattatct aagacccaca cacgtctatc  18180
tttaaatgga acaacttcta ggtctaattg accgcccgta atagctatac catttttcaat  18240
aaaaagtgaa tctataggtc cttctagaac atatacatca ccatctttaa ctcgttcgac  18300
tccatagatt tttgttgcct caggataagc ttcgatggtg atatattttt gaggagcatc  18360
tttctttaat gcacgtcctt gaaaagactc agcttttcca ttagcattat aaattggaat  18420
aacaagacga ggctcagaaa tttccttttt gtatgttccc ggtgctatgc tattaactaa  18480
tttaggccat tcggttgtaa accaaagata tttccattta tcctttggaa tacaacgagc  18540
ttttacgtat tttataattg gatggtcttc cgccagttta tctaatctaa cacatgacgg  18600
aagagattta attattttct tctcgggttg tttaggaagt tctttaggtt tttctattgg  18660
acgactttta ccttttttctt ttcttatttc aaagatatac tcacgatata aatcgggttc  18720
aaactccttt aaatatattc cgattggtgc atgatagtta cagttataac aatgaatatt  18780
tccttcatta ttatcaccat aataccatcc acgggcttta ttctggtcgg tttttgaatc  18840
tccacaaaca gggcatctaa accgtaattt aaaagttgaa ctattattta cttgtgtgaa  18900
tttaggtaaa tgagctaatg cacggtatgc aaactcatta tcaatccaag gtattgatga  18960
catttttact cttcttttttc tttagattcc tcttttttct ttttaggaat ctgttcagga  19020
cctttattta ctacagcgcc tgatgttgtt ccaatagaga tattttcagg attaccacct  19080
gaatctccag cgaccatatc ttctttgata aattctttaa atgttttcat attaacctct  19140
attcataaaa gcattaaaaa tttggtcatc aatagaaaca tttactttag gctgtttttc  19200
agatggcaat tcatatccac atattacaat tttatgatca atatcaaaat acacagaagc  19260
aatatgatta atgatatttt cagtaaagtc taaatcaaca tcaatatctt tttgaccaaa  19320
gcccaaagga taaataatgc gagtaattcg attatcttta acaaagattc caccgacata  19380
ctctgtgctg cgtttaaagt ctacacgccg acgaaatgaa aaatattcag gctctttatg  19440
agctcggctc ataggacaca acgaataact agaataagag atgtcaaatc ctacgccttc  19500
aatatgaact aaattgtcat gattaaacca attataatca tatgccaagt ccattagatt  19560
gtcatatgtg aaaagcaccg gattaacatc attggtcaca agcatataat tagcaactgc  19620
tataatttca ttatttttaa cgaatacaaa ccgtgattga tgcgaatggc ctggacctgc  19680
gttttcacga ttaatgatat aacactgggc acctttatat ttgtacgtgt ctttacactt  19740
gtgcatttga taaagcatta ttcacctacc acttcagcga tgatattttt gttattaaag  19800
tttttatcgc aatacagaac ataattatac tgcattacac caccagactt aagctgtttt  19860
tgcacttcag ctttcatttc aggacgatca cgcttaacga tattcataat atctgcttca  19920
atttgagttt caacctcagt ctgatccgca gtcatagacc attcgcacaa atctttatca  19980
taacctgcca tagcaggctg agcagcacaa gaagctaaag caaaaattgt agcaaagatg  20040
aatttttttca tgataatctc ctcagtagtt tatgtttata tagtatctca atttccaaca  20100
aaagtaaaca gttattttaa aatttctgcg taatcacatg ttacaaactg tttctctaac  20160
ttgacgattt tacgaaagta tcttttgcat tggcgaatct gcctcttcgt agggcgaaca  20220
gcaaacttaa taaattccac tcgaccaaat ggagggcttt cttctgctgg aatatctaac  20280
accaattccc acgtatctgc aataagtgct ttgaattgcg tatttttcct gacgttatac  20340
ggagtaggtt taaataaaac aatatgcata ttatcctcgg caatccactt cacatacttt  20400
cttgtcatca atgaaagctt taactaatgc tttattaact tcagcatatt gagtagtagc  20460
ccattgaacg tcatctttca tcattgtgat ttctttagta aacatgcttt cattcttaaa  20520
ccaccccata aaaactacct ttaccaattc cataacaatc tcctcattta accgacaaga  20580
ctactatacc atagtcttgt cagcttgtaa actaaaattt taattcattc gccaaagcat  20640
ctaactgagc tcgagtcgat tcatttcttt gatagcgatt ctgctcagcc tgaatctgtt  20700
gtgaacctgc tacttcgttc acttcagttg gagtagaatc ttgttcaatt tctacccatt  20760
tttgatttcc tttttgaaca cccatcaaaa acttattcca cttattctta tcaccatatc  20820
gtgatttgat ttgcttaatg agttgttgtt cagcagctgc tagctcctcg gtttcaatga  20880
ccgcaagcat aaaatcggct gttgctggaa gaccggcaga ttctgcaata tcgctcatgt  20940
```

```
taacatcgga agagtcccaa gcttgtttac caacctgtgc tgcagtccaa agaacagttt  21000
cggtttcaac agccagagca cgtaattcct ctgcaatagc tttaacagtt gtgtaactat  21060
tttctgaata aactctaatg cggcaagatt tacaaatacc tagatagtcg acaataatga  21120
ttgttggaac aaaattcttc ttgagcttca attcgtttaa aagtgatcga aatgtattag  21180
cgtctgctcc accagtagga tactgtttaa cgattaaacg accaagagta gatttctcac  21240
gccatttttc catttttcct ttatactcag cgtaagaaat atgcccatca tcaatgtcat  21300
caagagaaac atcaagcata ttagcgtcaa tacgtttagc acagacttct tctgccattt  21360
ccatggaaat gtaaagaaca ttatgtccga gctgtaaata atctgccgct aatgaacaca  21420
atcctaatga tttaccaacg ttaacgccag ccattaaaac gttcagtgtt ccagtttcag  21480
ctccgccttt cgtaattttg ttcagaattc tgagtttaaa tggaacctta cgagctttat  21540
tcatataaga tagccaacgt gcttcgtagt catccatcca atcatgacca acgtaactat  21600
caaatgaaat tgataatgcc tggcgcatga tgtcaggaat agcaccaaca tccggcattt  21660
tcttatttcg tttttccgga ggaagctcag cattagtttg aatttcgatt attttagacg  21720
tagcattaaa catcgccctt tgctgaacat atttttctgt ttcttttact aaccagctgt  21780
ggtcttccgg agaatcagcc agttttgaaa taagtgtttt tacaccagaa tattctgttt  21840
cagtaaatga actattttct aatgcaacat ttaacgcatt aatagatgga acgctatggt  21900
actcattaac atgagattta attaatttga atgtattttt agctggacca ctttcaaaat  21960
attctgaatc catatatggc caaacttttg aaaaataagc ttgatcaaat atgagatgag  22020
aaagaataat ttctaccaca cttactcctt aaaagaattt aaattttttc tttgaccttt  22080
tattaaatgc atcttgcagt tgcattgtaa tacatttttc tacatgagga gctaactcag  22140
cttttctttc ttggtcaaga acagcaaagt ccattacaac ctttccatca acccaatcca  22200
gtttagttac atacactata tgcgtagaac catcttctag tttaatgaca atctcctgga  22260
taacatttc catagcagat ttaattatct taagagactc attaaaaaga cgttcttttc  22320
tttcttcttc cccctccgaa gagggggatt catcgataat ttctagatct aaatctaaat  22380
catctttatt cattaaattc ttccatatca cttagctgtt cgaggtcagt ttctaaatca  22440
gcagctgatt tacttttact ttctggagat ttaaattttt caacctttga gttaatcaat  22500
tcatcaactt cagcttcaac aatttcatta ctatcaatag cacctaactg ataagcacgt  22560
ttaatagcat ctcggaatgg ttgatgctta aataaaggac cccagaatgt agtgcagttg  22620
gtatcttttg cacgccaaga tttttcttcg cgaatcatct cgccagtttc ttcgtcaaga  22680
aattcacgag cataccagcc atttttaggt tttaccacga atcctaattc tagagccata  22740
tctaacaatc cagaataagg atcgatacca ccgtcaaatt taacatcaat aaagaattta  22800
ctttttttctt taacggtacg agatttttct acatttagaa caaattgata cccctgaaga  22860
tcagaaccat ctttaatctg gcgtttaccg ataatgaata cggtatcagc cgaatacatc  22920
ggtccagtac cacctcccat aactgtttta ctaaacattt cttgtgtttc gtatgtatgg  22980
ttaatagcaa tacatggaat atttttagta ctaaaatagg gagttacgat acgaaataag  23040
cttttcattg ttttagctct agtcatatca ctaacaactt tttcatttaa agcatcttca  23100
gtttctttct tagaagctaa gttaccaagt gaatcgataa aaacgactac cttttcgccg  23160
cgttcaattg catccaattg attaaccatg tcaatacgta attgctcaag tgattgaacc  23220
ggagtatgaa ttactcgttc tggatcgact cccatagacc gcaaataagc aggagtaata  23280
ccaaattcac tatcataaaa caaacatact gcatcaggat attgacgcat gtaagatgac  23340
accattgtta atccaaagtt tgatttaaat gattttgatg gacctgccaa aattaacaga  23400
ccagattgca taccaccagt aatttcacca gaaagtgcaa tattcatcat aggaattttt  23460
gttcgaacta catctttttc attaaagaat ttagatgctg ttaattctgc agtcaattta  23520
gaagtagaag ctttaatcaa acgagatttt aaatcagaca tataatacct tatagtagtg  23580
ttcttgttcc acgaaatact tcgagcattc ttgcataaga tttatttgga aatccagctt  23640
caattgctaa ttttttaagc ttaatagcac cggattttcc agagttttcc catatttctt  23700
taatcttttc aatgttatcc cacattattg ggtcacgttt atgtgatggt ttatttctat  23760
tataaccata tggattatta agcaaagctt cttttcgttt tgctttagtt tcttctgact  23820
gctttttgcc tagctgggct ttccggcaaa catcactaaa tccaagatgt tttggttttc  23880
ctttttgagc ttttgaaatt ttttctttgg tttctgatga aactctataa ccaattcttc  23940
taccaccctc tccaccaatt tttaaattat aagtcatagg atcatttacc acatctattg  24000
ttactaattc tctttcagca tcacgggctg atttaaaatc tttataaaac ccaagaatgc  24060
ttaaattaaa atttttctta ccatactttt tcttggcttg tgctaataaa gttcctgatc  24120
ccatataacc atcatttaaa tcatcggttg aatgagttcc atagtaaatt ttattattaa  24180
ctaaattagt tataacataa gtataattat atttcttttc tttatgtctt ttcatgtcat  24240
taatcaactg ctattcgatg aacttctctc ttttctaatc aatataacaa aagaagtccc  24300
aaaaagcaaa cagacctaaa ccgataataa gcaataaagg tcctaacatt tattccaccg  24360
gttaaagata aataactttc taataatagt tcataatttt tataaatcaa tagctttttt  24420
gaacgcatct tgccattcgg ctttctttgc acgggtttta tttaaaatat catgttgaat  24480
agaaagcatc tctttacgca aaacatcact gtgttttaac tcattgactc tatcaatgag  24540
ttcagcacga ttatttacat aaaaacgagc atcattaata attcgatgtt tggtatcaaa  24600
ttcttcgtca attagcatca ctgcatcaga tgccattgtt tcccagacgc gtaaggtaat  24660
aaagttgtca ttataattct tgtcaccaat aattaatgca gcaatagctt gactattctt  24720
ttcagatacc atgttcatag gaatttttcc agtgaacacc ggagctttgg tccaaggata  24780
tttaggattt ttaaactgtt tttctcgtgc attgccaaaa aactcaatat ttaaaccggt  24840
gtcaaataag aattctacca tcttggattc gcgttgaccg gaccgaaatg aaccgccata  24900
aataacatcc aaagttttct tggtaggctt agataattga aaatcgttca tatgaatttt  24960
atattgttca ataggaaaat attcaaattc aataacatta tcaactttct tatgcgcagc  25020
cttagcaatg tctaaattta taccttggga aatcacttta attggtgatt taattaatag  25080
ctcttcttca gtgtacaaat atgcccatgg tctattttta acatttggcc aagactgcga  25140
aaacggcaaa cgtatatctg taaataaata ataaatttta cttttgtatt ttgccataaa  25200
tttttgcgca gataaaattg ctaaattagg tttaccgcca aaaaagttaa tagaagaatt  25260
aacaactatc aaacggtcat aatcattaac atctacttca tcaaaagatt tagtgtaaac  25320
accattttta agagaaataa tgtcgacatt aagacccatt tcagaaataa ctttaaaaag  25380
ataaatagtt tcagaagatg gaacagtttt aaaattaata acattattac ccatattaat  25440
tatagcaatt ttcatattat tccttttatg ttaaacgatt aagcgtattt tcctacataa  25500
tctttttttcg aaatatgtgt ttcgccagtt ttccaccaat gatcaaccaa ataaaaatga  25560
cgagaataca catgtaggct tccaacattc catataatgg aacctgcttt atactggcga  25620
gttgaatcac ctgcattcaa atcagatact aatttatcta atacgtattt ttgccatgca  25680
```

```
taatcattac ggaatccgaa gaccacgtca tttgagcgca tgttaacaac cgcattgatt  25740
ttcttgtcac gaatcaggta ttgtactgta ttcgtgcaca tgaaatctga cataccatct  25800
ttattatagt caaactgcat agatggacga gtataaatca tgataccacg tcgagaatca  25860
ggattttgac caagttcagc taaacacatg tcatactgag catagttatc ttctgaccag  25920
atagcccaac cataattcga gttaatttca cctttagaag atgctacttg ttgccaaatc  25980
ttcggtgttt cacccggaat atctttaacg aacaagcttt tagatttata ccattcaagt  26040
tcacgctgaa tgtattcatc attaagagcg ccaaaaataa acggttcatc tgctacaaat  26100
gatgcgccaa taatttcaat agttttaaca cctgttttat caactacgaa atctttttct  26160
tttaatgcaa gccccaaatg aagacggatt tcttcaactg tcatagagtc actaatcatt  26220
taaacctcaa ttgatacatt catatttaac ttgtaacagt aataaactcc aacctaaaat  26280
aatagttgga atcataagag gaaccgttac actatagtat atacttatta taatcatcaa  26340
gattaaaagc aatgctgcta taattttgct tttcattcct tctctctgat gataattacc  26400
tgatttggct gcgcagactt tttagtttca cctgcaattg accaaataaa tgtaataaac  26460
caaccaataa ttgaccagtt aaacagtaaa gatgcgaaaa agattcctac tgtcgatttt  26520
gacccacgca tcaaggcgat aaaccatgga agcatgtata taataatagc caacacgcct  26580
gaaactaaaa ccataaaaat tgaacctgct actaaagttt ccatgttttc ctcacttagg  26640
tcaaattttt tacacatgaa ttataagaat tcactacata ctccatcgga gcgtttttac  26700
ctgtacgcca ctggtaatta ttagcccaat ttgcccaaag ctcagcgcag tagttttcaa  26760
tttttcttc gcgtgtaatt acatctgaat tacgatatgc ttgagcagat tcatctggac  26820
gaatagcttc gtcaaaattc gcctgcattt gttctactgt ctgttttgga gcttctttat  26880
aacacttgac attaggatta taaaatttgc ttgaacagtt tacaattttt cctacatcag  26940
actgatttac taccggtcct tgagctacac aaccagcaag acctaatgca ataaccaaaa  27000
tagcgatttt catttcattc tccaaatccg tatcagtagt tgatagttgt atagtaccat  27060
ggaagaacag tcttgtaaac agttttgtga aaaaattttt agggaatcca aagggtccag  27120
aatcatctct ttttcataag tatagattta tattacttgt atgaaaaagg gacctggagg  27180
tcctagattt attctatcag ccaaacagga agtctaacga agctttttct tcatagtcca  27240
tgccagccga ttcacacata cccgcaagcg gtttaacaaa cgatttttgg aacaaagttg  27300
agtggtcaat ccaagatagc acatcagaac gaatttcttt tggaagttct gtacccgatg  27360
gccaagcaat gcacttgtca ccaaatggat ttccttcacg taatggaaga accattactt  27420
tatttccatc caaaattgga gctacaccta aaccgctaac agctcgacga taagttagca  27480
caccacgaat atggaacggg catttaaatc ctggccaacc tttatcatca tatttcgcta  27540
tatcgttcgc agtttttact tcagcaataa ctttatagtc aagttgacga tattctttct  27600
cgaagttctt gtagtattct tggacagact cttcaccttc ctgaagaata cgacgaatac  27660
tttcttcgag agcttcttgc actgcttttg gtgttgaact ctgctgagtt tccataccca  27720
tgatttttag atgcggttca gcaaatcgct tatcttccat atcataaacg ttcagagcat  27780
aacgcttttt cgctttccaa aatccaccaa cgccctttga accaagcgga gggcaagaaa  27840
tagcttcacg gtccatatgc atcagatgct cgcggttatt catataatca cataactcac  27900
gatatgcaac atcaatcata ggttccatct ttttcttacc gaactgattc atgaattcaa  27960
ccaaatcgtt ctgctctttg aatcggtcaa gaccaacttt ttcaataact ttatctacgc  28020
aaacatatac cgaatcagta tcacctgctg caatgaaatc ttcatcatta gttccgcata  28080
ctttattcag atattcatta attttacgag caatccactg aataccgact tggccgaaaa  28140
ttgtgatagc agtagcattt cgcaaatcat agtaacggaa atgaatatta ccaagagcac  28200
cataaagact gttaatgaga attttacggt tcagctgatt tgtattagca agtgtagctg  28260
ctttttcaca ttcttcaatc agactattga gaacagattc ggtgtaattc gatagttcat  28320
ttaagaaatc atcactgaac ttaacatatc gttcaacttc tggtttagtt gaacaagacc  28380
ctgcgccttt cataataatc tttttaatag cttcggcatt catttcttca gcgaacattt  28440
tctttttcca gtctttacgc tggaaaaata ctttagcgat ttcctttgga atgatacctt  28500
cttgatgttt atcatacatc catccattcg gagaacaaga atattcatca ctcggtttag  28560
gagctgttcc tgcgatatat tcatgaattg gatgaacttt aaactgacca cgaatagttt  28620
caggactaat gttaacctgg cgaataatgc tcggatacag agacgtcaag tcaaaactca  28680
taatgtatcg acgtgcaatt ggtttaggtt caaacacaaa tgcacccgga aaactctgtt  28740
taacgtgcga accttgttga ggaataacct tatgttcacc tttcaatgag ttaaaaataa  28800
tagcatccca agttttaata ggactcatta caccagaaaa aggcatttta gcgtaataag  28860
acatacttaa aactagatcg ataaacccac gaattttatc gattgcttga actgattcta  28920
cgtcaatgat gttataacta atgtatcgtt gatgattagt ctcacgaagt ttattaatag  28980
gaccgtcgta tggtaattta cctttttgg tttcatgttg agcaactgat tccaaagaga  29040
atgacggcaa attagtaaaa gcgaatttct tgtacaaatc taaataatca agaatagata  29100
cgccatcaat agaataaatt tctttgctac cgtacatatt ttgaattagt ttagatttta  29160
cccgaccgat tggagagaaa cgtttcatac tacgttcacc cagaatcatt ttaacacgat  29220
tcatgatata cggaacgtca aacccctcaa tattccaacc agtaaaaata gcaggtcgtt  29280
tctgttccca aagattgata tattccatga gcatatcacg ctcattatcg aatggcatat  29340
aaattactcg gtcaagaatt tcttgaggaa cttcatcacc accttcacag tcaagcttag  29400
cagctaactt tgcatcccat tttgatactg aaccgtacat tgaattcaaa aggtcgaaaa  29460
cataaaaacg atcgtcaatt gaatcgtaat gagtgatagc atcaatttca tattctgctt  29520
tcattgggtc aggaaattta tcaccagtaa cctcaatgtc acagttagct acacgaacaa  29580
atttcggtc ataaacaatt tctgaaccat atgtatcact tatataagcg agtttaaaat  29640
cgttcatacc gagagcttcg agaccgatgt cttccattcg cttcatccaa tctcgagcat  29700
ctttcattga tggaaatttt tgaggagcgc agtttttacc atagatgtct ttgtattttg  29760
actcttcctt acaatgccta aacatagttg gaagatattc tacttcacgg gtacgttcct  29820
ttccatttc atcaatataa cgttcaacaa tgttatttcc gactgtttca atagagatat  29880
aaaattcttt catagatatt ccttagttta tagcccgagt tattaggctc ttgatatatt  29940
atactccaaa taaggggccg aagccccttg cttaattacc aatcgtatat ttaggaacga  30000
gcttccattc atgtttttgt ttaaaagaaa taactcggaa gttattagtt aaatctttca  30060
taaaagttct ttgaccagga acgatttcaa ttagtcccca atcttctaat agccatgcaa  30120
tcgaatcacg acgaacttca tcttcttctg tcatttcaac ttgacgacca tccatacgaa  30180
gcatttcttt aaaatgaacg atatagtata gtcctttttt ctgaagaata tgacaggact  30240
gatatagaac tttatcttta ttattagcaa ttcccatacg agtcaaagtt tcttttactt  30300
tcagaaaatc ttcaggtttt ttaagagtaa tttcaatcat tttaccattc caatgctagt  30360
tttttgagtt gtttctgttc ttttacgttc ttagtcactt ctttcaaaaa atcatccgtg  30420
```

```
actaaacctt ttagttcttt taatactaaa ggaagttttc catttttagt aagaattgat  30480
ttatagttaa ttgcatcatt tgtattaact tgataccgct tagcaagtaa cttaataatc  30540
aatacttcgg tggaatcttc aaccagtttt gcccatttac catatctttt accacgagga  30600
actgcagcca ttagataatt aaaatgagct tcatcactta agcctgatcc aattaaattc  30660
atagcatata cagctggcat acactctgga aattgtgata atgcatttc aaccatgaat  30720
tttgaataat ctttttgagc aatagagcat ttagttttat tattaatagc tccaattatt  30780
tcaaaaaatt cattttctgc tttttcttta aaagaatcag cagcggattg gacagctgtc  30840
caatcttttg aataccaagc aacttgatgc tcgtttaatt gaatatcatc tttaaataag  30900
ctcatatcac ttccactgca tttcgcatgc taattgaatg aaaagataag ctaaatgcaa  30960
ttcagtatta gctgcaatac catgatactg attattttcg ccgacaattt cgtacatacg  31020
aataatactt tgtggagtta cacgtgaata gatttcttcg gcaagtttac ccacgaacca  31080
cgaataatca gccgcatatt ttggtgctaa agctctgagt tgtttaacat ctttattttt  31140
gagagactca agaacatcat caatagcacc acgatcgtta gtaaccagtg ataaaatacc  31200
agcatccaaa acacctttag acgaataact atcgagctcg ccaatagttt tacgaaaatc  31260
aggaaaattc tttttaacca aagctgctac aactttcata tcagctatag caattccttc  31320
atgcttgcag atttcagtca atcgacgaat catctgcttc atcatttcaa ttttatcttc  31380
atcagttggt tgaccgaatg taataactcg gcagcgtgac tgaagcggtt taataatacc  31440
atcaatatta ttagcagtaa taataatact acagtttgaa ctataagctt ccataaagga  31500
acgaagatgt cgctgagact ctgctaaccc tgaacggtca aattcatcaa taacgattac  31560
tttttgacga ccatcaaatg aagcggcgct ggcaaaatta gtcaaaggac cacgaacgaa  31620
atcaatttta caatctgacc cattcacaaa catcatatca gcatttacat catgacataa  31680
tgcttttgct acagttgttt tacctgttcc tggagaagga gaatgaagaa taatatgtgg  31740
aatcttacct ttacttgtaa tagatttaaa ggtttcttta tcaaaagcgg gaagaataca  31800
ttcatcgata gtagatggac gatatttctg ttcaagaatg tgttcttttt catttacagt  31860
aatcataatt tcctcattca agttttagtg taaattataa aggccgaagc cctctattaa  31920
aaatcgtggg tagaatcagc ttcaagagct accacataat tcgcgtgttc accttcaaat  31980
ttagcagcac cttgtttacc ttttgcccaa agcagaagtt tataatttcc tggttgcatt  32040
ttcatatttg ccatattgat aatgaaatta aatgtatttt caccatcata atcaccaaga  32100
gtcaaagaat atttaacacg ggtcagagca gaatcttcta ctttattaaa accgttaatt  32160
acgattttac cttcttttac cgtgatagca attgtatcaa tttgcagacc acgagataca  32220
cgcaacagct gttgaaggtc ttcagcttta atttcagtaa cagcagatgc taccgggaat  32280
ggaattggtt tattaggagc aactactgta ctcggatcgg ctgctggcca aaaaattgtt  32340
gagcgggcat cagcaatttt aatatttcca tcttctgact gggaaatttc tgcatcatca  32400
ttaactaaag acagaatacc gagaaaaccg ttcaaatcgt aaattgctac atcaaaatca  32460
ataacgtcag aaatatttgc ttccgcataa gttgtaccat taactgcgcg agtcataata  32520
aattgaccgg atttaagcat aataccagag ttaatagtag cgaaattttt aagcagagca  32580
gtagtatctt tagacagttt catgtaattt ccttcaattc aaatgagatt taattttata  32640
actaatttaa taaagcaatt aacgattaaa atcagccgca attgtttccg caacaatttg  32700
agcagcaaca attagacgtt catctgcatt accgcaataa tcatcttcaa ggcgttcacc  32760
acatgaagtc ataataaatt tagcaccggc gtttagggat tctgtagtat gtttgcgcat  32820
tagttcaatc catttattac ttacttcacg atcgatagct tcataatacg catgacgagc  32880
aggtgcagat ttaattttgt tctgaataac ttccattgcg ttatcagaaa gagacaaaac  32940
ccatgctcga cgaattttat tttggttttg tggatttgat tcagaacgca cgtgttttgg  33000
ctgaatatct tttacatcaa cagtataatt cacagtaatt ttagtcataa tacaccttta  33060
gtcataataa tcagtaacag tccaagcttc atttctattg gacattattt ttgtatattc  33120
tgctttaaat gcattcctaa gcatagattc agtaactata tgctcttcat tagaaaaatt  33180
atttctcaga atatatcgtt ttatttcagg aatagttaat agatgctgtc cagttgaata  33240
ttccatgttt ttcctccata gagattatac tctaataaat taaagcataa tctcttataa  33300
attaaaccat tacagtaaat cgaccaactt tcttcatttg aagatgctga ccatattctt  33360
gcgggtcatg gtctttatgc gaaattataa aaacgttagt gtttttcatt gaatttataa  33420
tattagctac acctttaata ccttcggcat caaatgaccc atcaaacact tcatcaagaa  33480
ttaatgtact aatactaaca ccagatacga tagaagcaat atcacgccaa gtaaataaaa  33540
gagcaatatc gattcgtgcc ttttcacctt cactaaatga agcataacta aaatcttcac  33600
gaccacggga tttaattgtc tcattaaatt cttcatctaa tgtaaacaca taatccgctt  33660
ccattatttt aagataatgg ttaatctgct tattaaataa tggaatgtac tttttaataa  33720
tagcaccttt aataccagaa tctttgagca tatcagtcaa aattcctcgg tggtattttt  33780
ccattactaa attagttttt gtcttaacaa ttttatcaag ttcttcttga agcagtgcta  33840
tttcatcagc atggtcaata aactcagaag atgcttttc tatagccgct ttaacttttt  33900
tagctttatc tactgctgcg atcagagatt gctttttatt gcgaatatca tttgccaacg  33960
actgctgggt tttaatatta tctcggtatt catcaacaag aacttttaaa ttatcacgat  34020
gtgttgaaag ctgttcaaac gaatgtgtgc attcagaaac tttatcttta attttagaaa  34080
caactttatc accggaactc aattgtgaca aacaggttgg acataatcca ccttcgtgat  34140
acatattaat gactttatta tacgagtcaa tttttgattt aattaaaaat gcttcttgac  34200
cgattttatt aaatgcatca gtcgggtctt cgtccaaaac aatattaact aatctttcgt  34260
tagcttcttc tatttccgat tttagcgttc tagcttcttt tgccaaatca tcatacatat  34320
tttgtagacg agtaaggttg tcacccgtta atttttctg gcgttcaaca ttatcattat  34380
atattttaat ttgttggata atactatctt ttttaacatc aagcacttgg ttctgcgaat  34440
ttaattcacg tattagtgct ttattaagct tatccatttc agctaatgtt cctacctcaa  34500
gcaggtcttc cacaagcttt cttcgcgcag gggtcgacaa acccatgaaa ggggtatacc  34560
ctgctgtacc aaggacaaca atctgcttga aactggcata tgacattccg ataagctgtt  34620
caaattctgc ttggaaatct ttactgctgg cagattcatt aagacgtgta ccgttaacgg  34680
tgatttcgaa aacgtttggt ttttgtcctc ttttgatata gtactttttc tcatcatatt  34740
ccatccacag ttcaactaaa agttctttct tatttgtgct gtttattaat tgacctttct  34800
ttacatcgcg aaatggctta ccaaaaagcc caaatgtgat ggcttctagc atagtagact  34860
taccaccgcc atttcgtcca gtaataagag ttttttgaac cttatctaat tgaatgtcaa  34920
tcccattttg accaactgac attatatttt tatattttac tctattaagt ttaaaattct  34980
tcacaaaaga ttccttttaa tgtatctttt agaccattct atcatatcat cataatctaa  35040
aaagtattca tcaaattcag ccatgcaaac aacgccttgt gctgtttttg atgtgatata  35100
aattattcca acatatctag aatcttcttc ggtataatca atatttgcta tgaattcatc  35160
```

```
attaatgtca aatgtcgaaa acttcacagt atgcatcctt aatacaagat acagccatat  35220
ctcgtaatga tttaggtgtg tcattatcta aaatgttgaa gttaaaagat acagcccagt  35280
cagtgcagac agtaaccttt ttaatacaat tatcttcaac ctctaacggt tcaaaccagt  35340
attcaataat ttctttatga ccaatatcat cttttacttc acatttaaaa tgctgactca  35400
tcataacatt tttaaattca tcaaaagtca ttgtgttgcc tctacatata gctgatttgc  35460
atattgaata agtgcttcac ggtcagaatc agtgatgtct ggaattgcat taatatactc  35520
ttccattaat gtctgaagcg attgaacttc aacttcttca ctgtcatctg actcgacaga  35580
gttatcaatc tttgacacaa ctcgtaatga atgcacaact ttttctagtt cagattcgaa  35640
cttcgtcaga tttttgtcta cttcagttac tataacacgt actgatagat ttgtaaaatc  35700
tttatagtca atttttcctt taaatggata atgaattcta cgatgccagg tagtattgtt  35760
tggaataaat tccgttcgtt ctgtttctgt atcaaacatc cagaacccac gagggtcatt  35820
ctcgtcacct gcggttagtg tccatggtgt cccaatatat ctgacgtttg cagcctcaga  35880
aatagtatgg aagtgaccag accacacttc tttataagtc ttaaggaaat cgggttcaag  35940
accatgagat ttcattcctt tataaaaata aaatccattc agttcccagt gaccaacaca  36000
aaaagaagca gatgaagttt tgatatgctc aagaatttca ccagtatttt cttcgcacat  36060
ccaaggaatc aaatcaatca aacacccgtc aaaatctact gtagtaggct tatcatacac  36120
tttaacatta ggatatttag ccaaaagctc agtagaagca tttggatgca ttacattttt  36180
atagtggaga tcgtgatttc ctacaatagt gtgtaatgta attccagcat catcaagcgt  36240
ttgaactatt tcacgggcaa actccatagt tttatgtgtg atcgcttttc gcacatcaaa  36300
aatatcaccg tattgaatcc aggtagtaat tccatttttc ttagaatatt ctatcgcttg  36360
cttaattcca tcaatttgaa taccgcgaat ccactcatca tcagctttaa cgcctaaatg  36420
ccaatcacct aaatttaaaa ttttcatata tcaagaaccg tcattgaaat gcaaaataaa  36480
attattgaaa taaatccatc tggagtgcta aagaacccaa tccaacatgc tctagtgaat  36540
agataaaatg caagaaaaag tatcacatat ccaagaaata tcattatatc aaactccgta  36600
taaagctaaa gggccgaagc cctttatttt gtaataatgt caaactgttc tttaaagcag  36660
aagcttgaat cttgatgctg atacaaaaat tcatatgctt tttctcgctc acggtcataa  36720
agagctcggt cagatgacag ttctttaata cgttcaaatg ttgattccat atcattttca  36780
tcaaaccaaa tgataccgct atcatgcgag gtcaaaggag tattatcaac acggaatttt  36840
aaattttcgc cagtagattt ccaaaatacc ggaattgttc cacatgcacc aagctcgaga  36900
tgagtatatt cgagtgagcg ttgtaagtat ttctggttaa gtttactcaa ctgatatcca  36960
aagccagatt tactcattcg ttcaagcatt tcactattaa tataacaatc taggatttgt  37020
gccggttgat tcggcgcgag attcatttta tcaatctcac gattaccgta atattcatac  37080
ggaatacctt tttccttaat tgcaataaaa gcaggggaac gttccagacc ttccattaca  37140
gtggatttac cagcaggttt taagaatttt tcatgaaaat caaacatctg gtaaaaacct  37200
ttccatgtag tcgtacgacc aatccaacgg ttgatattca tgttaatttc agaaacatct  37260
ttccaataag ttgaccgaac cttcacaata tccataggag gctgaaaatt atatactgtc  37320
ggtgcttctt caatatcatc aaacagagaa acagtttctg gataccattc tttcatcaga  37380
actttattaa aatcaccatt atcagaatgg ctaaaaataa catcagctcg acgaacagtt  37440
tcttctaatc ccaaatttcg acgcaaagaa agaacagaat gatcatgctg ataaactaca  37500
acacgaatag aaggtttaat attatctaaa agttttttat agttattaat cgtagcttct  37560
tgaacggaag tagcaggaac agaattaata attagaatat cacaatcatt tactagctta  37620
agtgctttat cgtattcttt agctaaaata actggaattg aaaatgattt gtggtcatga  37680
gaacttgtac gagtaaatga tttatcttta gcataaacca aagttacttc atgaccattt  37740
ttaataaacc aatcacgttg ctcgagtgag aattttgtta caccacaacc ttcaagacct  37800
cgagccataa aaatgcaaat acgcatagtt ttcctctttt catttaataa atcatgtaaa  37860
taatatttta ttttctataa aacgctacga ataggcccaa acatatccat aagcaatttt  37920
gctttttcca gatatgcact ttttaatatt agacatgcat cctttaacgg atacagctgc  37980
gtctttaatt ctaggaaata ctcgtaataa ttttccagta gtatcatatt gaaatactgg  38040
cacatttctt ttctgagtta tcccacgttt agatttagac atttttttgtt tagttgcatt  38100
agacatccta gagggctttc ctatgttatc agaataataa tatttccatt gaaatcctcc  38160
agcggttttc cttttaccat ctacacattg tttaattgaa gttgaacagc tatatgacat  38220
atcttctgca gcatctgtaa tacatctata tttgcgaata aaatttccat ttaaatcata  38280
ttgataaatt ggttttccag catttcgtct agcgttagac atgtattttt tattatcatc  38340
atctttccag aactctttca tgctttccga tattgaagaa gatacagctg ttttaatcca  38400
tccatacatt ttattattta gtcttgttcc gtcagaacta taacacatca tacgaatagc  38460
taaagccaat ttaggaagtc tataaatttt aaataataat aaatgcgcgg taaaatgttc  38520
ttctggtgtc aaaagaacta aattagtttt atcatctgta ccacccatac atctaggaat  38580
tatatgatgt gtttcagtat agtatgtcaa aagactttta tcattgcctc tgtttagtcc  38640
tttttcgatc agtaaattat atatgtttaa ataattcatt ttagtttatt ttaccaaaaa  38700
atttataaag caatatagga gccgaagctc ctatccacat aatacgccat acagaggctc  38760
gttagaactt ttaaatttta tgcgcttata tgttatagtt ccttctgctt tagctttatc  38820
atgagcctct ttaaagcgtc tcatcatttc ctctctagag gaacgaattt tattataatc  38880
tatttcagaa gtcggatgtt catctttcac agttgccacc attttttgac ttgataagaa  38940
tcaacccaca ctttcatatt agggtctgct cttacaatag gaggattaac ttctttgatt  39000
gaactatcac ggtattcttt ttcagaaatt ttcacgcaaa gatgaccatt caaagattca  39060
gtaaatcctg cattaatttt aagacgcttg aattttacgt gtgtaagcat caatcatatc  39120
ctcaatctgc gatctagtag tcttccaaag aatactgatg agttcatcgt tatatggctg  39180
ttttagaata tcccgacttt tcttgatagc atattcgtat tgagcaaaat tattattttc  39240
agctgcgatc tgagcgtgct tataaagacg attcagttcg cgtttgtttt tagacaataa  39300
cttatttgct tttctttctg cttcaagacg gttcttttct tcaatagaag aaataagctt  39360
ttccacttca tcattaattt cgggtttatc agtcatatta tttctctaat ataaaataaa  39420
aatcatcatc tgttaaatga taccgatagt ttaattctac accattagat ttaaaagcgg  39480
tatcatacgg attttctgga tcaatatcaa tgtcaagagc taaaacttcc ctgagataca  39540
ttttaagtaa atagggaata gcttcaactt caggtatttc ttccaagaat ccggagaggt  39600
taatcgttag cctcatataa aaaatccaaa ctaggagaat catctacaac acttttcttt  39660
tcagcccccg gtgttctata ggttgattct tcgtaatgcg tcattttatc atagatgtct  39720
tgaataaaag tttcatctac taacgcaacc atatcgtcgt cacggctgtc atagacattg  39780
tgaacgaagt aactatattt ctttgcaact tccttacgtt ctttttttaat acgttggacg  39840
aatgcattaa aacaagcttg agttatatac gcatgtgggt tttatattt cgtttcatca  39900
```

```
aaattgtgaa gcccccttaat agaagcttct ataccatctg caatcatttc ttgtttccaa  39960
gactgggtgt atcctgaaaa gttgaaacgt ttagataagc cttctgcaat aagcataatg  40020
gctaatccga tagtatcatt ctgacgaact actttatttg ggtctttatt atttgctaat  40080
tctgttttcc aatcaataat agcttgtaaa agctctttat tgtttacgta attatattta  40140
ggcttagttt ctgacatttt cacctcttag ctcaattcat agatctatta tatcataata  40200
tttgaagacc tatcttaaag catagaggat gaatcaattt caagcacttc atcagattag  40260
ccgctccaag agctgcatct agtgaatcaa attggtcaac atattcaatt aattcgccgt  40320
aattagcgta taaccaccat tggctaaatt catactcaag gatgaatcca tttccttcaa  40380
tttgagttaa accaatgcca tttgtattta cttcataccc agcgagacgt aaatcgttaa  40440
taagagcttc gttcataatt ataccttagt aattttcagg tctgcaaatt ttttcttgcg  40500
ttgatttttc atgcgacgaa tagttttatc ggaaatttca tgcttttgat aagctttaga  40560
ttctacacca aaagctttaa catcaaattc tgacaagata tattgaacca acaattcacg  40620
gacagtattg cgtccaatct tctgatcatt ctgtttcatc gtttgatgaa gctctttttc  40680
ccatttatcc aaaatttgag gagttacaat atcgcctttt tctagcaaag aaactacttt  40740
atcatatgcg taagaattga tggcgttttt aatttgaata gtcatacatt atcctcaatt  40800
acgttaaaat tttattatcc aaaaaggccg aagcccttag gctaaacttt ttggcaccct  40860
tccagccttc gtacatcatt gcgactgaca atgacaaagc tccttcacat gctgcatact  40920
tattattcca gaaccaattt agaaaaactt catcctcaat accgttgtgt ttcatgttct  40980
ggaaaaattt ggcgcgttct tcagcaattc gctgcgataa tttagattca ggattcattt  41040
aaatttccca attgccattt tcatcaataa atttaatcca gtcatttact gaccacttgg  41100
tcgtatcgcc ttttggagta acatttaaag tgtatagccc ttgcttaaaa agcatgcgtt  41160
tgatattcat attttcctca gctgtaacga taacactcgt ttgatttacg tttagcaact  41220
cgttgagaag tattataatc aaaatcatca tcaatgtaaa ctgatttttt caactttctt  41280
acttcaccgc gtaattgacg atttaactca tctttaactt ctgaatcaat acctttcatt  41340
ctacgccatt tatctgagcg aaaaatgttt tcaaccatat ctttatgact taccccatca  41400
ggagctttac gctttccgaa atagtcataa tcacgcactt ttaagtcttt acgacgatac  41460
gttttaccca tggagtttaa tttccttagc aactgaacta aatacagcac gatcacaaat  41520
catacgttta tgtaacttga gtataagata gtaaacatca aaaccattta cataagtaac  41580
acgaacaaca ttaccattca cgagataata ctgtcccttt ttaatctctt tatcaaccac  41640
aaccatatca attcctcaaa ggtaattcat atgttaataa taccacggtt tgaacttgtt  41700
gtaaacaact ttgtgaaaaa tattttaggg aatgataaga aaggaacgat agcttagaat  41760
ggtaatatac agaatgtgag aaagaaaggc ccagagggcc cgtcttaatc ttctatgata  41820
tctctatcat atccaagtga aatgagagtt tctttgaagt gtttaatgtt cttttgtcta  41880
gaatcattaa tgaaaatgac tggataacga atgttaagag atgtgaatcc agcgcgttta  41940
gcaagagata caatcagcgg acgatcatac tcaatcttac cattatttgt aagaacttta  42000
tagaaagtaa aaggagcatt gagctccttt agaagttttg taactgattg acatccagga  42060
caacgaccta cttcatctgg aattccatag acttcaatct tattttgttt cacaactatt  42120
ccttactaag agcagcattc agcttgttag taattttatc cagacgctca ttgaattcac  42180
tagaagataa gcccttttct ggagaaatca aactaatcac gaaaaatata gcaataaaag  42240
gaataaggaa aatagctcca actgccataa acagaaagaa tgttacagtt gtaagaaaat  42300
cagctaaacc tttacgaaat ttatacattt acatttacct ttaattgatt aaccaagcat  42360
tgataagcac taaactatac tgcgaataaa attctggacc aaaatgaaaa tcatatcatt  42420
tatagtatcc ataatgtaat tcaatttaat catgtttcca cacccccatcg gtatttgacc  42480
aaagtcgctg attatctgat cctcgccaca gctttttggt cggaagattt ttctcatact  42540
tcccatcaat aataacatca acatatttaa gcatttctag ttgtttaata tcttcaaact  42600
tatatcctgt ccacaaccag atatctttct ccggaaatct tgctttaacc caagaaacta  42660
aatttgaaat ctcttctcgg ttctgtggat aaagtgggtc accgccggtt aaggtaaggc  42720
cttggatata cgatttgctt aaatgggacg caagttcttt aacggtattc atagtgaata  42780
actgtccgtt acgagcattc caagtactac gattataaca accttcgcat ttatgcaaac  42840
atccagtgac gaagagaacg accctacatc cagggccgtt aacgaaatcg catggataaa  42900
ttctatcata attcatcttt atatttccaa gtatatccct tatgaataga ttgaattcct  42960
ttgcaacatt tataaacagc agaatgaaaa aatcctgcat ttcttatttc agttgctcca  43020
gttagttcta ttgtatttcc gtctggtgaa tagccaataa ccgttttggt gttaaagcga  43080
tttctagaac tatttttgat atgctcttta tgattagtag acaaagttct tcctgttagc  43140
ccatcagata tcctttttcc aaaatcatca ggaagagtta ctttagacct agctatgctc  43200
attagcttct tagttttatc gcttcttttt gcgccacgct gattttcaaa tttcttagct  43260
tttgcatacg cgtattgtga agaagtaact tttctatgct tactattact cattatccaa  43320
tatgcatcat acatctttcc accatatatt ttagccaata aatggtgagc agtatagtgg  43380
gccttataag ttaaaaatac taagttgtct aaatcatctg aaccacccat acttcttgga  43440
attatatgat gaagttcata cccggcttta gtttgacggg gcttagatgg gtgttcagca  43500
gaattaacta gatttgaata gattctgtca taattcattg gtgcttaacc ctatgcatga  43560
tttctttatt tttaccgaga ttaaatccgc gttcgttcgg atttcccaaa taaccacatg  43620
ttcttcttat ggtattcatc tttttaggat cagtttctcc acaaatagaa caaacaaatc  43680
cgttttcagt aggagtcatt tcatgggtac ttccacatgt aaaacattta tctactggca  43740
tattaacacc aaaataatct aaatgctgtg cagcataatc ccacacggcc tcaagacctt  43800
ttaagttatt tttcatatca ggaagttcaa cataagaaat gtgaccacct gtcgcaatga  43860
aatgatatgg cgcttcacga gaaatctttt caaacggagt aatattttct tctactgaaa  43920
catggaaact gttagtgtac cagcctttat cggtaacatc ttttacgctt ccatattttt  43980
ctgtatcgag tttacagaag cgataacaca ggttttcagc aggagtcgaa tataaactaa  44040
aagcaaatcc ggttctttca gtccactgtt taagatgagc attcatttta gttaaaattt  44100
ctcgtccaat atcacgaccg acaagaatat tcaattcgtg aataccaatg tatcctaaag  44160
acactgaact tctaccgttt ttaaataact caattatgtc gtcatcaggt ttaagacgaa  44220
ccccgaatgc accttcttgg taaagaatag gagcaacagt agctttaact ccttttaagg  44280
aactaattct acacatcaaa gcttcaaaac ataaatccat tcgttcatta aatagctcaa  44340
caaatttctg ttcattgaac tgtgttccaa tataagaatc taacgcgatg cgaggaagat  44400
tcagtgttac aacaccaaga ttattgcgtc catcaagaat ttcattgcca gtcgaatctt  44460
tccatacgct caagaaacta cggcaaccca tcggagaaac aggaacagat gaaccagtga  44520
tagctttatt gttcttagct gaaataatat caggatacat ccttttgctt gcgcactcta  44580
gagcaagctg tttaatatca tagttcggat cgtctttata aagattaaca ccttcttcaa  44640
```

```
cgaacataac aagcttaggg aaaataggag ttatcccatc acgaccaaga cctttaatac  44700
gatttttcag aattgctttc tgaatcattc gttcagtcca gtcagttccc gtaccaaatg  44760
taattgttac aaaaggagtc tgtccgtttg aactgaataa cgtgttcact tcatcaatgt  44820
gttcagtaga gttcgctact tctctacccg tttatatgaa acaatgtaat ttggataatt  44880
gtcatctaaa cacaaatctt taatacgact tgggtggagt tttaaatctt tagcagcatc  44940
cacaaatgat ttatagatat tgtcatttat tttaacatat tctgggacgg gatgaattgt  45000
tatttttata tctataacat ttggatgatt actaacctgt tcttcagagc atttaagaaa  45060
ttttgcagct gatttaaaac ttctaaattt atttccggat tttaaagcta tagaaacagt  45120
ctttttagcc gttctactac caatattatt tttaacatga gcttcacttc tactattatt  45180
tttataatgc tcaatcaatt tctctcgtat cttatcttta tgttttaaag ataagatttt  45240
acctttatgg gcattactaa gtttttgctt atgttcttct gaatccggat atttgttaaa  45300
tttatatcca cctatagatt tattaagaat aaattcgtta ttaaaatatt tcctaataag  45360
catttcttca tgtttaaggg ccgattcata agaatcaaaa acttgaagaa ttatccactt  45420
agctttataa tctttaagct tttctttaac aagcttagat gacgaattgt attctttcca  45480
atttgtatct ttaccatata tagttttgaa ttttttaaaa cctatataaa aagacttatc  45540
aggaaatctt accatatagg taaatgctac agaattggca atttttaagc tttttcttaa  45600
tttccatttc atcgtttcac ctcgtattca tatttatacg aggataaaca gctgcatgtc  45660
accatgcagt tcagactata tcttcaactc ttagagttgt ctgccgtttc gggtcgcttg  45720
accctactcc cttacattca tcagggatag tcgttgggca tttacagcta ctgctgattt  45780
agcaacggat tgtctcagtg agagtttccc gttttaggca gattttacat gagcttgact  45840
tacgttaact cataagcttg gaatgcatcg tatacgtctt tttctgtttt agattgagca  45900
taattcaacg catcagcgat ttgccatttt tctgcatcct caatatgttt tgcataggtg  45960
cgtttaacat aaggagaaag tactttatct acattcgcaa aagtcgttcc gccgtattgg  46020
tgagaagcaa cttgcgcagt aatttgtgcc ataattgcag tagcaactcc aattgattta  46080
ggagtttcaa tctgcgcatt accaagctta aatccgtttt caagcattcc ttttaaatct  46140
actaaacagc aattagtaaa tggaagagca ggggaataat caatatcatg cacgtgaata  46200
attccgcttt catgcgcttt cataataaaa gacgggacca tatttttggc aatgtgttta  46260
gacacaatac cagccataag gtcccgttga gttggaaaaa cacgagaatc tttattagca  46320
ttctcgttta aaaggtcttt attagtttta tgaattaatc cttcaatttc tttttcaatt  46380
gtcattttaa actctttcta agctgcttct tgaatgaagc tattaattgt gttttggtgt  46440
cagattcatt atattcaaat cctctttgaa gcatctcggc catcatttcc tcttttccta  46500
aacgagaaaa ttcctttgat ttatctccaa caaagttagg gtgaatatta ttttgggtgt  46560
aatcggattt taaataagta agtaaatttt ctaaccattc aagataatca acaccttgtc  46620
cctttaagcc agaacgatta aatttatgct tcatttgacc ttctgcagca ttgcatagat  46680
tacaaagcaa tccacgcacc tttcctgctt ttggtccatt taattcatgg tcatggtcga  46740
ggtgattagc ttgaacatca ggatttagtt ctcgttggca aattaagcat ttaccgtttt  46800
gtgcatcata aaatttctgt ttttcttctt tgtataattt gccagtcaat aacataataa  46860
acccttacct taaatagata aggtatttta ttattttcaa gtattgtaaa acatttgatg  46920
caatcgctta tattgctgaa tcattcggtc agaaaaagaa atttgagttt caagccattc  46980
aatgtactct gcggcagctt gcattaaatt tccttcatag ccatcgttat tttcttgtgc  47040
agctaattta gctaatgcgt atgaaatacg ttcaccttga aaatcggctt taggcttctg  47100
aacaacttga ttagttcgct ctacaacttc ttcaatttcg ccatttttcta ctgattcagt  47160
attccacaaa caccaatacg taattggctt atcgtagatg ttaataatct ttccatcaga  47220
aagttcaatt tcaataattc cagtgtcagg ctctatatca tcttcacatt cttttacaag  47280
ttcacgaact ttaaagacag tacctgcact aagttccggc cagtaattac acagccctgt  47340
atcagcacga ttaattctaa accatttatc tactgtaatc atgtcccatc tccatatcaa  47400
ttaagtcatt tatcgttggt tcattataca ccgtttcttc atcagtgtaa accggttctt  47460
ccggctctgg ctctacagtt tcccatctag ccgcccacca aggttttata gcgtaatcca  47520
ttctcgtact gtctgagtta ctacacgttc tcgaagctca accagttcaa cagtaggaac  47580
tgcataatac cagtcagaat ggtaagaacc tgagcgagat tcatttacag ccacatgtac  47640
attatgtttt ggactaaaat aaacacactg acgatattgg catttaccat cttgcaccca  47700
gtcttctatt tcgataggtt taagatagtc ggaaaaatcg aaatcatagt tttccgaaaa  47760
tgcatcatgg tcttcaatga tttcgctcag aactgcatca acatctaatt tattttcaat  47820
attcattttt cacaccacca actgcttact tcaaaatcgg gttcgccatg ttcccagaac  47880
caggggccga taggaatcca cttaccttca tcggtgacgt catattcttc ggatttaagc  47940
ccaacgtatc gccattcgac ttcataagcg gtaccaccga ttacaactgt gttctcgcca  48000
tacgggttag acacaacaaa gtctatacct tctgctttag ctaaccaaat catgtattca  48060
tagagtttat attccaggtc gccttctgtt ccatcgccta gaaaaataat ttgttcattt  48120
aattctatca tttaaagtat tcccgcaatt ggtcaaatcc accaatatga cttccatcag  48180
gagcaaatac ctgaggcatt gttaagccga tttgagtatc acgacctagt ttagtcagaa  48240
gctcagcaat tttctcatca tcaaaaacac ctttttccgg cataatgttg ataaattcaa  48300
acggctgttt cttcacagtc aaaagacgtt ttgcattatc gcaatacaca catttatgaa  48360
tgttgctatc ataaccatat actttaaaca tattattcct taattcctag tacttgttta  48420
aaagtctcgt cgtaatcaag actttggccc gtttgttctt tatgcttgta tataatatca  48480
cttacttctg atagcatatt tttatatgaa cgagttaaag cagatttaag cacgctgtat  48540
ctatcaggaa atttaccgtg ttcattataa taagctattg ctaattcacg gactgccttt  48600
tcagcagtct ccatatattc tttacgcttt gtcattttct tctcggtcaa atcggtgttt  48660
acaatggcga catttataac gaagattatt agtctgccaa tggaccaatt gcacctgttc  48720
agttccacat tcagggcaat taggaacgtt tttagaagcc ctttcgcgac gttcaaccat  48780
gaccattaca gaatcccaat taacaggagg gctataatca tcacaaccat aaatctttcc  48840
acgcatttcc agatcgtctt cttcaccagc cataataatt ttaattagac tagaattact  48900
tgaagctgca atgtcttcta atagacgctt tttcatttca atacctcaat agcattacgt  48960
aaaccatttg ctttggcggt taaatcctta agaactttag tatgctcttc aatctgtttt  49020
tcaacttcaa tcaaacgggt actgagatat tcgcgttctt ctttcatagt atcattccca  49080
tgattgggct ttggcgtagg tttaaattta ttagggtcct ttaacttaat aacaacttta  49140
gtttcaaaca gtgaaagacc ataattcgta ttatcatcaa aggattcaac tacgtccatt  49200
ttagacaata acgtacgaag tttataagtc aaagaacgaa tcgttttatt atgtttatta  49260
gcttcacatg gtttcatata tggaagattt ttatatattt catgcggagc acaaacaata  49320
attaacaatt caaatggtcc attctgagat gatggaatga atttagccgt aacccaatct  49380
```

```
tttacattta cattaatagt acgatcatcg ccatgacaaa acagtctacg agaatgctta  49440
aaaagcatat tcacattatt attaaattcg tgtgaaaact cactggcaaa tttttcttta  49500
ctatctttag aaaaccattc ttctaaataa gttcttttca cgtcgttaat aatattaaat  49560
gtaacaacat tatcatttga tacattagtc tcaatgtagc ttggatacat aaatttttta  49620
acattattaa cagctatcac agaagatagt aatcgggaac gtttgaacca ctcgagcaaa  49680
gaaccaagag aatgtgaata cgcattttgt gtatctttac aaatatggtt ttcccatcca  49740
atatagtcta aaaaatcacg aagaatatta ttgattactt ctctatgtcc tttctgataa  49800
tcacgatgtt tagtaataag actgtcaaaa taatcaatat aatgtttacg agttttcatg  49860
ttcttctcac ttggttaatg atttatactc cgagccatcc ttggctttaa attttactta  49920
attaactgca aagcttgttc tagacgatca agacgattaa cggattcttc ccaaatcttt  49980
ttagcctgct catattcttt ctgcgcttta ttagaaattt ctagaacttc tttataagct  50040
ttttctagtg caataacttc tggacgaatt tctatcggtt caggtgaatc atcaagacat  50100
tccattagtt cctcaagggt agtttcttct ttaggagtat tcacaatttc atcacatttt  50160
tgttggtaaa tttctttact agtaggtgaa taagcacatt tcacttcacg aaggctaatt  50220
acgagtttat atccttccca accgcatata ttcttaaaag gatatgtatg aatatttttct  50280
actgtttcca tacaaagtaa tgcggtctct aattgacgag ttatagtgct agcaattgag  50340
aaaaatttat taatattctt ttggttagtt tctggtgtaa aaaatccata attcacaaaa  50400
atagatactt tatttttatc aagttcatat tcttttatga taatcatatc agaagccaaa  50460
ggatgaattt gacgataatc gccataacat aatttagaag ctgattttag aatttgcttc  50520
ttgaaaagtc tgaaattact aatccaacga cgagtaaaaa tattctcagg gtcttcttta  50580
ttattgagat gataagaatt aacatcaccg aaccaattat atcctactac atctttagtt  50640
cgtttaattt ctttcccaaa attaccaaga atatcccgat taaccaaata tgaaagaaga  50700
cgagactctt taaaggtttt cttgataaca tctttatcta cacggctaga aatttacga  50760
atttcatgaa taaatttagt agaagaaaca atacttgcat caacactatt gagccactga  50820
ttgataatag aaagaacgct attttggcca aacatcggta tagctttatc atcaataacg  50880
ctattgaatg atttgatata ttcgttacga gtcatattaa tctcctcagt agaaagtaag  50940
aacattatac cacatccttg tggcaaagta aactagttca gtgcatttag tgcattgttc  51000
agtttagaac gttgctttgt cagattttga acccttgact gagcttgttc taacgccttt  51060
tcagcttcta gcacttcatt ggtcgcttta actaattcag catctactgc cttaagagac  51120
ttctcaatcg catccgcgtg ccatttttca acaggtttaa gacttggatt ttcaacagga  51180
agaaaattca ctttattgaa tttccatgca tctttattac ctgagctata catccaaaat  51240
ttaggatcgt ttgataagta attagataaa tttaagttat cttgcacttc ttgcttttttc  51300
tcttgtgtga cttcgtcctt tctcaaaaat tcatatttaa atgaaacgat catatcaagt  51360
tcatatgatg ttgtatctaa cttaaatcgt tcaaaacgag gtaaaatctt agattgaaca  51420
gcagcaacaa catccatata cttaaatgct tctgtcaact gcgatttaag gcattcgcaa  51480
attgaaagag aattttttgt attaggttta aagctaattc gtgcagttct attattttct  51540
tttaacggtc ttacttccat ctgaagagta taaccatcaa atttcagatt ctttaagtta  51600
atgtcagagc cttttaatcg actagcagta gacaaaattt gctttaattg tctacggaac  51660
agagcaataa atctccattc aatacgataa tgatttggat tgaaaaatcc agatgataaa  51720
tcgaccttac tttgaccaac gccttgaaca aatagaggat ttttataatc aatagtttta  51780
cagaaatcgg tgagctgttc acgagcagtc atttgagtaa tataccctgc tttactaaaa  51840
ttacgcaccc attcactgct attcgtatac ttaaagtgat gaataacacg attaacttta  51900
tcagggtcta aattattttc acacaaaaat gtcataacat cacgagtata gctggcatta  51960
cgaaccatat cttcaatttg agaacgagtt ttcatggtgt tccttaagat ttaagtaaat  52020
caacaatttt aattaacttt tcacgctcag atttagcttt actactcaat ccagatagtc  52080
tgaaaatttc atcatcatat tgttgaatag aaatatcagc tcttcaattt gcttattaaa  52140
ataatcaatt tgttcagaat gtttttcgtt actacgaact ggtacaggtt ttgtaggcaa  52200
tttagttgaa ctggattcat tcgggcgata aattaaaatg caatttgaac caatcgggca  52260
tttagcacca gatgaatatt ctaacgttcc agcttctttt aaaacttcaa aagctaaaca  52320
gagatgatgc cccatattaa cataatcagt agagcgagct ctgatgtaat aatcatctcc  52380
acgagtgcta aatttaaagc atttaaggtc ttctgtatta ttagttttaa aaatcatttg  52440
tttatctaga cctttagcca atcgagcacc taatgctaat aatcgtcgtt gatttcccca  52500
caaatctgcg atcatttggt caaatgataa tttcggcatt agccgaccat aaaggtcata  52560
tcctttatta taattgcgaa ggatttcact cgcattaata cgagacaacg ctccaatttt  52620
attaagggct ttcataatac gattagataa actcattcca gacccgtttg ttcgctgtaa  52680
atgtttttct aatccaaatc caatatcaac tttaaattta tctaaaattt cagcatgaac  52740
atctctgtca ataacattca aatccaaagt tgggttaaat ctatgaaaaa atttatctgg  52800
ctctccacga cgtaaaacag tccattcatt catcattttt ttattaacta aagatttaat  52860
tactgcgttg acattattaa ttactactga catattttcc tcactcaatt ttaccaatta  52920
cgcggaataa gattgaacag actatataag taccacatat agattgaact aatgccattc  52980
caaagaacca aacaatatta tcaaaccatg tctgttttac gtcgaaagga cgtaaactta  53040
cagtaatatt atcacctttt tctattgaag aatacgtctc tggggaaata tattcactaa  53100
atctataacc gtctttgagt tcatatacag caataaacga taaactagac ccctttcctt  53160
gagttcctgt aagggtatta actacagtaa catcataatc tttataatgc atataatcat  53220
taattgcgta ataaccatat gcaattacta tacataaaca acatatcaat aaattcaatc  53280
ttttaattat caactgtttc ataataatct caattaaaag ggcttagaac cattatacca  53340
tccttggtat aaagcggtta tgcgagtacc gtatttaacc gttcttcaaa cttccgaaga  53400
gtgttctggc gttcagctct ttgctttttg taagtttcaa tacgctctga aatgagagtg  53460
tatcgttcat ttactgattc tttcataaaa tcaggaattt ctcgagaagc tttaatctcg  53520
tcaaatttat caataacagc ttgctcttca gcaattaagt tatcatacat caaaatatct  53580
ttcttgatga actcaatatc ttcttgagtt acacgagata atttagatgc tttatccttt  53640
ttgtactgtt cgttagtatc acgagaccag tgtaatgtac gatttttatt cgtattcttg  53700
taaatttcta caataccaat ctcatcgata ataacgatcc aattccaacg ggatttgtaa  53760
atttgtcctc cattaacagt gatttcacct ccgattgaga tgtcattaaa gaacttgctt  53820
tgtgcttctg atttaaattt accatcgttg taatttacca ggttgaaaat atctttagcg  53880
ttcattttgt gttcctccgt agttgatagt tgtatagtac cacagaggaa cggtcttgta  53940
aacaactaaa agaaacttct ttcacaattt tttccactga accaagcgct cactgctttc  54000
ttagtttcag gagcagtgtt atccataaac cattcaaagg cagccttttt atgattctgg  54060
agggcttctc gggctttaat ctgctcacgg tctattaaca ctaacatatg agcctttctt  54120
```

-continued

```
gtcaccaggg gcttcttatg attttttgaa tactcccaat catttgtcca tcgcatcgtt  54180
gttgcgaatt gaaatacagc ttctttaatc ttagtttcgt aaatttcacg agcctttgag  54240
tataacatca ttacctccat ttaccagttt aattctagtc atctttttga tggcagtcca  54300
tataatctat ttctgaactg ccttttttgtc ttagaaggcc tcttatgaat ttatttcaga  54360
agagtaaccc gtagcgattt cttcccaacc gtttttgtcg gtcataataa agtcagcaag  54420
ataaagtgca gtacgcagtg aaacattacg taaacggtta acattgactt tcatccatga  54480
taatgcttta taagtttctt catcagaaag accacgcttt tgcatcatgt cggttgaaag  54540
aataacatct tcaaccctga ccataatttc ttcattagtg tgaacaccca aatccaaata  54600
aactgagcgg gacactaatg cttgtaaatg tggagcaagt ttagtaccac ggtctaattc  54660
gcggtcaatg tcaacgtttg tgataaaaac aattgttcct ttaaattcga gctcacgctc  54720
aatgcctttt tcttctaagt aagaagatgc agtgctccag cagactttac gggtctctcc  54780
agtgtccaga gcagctttca gaagattaag aatgtccata tcagagaaaa catccacatc  54840
atcaatcaaa aggacagaat tctcttcacg attattccaa agctgttcat aaagaccgat  54900
accagagatt ttaccgttaa tgcttttata ctcaatgtat ccaatatcat ttgctttatt  54960
caaagcttta tctaaagaat atgttttacc aatacccgcc gcaccagaga taattaatga  55020
acgaatattt ccgttaataa taccattcgt catcattccc ataacattaa atcttttatt  55080
aatgcgggtt ttcatatctt catatgattc tttaacttct tcaactttta caccatcata  55140
tgaaatgtct gatttgtaaa cccaaacacc gcgacgttta ccgtcaattt caacaaaaac  55200
tttaccatct ccttgtgcat ctaccggagc attatcaggg aaccattcac ctaagagctc  55260
aaaagttcca gagatttctt taccgaagta catacccttta ttgatagtta cagttttcat  55320
tttattctcc aaatccgtat cagttgatag ttgtatagta ccataaagct ttatgcttgt  55380
aaaccgtttt gtgaaaaaat tttgaaataa aaaagggagc ccgaaggctc cctatcattt  55440
ataataactt cgatggtttt caagataaac cctctcaagg aagtcatccc agaaactcat  55500
gtctactttt tgctgcatac cgttcttaga agcttcagta gatgctgctt ctacttgatc  55560
gaccacatct tccaaaaact cttgaacggt tttaaatgga tgcttaccca acttcacgtc  55620
gagaataaat ggagcatctt ggagtggata aaccaagtca ccagttttgt aaatttccaa  55680
tagttgaagt ccaccacgac aagcatggct cagagctttc cagtcaatgc cttcattggc  55740
ttcggcctta cgagcacgtt cgccgtattc agcatctaat ttgttcagtg actgcttaag  55800
ctcaataaga gaaagcgttg tctgatattt acgacccaac actgtgtaaa acgtttgtgg  55860
gcctgttttc tcatgattat ggaacaccca ttcacagaat tcgttttctg gaagacgatg  55920
cttaatatct tcaactttag tacgacgctg cttaatggaa ccatcttctt ggtaatcaac  55980
ccattgctca gggatttgat taactacttt caatacatcg cgtaatgcag ccaaacgaga  56040
acccttgacg ccgtatttag aagcttgctt gcggacatat cctaaatatg atttcatgtt  56100
agtcgtataa aaacgagaac ggttgtcttg aataaacttc camacatcag gcaaatcgga  56160
tttaaccact agttcaggtg gagtgtgaag catatccaat gctacaggtt caccatctgc  56220
tgctaattta aagaaatact taagactata caattcgtgg tcaatattat ctttagtgtt  56280
tttagatgat gtgttgttgg tatttttact catgtgctct ttgacgtttc caataagaat  56340
atcgcgagca ggaggaacaa agatttcttt aaaatctaca tcagattctg gagtagaagt  56400
tccataaaga tgactaccaa aataagactt aactacagtt ttcattatta gacctttcat  56460
aatcttcatt aaattgtaca atcaatcgat gataattaga ttttggatat cctaatttac  56520
ttatataagt tccgaatgac ccacgtttag gtctatttaa tttaatccat aacttataaa  56580
gtaagtcata gtcttgccaa tgtttaccag ttctttgtct aattttagat gaatttgatt  56640
gtttcttttt agcttcaaaa ttattcaaag attttttgac tgcagcagag tgtttttctt  56700
taactcccgg tcgtttaaaa gcagctttca cccctttaga tatttttttct ttaacttccg  56760
gtttgttttg tgcttctaac tgggattctg aaattttagc ccttatttca ggaagactta  56820
atgttatcga acgtttttct ctgtattcat tagacttcca catttctttc attgtattag  56880
aatgtatttt tgaaaatttt tctctaacta actgatatcc tcttgaagtt aatttgagat  56940
ttcttcctaa agaatcttct ccaaaattat aaaatgacca ccatgcataa attaatccag  57000
gcgaattgta atgaatttta gctaaaagcc aatgggctat aaaatgctct ctagctgtta  57060
ataaaactag attatcagaa tcatcattac caccaataca agatggaata atatgatgct  57120
tttccgtata aaaatttaat ttagatttat ctaattttct gagttttcct ttcttaatta  57180
aattattata tactttagta taattcattg gttcttcgtc tcatttaatt ttgctttgca  57240
tttataacac atgtctgttc cacttgaaat aaacatattt cctcactttg aaatcatagt  57300
tggaataaca gaatcaagat aagtctttag tgcaatagct tcctctttct ttaatgtaat  57360
gatatgtgat cgaaaatcat caatttgacg aatagatact acatctccct cttcatagca  57420
ttttgaaaca tttaaaatag tttcatcatt ctgattacag gagttagtaa taatagcatt  57480
acattttttta aaccatttta aattatgttt tcttttagta gaatcataaa aatatttaat  57540
gttagttata aaattatccc aattattaat tgataagcac attgactcgc ttttaatatt  57600
aaatcctggg catgaagaat aaaaatgaat tttatgctca tcattaatgc ttacaatttt  57660
atcagtgtaa gcatattcaa tttgggttaa acgaacaatt tcgctaggcg taaaatataa  57720
catgtcatct tcttgcgtca aacgatacat gttatttact ttttctatag ccaattcacc  57780
aaaaagtgga ctaacttcta atactagtcg tttcgcctcg ctcatcatta catactcctc  57840
tgaatcatat taataatgtt attcaccaga ttataagtaa acattgggta attatattga  57900
atcatcacat atataacaaa caaaactttc attctcttct ccttggcagt tgacaagatt  57960
actataccat aatcttgtca acttgtaaac cattaaatga cgttttcgat aaaattttga  58020
agctttgtat gagcatcaac catgatttc atttcttcct tggaaaagct gtgcctcttt  58080
cccgagaaga acattcatag tcagaaactg cattagcata ttcttcaatt agcttcatta  58140
aaaacatctg tttttcagtt ttcattattc cacctaatca tttcaagata ttgaactaac  58200
ttagctttgg atttatccaa atccctttta gctgcttcta taccgtcgta tgaatatcct  58260
tcacaatgct caactgctaa ttgatatgaa tctatttcaa tatcatgcgc taatttaatg  58320
attttttcaa actgttcgcg tgttagcata cttaaactct cgtattatga tcgataattt  58380
catcaagaaa catatctaac gcttctacag cattattaac tttagcttca aattcttcaa  58440
tacctgataa ggcaaagtta atgcgttcct catctgcttt acgaattaaa gctaccaatt  58500
ccttaatttt atccgcttgt tcgatactaa tcattattcc accacatatg aaagagagaa  58560
tattgcacac gccatgtgag ttgcaacttc atcacacata ttataacgtt tcttaagaag  58620
ttctacaagt tcttcactag taacttcatc catgtcgacg aaaaaatcac cattaatgat  58680
gacgtagata tttccttctt gattgagtgc ttcaattttc atgatgttct cctctttatc  58740
cgatggttgt atagtaccac agctcaaacg gaaagtaaac cggtaaaatg aaaaaaagtc  58800
tcccgaagga gactaatgtt attcgaggga aagaagatac ttactctggt aaaacattcc  58860
```

```
agtaatatca tctatcgtgc tttggatggc tggaggcatt tctttataaa tgctgttaga  58920
ttggtctagt atgcgatcaa tcattttaat tgtgtcggta ggaagtttac tggcatctgg  58980
aattgaaggc gtgtatttc gaccagaata ccccaaatat tgctcaccaa atttatcaat  59040
caaatctggc aactcggaaa aaataaaatc gtatgctttg tgtctagcat aacttttagt  59100
ttcaaaatgt gcagaatgaa aataagcttg tgcagccatt aataaaccta agtattcatc  59160
tgcctttgaa ggttttccac tttgtgaaaa gtcgctgaat ttcattcagt ctccaattta  59220
atgttcataa ttctagcgta tgattgtgcc atctccgcgc ctcgctctat acattcaaaa  59280
tcagaagagc acgggtcatt tttataggtc gttctcataa aactatagaa ttgttcagac  59340
gattctacgc ttttatttc aaaaagcata taaacgtgcc taataccaga ttccataaat  59400
ttatcaaaat gaggatcgac attcgcttca atcgatggag ataaaacaaa tgacaatcct  59460
agcatggcaa aaagtgctgt tgcttttaag gccataaagg cctcctatca tttttgtcct  59520
gtatttactt tgtgccgatg cacggcctta actttatcaa ggtatttttc aaaatttcgc  59580
aatctagtat agtctgccgg agattggttg agtgatactt ctcgacgcaa agctgaaatg  59640
atatttccaa cttccctacg aatttcatct aattgaagaa cagtaagatt gcgaagttgc  59700
ttttcagtta attgtagcat atatacccct ttagttagat aaacctattt ataacttttg  59760
cactaaccga gctttttagt taattcattc caatgtttc tacacaaaga aacataaatt  59820
tcatcaccaa tacaaatttg attaccttct ttaactggtg ttccatcttc cattaatcga  59880
gctgtcataa tcgctttttt accacaatga caaactgctt ttagttcaat aagtttatct  59940
gcaatcgcta aaagttcttt agaaccttca aataattttc cagcgaaatc agtccttagc  60000
ccataagcca taacaggaac attatatgta tcaacaattc ggctcaattg atgcacctgt  60060
tcagttttta aaaactgagc ttcatctaca aatacgcaat gaatatcttt ttgtgcttca  60120
gcccatttat agaactcgaa aatatccata tcatctgtaa taatattcgc ttcctgctta  60180
attccaatgc gagaaacgac ttcacagaca gaatcgcgag tatcaatagc aggcttaaga  60240
actaatacac tcattccacg ttctttataa ttatgtgcag caatcaaaag agaagcagat  60300
tttccagcat tcattgctgc ataagtaaaa attaaactcg ccatcttagt ccttagttaa  60360
attttctaaa tatgtttcta aatcatttc agctttatcg atagatttta ctaattcgta  60420
atatgtttcg gcatctccat attcagaaga tatttcaaaa gacaaatcct tttctaaact  60480
aataatttca ccaactaaaa ataatatttc gttcttttgt tcgcgagtaa tcataaggaa  60540
tttatataat caatgagttc ttgttcttta ttatcgaatt ctttagaaag ttcttcgtac  60600
tcgtttgcgc taaaaggacc gcattcatta caaacttttt ccaattcact atttttatcc  60660
ataacttcgt ggataagaga aaagagtgtg tctttttgtt ctttgcttaa actcataacc  60720
atgtcacctt taagcagtat tcttctacat gctgtttacg acctttctta tcaataaagg  60780
tatattcaac gaatgttcca atgtagtctt tatctacatc atgtggacta ttaattggac  60840
atttagtgcg acaaatgcgt tcccattgac gaataattac tgccttattc tttgggtcat  60900
atggatgtgg ataatgtata ttcataataa tggttcccaa tcaacaatca caatttctaa  60960
tttagaggaa tatgtatcta aaatcccctc aataatatcc cagttccctt tacctatgcc  61020
tgcaccaatc ctaggcatat agattgtagg tttaatcagt ttattttcac caaactcatt  61080
taattctaac atacaattca ttaaagcgga atactcaaaa tttggccctg gttgaaattg  61140
agtataaaga ttgaagcagt aagctttatg agtcctaaag tatttttcat agactgagta  61200
agaaccgagt ttagttacat caccccattc agtctgtaat ttatcagctt ccaaaatttt  61260
agggaaagct ttggttaatt gacccgctac gcctgaaccc atagtatgaa aacaattaca  61320
tccatgtgca atatttttac cttcagcgaa aagggcgaca atatcgccct tgatatattt  61380
tacaatcatc tagtactcaa tcctcgatta taagaatcta ccaaacggtc aaccattgaa  61440
tgacaagcgg ctttatcttt ctcctccgca actgaacatt ctaaggtatt ccactttta  61500
gcatatcgtt ttaacaatgt atcgtttttg tatctgcttg atttatctct ttctccgtct  61560
ttatatgcat atattaattt ctgtgcaaat tcagcttggc atgccttatt tttcccacaa  61620
taatctgccg cagtgcggtt tacatattct ctaatttcag tatatgatgt atctgctgac  61680
gcagaagcag aaaatgaaat taatcctata cataaaacca aaattttagt catttactat  61740
ttccaaaagt ttattatttt taaggtaatt agccttttct aggacttcag aagcatattt  61800
agaacctgct ttaacattcc atcccgaatt ataagaggat attgcttttc ttatatcgcc  61860
cttatgtata tttaaccaat aagaaagttc aatgtacgcc caggaagctg aattggatcg  61920
tttattcaac attcttttta tttcagcatc ggtcatatta taaccaagtt ccttaactct  61980
tgctcgcata gtaggcaaat aattttggaa cattccgtag gcgtgatgct ttggtttaga  62040
ttttaaatta actccgccag agctttcttg ccataaaatg gcagccatta tatgacctaa  62100
tccgctcttg tggatatttt tgtgtgtttt atattttcca tccttagaaa attgttcccc  62160
gaattgatac gcgtaacgca tgttatcgag ttggacatta ctgaaagtat gctcggagct  62220
atgtgccatc attgaaatgg ccaatagacc agcgagtagt gcttttctca tgcttacctc  62280
attgagtttt aattactgct ttagaagcct ttcctggtaa acgacgactg ttgataattg  62340
ccatcctaca ttgaagtgac gggtctttga acttctcgtt aggtttacaa actgtaaatc  62400
caagccaaag atttccatct gtgatttcta aacgtccagg acgatattca accccatcaa  62460
taaaatcctc gtcaatgtca ggacgcggag gcatactcag gaattcatta acttctaaaa  62520
catggtcttt tattttatgg aataattcaa aaacgtatgt ctcatcaatc tcccgttgaa  62580
ttgcgcgatc aagaagatgt tgagaatatt ttagatgaaa cgatgagact cctgctgctt  62640
ttgatgcctc acgaatctca ttgttaattt gacgaaactc cgactcaaag tgacgacgaa  62700
gcttatttcg acggataaaa acttctgtat tgatagtcat gttattctcc tcttaactga  62760
tagaaaaatt ataccacagt caagaggaaa agtaaacagt tattctttaa atctaatcaa  62820
tttattcata gactttgaaa cttcggcacg aacctcatgt agatttttga gctgttcaag  62880
acgctgcgta tagtaagcaa tttcatcttc ttcgagacag tcctgcgaat cttctttaag  62940
ataacgtgca tagtcctgga aagcgttacg gactacttcc tggaagtcat caagactttg  63000
aattttctta ggagcaacag atacacgacg aggggcagta taatactcat aaccaaaccc  63060
tgcgcttaat tgagccatta gtatttttcc tctggttgga acactgcacg acaagcccac  63120
atactggctt ctttgagttt cgttttagca atagttaact gatcgagact ttcagcataa  63180
ttcttcgcga attcacagtc ttcgcaatta tctagtgctt cccagaattc atcatataaa  63240
gcatcaaaga taagtcctaa acgaacttca gcgtctttaa tagcatttac tttaccgatt  63300
ttctcttcag tatgtggttt ataaccctta atatcttcaa tcatatttga cttcctcacc  63360
agtacataat acgtattcaa ctaaacgaat aggttcatga atgccatagc cttgaacaga  63420
aatttctgtc gtaggataaa ttccatcaat atcacccata ttccacgctt cattaaattg  63480
ctgttcgcct gagttactaa accactcgcg aaagcattta gcacatcttc agaaccttca  63540
ataattatct ttgccattac aaactttcag taaaggtacg agcgataacg tcgcgctgct  63600
```

```
gttccggagt cagagagtta aagcgaactg cataaccgga tacacggatg gtcagctgcg  63660
gatatttttc cggatgctta actgcatctt ccagagtttc atgacgcaga acgttaacgt  63720
tcaggtgttg accaccttca attttaactg taggttgtgg ctcaatttca atttcacggg  63780
catgcaaacc atagaaaatt tctgggtcta caaaagagtc ctctttaaag gttttagaga  63840
caataattcg tgcttgaata ccatcttcaa aataaatagt acctttatgt gtgccttcaa  63900
gaatttgata tgctttcata taaacctcaa ttagaaaata aatttatcca agattgttct  63960
ttaattaaaa atggctcaga atcatatgcc attaaacttt gcgtaattaa tcctttaaaa  64020
ggtccatcaa taaattccat ggtaaaatat ggaattttat tcattagccg tgcattagga  64080
gcagtgcaca aaactctgca tcctttgaat acgccttttt gtaatttgta ttgcttggga  64140
taaaattcgc tcaaaatgtt attttttgcc aaaatttcaa aatgattcac caatttattt  64200
ttaatagttt ttggcgaaaa ataaagatat tcgaaaagct gagtgtctgt catcattgca  64260
ttccgattac gaaaaactgt ggacgagtaa taccaccaat gcaacattta ctattacagc  64320
agtagtgtac ggtgtcaata tggacactat aaatcttatc catatcagga gatttgacag  64380
gctcatcaat tatatacaaa attcgcgaaa gctttaaacc tctgaacttg cttcctttat  64440
taccaataaa actgcgtaca gaatcagtaa ataaacgaaa acgtatatca tcattagaat  64500
aacgcgaaaa ttcctttttg atgttatttg cagaaatttt agcataagct gaagtattag  64560
aaagaacaat aactgttccg ccatcataca accaattagc agcaaagtta gtcacagcaa  64620
ttgatttacc ggattgacgt ccaccatcta gtcgaagtgt acaatactgt ttaagtaagt  64680
cttcaaatgg cgggatatat tcgtttttac aaatttcttc tactctagca tcagaatggt  64740
gtgtaaaagc attcatcagg gatagataag gaccagttaa aaatgttctc atttcttctc  64800
tataagctct ataagtttgg gccattccgt ggcacatgaa ttgtccattt ctgtatttac  64860
ccattaccgc gcttgggctc gaccttatta caggttggcg ggaatccctc atataatcat  64920
gaggtccagg ttgttccctt atgcataaat cgccttaccg tagtatttgt accaagtagg  64980
acgttgtgca atttttcat ctaaacgagc ttgtgatata gcaatagaag cttcatgggg  65040
aatataatca ccacggaatt cctgaggaat atcactaata tcctggactg tagtatcctt  65100
gatattaaaa ccacgtttta aacattcagc tataagctca atttgacgtt tacgtaagaa  65160
ctcgagctta tcgtaaaaga atgtaacatg acctgcgcca aggataaaag taggactgat  65220
tttaaaatca cgaacacgtt taccgttagc aacatgctta cgaactgcac caaaaacacg  65280
cggcaattca cgatattcag ccattaagtg ttggtcagcc aattcagata ctaaagtaag  65340
gttgatacga gtcattttag tgttctcctg tagttgatag gtctatagta tcatacctac  65400
aggagatgta aactgttatt tatctttaat tgctttagct gcttcgatag ccgcttgctg  65460
aaggtcatcc atagacatgc cgaacttaga agcaaagtta tcaattttct tttcgacggc  65520
attcaaaggc ttggcctgtt taccttcatt agcgccagga agagcgagaa tacgctctct  65580
gtcaatataa aggcttacaa gtttcttacg gtctttatcg ggcaaatcat gaaatgaatg  65640
ggcctttta tttacagcgg cttctaattt acctgcgccc actcgcgctt cggcaataaa  65700
ttcttgatat gttttcatat gtttccttta aatgtaaata tttttattat tctatcctag  65760
aattgtgata atatattcac aattctagga gttgtaaact gcttttattt aagcgtccca  65820
agtataagct ttattaagaa ttaccacggg ctgcattagc aacggcgtaa gcgtactgaa  65880
tattagcgtc tttaaactta cctttagagg tatctatttc tgccttaaag ccgcctttag  65940
tcataacatc ggcaaattct ttacggaaag ccattgcatc aagacctttc catgatgatt  66000
tatgcttggc aaattcaaga cctgcgaagt tgacagcttt agccaattta ttatcaatga  66060
cccatttacc ggctttaggc acaaacttcg ggcctttctg tttagagaac agttttaaat  66120
tccagcggcg aaggtctgca tcagctttaa caaattctga gtctaagtta ctagcaacaa  66180
catcttcaat atgagcaaat ttaagtccgt caacttcaat atttaaatcg gtacgccagc  66240
gaagtccttc ccaagcgaag gctttaaagt cggaagcctt tgtagctaag taccgttcaa  66300
taggagctgt tttagggtca aagccgtttc ctgatcggta ggtccactca tctttgttaa  66360
tgcctttggc ctttactaca gaagcttcgg caataaattc ttgatatgtt ttcatatgtt  66420
tcctttaaat attttaatta gtaattgtct attcaagtaa ttgtgaatat actatcacaa  66480
ttccaagaga aagtaaacag ctttatagat ttttatacgc gtcccaagtg ccagttctaa  66540
acgttgtaat gactcgtttt gcgcgattag gtgtttgatt ataccatata cttttagcta  66600
agttaactgc tgcttcatcc cagcgttttt gttgaagcat acgtaaagag ttagtaaatc  66660
ctgccacacc ggtttctccc atttggaaaa ccatattaat caatgcacag cgacgaaccg  66720
catcaagaga atcataaacc ggttttaatt tagcatttct cagaattccg cgaacagcag  66780
catcaacatc ctgattaaag agttttcag cctcatcttt tgtaattaca ccattgcaat  66840
tacgcccaat agctttatct aattcagatt tagcagcatt aagtgatgga ctttttgtaa  66900
gcaaatgacc gatgccaata gtgtaatagc cttctgtgtc tttatagatt ttaagtctaa  66960
gacgttcatc tatacgtaac atttcaaata tattcataat acctcctaag tatttataga  67020
aggtatttat aaaattaaaa gaggttgttc attattcggt aaagtgaagg acccatcaca  67080
tattgccact gagtacgagg aataagagca aaagcgtcca tctctggaat cataacgcca  67140
tctttatttt caaaataaga ctcgcaacgg caatttctga acatctcatg ctctactgga  67200
atcgtgtaat aaaataactg taggtcttta ttactagaat atttaaatac acctaggtct  67260
tctagaaggt ctggattata attgctaaaa ccagtctctt ctaaacattc tcttcgtgct  67320
gcatctaatg cgcttaaatc agaattttct acacggccct ttggaatatc ccaacgatgt  67380
gccatcattc cagtcttacg agaaccagta acccgaccca taaataaatc tttatcttct  67440
gtcataaaga taataccagc tgataatgtt ttcattttaa tttcctgcat tcagtgataa  67500
agttatttaa attttgagca tatttctttt catcaaaaat cttttgctgt ctgcgtaacc  67560
gccatggcat ttcaatgaac atacgccata tccctagata ataccgctgc tgtaaaaata  67620
ttaacaagta tagttaaaag aatccaatcg cctattctgt ccattggatt tttataaaaa  67680
agtaaaatac gaatgatgat ataggaagac taatgatata ccacagaaga accttcttat  67740
ctgtgaacca atcagcattc gttaacttag cgcgaccatt ttgaatacac acgaatttat  67800
catctgttac agtaaatggc ttagctgctt gatatcccat tctaaactcc ctaattaatc  67860
gtttctttgt atcttcggaa caaccattcc aatcaactct atcaactgga atgccatcat  67920
ccccatcatc taaatcatac cagcgagttt ttaaaatcat ttaattttcc tgcaatcaat  67980
cacaaactct ttcattgatt cattttcaat ataagacatg tagctattat attcttttaa  68040
ttgtattttg taatcctttt ttctttgcca atttatttta aaattatcat aatgaaaata  68100
taaaatgata ccaaagaatg aaaacaatga aataatttta gtataacaaa gctcgctcca  68160
aacttctatt atatctactg taccactgat ttttaaaata aaacagtcaa ttaatagtcc  68220
aataagacta cctgtaagag ctgcagccaa cgccacagca aaaattaaaa atgactcaga  68280
aaacgaatat ttgactttat ttagctttgg cttttgcatc gtgattcctt aacaaatttc  68340
```

```
ataatttcat taaattcata ctcagcaagt ttaagctggt gttccttttt aatcttttg  68400
cactgggctt tccaatcacg tacgcgttta cgataatgtc ttccttgata ccagtatcct  68460
atccaattta cgggtactaa taaaaatgga actaccaatg gaagagttag cattaacata  68520
attattacgc cagaatcaat atcagtcata acatctaaaa cacctccaat aatcaataga  68580
attacaaatg atatagctat cacaggacct attaatacat cagtagaaat tatctggcgc  68640
tttaattcat acttcaaagg tttacttgga aggtatagtg atggctttga catattctct  68700
acattcctta acaaattttt ctagtaataa atcactttca aaattaggat tttccactaa  68760
tttatcaaaa agatcatcaa caatattcaa gatatttctt ttactaagaa tacgtttatt  68820
ttcatgcttc gtttcagaat caactataag agtaaagaaa tatttctttc cctgaaattt  68880
taccgtagta tcaatataaa ataaatttga cttttgtaaa ttacgtttaa accatgcgtc  68940
acttaaacta taaacaccga gataatcaaa atcgtcgttt aaataacaaa ctgaccattc  69000
aggagaaatg aaatcagtaa attcaacatc aaaatcacat gtcaatgaat gaattgattc  69060
aatactgtta ataagtattc caggacgtat taaagacttt ttacctctgg aaaatcttcc  69120
agaaagactt tcatcagttt catatgaaga accccaataa taattacgtc cttttgccat  69180
atgtttaaga gcatttagta attggtctgg aacatcaacg tgtctttgga actcttcaaa  69240
cattgaattg aaatcacttt gcattttcat tcctatttac tccaagtaat aggggccgaa  69300
gccccttatc attatttcag agaattaata tattcctgaa catcggcaga ggtagtttca  69360
accccagaaa tattaccatt aaaggtttca actcgagcaa gagtatcttc aatatcaacc  69420
ttagtcagtg ctgcaatttc aactacatca tcagcagtac taattccaag ggcatttgct  69480
gcacgagttt cacggatata ttccaattta actgcaagtt cttggcgagc atcatctaac  69540
tcaactactt tcttggcgat ttcaattcgc atttcagcat aaccatcagc tttagtagtc  69600
agctgttcag ctgttcgacg atatagcaag ccgagtttag catgcattgt tacatcttga  69660
ccttcggaaa gaagcttgcg aatttcacgc tcttttgatt cggcctgttt attcttttca  69720
acaataagtt cacgaatacg tttttcttca ttaatagatt taacagaagc agtttttagg  69780
tctttaattt tatcaagtag ttttgctgct gcagcagtat actgttcttc aacagataga  69840
tttttagcca ttgcagaacc aagtttagtg cgaataaact caacaatttt cttcagtgtg  69900
ttcatagtat ttccttaggt tggtataatt agataatata atatcacgtt tctaatagat  69960
tgtaaactta ttcttcgtct agctcgtcga taaaggcgtt gatggcctcg ataatggcat  70020
cattgatagc caataaaata aaatcatcgt cagtaccttt agaagattct aaagcattga  70080
tatatgcttg gttgacgagt tcccaagcct ttttaaaata aggagcttca tcatcaggac  70140
aaatatcccg cacgccttca aagatacgtt tggcataatc taacacccat tgtacaggca  70200
tgttttgaga acgttcgtta aactctttaa agtccttaga ttcaaaaagc tcttcaggat  70260
aattatttct attacaaaaa gctttactaa agttacgttt cataatgttt tcctcatttg  70320
tataggctca taatatctca atcatsagcc tatgtaaact tatttcatat tattgaaata  70380
ttcttctgcg atttcgtcgt tatcatggta aactttagaa gacagtttaa cataactttc  70440
agcagtgaac atgttaatca caacctttac agtataccac tgaccgtctt cattacccat  70500
tactgcgtaa gtttcaaaca tcggatggtc aggaccgata actttaatat cattcaccgt  70560
acgaccgaaa tcttctgaaa cacatttcat aaagaagttg aaaagttcac cgtaattatc  70620
cattttattc tccaagttat tttctgtatc agtagttgat agttgtatag taccatggaa  70680
gaacaaggat gtaaacagtt ttgtgaaaaa atttttaaaa agttttaggg aattctaggg  70740
cggagagggg caattaaaag ataggataat atattataaa gggtataaac taaatgatgc  70800
ctagagaggt ctggaaaggc ttagatacca aaaagcccca acctttcggt cggggctaac  70860
cgttgcggca accttgtcgg ggttccacct gccaaggcaa gtgtttgtac gaaacgccgg  70920
gattcgaacc cggttattaa gtagttgacg ctactcaata tttttaaaag gccatatctc  70980
aaccatatcc gaacgttccg tcaaaaacgc tactcggctt acggcaaaga tatttcctcg  71040
aatcgataat ttggtgcgcc gtttctgctg tgatgtaaga gggcatcaat aaacgcaaag  71100
attattaacg caattcctta ctcagggaac catcagtccg acgacttacc ggtagcgacc  71160
cggtttctca tttggtatcc cgccctggga tcgaaccagg accgcaaact tagaaggatc  71220
gtatgctatc cattacacca gcgggacgta atttaaaatt tcatttttcg acctttaaac  71280
catccttctg gaattgggtc agttttctta atacgtttag aaactttttc atctaatgaa  71340
tgaatccaca tcataccgaa ttgggaattc ttttcacctt tctggtgatt atttttggcg  71400
tgagattctt tcattttatt aatagtttca ggagtatgat gcttatttag aaatctgcta  71460
ttatttaaaa atttttccct gtattcagga gttgaccaca aacgtttaaa tacatttgaa  71520
ccaatttttac gatattttttc ttgaagtaaa atatcatttt caaaacgtga cttaaacgat  71580
ttagctcctt ttaagctagc atctttcttc tggtttagca ttccaggaat atttacatga  71640
tcccatccac cttcaccgcc aagttttaaa ttatacacat ctggtctatt taaaaactct  71700
tctgtgacaa tatttttctc ggcttcaagc atagattctt tatcgtcaaa atactctaat  71760
atttctttag aaaaatttc tataccatat ttatcttggg ctctttttaa taatttacca  71820
gaacccatat atccatcatc taaattttcg gtagaatgca caccaatata aattttatta  71880
ttaattttat ttgttatttt ataagtgtaa tagaacataa atatctccta tttctaagag  71940
tatttatgtt ctcaaaatat gacccagacc agatttgaac tggtaacctt tcccttatga  72000
ggggactgct gctaaccatt gagctacagg gccttggtgc tgattgacgg aatcgaaccg  72060
ccgacatcct cattacaagt gaggtgctct acctactgag ctaaatcagc aaaattacgg  72120
aggcgatagg atttgaacct atgagtcgcc ggagcgactg ccggttttca agaccggtgc  72180
attaaaccac tctgccacgc ctccagtctc catacaagga tttgaacctt ggacctcctg  72240
atcccaaatc aggcgctcta ccaaactgag ctacacggag taaattaaat tggagcggat  72300
aatgagaatc gaactcacat catcagattg gaagtctgag gtaataccat tatacgatat  72360
ccgcaaattt ggtgcgagaa gtgggactcg aacccacaag gaaatcattc cgcagcattt  72420
taagtgctgt gcctttacca atttgaccat tctcgcgctg ggaataaagg actcgaacct  72480
ttgcatctag cagtcaaagt gctatgcctt accaacttgg ctaattccca attattaaca  72540
aaggctctct aacaagaacc cttgatgata gagggtatta atcagtgcgg tatgagttaa  72600
taataacaaa taattcttaa agcatattta ccatttatga tgatacgtat ttacgataca  72660
ttcaagaccc aaaggattct tgaaaatatc atattcaaga ggaccttttt ctgtttcaat  72720
aaagaaatca aaatttactg tattaaattt acggtcttcc tttactaatt taacttgaga  72780
agatgaacga tcaatgtaaa ccttttcaac ttcaaaacac gttaaaatgc cataatcatc  72840
aatcaaggct ttagctgctt cttgatcata tttatatcca ttttcaacgg atgatacttt  72900
cgcataaaga atcatcatca acctctatca acaatagcat gagtatgggc atttacgatt  72960
tgccaccagt cgaaacgatt ggaaccataa tctggtttat tttcattttc tttaatgata  73020
tcacgcagtt tatcttctgt ttcagcatac gcaattaaat catcatatcc accacaagga  73080
```

-continued

```
taataattat cacctgcgaa taaaagaaaa tttaccttag atggatttac gtaataatgg  73140
tctttaggat atttagttcc tctccaatca gttacttcaa cataacggta agaaaatcca  73200
tttttacttt caatccaact ccacgcttca aaaggagtat taaaaacttt atcaggtatt  73260
aaattacctt caaaatgaga aggatttgca taatccccgg cataaacata atattcgtta  73320
atactcattt attcaccttt agaaatttta tccataacga tagcaattaa accaattaaa  73380
aatgctacta caagtgaaaa cacattttct gctgtagtta ataatccgca tataaatcca  73440
acaaacattg aaaaactaaa agcagaagca gaaattgcaa tagcaacatt tcgaattaat  73500
tcacagcgtt tcattttatt ctcctcagta gttgataggg taatagtatc acagctaaaa  73560
ccctatgtaa acaactttgt gaaatattta ttacaaaaga tttttagcaa taatcttgag  73620
atgtgccgca gaaatgtgtt tagctttaaa caacgcagtt tcttcagcag gagagataac  73680
gattgtagca ccatcctttt tagcagacca cccatcacct aggtaaacag tacctttgat  73740
ttcttcgcca tcaaccagac taatcattgg tttaccttct cgtcctttat ttgctttaat  73800
aacttcagaa gtaagagtag cttcggtaat ggtagaaacc ggggtagttg tagaagtaaa  73860
ttctttaaat gttttcattt ttattttcct aattaatttt gatgaggtaa tagtatcact  73920
acctcatcag tatgtaaaca actttgtgaa attattttaa atcatctgcc caatcgagtt  73980
taagaggctc tttgtattca cgatctaata cgaccggaat ttgtacatca ccgctaaatg  74040
ataagggccc aacattataa gacaatgtta tatgcggtgt gtaatcatca aaatcatgtg  74100
tagcacctag tgcccgcgca tacatgtgtc gacagcgcag atattcagaa tctagcacaa  74160
gtacaagagt cgatccatct tgtgttttcc atacttctaa atgtccagaa gaagctactt  74220
caaaacttcc actcgatgga acatatggaa catttactct tgaataacat atagtcgaat  74280
gaatttttc tctaggaact ggattaggaa cacgtaaaga gcgctgaagt tcttccagcg  74340
catcaagtgt taattctgaa aacttagctg ctacataaag acccgttgaa aagtctttaa  74400
attccatcat tcttcatctt ttgcttcatc tgcagattca gcagtaagat ttttgacagc  74460
ttcaacgatt tcttcaactt tgatagtatc gccagtgata cctactgcac gagcaatttc  74520
agccaaagtt ccttgcagaa ttttggattc ttccatcaga cgagcagctt gatcctgcgt  74580
atcaagaatg cgagatttca gagttacgat ttcagcagac agtttttgtt caacagtttg  74640
ttcagacatt atagtacctt tagtgtattt ttaattttag aaaaaagttc ttcaagagaa  74700
ccatcgtttg taattactaa atcgccatca cgaattggca atccagcttc tgtaatatgt  74760
gtatcattgg atttttgacc aggacgaact acatgaatta ctgtagcacc catcgcccta  74820
gccgcatcca tttcatgatc ttgacgggta tcaggaacga tataataatc ataacctgag  74880
ttaaatttat caagataatc taaagcaaat aattttaccc agtacatgcg gtcgaagtta  74940
ttaacaatca aatccgtacc tagggcttgc atcagacgac ggactgacca ttgatcttca  75000
atattattta taacgtcagt aatcttatta aatgctacga aattaactga ttcttttcct  75060
tcgtcatcaa aaacaaacac acctttaatt gggcttttac cattaagata acaaaatgct  75120
tgttccataa tcgtgattac ttctaattta gtcagattta aattagtctc acgatcatag  75180
tcaattcctt caaactcttt acgagttaag caaggatagt cagtgtttgc tgcaaatact  75240
ccccatgcat aagccaatgc atccttaata ggaccagcaa gttggtattt aactgcagaa  75300
taattgctca tgataaaatc agcagtagta tcttttccac tacgctttac accgcttaaa  75360
aagattagtt tcatgtgttt ctcctcaaat ttaattaaga ttataacaca caaaactgaa  75420
gcattaaact tctgctataa ttttaccatc tttttctact tgaaaatagg tgtaaggaat  75480
tgttgcagta catactaaag ccgggtctga atcttccgtg tagctaaatt ctacttcaga  75540
taggtcagaa acccaaggct tataaaaatt tattgacatc acgatttcag ttttgctatt  75600
atctaagatg taaagcgtaa tgtactcagg acctgttttt tgggcagtat tttcacctgt  75660
aagatagttg ctagttccta gcatccattc atacattcct atccacgact taagttcttc  75720
atcaactata aatctcacaa tgagtggatc atactcaaat gtaacacctg gacgttgtgc  75780
tcggcccagt ccaaacggcc cagtcacggt atcagtaaca ggtattctaa ttcctggaat  75840
aggaactgac tgagcattta aagtaaaagc agatgtagta ttactatgtg gtattgatac  75900
tacaaagtta gttgtatttg cttggttaaa aatttgttgc agagcttgcg acatatattc  75960
ctcataatgc tttataactg ttggtggtat aatgggtcta agtcccttcc attcaattcc  76020
atttagaaca aacaacagaa aagaatggaa gataatagaa ttagatattt gaccagactt  76080
tgtttgcaga gaaacgtttt ccttttgaaa cgaactgctg aagtggcatc aacacaacgt  76140
tcgcccagtc tttcggggcg atttcaacaa ggctacccat aatattacca ggtatatatg  76200
ccttaatcat ttggtctgca ccccctaaatc ctttcacttg actccaatca atttttaatt  76260
tcgttttatt agtaatagta ggtgtatttg catattgctt taaaagctct tctaggaatt  76320
gctgacgagc tttaggtgga atatagtgca agtttaatcc gtacattaaa ttatgcttac  76380
ctaaaccaag gtaaattatc aaaggaaatt tatcccagta aggaagagtt tccttgtgtt  76440
tagcatcata agcaaaagca tatattcgtc ccggctgcgg gcgaacaact ttatgtcctt  76500
ttacttgctt aatagtttca gcaaaccact ttctggtttt attattaatt gctgcgcctt  76560
cattacgaat tttatcacgc aatgtttgtc tgaatgaatt tatcataagc agttgtcttt  76620
cttgcttatt gagtttattc attggttttg attcaagttt ttgaatcttt tcagccgttt  76680
taattcctga agcatatttt gacattgctg aagtaaacgt agagtatttg attcctcttt  76740
cttcagcaaa ttgctttcct gtcattcctt ttgctttggc ctttttatat tcaagaccta  76800
tctgaatcca tttcttttcg tttaatgatt gcttaacctt tggaacttgg ggagtgcttt  76860
cattaattat ttgaaaaata gccattatgc cccccttaaag ccaagagctc gtaatccatc  76920
ttctgttaga attctaaatt ttattccacg cttttcagct aaagattgtg ctgctttcca  76980
tttgtcagtg ttcacagacc aggtataaat ttcattcata aatcttttct tcgctgcggt  77040
cgttagatgt gctggtttaa ctggtggttg tgtttctttt ttaggtttta tttcaataaa  77100
aaattcttgt ccagaagaat ctttcatcca aatatccatg aagtatctac gttttttccc  77160
ttctgcatta caaaaataag gaattactgc tgtttcacta ccccatgcaa taatttctgg  77220
atttttatct aaccattcaa aaaagaattt ttcccaattt gatctatacg taattttttt  77280
agggtcacct ctatactttg atatattttt aggaacccat tttccagaat atgccattgg  77340
attctcctta taaatagata atatatttat aaacaggagg gcccatgctc tttacatttt  77400
ttgatccgat tgaatatgcg gccaaaaacgg tgaataaaaa cgcgccgact attcctatga  77460
cagatatttt tagaaactat aaagactatt ttaaacgcgc tcttgcggga taccgcttac  77520
gtacttatta tattaaaggt tcaccacgcc cggaagaatt agcaaatgct atatatggaa  77580
atccacagct gtattgggtt ttattgatgt gtaatgataa ttatgacccg tattatggat  77640
ggattacttc gcaagaagct gcttatcaag catctataca aaaatacaaa aacgtaggtg  77700
gagaccaaat agtatatcat gtgaatgaga acggtgaaaa atttataat ttaatatcat  77760
acgatgataa tccatatgtt tggtatgata aaggcgataa agctagaaaa tatcctcaat  77820
```

```
atgaaggagc gcttgctgcg gtcgatacgt atgaagctgc tgttcttgaa aatgaaaaac  77880
ttcgtcaaat aaaaataata gcaaaatcag acatcaattc atttatgaac gaccttatac  77940
gtataatgga gaaatcttat ggaaatgata agtaataacc ttaattggtt tgtcggtgtt  78000
gttgaagata gaatggaccc attaaaatta ggtcgtgttc gtgttcgtgt ggttggtctg  78060
catccacctc aaagagcaca aggtgatgta atgggtattc caactgaaaa attaccatgg  78120
atgtcagtta ttcaacctat aacttctgca gcaatgtctg gaattggagg ttctgttact  78180
ggaccagtag aaggaactag agtttatggt catttttag acaaatggaa aactaatgga  78240
attgtccttg gcacgtatgg tggaatagtt cgcgaaaaac cgaatagact tgaaggattt  78300
tctgacccaa ctgggcagta tcctagacgt ttaggaaatg atactaacgt actaaaccaa  78360
ggtggagaag taggatatga ttcgtcttct aacgttatcc aagatagtaa cttagacacc  78420
gcaataaatc ccgatgatag accgctatca gagattccga ccgatgataa tccaaatatg  78480
tcaatggctg aaatgcttcg ccgtgatgaa ggattaagat taaaagttta ttgggatacc  78540
gaaggatatc cgacaattgg tattggtcat cttatcatga agcagccagt tcgtgatatg  78600
gctcaaatta ataaagtttt atcaaaacaa gttggtcgtg aaattacagg aaatccaggt  78660
tctattacaa tggaagaggc gacgacttta tttgagcgtg atttggctga tatgcaacgg  78720
gacattaaat cacattctaa agtaggacca gtctggcaag ctgtcaaccg ttctcgtcaa  78780
atggcgttag aaaatatggc atttcagatg ggtgttggtg gtgtagctaa atttaacaca  78840
atgttaactg ctatgttagc aggagattgg gaaaaagcgt ataaagccgg tcgtgattca  78900
ttgtggtatc aacaaacaaa aggccgtgca tcccgtgtta ccatgattat tcttacgggg  78960
aatttggaat catatggtgt tgaagtgaaa accccagcta ggtctctatc agcaatggct  79020
gctactgtag ctaaatcttc tgaccctgct gaccctccta ttccaaatga ctcgagaatt  79080
ttattcaaag aaccagtttc ttcatataaa ggtgaatatc cttatgtgca tacaatggaa  79140
actgaaagcg gacatattca ggaatttgat gatacccctg ggcaagaacg atatagatta  79200
gttcatccaa ctggaactta tgaagaagta tcaccatcag gaagaagaac aagaaaaact  79260
gttgataatt tgtatgatat aaccaatgct gatggtaatt ttttggtagc cggtgataaa  79320
aagactaacg tcggtggttc agaaatttat tataacatgg ataatcgttt acatcaaatc  79380
gatggaagca atacaatatt tgtacgtgga gacgaaacga aaactgttga aggtaatgga  79440
actatcctag ttaaaggtaa tgttactatt atagttgaag gtaatgctga cattacagtt  79500
aaaggagatg ctaccacttt agttgaagga aatcaaacta acacagtaaa tggaaatctt  79560
tcttggaaag ttgccgggac agttgattgg gatgtcggtg gtgattggac agaaaaaatg  79620
gcatctatga gttctatttc atctggtcaa tacacaattg atggatcgag gattgacatt  79680
ggctaatata cttccaatga gcgctgattt aggagaatcc atggaaggtt cttctatcga  79740
cgtcaccttt accgctcaat tagaaacagg tgaaacgtta gtatctataa atataactag  79800
ttacgaagaa actcctgggg ttttagtaga agaaaatcgc ttatatggaa catatgaatc  79860
tgtatttggt ttcggaaatg acgcgttgaa atatcgttta ggcgatgaat ttaaaactgc  79920
tgcttcatgg gaagaacttc ctactgattc tgatactcag ttgtatttgt ggaaagctcc  79980
tcaaaacctc cagaagacat tcacttacga agtaacatta atatatgact accaagaaca  80040
aagtgaatct gggggttctg gcagtaattc taggtcatct tctgatacta ctgaaccgac  80100
agatcctcct gctccagtaa gaaaaactct agttaaaaat tatactaaaa ctatagttgg  80160
aaattggagt cgttgggcta ataaactgag aaaatatgcc tatgcaagac cataaatatt  80220
tttatttgta ttcaataact aataaaacaa cagaaaaaat ttatgtaggc gtccacaaaa  80280
cttcaaattt ggatgatggg tatatgggtt ctggcgttgc cattaaaaat gccattaaaa  80340
aatatggcat agataatttt tataagcata ttataaaatt ctttgaatct gaaaaagcta  80400
tgtatgacgc agaggcagaa atagtcacag aggaatttgt taaatctaag aaaacttata  80460
atatgaaact aggcggtatc ggtggcttcc caaaacataa cacagcgggt gctaaaaatg  80520
gattttacgg taaatctcat tcgcgtgaaa ctagattgaa aattagcatt aaatcgtcta  80580
gaaaaagagg gcctagaggg ctagaggtaa aactctgaag atgtgtggcg ccaataaccc  80640
aaggtatggc aaaatagccc ctaatgctaa atctgttatt atcaacggcg ttttatataa  80700
aagtattaaa atcgcagcta aagctcttaa tataaattat agtaccttaa aggggcgagt  80760
taaagcgggg tattataaat gtcaggatta agttatgata agtgtgttac tgctggccat  80820
gaagcgtggc ctccaacagt tgtgaatgct acacaaagta aagtattcac tggaggaatt  80880
gctgttctcg tagcaggcga tccaattaca gaacatacag aaattaaaaa gccgtatgaa  80940
acacatggcg gagtgacaca acctagaact tctaaggtat atgtcactgg aaagaaagct  81000
gttcaaatgg ctgatccaat atcatgcggt gatactgtgg ctcaggcatc atctaaagta  81060
ttcattaaat aggatttaaa atggcaaata cccctgtaaa ttatcaatta acaagaacag  81120
caaatgctat tcccgagata ttcgtcgggg gtacatttgc tgaaataaaa caaaacctca  81180
ttgaatggct taatggccaa aatgaatttt tggattatga ttttgaaggc tcaagattaa  81240
acgttctgtg tgacctttta gcttataata cattatacat tcagcagttt ggtaatgctg  81300
ctgtgtatga aagctttatg cgtactgcta acttacgaag ttcagttgtt caagctgcac  81360
aagataacgg atatttacct acttcaaaat ccgctgcgca gaccgaaatt atgttaacat  81420
gcactgacgc attgaatagg aattacatta ctattcctcg cggaactcgc tttttagcat  81480
atgcaaaaga tacttctgtt aatccatata acttcgtttc tagggaagac gttattgcta  81540
ttcgtgataa aaataaccaa tattttccgc gtttaaaatt ggcccaggga cgtatagtaa  81600
gaactgaaat catttatgat aaattaacac ctattatcat ttatgataaa aatattgata  81660
gaaaccaggt taaattatac gttgatggag cggaatggat taactggacg agaaagtcaa  81720
tggttcatgc tggttcaaca tcaacgattt actatatgcg tgaaactatt gatggaaaca  81780
ctgaattcta ttttggtgaa ggtgaaattt ctgttaatgc ttctgaagga gctttgaccg  81840
ctaattatat cggaggtctt aaacctactc agaactctac gattgttatt gagtacatta  81900
gtactaatgg tgctgacgcg aacggagcag tcggattttc atacgcagat acattaacaa  81960
atataactgt catcaatatt aatgaaaatc caaacgatga tccagatttt gttggggcag  82020
atggaggcgg tgatccagaa gatattgagc gtattcgcga attgggtact attaaacgcg  82080
aaacccaaca acgatgcgta actgcgactg actatgatac attcgtttca gagagatttg  82140
gttctattat tcaagctgtt cagactttca ctgattctac taaacctggg tatgcattta  82200
ttgctgctaa acctaaatca ggattgtatt taactaccgt acagcgtgaa gatattaaaa  82260
attatctcaa agactataat ttagctccta ttacgccatc aattatttct cctaattatc  82320
tttttattaa gactaattta aaagtcacat atgctttaaa taaactgcaa gaatccgaac  82380
agtggcttga aggtcaaata attgataaaa tagatcgcta ttataccgaa gatgtagaaa  82440
tttttaactc gtctttcgct aaatctaaga tgttgacata tgtagatgat gcagatcatt  82500
ctgtcattgg ttcatcagcg actattcaaa tggttcgtga agtacaaaac ttctataaaa  82560
```

-continued

```
cgcctgaagc gggtattaaa tacaataatc aaataaaaga tcgttctatg gaatctaata  82620
cgttttcatt taattctgga cgaaaggttg taaatcctga tactggttta gaagaagatg  82680
tattatatga cgttcgtata gtatcaacag accgagattc taaaggaatt ggtaaagtta  82740
ttattggtcc atttgcttct ggcgatgtta cagaaaatga aaacattcag ccgtatacag  82800
gcaacgattt taacaaatta gcaaattctg atggacgcga caaatactat gttatcggtg  82860
aaataaatta tccagctgat gtgatttatt ggaatatcgc taaaattaat ttaacatctg  82920
aaaaatttga agttcagacc attgaattat attctgaccc aaccgatgat gttatcttta  82980
ctcgcgatgg ttcactgatt gtatttgaaa atgacttacg tccacaatac ttaactatcg  83040
atttggagcc tatatcacaa tgacagtaaa agcaccttca gtcactagtc tcagaatttc  83100
caagttatcc gcaaatcagg tgcaagtacg ctgggatgac gttggtgcta atttctacta  83160
ttttgtagaa atcgctgaga caaaaacaaa ctcgggggaa aatctcccga gtaatcaata  83220
tcgttggatt aatttaggat atacagcaaa taatagtttc tttttgatg atgctgatcc  83280
attaacaaca tacattatta gagtagccac agctgcgcaa gattttgagc agtctgattg  83340
gatttatacc gaagagtttg aaacttttgc tacaaatgct tatacatttc aaaacatgat  83400
tgaaatgcaa ttagccaata aattcattca ggaaaaattt actcttaata attctgatta  83460
tgttaatttt aataatgata ctataatggc tgcattgatg aatgaatcat tccaattcag  83520
cccatcgtat gttgatgttt catcaataag taattttatt attggtgaaa atgagtatca  83580
tgaaatacaa ggttctattc agcaagtatg taaggatatt aaccgagttt atttgatgga  83640
atcagaagga attctatatc tttttgagcg ctatcaacct gtagttaaag tatccaatga  83700
taaaggacaa acctggaaag ctgtaaagct cttcaatgac cgtgtaggat atcctttatc  83760
taagacagta tattaccaat ctgcgaacac aacatacgtt ctaggatacg acaagatttt  83820
ctatggccgc aaatctactg atgttagatg gtcagccgat gatgtcagat ttagttctca  83880
ggatataaca tttgctaaac ttggcgacca attacatcta ggatttgatg tagaaatttt  83940
tgccacttac gcgactttac cagcgaatgt ataccgcatt gcagaagcta ttacttgcac  84000
cgatgattac atttacgttg tcgccagaga caaagttaga tacataaaaa cgagtaatgc  84060
acttatagat tttgatccat tatctccaac atattcggaa agacttttg aacctgatac  84120
catgactata accggaaatc ctaaagcagt atgctataaa atggattcta tctgtgataa  84180
agtttttgct cttattattg gtgaagttga aacattaaat gctaatccta gaacatcaaa  84240
aataattgat tccgctgata aaggaatata tgttttaaat catgacgaaa aaacatggaa  84300
aagagttttt ggtaataccg aagaagaaag aagacgtatt caacccggat atgcgaatat  84360
gtcaactgac ggtaaattag tttctctgtc ttcgagtaat tttaaatttt taagtgataa  84420
tgttgttaat gaccctgaaa ctgcagcaaa atatcagtta attggcgctg ttaaatatga  84480
atttcctcgt gaatggttag ctgataagca ttatcatatg atggcattta tagcggatga  84540
aacatctgat tgggagactt ttactcctca accaatgaaa tactacgcag aaccattctt  84600
taactggtct aaaaaatcta acacacgttg ttggataaac aactctgata gagctgtggt  84660
agtttatgct gatttaaaat acactaaagt tatagaaaat attccggaaa catcaccaga  84720
tagattagtt catgaatact gggatgatgg tgattgcact atagtaatgc caaatgtcaa  84780
attcactgga tttaaaaaat acgcatcagg aatgcttttc tataaagcct ccggtgaaat  84840
aatttcttac tatgatttta actatcgtgt gagagataca gtagaaatta tttggaagcc  84900
aactgaagta tttttaaaag cattttaca aaaccaagag catgagactc cttggtcacc  84960
agaagaagag cgtggattag ctgaccctga tttaagacca ttaattggca caatgatgcc  85020
tgattcttat ttgttacagg attcgaattt tgaggcattt tgcgaagcat atattcagta  85080
tctttctgat ggatatggaa ctcaatacaa taatttacga aatttaattc gtaaccaata  85140
tccacgagaa gagcacgcat gggaatattt gtggtcagag atatataaaa gaaacattta  85200
tttaaatgct gataaacgcg atgctgttgc gagattcttt gaatcacgta gctatgattt  85260
ttattctact aaaggaattg aagcatcata caagtttctt tttaaagttc tttataatga  85320
agaagttgaa attgaaattg aatctggggc tggtactgaa tatgatataa tcgttcaatc  85380
tgattctttg actgaagatt tagtaggaca aacgatttat acggcaacag gaagatgtaa  85440
tgttacttat atagaaagaa gctattctaa tggtaaattg caatggaccg taactattca  85500
taatcttttg ggacgattaa ttgctggtca agaagttaaa gcagaaagac tccctagttt  85560
tgaaggcgaa attattcgtg gggttaaagg aaaggatttg cttcaaaaca atatagacta  85620
tattaataga agtagatcat actatgtaat gaaaattaaa tccaatttac cttcttcccg  85680
ctggaaatct gacgttattc gttttgttca tccagtagga tttggattta tagcaattac  85740
ccttttaaca atgtttatta atgttggttt aactcttaaa catacagaga ctataattaa  85800
taaatacaaa aactataaat gggattctgg attgcctact gaatatgccg acagaatagc  85860
taaattaact ccaaccggtg aaattgagca tgattcagta acaggcgaag caatttatga  85920
gcctggccca atggctggtg taaaatatcc tcttcctgat gactataatg ctgaaaataa  85980
taattcaata tttcaaggtc aattgccgtc tgaacgacgt aaattaatga gtcctttatt  86040
tgatgcatct ggaacaacat ttgcgcaatt tagagattta gttaataaac gtctaaaaga  86100
taatatagga aatccaagag accctgaaaa tccaacacag gttaaaatag atgaatgatt  86160
caagtgttat ctatcgtgcg atagttactt caaaatttag aacagaaaaa atgttgaatt  86220
tttataattc aattggaagt ggtccggata aaaacactat ctttatcaca tttggaagat  86280
cagaaccgtg gtcatcaaat gaaaatgagg tgggctttgc cccaccttat ccaaccgatt  86340
ctgtattagg cgtaactgac atgtggacgc atatgatggg aacagtaaaa gttcttccat  86400
caatgcttga tgctgttatt cctcgcagag attggggaga tactagatat ccggatccat  86460
acacatttag aattaacgat attgtagtgt gtaactcagc tccttacaac gctactgaat  86520
caggcgctgg ttggttagtg tatcgttgtt tagatgttcc tgataccgga atgtgttcaa  86580
tagcatcttt aactgataaa gatgaatgcc ttaagttagg tggaaaatgg actccttctg  86640
ctaggtcaat gactccgcct gaaggtcgag gagatgctga aggaacaatt gaacccggag  86700
acgggtatgt gtgggaatat ctatttgaga ttccgcctga tgtatctata aatagatgca  86760
cgaatgaata tatcgtggtt ccttggcctg aggaattaaa agaagacccg actagatggg  86820
gatatgaaga taatctcact tggcaacaag atgattttgg attaatttac cgtgttaagg  86880
caaatactat ccgttttaaa gcatatttag attcagttta ttttcctgaa gctgcattac  86940
caggaaataa aggatttaga caaatatcaa taatcacgaa tcctcttgaa gctaaagctc  87000
atccaaatga cccaaacgtt aaagctgaaa aggattatta tgacccagaa gatttaatga  87060
ggcattcggg tgaaatgatt tatatggaaa ataggccacc tattattatg gcaatggatc  87120
aaacagaaga aatcaatatt ctgtttacat tttaaattaa gggagcccat gggctccctt  87180
tttctttata aatactataa actcataagg aaaccgctat gttcattcaa gaaccaaaga  87240
aattgattga taccggcgaa attggtaacg cttctactgg tgatatctta ttcgacggtg  87300
```

```
gtaataaaat taatagtgat tttaacgcaa tttataatgc gtttggcgat cagcgtaaaa  87360
tggcagtagc aaatggcact ggagcagatg gtcaaattat ccatgctact ggatattatc  87420
aaaaacactc tattacagag tacgcaactc cagtgaaagt tggcactaga catgatattg  87480
atacctctac tgtaggtgtt aaagttatca ttgaaagagg cgaactcggc gattgtgttg  87540
aattcattaa ctctaatgga tcaatatcag ttactaatcc tttgacaatt caagctattg  87600
attcaattaa aggtgtttca ggtaatttag tagtaactag cccatatagt aaagttactt  87660
tacgctgtat ttcatctgat aattctacgt cggtttggaa ttattctatt gaaagtatgt  87720
ttggacaaaa ggaatcacca gctgaaggta catggaatat ttctacatct ggatcagttg  87780
acattccatt atttcatcgt actgaataca atatggctaa attgctagtt acgtgccaat  87840
cggtagatgg aagaaaaatt aaaacagcag aaataaatat tcttgtggat actgttaatt  87900
cagaggtaat ttcttctgaa tatgctgtca tgcgagttgg gaatgaaacc gaagaagacg  87960
aaatcgctaa tattgcattt agtattaaag aaaattatgt aacggcgact ataagttctt  88020
caactgtcgg tatgagagca gcagttaaag ttatcgctac gcagaaaatc ggggtggctc  88080
aataatgaaa caaaatatta atatcggtaa tgttgtagat gatggtaccg gtgactacct  88140
gcgtaaaggt ggtataaaaa taaatgaaaa ctttgatgag ctttattatg aactcggtga  88200
tggtgatgtt ccatattcag ccggtgcctg gaaaacttat aatgcttcat caggacaaac  88260
attaacagca gaatggggaa aatcatacgc tattaataca tcttctggaa gagtgactat  88320
aaatcttcca aagggtacag ttaatgatta caacaaggta attagagcta gagacgtatt  88380
tgctacatgg aacgtcaacc cagttacact agtagctgct tccggcgata cgattaaagg  88440
gtctgcagta ccagttgaaa ttaatgttcg attcagcgat ttagaactag tgtattgtgc  88500
cccaggacgt tgggaatatg tcaaaaataa acaaattgac aaaattacca gttcagacat  88560
tagtaatgta gctcgcaaag aatttttagt tgaagttcaa ggacaaacag actttttaga  88620
tgttttccgt ggaactagtt ataatgtaaa taacatcaga gtaaaacatc gtggtaacga  88680
attgtattac ggcgatgtgt ttagcgaaaa cagcgatttt ggctctccag gcgaaaatga  88740
aggagaactg gttcctcttg atggatttaa cattcgatta agacagcctt gtaatattgg  88800
tgacactgtt caaattgaaa catttatgga tggtgtatca cagtggagaa gttcatatac  88860
aagacgtcaa attagattgt tagattcaaa attaacgtca aaaacttctt tagaaggaag  88920
catttacgtt actgatttat caacaatgaa atcaattcca ttttctgctt ttggattaat  88980
tccaggagaa cctattaatc ctaactctct tgaggttcgt tttaacggga ttttacagga  89040
attggctggc acagttggaa tgccattatt tcattgtgtt ggtgccgatt cagacgatga  89100
agtagaatgc tctgttttag gtggaacttg ggaacaatct cataccgatt attcagttga  89160
aactgatgaa aacggcatac cagaaatttt acatttcgat agcgtatttg agcatggtga  89220
cattatcaat atcacctggt ttaataatga tttgggtaca ttattaacaa aagatgagat  89280
tattgatgaa actgataatc tctatgtatc gcaaggacct ggagtagata tttctggtga  89340
tgtaaattta acagacttcg ataaaattgg ttggccaaat gtagaagcag ttcaatctta  89400
tcaacgcgca tttaatgctg tttcaaatat ctttgatacg atttatccta ttggaactat  89460
atatgaaaac gctgttaatc caaataaccc tgttacatat atgggattcg gctcatggaa  89520
attatttggg caaggaaaag ttttagttgg atggaatgaa gatatttcgg accctaactt  89580
tgctctaaat aacaacgatt tagattcggg tggaaatcct tcacataccg caggtggaac  89640
aggtggttct acttctgtta cattggaaaa tgctaatctt cctgcaactg aaacagatga  89700
agaagttcta atagttgatg aaaatggatc agtcattgtt ggtgggtgtc aatacgatcc  89760
agatgaatcc ggtccaattt acactaaata ccgtgaagct aaagcatcta ctaactctac  89820
tcacactccg ccaacatcaa taactaacat tcaaccatat attacagttt atcgttggat  89880
aaggattgca taatgagttt acttaataat aaagcgggag ttatttcccg cttagccgat  89940
tttcttggtt ttagacctaa aactggcgac attgatgtaa tgaatcgtca atcagtcggg  90000
tcagtgacaa tatctcaatt agcgaaagga ttttatgaac caaacataga atcagctatt  90060
aatgacgttc ataattttc tataaaagac gttggcacaa ttattactaa taaaactggt  90120
gtttctcctg agggtgtttc tcaaactgat tattgggcat tttctggaac tgtaacagac  90180
gattctcttc ctccgggttc tcctattacg gtattagtat ttggtcttcc agtttcagca  90240
acaactggaa tgacggcaat tgagtttgtt gcaaaagttc gcgttgcact acaagaagct  90300
attgcgtcat ttactgctat caattcatat aaagaccatc caactgatgg tagtaaatta  90360
gaagttactt atttagataa tcaaaaacat gtattaagca catattctac atatggaata  90420
actatttccc aagaaattat atctgagtct aagcctggct atggtacatg gaatttattg  90480
ggcgcacaaa ctgtaacttt agataatcag cagactccta cagtatttta tcattttgag  90540
agaacagcat gagtaataat acatatcaac acgtttctaa tgaatctcgt tatgtaaaat  90600
ttgatcctac cgatacgaat tttccaccgg agattactga tgttcacgct gctatagcag  90660
ccatttctcc tgctggagta aatggagttc ctgatgcatc gtcaacaaca aagggaattc  90720
tatttattcc cactgaacag gaagttatag atggaactaa taataccaaa gcagttacac  90780
cagcaacgtt ggcaacaaga ttatcttatc caaatgcaac tgaaactgtt tacggattaa  90840
caagatattc aaccaatgat gaagccattg ccggagttaa taatgaatct tctataactc  90900
cagctaaatt tactgtcgcc cttaataatg cgtttgaaac gcgagtttca actgaatcct  90960
caaatggtgt tattaaaatt tcatctctac cgcaagcatt agctggtgca gatgatacta  91020
ctgcaatgac tccattaaaa acacagcagt tagctattaa attaattgcg caaattgctc  91080
cttctgaaac cacagctacc gaatcggacc aaggtgttgt tcaattagca acagtagcgc  91140
aggttcgtca gggaacttta agagaaggct atgcaatttc tccttatacg tttatgaatt  91200
catcttctac tgaagaatat aaaggcgtaa ttaaattagg aacacaatca gaagttaact  91260
cgaataatgc ttctgttgcg gttactggcg caactcttaa tggtcgtggt tctacgacgt  91320
caatgagagg cgtagttaaa ttaactacaa ccgccggttc acagagtgga ggcgatgctt  91380
catcagcctt agcttggaat gctgacgtta tccagcaaag aggtggtcaa attatctatg  91440
gaacactccg cattgaagac acatttacaa tagctaatgg tggagcaaat attacgggta  91500
ccgtcagaat gactggcggt tatattcaag gtaaccgcat cgtaacacaa aatgaaattg  91560
atagaactat tcctgtcgga gctattatga tgtgggccgc tgatagtctt cctagtgatg  91620
cttggcgctt ctgccatggt ggaactgttt cagcgtcaga ttgtccatta tatgcttcta  91680
gaattggaac aagatatggc ggaaacccat caaatcctgg attgcctgac atgcgtggtc  91740
tttttgttcg tggttctggt cgtggttctc acttaacaaa tccaaatgtt aatggtaatg  91800
accaatttgg taaacctaga ttaggtgtag gttgtaccgg tggatatgtt ggtgaagtac  91860
agatacaaca gatgtcttat cataaacatg ctggtggatt tggtgagcat gatgatctgg  91920
gggcattcgg taatacccgt agatcaaatt ttgttggtac acgtaaagga cttgactggg  91980
ataaccgttc atacttcacc aatgacggat atgaaattga cccagaatca caacgaaatt  92040
```

```
ccaaatatac attaaatcgt cctgaattaa ttggaaatga aacacgtcca tggaacattt  92100
ctttaaacta cataattaag gtaaaagaat gacagatatt gtactgaatg acttaccatt  92160
cgttgacggc cctcctgcag agggccagag ccgcatttcc tggattaaaa acggcgaaga  92220
aatattagga gctgacacac agtatggaag tgaaggctca atgaatagac ctacggtttc  92280
tgtactaaga aatgttgaag ttcttgataa aaacattgga atacttaaaa catctttaga  92340
aaccgcaaat agtgatatta aaacaattca gggcatctta gatgtatctg gtgatattga  92400
agctttggcc caaataggta tcaataaaaa ggatatttct gacctcaaaa cgctaaccag  92460
tgaacacaca gaaatattaa atggaactaa taatacggtt gacagtattc ttgccgatat  92520
tggtccattt aacgccgagg ccaactctgt atacagaacg atcagaaatg atttactgtg  92580
gataaagcgt gaacttggac aatacactgg tcaagatatt aatggtcttc ctgttgtagg  92640
aaatcctagt agtggaatga agcatcgcat tattaataat actgatgtca tcacttcgca  92700
gggaatacgt ttaagcgaat tagaaacaaa atttattgaa tctgatgtag gttctttgac  92760
cattgaagtt ggtaatcttc gtgaagagct tggaccgaaa ccaccatcat tttcacagaa  92820
cgtttatagt cgtttaaatg aaattgacac taaacagaca acagttgagt ctgacattag  92880
tgctattaag acctcaatag gatatccagg aaataattcg attatcacga gtgttaatac  92940
aaacactgat aatattgcat ctattaattt agagctaaat caaagtggag gtattaaaca  93000
gcgtttaacc gttattgaaa cttccattgg ttcagatgat attccttcga gtattaaagg  93060
tcaaatcaaa gataatacaa cttcaatcga atctctaaat ggaatcgtcg gtgaaaacac  93120
ttcatctggc ttaagagcga atgtttcatg gttaaaccaa attgttggaa ctgattctag  93180
cggtggacaa ccttctcctc ctgggtctct tttaaaccga gtttctacaa ttgaaacttc  93240
tgtttcaggc ttgaataacg ctgttcaaaa cctacaagta gagattggta ataacagcgc  93300
aggaattaaa gggcaagttg tagcgttaaa tactttagta aatggaacta atccaaacgg  93360
ttcaactgtt gaagagcgcg gattaaccaa ttcaataaaa gctaacgaaa ctaacattgc  93420
atcagttaca caagaagtga atacagctaa aggcaatata tcttctttac aaggtgatgt  93480
tcaagctctc caagaagccg gttatattcc tgaagctcca agagatgggc aagcttacgt  93540
tcgtaaagat ggcgaatggg tattcctttc taccttttta tcaccagcat aacatggggc  93600
cgcaaggccc caaaggattt taaatgtcag gatataatcc tcagaatcca aaggaactca  93660
aagatgtcat tctaagacgt ttaggggctc caattattaa tgttgagtta acacccgatc  93720
aaatttacga ttgtatccag cgtgccctag aattatacgg tgaataccat tttgatggac  93780
tcaataaagg ttttcatgtt ttttatgtag gggatgatga agaaaggtac aagaccggag  93840
tcttcgattt aagaggttct aacgtatttg cagtaacccg cattttacgc acaaatattg  93900
ggtcaataac atctatggat ggaaacgcta catatccgtg gtttactgac tttcttttag  93960
gaatggctgg tattaatggc ggaatgggaa cgtcttgtaa tagattttat ggaccaaatg  94020
cctttggagc tgatttagga tattttaccc agcttaccag ttatatggga atgatgcaag  94080
atatgctctc tcctattcca gacttttggt ttaattcagc aaatgaacag ctcaaagtca  94140
tgggaaactt ccaaaaatat gatttaatta tcgtagaaag ctggactaaa tcatacattg  94200
atacaaacaa aatggttgga aatacagtag gatatggaac agtcggtcca caagatagct  94260
ggtcattatc tgaacgatat aataacccag accacaattt agtaggtcgt gttgtcggcc  94320
aagatccgaa tgttaaacag ggtgcttata ataatcgttg ggtgaaagac tatgcaacag  94380
ctttagctaa agaattgaac ggtcaaattt tagcacgcca ccaaggtatg atgcttccgg  94440
gcggtgttac aattgatggg cagcgcttaa tagaagaagc cagattagaa aaagaagcac  94500
tgcgcgaaga attatactta cttgatcctc catttggaat tttggtaggt taatatggct  94560
acttatgata aaaatctttt tgctaaattg gaaaaccgca caggttattc tcagaccaat  94620
gaaactgaaa tattaaatcc ttatgtaaat ttcaatcatt ataaaaacag ccaaatatta  94680
gctgatgtat tagtagctga aagcattcaa atgcgaggtg tagaatgcta ttatgttcca  94740
agagagtatg tttcccctga tttgatattc ggcgaagact taaaaaataa atttactaaa  94800
gcttggaaat ttgctgcata tttaaattca tttgaaggat atgaaggagc taaatcgttc  94860
tttagtaact ttggtatgca agtacaagac gaagtgactt tatctattaa cccaaattta  94920
tttaagcatc aagttaacgg aaaagaaccc aaggaaggtg atttgatata ttttcctatg  94980
gataacagct tatttgaaat taactgggtt gaaccatatg atccatttta tcaattaggc  95040
caaaacgcta ttcgtaaaat tacggcaggt aaattcattt attctggaga agaaattaat  95100
ccagttctac agaaaaatga aggaattaac attccagaat ttagtgaatt agaattaaat  95160
gctgttcgca atcttaacgg tattcatgac attaatattg atcagtatgc tgaagtagat  95220
caaattaatt ctgaagctaa agaatacgtt gaaccttatg ttgttgtcaa taacagaggc  95280
aaatctttcg aatctagccc atttgacaat gatttcatgg attaataaat attataaact  95340
aattaaagcc cggattagga gaagtcatgt ttggttattt ttataattcg tcttttagac  95400
gatatgctac cttgatgggc gatttgtttt caaatatcca aatcaaacgt cagttagaat  95460
ctggtgataa gtttatacgt gttcctatta cgtatgcatc aaaggaacac tttatgatga  95520
aattgaataa atggacatca ataaattcac aagaagatgt agctaaagtt gaaactattc  95580
tacctcgtat aaatttacat ttagttgatt ttagctataa tgctccattt aaaacaaaca  95640
ttttaaatca gaatttactg caaaaaggtg caacttctgt agtatcgcag tataatccat  95700
ctcctattaa aatgatttat gaattgagta tctttactcg ctatgaagat gatatgtttc  95760
aaatagttga acagattctt ccatattttc aacctcattt taatacaact atgtacgagc  95820
agtttggaaa tgatattcca tttaaaaggg atattaaaat tgtactgatg tctgctgcta  95880
tagacgaagc tatagatggg gataatttat ctcgtcgtag aattgaatgg tcattaacat  95940
ttgaagtaaa tggatggatg tatcctccag tagatgatgc agaaggatta attcgtacta  96000
cttatacaga ttttcacgcc aatacaagag atttgcctga cggcgaaggt gtttttgaat  96060
ctgtcgatag cgaagttgtt cctcgagata ttgacccaga agactgggat ggaacagtaa  96120
aacaaacttt cactagtaat gtaaatagac caacaccgcc agaacctcct ggcccaagaa  96180
catagaggtt attatggaag gtcttgatat aaacaaactt ttagatattt ctgacctccc  96240
cggaattgac ggggaggaaa tcaaagtgta tgaacctctg caattagtag aagttaaaag  96300
caatccacaa aaccgtactc cagacttaga agatgattat ggagtagttc gtcgaaatat  96360
gcattttcag caacaaatgc taatggacgc tgccaagatt tttcttgaga cagcaaagaa  96420
tgctgattct cctcgtcaca tggaagtatt tgcaactctt atggggcaaa tgactacgac  96480
gaacagagaa atactgaagc ttcataaaga tatgaaagac attacatctg agcaggttgg  96540
caccaaaggc gctgttccta caggtcaaat gaatattcag aatgcgacag tattcatggg  96600
ttcaccaaca gaattaatgg acgaaattgg tgatgcttac gaggctcaag aagctcgtga  96660
gaaggtgata aatggaacaa ccgattaatg tattaaatga tttccatccg ttaaatgaag  96720
ctggaaaaat tttaataaaa cacccaagct tagcggaaag aaaagatgaa gatggaattc  96780
```

```
attggataaa atctcagtgg gatggaaaat ggtatcctga aaaattcagt gattaccttc  96840
gtctacacaa aatagtaaaa attccaaaca actctgataa gcctgaatta tttcaaactt  96900
ataaagataa gaataataaa agatctcggt atatgggtct tcctaacttg aaacgagcta  96960
atattaaaac acaatggact cgtgaaatgg ttgaggaatg gaaaaaatgc cgagatgata  97020
ttgtttattt tgcagaaaca tactgtgcca ttactcatat tgactatggt gtcataaagg  97080
ttcaattacg tgactatcag cgtgatatgc tcaaaataat gtcatctaaa cgtatgactg  97140
tttgtaatct atcgcgccag ctcggtaaaa ccaccgtagt agctattttc cttgcacact  97200
ttgtatgttt taacaaagat aaagctgtag gtattcttgc acacaaaggc tcaatgtctg  97260
cggaagtttt agaccgtact aagcaagcaa ttgaactgct tcctgacttt ttacaaccag  97320
gaattgttga atggaataag ggttcaattg aactagataa tggttcttca attggcgctt  97380
atgcttcctc tcctgacgca gttcgtggta actcgttcgc aatgatttac attgacgaat  97440
gtgcgtttat tccaaacttc catgattcct ggcttgctat tcaaccagta atttcatctg  97500
gtcgtcgttc gaaaattatt attactacga ctcctaatgg attaaatcat ttttatgata  97560
tttggactgc tgctgtcgaa ggtaaatctg gatttgaacc atatactgct atttggaatt  97620
cagttaaaga acgtctttat aacgatgaag atatttttga cgatggatgg caatggagca  97680
tacaaaccat taatggttct tcattagctc aattccgtca agaacatact gcagcgtttg  97740
aagggacttc tggtacatta atttcaggaa tgaaattagc tgttatggat tttattgaag  97800
taacaccaga tgatcatggt tttcaccaat ttaaaaaacc tgaaccagat agaaaatata  97860
ttgcaactct agattgctca gaaggtcgtg ggcaagatta ccacgctttg catattattg  97920
atgttactga tgatgtgtgg gaacaggttg gtgttttgca ttcaaacact atttctcatt  97980
taattctacc tgacatcgtt atgcgttatt tagtagaata caatgaatgc ccagtttata  98040
ttgaattaaa tagtactggt gtgtcagttg caaaatcgct ttatatggat ttagaatacg  98100
aaggtgttat ctgcgattca tatactgatt taggaatgaa acaaactaaa cgcacgaaag  98160
cagtaggatg ttccacgcta aaagacctta ttgaaaaaga taagcttatt attcatcacc  98220
gagcgactat tcaagaattt agaacgttta gtgaaaaagg cgtgtcttgg gcggctgaag  98280
aaggttatca tgacgattta gtaatgtctt tagtgatttt tggatggtta tcaacgcagt  98340
caaaatttat tgattatgcg gataaagatg acatgcgatt agcatctgaa gtattttcaa  98400
aagagcttca ggatatgagc gacgactacg cgccagttat atttgtggat tcggttcatt  98460
ctgctgagta tgttccagta tctcatggta tgtcaatggt ataaatatat taaagcatat  98520
taaagaggat taaaaatgac tttattatct ccgggcattg agctcaaaga aactacggtt  98580
caaagcaccg tagttaataa ctctactggt acagcagctt tggccggtaa attccagtgg  98640
ggtcctgctt ttcagattaa acaggttaca aatgaagtag atttagttaa tacttttggt  98700
caaccaaccg ctgaaactgc tgactatttt atgtctgcga tgaatttctt gcagtacgga  98760
aatgacttac gagtagttcg tgctgttgat agagataccg ctaaaaactc atcgccaatt  98820
gctggtaata ttgattacac aatttctacc ccaggtagta actatgcggt tggagataaa  98880
atcacggtca aatatgtttc agatgatatt gaaactgaag gtaaaattac tgaagtagac  98940
gcagatggaa aaattaagaa aattaatatt cctactggca aaaattacgc taaagcgaaa  99000
gaagtcggtg aatatccaac actaggttct aactggactg cggaaatttc ttcatcttcc  99060
tctggtttag ctgcagtaat aactcttgga aaaattatta ctgattctgg tattttatta  99120
gctgaaattg aaaatgctga agctgctatg acagcggttg actttcaagc aaatcttaaa  99180
aaatatggaa ttccaggagt agtagcgctt tatccaggcg aattaggcga taaaattgaa  99240
attgaaatcg tatctaaagc tgactatgca aaaggagctt ctgcattact cccaatttat  99300
ccaggtggtg gtactcgtgc atctactgct aaagcagtgt ttggatatgg accgcaaact  99360
gattcacagt acgctattat agttcgtcgt aatgatgcta ttgttcaaag cgttgttctt  99420
tcaactaagc gtggtgaaaa agatatttac gatagtaaca tctatatcga tgactttttc  99480
gcaaaaggtg gttcagaata tatttttgca actgcacaaa actggccaga aggcttctct  99540
ggaattttaa ctctgtctgg tggattatca tcaaatgctg aagtaacagc aggagatttg  99600
atggaagctt gggacttctt tgctgaccgt gaatctgttg acgttcaact gtttattgca  99660
ggttcttgtg ccggtgaatc tttagaaaca gcatctactg tccaaaaaca cgtcgtttca  99720
attggggatg ctcgccaaga ttgcttagta ttgtgctctc ctccgcgtga aactgtagtt  99780
ggaattcctg taacccgtgc tgttgataac ctagtcaatt ggagaactgc ggcaggttca  99840
tacactgata ataactttaa tatcagttca acctatgcag caattgatgg taaccataag  99900
tatcagtatg acaaatataa tgatgtgaat cgttgggttc cattagcagc tgatattgct  99960
ggtttatgcg caagaactga taacgtatct cagacttgga tgtctccagc tggttataat  100020
cgtggtcaga ttcttaacgt tattaaactt gctattgaaa ctcgccaggc tcagcgcgac  100080
cgtttatacc aagaagctat caacccggta accggtacag gtggtgatgg ttacgtattg  100140
tatggtgata aaacagctac ttctgttcct tctccatttg atcgtattaa cgttcgtcgt  100200
ctgtttaata tgttgaaaac gaatatcgga cgtagttcaa aatatcgttt gttcgaatta  100260
aacaacgcgt ttactcgttc atcattccgc acagaaactg cccagtactt acaagggaat  100320
aaagctctcg gtggaattta tgaatatcgt gtagtttgcg atacaacaaa taacactccg  100380
tcagtaattg atagaaatga gtttgttgca acattctaca tccaaccggc tagaagcatt  100440
aactacatta ccttaaactt cgtagcaact gctactggtg cagatttcga tgagttaact  100500
ggtcttgctg gttaatacgg tgcattctaa aggcctgttt cggcaggcca tataaataca  100560
ctatatcctt aattctttaa ttctatatgc cctaggttaa acatagggat ataaatacta  100620
cagaggctaa tatgtttgta gatgatgtaa cacgagcgtt tgaatctggt gatttttgctc  100680
gacctaactt attccaagta gaaatttctt atcttggaca aaattttacg ttccaatgta  100740
aagctactgc tctaccagct ggtattgtag aaaaaattcc agtcggattt atgaaccgta  100800
aaattaacgt agcaggcgat cgtacattcg atgactggac tgttacagta atgaacgatg  100860
aagctcatga tgctcgtcag aagttcgttg attggcaaag cattgctgcg gggcaaggaa  100920
acgaaattac tggtggaaaa cctgcagagt ataaaaagag cgctatcgtt cgtcaatatg  100980
ctcgtgacgc taaaacagta acaaaagaaa ttgaaattaa aggtctgtgg cctactaacg  101040
tgggtgaact tcaattagat tggattcaa acaatgaaat ccaaactttt gaagtaactc  101100
ttgctctcga ttattgggaa taaaatgaat ggggagaaat ccccatcctg cttaaagcag  101160
agaagtccat tataaatata actataattc ccatttggag aatacaatga aatttaatgt  101220
attaagtttg tttgctccat gggctaaaat ggacgaacga aattttaaag accaagaaaa  101280
agaagatctt gtttccatta cagccccaaa gcttgatgat ggagcaagag aatttgaagt  101340
aagctcgaat gaagctgctt ctccttataa tgctgcattc caaacaattt ttggttcata  101400
tgaaccagga atgaaaacta ctcgtgagct tattgataca tatcgtaatc tcatgaataa  101460
ctatgaagta gataatgcag tttcagaaat cgtttcagat gctatcgtct atgaagatga  101520
```

```
tactgaagtc gtagcgttaa atttggataa atctaaattt agcccaaaaa ttaaaaatat  101580
gatgttagat gaatttagtg atgtattaaa tcatctatcg tttcaacgaa aaggttctga  101640
tcattttaga cgttggtatg ttgattcaag aattttcttt cataaaatca ttgatccaaa  101700
acgtccaaaa gaaggcataa aagaattacg tagattagac cctcgccaag ttcagtatgt  101760
tcgtgaaatt ataacagaaa ctgaagctgg cacaaaaata gttaaaggtt acaaagaata  101820
ttttatatat gatactgccc atgagtcata tgcatgtgat ggtagaatgt atgaagctgg  101880
cacaaaaata aaaattccta aagctgccgt cgtttatgcc cattctggat tagtcgattg  101940
ttgcggtaaa aatatcatcg ggtatttgca tcgtgctgtt aaacctgcta accaattaaa  102000
attattagaa gatgctgtag tcatttatcg cattactcgt gctcctgacc gtcgtgtttg  102060
gtatgtagac acaggtaata tgcctgctcg taaagctgct gagcacatgc aacatgttat  102120
gaacacgatg aaaaaccgtg tagtatatga tgcatcaaca ggtaaaataa aaaatcaaca  102180
gcataatatg tctatgaccg aagactattg gttgcagcgc cgtgatggta aagctgtgac  102240
agaagttgat actcttcctg gtgctgataa tactggcaat atggaagata ttcgttggtt  102300
tagacaagct ctttatatgg cattacgtgt tcctctttca cgcattccgc aagaccaaca  102360
aggcggtgtg atgtttgatt ctggaactag cattacacgt gatgaattaa cgtttgctaa  102420
atttattcgt gagttacagc acaagtttga agaagttttc ctagatccgc ttaaaacaaa  102480
tcttttgctt aaaggtataa tcacagaaga tgagtggaat gatgaaataa ataatattaa  102540
gatagaattt catcgggata gctactttgc tgagctcaaa gaagcagaaa ttttggaacg  102600
aagaattaat atgctaacca tggcagaacc atttattggt aaatatattt ctcacagaac  102660
tgctatgaaa gacattttgc agatgactga tgaagaaata gaacaagaag ccaagcaaat  102720
tgaagaagag tctaaagagg ctcgtttcca agaccccgac caagaacaag aggattttta  102780
atggaaggtt taattgaagc tattaaatca aacgacctcg tagccgctcg taaattattt  102840
gctgaagcca tggctgcaag aacgattgat ttaattaaag aagaaaaaat cgctatcgct  102900
cgcaatttct taatcgaagg tgaagaacct gaagacgagg atgaagatga agatgacgaa  102960
gatagtgatg ataaagacga caaaaaagac gaagactctg acgaagacga ggatgatgaa  103020
taatgcttct gatccctgaa actcatgaat tagttctcga gaatgtcgaa gcacttattc  103080
ctgaagcaca gggtcgcttt gacgaattgt cttctgcttt aaataaagac gatataaata  103140
caattgtcga gaatatgctt gatgatgaaa ctgatttagc ggttgcatta gcttctatta  103200
atgaaaatat gccgttaaat gaattcatcg ttaaacatgt ttctgcccgt ggtgaaatta  103260
ctcgcactaa agaccgcaaa acgcgtgaac gaaatgcatt tcaaaccact gggctgtcta  103320
aagcaaaacg tagacaaatt gctcgtaaag ctaccaaaac gaagattgcc aatccagcag  103380
gtcaatctcg tgctcagcgt aagcgtaaaa aagctcttaa acgccgtaaa gcattaggat  103440
taagctaatg aatgaacccc aattactaat tgaaacttgg ggtcaacctg gcgaaattat  103500
tgatggcgta ccaatgcttg aatctcatga tggaaaagac ttaggtttaa aaccgggttt  103560
atacatcgaa ggaatattca tgcaagcgga agtcgtcaat agaaataaac gtctttatcc  103620
aaaacgtata ttagaaaaag cggtaaaaga ctatattaat gagcaagttt taactaaaca  103680
agctctcgga gaattaaatc atcctccacg cgctaatgtt gacccgatgc aagccgctat  103740
cattatagaa gatatgtggt ggaaaggaaa tgacgtatac ggacgagctc gtgttattga  103800
aggtgaccat ggtcctggag ataaattagc agctaatatt cgtgccggat ggattccagg  103860
agtttcttct cgtggattag gttcattgac tgacacaaat gaaggttatc gtatcgtaaa  103920
cgaaggattc aaattaactg taggtgttga tgcagtatgg ggtccaagtg ctccagatgc  103980
atgggtaact cctaaggaaa ttaccgaatc acagacggcg gaagccgata caagtgccga  104040
tgacgcctat atggctctcg cagaggccat gaaaaaagcg ttataaatat tattatctaa  104100
acaacaggac tacaaaatgc ttaaagaaca actgattgcc gaagcgcaga aaattgatgc  104160
ttccgttgct cttgatagta ttttcgaatc agttaatatt tctccggaag caaaagaaac  104220
tttcggcact gtattcgaag ctaccgtcaa gcagcacgcc gttaaattag ctgaatctca  104280
tatcgctaaa attgctgaaa aagcagaaga agaagtagaa aaaaataaag aagaagccga  104340
agaaaaagct gagaagaaaa tcgctgagca agcttctaaa ttcattgacc atcttgcaaa  104400
agaatggctc gctgaaaata aattagcagt tgataaaggc atcaaagccg aactgtttga  104460
atccatgctt ggtggattaa aagagctctt tgttgaacac aacgttgttg ttccagaaga  104520
atcagttgat gttgtagctg aaatggaaga agagctgcaa gaacataaag aagaatcgcc  104580
tcgtctgttc gaagaactga atatgcgcga cgcatatatc aattatgtgc agcgtgaagt  104640
ggcattgagc gaaagtacta aagatctgac tgagtctcaa aaagaaaaag tctctgctct  104700
ggtcgaaggt atggattatt cagatgcatt ctcaagtaaa ttgagtgcaa tcgtagaaat  104760
ggtgaagaaa tctaataaag atgaaagcac tattactgag agtataaata ctcctgatac  104820
tgaagcagcc ggactgaatt tcgtcactga agctgtagaa gataaagctg cacagggtgc  104880
agaagatatt gtaagtgtat atgcgaaagt cgcatctcgt ttctaatttt aaaggttaac  104940
acaaatgact atcaaaacta aagctgaact tttgaacaaa tggaagccat tactggaagg  105000
tgaaggttta ccggaaattg ctaatagcaa acaagcgatt atcgctaaaa tctttgaaaa  105060
ccaggaaaaa gatttccaga cagctccgga atataaagac gaaaaaattg ctcaggcatt  105120
cggttctttc ttaacagaag ctgaaatcgg tggtgaccac ggttacaatg ctaccaacat  105180
cgctgcaggt cagacttctg gcgcagtaac tcagattggc ccagctgtta tgggtatggt  105240
acgtcgtgct attcctaacc tgattgcttt cgatatttgt ggtgttcagc cgatgaacag  105300
cccgactggc caggtattcg cactgcgcgc agtatatggt aaagacccag tggctgccgg  105360
tgctaaagaa gcattccacc caatgtatgg tccagatgca atgttctctg gtcagggtgc  105420
tgctaagaaa ttcccagctc tggctgctag cacacaaacc acagtaggtg atatctatac  105480
tcacttcttc caggaaactg gtactgtata tctgcaagct tctgttcaag taacaatcga  105540
tgctggtgcg actgatgctg ctaaattaga tgctgaaatt aagaaacaaa tggaagctgg  105600
tgcactggta gaaatcgctg aaggtatggc tacttctatc gctgaactcc aggaaggttt  105660
caatggttct accgataacc catggaatga aatgggcttc cgtatcgata agcaagttat  105720
cgaagctaaa tctcgtcagc tgaaagctgc ttactctatt gaattagcac aagacctccg  105780
cgctgttcac ggtatggatg ctgatgctga actgtctggt attctggcta cagaaattat  105840
gctggaaatc aaccgtgaag ttgttgattg gattaactac tcagctcagg ttggtaaatc  105900
tggtatgacc ctgactccgg gttctaaagc tggtgtattt gacttccagg acccaattga  105960
tattcgtggt gctcgctggg cgggtgaatc ctttaaagct ctgttgttcc agattgacaa  106020
agaagcagtt gaaattgctc gtcagaccgg tcgtggtgaa ggtaacttca ttatcgcttc  106080
ccgtaacgta gttaacgttt tggcttcagt tgataccggc atttcttatg ctgcacaggg  106140
tctggctacc ggctttagca ctgatactac caagtcagta tttgctggtg ttctgggtgg  106200
taaataccgc gtatatatcg accagtatgc taaacaggat tatttcactg taggttataa  106260
```

```
aggtccgaac gaaatggatg ctggtattta ctatgctcca tatgtagctc tgactccgct  106320
gcgtggttcc gatccgaaga acttccaacc ggtaatggga ttcaaaactc gttacggtat  106380
cggtatcaac ccatttgcag aatccgctgc tcaggctccg gcttctcgca tccagagcgg  106440
tatgccttct attctgaata gccttggtaa aaacgcttac tttagacgtg tatatgttaa  106500
aggtatctaa tctctaacga tagaaacaca attttaggga accttcgggt tccctttttt  106560
ctattttata cgatagcaat caggcatatc atccgcattt atccaattgc gaatagtttt  106620
aggactaact ttaaaatgct ccgctgcgta atcaggatta tcaaatttaa cgccctttat  106680
acatattgga ataaattttt taataccacc aagtttttca gaaatagctt tacgatgtga  106740
aatcgatata ggtttgtttt ttcgtggatg aacatgtgtt ttataatatt cattgcgccc  106800
tttaactcgc ttcgcaatag tttcatcaga ttgcttaacg cctgtttttg cctttgatat  106860
ttttcgttta gcttccacag tcattccttc ttttgttcgt attgataaca tattacgata  106920
tgaaggatct tgcaaatgaa ctataactgg atttcctctg ccaccaatag cagcattata  106980
ggtatcagtt ctcataacga attcctcatt aactagtaaa gcttccattt tatacatctc  107040
ctcagatgag gagaaagaat aaagaatttc tttttaaag ttatgaatac catattttt  107100
gatggatttt ttgatgttta cgccagaacc catataacca tcgttttcgt caagagtagc  107160
atgagctccg atgtaaattt ttccattgat gatattagta atttgatata ttaaatattt  107220
cattttaaac atcactccgt ttgtatatga ttataatatc atattacttt ggtcttgtaa  107280
ataactttat aaatagtatt atatttcaac aaggaaaata caatggctaa aatcaacgaa  107340
cttctgcgcg aatcaaccac aacgaatagc aactcaatcg gtcgcccaaa tctcgttgct  107400
ttgactcgcg ctaccactaa attaatatat tctgacattg tagcaacgca aagaactaat  107460
caacctgttg ctgcttttta tggtatcaaa taccttaacc cagacaacga atttacattt  107520
aaaactggtg ctacttacgc tggcgaagct ggatatgtag accgagaaca aatcacagaa  107580
ttaacagaag agtctaaatt aactctcaat aaaggcgatt tattcaaata taataatatc  107640
gtttataaag tattagaaga tactccattt gctactatcg aagaaagtga tttagaatta  107700
gctcttcaga ttgcaatcgt tcttttaaag gttcgtctat tttctgacgc agcgtcaaca  107760
agcaaatttg aaagctctga tagtgaaatt gcggatgcta gattccagat taataaatgg  107820
caaactgcag ttaaatctcg taaacttaaa actggcatca cagttgaatt agcgcaagat  107880
ttagaagcaa atggattcga tgctcctaat ttcttggaag atttgcttgc aactgaaatg  107940
gcagatgaaa tcaataaaga cattctgcag tctttgatta cagtgtcaaa acgctataaa  108000
gttacaggaa ttactgatag tggattcatc gatttgagtt atgcatctgc tcctgaagct  108060
ggtcgttcat tataccgaat ggtatgtgaa atggtttcgc atatccaaaa agaatcaact  108120
tatacagcaa cgttctgtgt tgcttcagct cgtgccgctg cgattcttgc tgcatcaggc  108180
tggttaaaac ataaaccaga agatgacaaa tatctttcac aaaatgccta cgggttctta  108240
gctaatggtt taccgcttta ttgcgatact aacagcccat tagattatgt aatcgttggc  108300
gtagtagaaa atatcggtga aaaagaaatt gttggatcaa ttttctatgc tccgtataca  108360
gaaggtctcg acttagatga ccctgaacat gtaggtgcat ttaaagttgt tgttgatcca  108420
gaaagcttac aaccatctat cggtttatta gttagatatg ctttatcagc aaatccttat  108480
actgtagcaa aagatgaaaa agaagcaaga ataattgacg gtggagacat ggataaaatg  108540
gcaggtcgtt cagatttgtc tgttttatta ggtgttaagc taccaaaaat tatcattgat  108600
gaataaaaca aagggacctt tcggtccctt tttatttaac ttaccaactc aatccaagct  108660
ggacgaagta catcttgtac cattttaact aattcctttt taatcaaaga aggattatct  108720
gcttgagtta gagtaatacc ttcacgagaa gtttcttcca aaatatcttg aacagttagc  108780
cccatcacct ttccaaaatc ctttggacca atttcgccaa ttttagaaat aacgttattt  108840
acgcggttca gtgtaacgta acaagctaaa attcccacca atttgttatc agcttctgat  108900
agctcaactt tagctttaat aggcttatca gactttttct tttcactaaa tttagagttc  108960
ttgcatttaa tcgctacacg atttccatta cgaagccaag aaggataaca aggtttcaat  109020
acatatcctt cagcagtaaa tacttcgcct tttgcttcgg cattccaaac gcatttattt  109080
gcatcaacta atccagcatg gtctactgta aaattataat cttggacgac agaatctaaa  109140
tcatttggca atttaataag ctcttcaaat ttaccgcgac ctaaaagtgg agccatttta  109200
aatttaaatg tattacagaa tgattccatc atataatcat ctacataagt cacatcaccg  109260
ctttctgtag taacaataat gtcaaataca taaaaatctt tatcacaata atcaacattc  109320
ttctgaatgc caggtccagc gaattcgcca aagacttgat aagatacaac cgctgaggtt  109380
tccataatat cttgtacagc tttaatggaa tcagcataat tcttcaaaat aatttcatac  109440
ccaaagaaat cttcagcagg aagaatcggt ccagtgcgtt tagcgcaagt cactttatca  109500
cgctcaataa tcaatgagaa atttgtgccg tgaatctttt cacgagctac ccactcccca  109560
ccagtcaatc ccaagctata aagtttttca ataaatttag agttgtaatg attttcaaga  109620
ctgctatact ttttaaacat aattaatcct caaaatgtaa tttctaacca atcaccatca  109680
cgctgatcac tattgacttt aaagctgaat ccttcttttc tcagccaatc accaatttct  109740
tctgtaatca atttatcacg agcaatacaa taataattaa aatgtgtttt accttgttca  109800
gctgctttat tagcaagttc tgaaaaatct ttaataaaac actctagctt aaactgttta  109860
ctttttaatg ctttttcgcg taattgatta gcaaaagatt cattttcata aagatcatac  109920
tgttccattt ttcacctttt tattgatatg tctttttcta tagacaactt tttctcgagc  109980
ccataataca gccacttctt ttgcctgtaa gtttaattca cgagcaattt caatgaatga  110040
ctttccagac tcatgaagag taaacaccac aacctcagtt ctcataatca atctcatgtt  110100
atcgagttgg tgccattata tacatcattt tctgattgtg ttttgtgtgc tttcaaaatg  110160
aagaaagggg ccgaagcccc ttatgattat ggataggtat agatgatacc agtttctaaa  110220
gcagttttat gaatgatgta tccattacgc gattcttgga catcaacttc tggatagtct  110280
ttcatcatct tctggagagt gtaacgatgc aggtaatatt tactatctgg gtcgtcagtt  110340
ttccaatctt taccttcttc ggtcattttt tggatttcat ccataaccca ccaaccgcac  110400
cagatgtaag ctgagctacg gtgtggaaga ggatgaacat aaggtaattc accttctggt  110460
tctggagcaa ctttagccgt gactgttaca ttaccagttt tggtaacggt tacagggtta  110520
taatctgcag cagtaacagt tgcagtaact tcaatagttt gacttccaac agatgaggta  110580
tcgacagtat atacgttagt tgacccttct acaggagaag aatctttctt ccatgagtaa  110640
gtaatttgtg cttcttctgg agcacccgta acattagccg taaatgtagc cgaagcatct  110700
tgctgaacat taatagaagg aggagtcaat gtaacctgtg gattcattgt cttcttatta  110760
accgttaatg atacttcatt agaagtaacg cttagtgcat cataatctgt cgcggttact  110820
tgggctacgc atttaattct ttttactcca cttgtagttg gagtatagct aaatgtagag  110880
ttagtttctc caccaacttg tgaatcatct acataccact gatacgtagc agatgctcca  110940
tcaggttgag aagctaaggc agcagtaaat tgaactgggg ttccaatcac tccagccgca  111000
```

```
ggactagcag gagttacggc taaggtagtc gtctgtgtct tatttttaac tgtgatagtt  111060
gttgtcgctt cagccgtttc cgggcctcct tcagaaagtg tatttgttgc aactacttta  111120
atagtctttt gaccggcagg tccttttagt acataactaa aagttgcttc agctccatct  111180
tgtggaacat tatctacgct ccaagcatat gtaatagttc cgcctccagt ttgaccactg  111240
ggtgtagcag taaactgctt agtttcatca ataacccctg taggtgtttt aggagttata  111300
tcaactgtaa aagtcataag ttatccttat tttaatgtta cgaaagaaga gttgcgtgtt  111360
tcacgaatta aaactgatcc atcgcgatta atgtaataaa ttaagctaaa taaagtttgg  111420
tgtgctgacg catgttcaaa actagttggg tgagatttcc aatcaggagt ttcagcaatc  111480
cattgataaa tccaccaagg aacagtacag aatcctagat tttttccaat cagttgaaga  111540
ttcggactaa agttttccgg aagagtaaat acagacggct tttcagattc aataatctca  111600
gctacagcct gttcgaattt ttcttcaaca aaaggagtat cttcaatcaa aacatcggta  111660
ttttcaggaa ttttatccgt ttctactact tcaattttaa tgtcagattt aatcggagaa  111720
tcaatcagaa gtgctgcttc tggattgact tcttcatcgt catattttaa tccctctgcg  111780
gcatcagcag catcaattaa gtctttaata gataacccat cagtctctgg cataggttca  111840
ctagcgagct tctggagggc ttcttcaata tcaacaacga tattatcaaa agatttattc  111900
tttttgacct ttataccaaa ctgttcagca tattcagcta atttagcttt agcttctttg  111960
ttatcatcaa gagccttcag ctctgcaata taatctttat ctatcataat atttcctcag  112020
tataaatata gatatattta ttactcggaa aatagtatgt accactttgt atatgaaaca  112080
acaaatctaa taaatggtaa aaagtatata ggaaagcact ctactgatga cttgaatgat  112140
ggttaccttg gttccggtaa ggcaattcag caggctataa agaaatatgg tgaaaacaat  112200
ttctctagaa caatactaaa agagtttaaa acttccgaag aagcgtacat gtatgaagaa  112260
gaaattataa ctcctgaact aataaaaagc aaaaattatt ataatatgaa acctggtgga  112320
attggtggaa ttgttatgac tacagatgtt atagcaaaga tgaaagaatc ttccgctaaa  112380
agatttgaaa actcaccggg cacggtatta ggtaaaactt gttatactaa tggaactaaa  112440
aatattttta ttaaacctgg agaacttgtt ccagaaggat ttgtaaaagg gatggttcat  112500
cctaatagaa agtccagaaa aggatgtaaa gtcaaaccga ctaccacagg aactttttgg  112560
gtcaataatg gcgcaataaa taaattaata caaccagacg gtattattcc cgacggattt  112620
attaaaggtc gtctcatgaa aagagattct aaaggcaaat ttagtaaggc ataattatgg  112680
atattaaagt acattttcac gacttcagtc atgtacgcat cgattgtgaa gagagcacgt  112740
tccacgaatt aagagatttc ttttcgtttg aggccgatgg atatagattt aatcctcgct  112800
tcagatatgg caactgggat ggacgaatcc gtcttttaga ttataatcgt cttcttccat  112860
tcggcttagt cgggcaaatt aaaaaattct gtgataattt tggctataaa gcctggattg  112920
acccacaaat taacgaaaaa gaagaattat caagaaaaga ttttgatgaa tggctttcta  112980
aattagaaat ctattcagga aataaaagaa ttgaaccgca ctggtatcaa aaagatgcag  113040
tgttcgaagg attagttaat cgtcgtagaa ttcttaatct tccaacatct gcaggtaaat  113100
ctttaattca agctttgctt gcgcgatatt atttggaaaa ttatgaaggt aaaattctta  113160
tcattgttcc aacaactgct ctgacaactc agatggctga tgacttcgtc gactatcgtt  113220
tattcagcca tgcaatgata aagaaaattg gtggcggagc atcaaaagat gataaatata  113280
aaaatgatgc accagtcgtt gttggtacat ggcaaactgt agtaaaacaa ccgaaagaat  113340
ggttctcaca gtttggaatg atgatgaatg atgaatgcca tcttgctaca ggaaaaagta  113400
tttcatctat catatcaggt ttaaataact gcatgttcaa attcggtttg tctggttcat  113460
tacgtgatgg caaagccaat atcatgcagt atgttggaat gtttggtgaa atatttaaac  113520
cagtaacgac ttctaaatta atggaagatg gacaagtaac tgagctaaaa attaatagta  113580
tttttcttcg ctatcccgat gagttcacta ctaaattaaa gggaaaaact taccaagaag  113640
aaataaaaat tattactggg cttagtaaaa gaaataaatg gatcgctaaa ttagctatta  113700
agcttgcgca aaaagatgaa aacgcttttg tcatgtttaa acatgtatcg catggtaaag  113760
ctattttcga tttaattaaa aatgaatacg ataaagttta ttacgtatca ggggaagttg  113820
ataccgaaac ccgcaatata atgaaaacct tagctgaaaa tggtaaagga ataattatag  113880
tagctagtta tggtgtattt tctactggta tttcagttaa aaatctgcat cacgttgttt  113940
tagcgcacgg tgttaaatca aaaatcattg tattacaaac aatcggtcgt gtattacgta  114000
agcatggttc taagacaata gcaacagtct gggacctcat agatagcgca ggcgtcaagc  114060
caaaatctgc taatacgaaa aagaaatatg ttcatttgaa ctatctttta aaacacggca  114120
ttgatcgtat tcagcgctac gcagatgaaa aatttaatta cgtaatgaaa acagttaatt  114180
taataagctt cggccctttg gagaaaaaga tgttactaga atttaaacaa tttctttatg  114240
aagcttctat tgatgaattt atgggtaaaa ttgcctcttg tcaaacatta gaaggtttag  114300
aagaacttga agcttattat aagaaaagag tcaaagaaac tgaattaaaa gatactgatg  114360
acatctctgt gagagatgct ttggcaggaa aaagagctga attagaagat tcagacgatg  114420
aagtagaaga aagcttttaa attaaaaaag gcccaaccaa aaaggaaggg ccaaaactat  114480
agactaaagg tcacactata gcaaaagttg tgtttcattt aattgttctt ccgaactttc  114540
tgaaactggt agttctttaa tgtaattata gcaaggccca ggatgtacag gacctttgtc  114600
tgtttcaaca accaatgcag aatcgattgg agttttacag acaacacaaa tcttatctga  114660
catgattgtc tcctctgaat tatatctatt tatacaactc tcatatgcat atcaatgccc  114720
atatctttag aataaaaata ttcatcaaga tatccggcaa attttccttt aatataaagg  114780
acatcttcac cacacgggtg gtcggccagg atacgaatat cctgacgctt aagattatgc  114840
tttttcatta agaattgaat ttccgtttca aattcttctt cataattaaa agcatcatca  114900
atgctatatc tcattatttt ccagcctcaa atgctcgcat gtcttgaata tgcttaatag  114960
caaatccacg tgatttaata gcatcaagag ctccgctaca gaaatctaat aaaatccccc  115020
aatactgcaa cgaggtatca acctttaaaa catccttatc cgctgataga actgtcttca  115080
tttctgattt ctcgtaacga tccatactaa attcatcacc atctcctcgt cccgagtagt  115140
agtctaatct agctttaaga gcaacttttt tctgtgcttc aattctaagc atttcctttt  115200
taatacttga atgcttatta agccatttac tatataacat cacattatta gctgcttcat  115260
actgtaattt agtcgaatct ataaacacat ctttcttcaa ttcttcttga agatcttcta  115320
atctcatatt gttctctatt caattgttat tggttgttat tggatggact tagattcatt  115380
ataccacgtt ttaacgtgaa gcattatact ctattactgg aagccagctg cagttttatc  115440
tgctcaatat catcaggatt atcgatgacc gaaaagcgta tttctactat cagagtataa  115500
tcgtcataaa cgggtatcac attaactgct aatttatcaa tacgtggctc atagtttctt  115560
actgcgcttt cgatattgcg ttcaaccgtg tcagcagtaa gaggagtcat attttcaaaa  115620
agctggtctg ataaatcaca tccaaattca gggtcaaacg gtcttgaacc ttttcttgtt  115680
gtaataattc ccaaaagact gtttttaatt gaccttaatc caagcgatct ggaaacgtct  115740
```

```
ttgttccaat ccattttcat ttccgggtca atatcagaat aaagcttatt aatatttgcc  115800
attatagtaa ctcaaagaac tctttgaggc ctcttattac gtgagcatgg gtttttccac  115860
actctggaca cttaattgga acagccaaat aaacggtagg ctttaaaagc atatctttta  115920
tagctacaat atctgactct gtgatgatag aatataaatc ttctagttcc ttttcattta  115980
agtcttcaac tggaatgctt tccccgttag catgaatcgt ttctatacat gatactatca  116040
tgtgggctat atttttatca tcaaaaattt tagggtatcg gaatttaatt ttaatgtcac  116100
ctagtgtata ccagaggtct tctggtgcat ctatttgtgt atgtaataga tttatatggg  116160
ttggtatttc agttccacag gtgcacttcc aggagtttc gtgattaact tcaccgagag  116220
aatgtgccca taaatgaatc aacaatagtt ctgattcttg gcggtttaaa tcttttgcat  116280
ttgtgcagtc tttgattagc tttttaacaa ttacttctac ggaaccatta tttttggcag  116340
taataagttc tagatattct ttaagcgtga atgcgcgaca attgattatt ttagaaccaa  116400
ctctcacatc aaatttgtat tcatacatat ttagctcctt tatttatcat atttataaat  116460
agaataaaag gagcatctat ggcaaacatt attcgttgta aattaccaga tggtgttcat  116520
cgttttaaac catttacggt agaagattat cgagattttt tgttagttcg aaacgatata  116580
gaacatcggt caccacaaga acaaaagcaa ataattactg atttaattga tgattatttt  116640
ggagactatc cgaagacttg gcaaccattt atatttttgc aggtatttgt agggtcaata  116700
ggtaaaacta aaagtacggt cacatttata tgtccaaaat gtaaaaaaga aaagacagtt  116760
ccatttgaaa tatatcaaaa agaattaaag gaccttgttt ttgatgtagc taatgttaaa  116820
attaaattaa agtttccttc tgagttttat gaaaataaag caaagatgat tactgaaaat  116880
attcattctg ttcaagtaga tgaaatatgg tatgattgga aggaaattag cgagtccagt  116940
caaatagaac tagttgacgc catcgagata gaaacattag aaaaaattct cgatgcaatg  117000
aatcctatta atttaactct acacatgtca tgctgtaata agtacattaa aaaatacact  117060
gatatagtag acgtgtttaa gctattagtt aacccagatg agatatttac tttttatcaa  117120
attaatcaca cactcgtaaa aagtaattat agcttaaatt caataagtaa aatgattcct  117180
gccgagcgcg gattcgtatt aaaactgatt gagaaggata aacaataatg agtatgttgc  117240
aacgccccgg atatccaaat ctcagcgtta aattatttga tagctacgac gcttggagta  117300
ataatagatt tgttgaatta gctgctacta ttaccacatt aactatgcgg gattctcttt  117360
atggccgaaa tgaaggaatg ctgcagtttt atgattctaa aaacatccat acaaaaatgg  117420
atggaaatga aataattcag atttctgtag ctaatgcaaa tgatattaat aatgttaaaa  117480
cacgaattta tggatgtaag catttttccg tgtcagtaga ttcaaaaggt gataacatca  117540
ttgctattga attgggaact attcattcta tagaaaatct taaatttggt agaccatttt  117600
tccctgatgc aggtgaatct ataaaagaaa tgcttggtgt catttatcag gatcgcacat  117660
tattaactcc agcaataaat gctataaatg cttatgttcc tgatattcca tggactagca  117720
catttgaaaa ctatttgtca tatgtaagag aagttgctct agctgtagga agcgacaaat  117780
ttgtatttgt atggcaagac atcatgggcg ttaacatgat ggactatgat atgatgataa  117840
atcaagaacc atatccaatg attgtcggtg agccatcttt aataggtcaa ttcatccaag  117900
aattaaaata tccattagca tatgatttcg tttggttgac taaatcgaat cctcacaaac  117960
gtgacccaat gaaaaacgct actatctatg cgcattcatt tttagattct tcaataccaa  118020
tgattactac aggaaagggt gaaaactcta ttgtggtgtc aaggtcaggt gcttattctg  118080
aaatgactta taggaatgga tatgaagaag ctattcgtct tcaaactatg gcacaatatg  118140
acggctatgc taaatgttct actatcggta attttaactt gactcctggt gttaaaatta  118200
tttttaatga tagtaaaaac caatttaaaa cagaatttta cgttgatgaa gttatccatg  118260
aattatccaa taataattca gtaactcatc tatatatgtt cactaatgca acgaaactgg  118320
aaacaataga cccagttaag gttaaaaatg aatttaaatc tgatactacc actgaagaaa  118380
gtagttcttc caataagcaa taaagaagtt tctattccta aaatgggtct taaacattat  118440
aacattttaa aagatgttaa aggtcctgat gaaaatttaa aacttctcat tgattctatt  118500
tgtccgaatt tatcaccggc agaagttgat ttcgtttcta ttcatttatt ggaatttaat  118560
ggaaagatta aatctcgtaa agaaatagat ggttatactt atgacattaa tgatgtttat  118620
gtatgccaaa gattggaatt tcaataccaa ggaaatacat tttattttag acctcctgga  118680
aaatttgaac aatttttaac ggtgagcgat atgttatcta aatgcttact tagggtcaac  118740
gatgaagtta aagaaattaa ttttcttgag atgccagcat tcgttttaaa atgggcaaat  118800
gatattttta caactttagc aattcctggc cctaatggtc caataactgg aattggcaat  118860
attattggat tatttgaatg aaaaagccac aagaaatgca aacgatgcgt agaaaagtta  118920
tttcagataa taaaccaaca caggaagcgg ctaaatccgc ttctaatact ttatctgggc  118980
ttaatgacat atctacgaaa ttggatgatg ctcaagctgc ttctgaatta atagctcaaa  119040
ctgtcgaaga aaaatcgaat gaaataattg gagcaattga caatgtagaa agcgcagtga  119100
gtgatacatc tgccggttct gagttaattg ctgaaactgt cgaaattggc aacaatatta  119160
ataaagaaat cggtgaatcg ctcggaagca aattagataa attaacaagt ttactagagc  119220
aaaaaatcca gacagctgga attcaacaga ctggaactag tttagctacg gttgaaagcg  119280
ctattcctgt taaagtcgtt gaggatgata ctgctgaatc tgtgggtcct ttattaccag  119340
ctcctgaagc agttaataat gatcctgacg ctgatttttt ccctacccct cagccagttg  119400
agccaaagca agaatcacca gaagaaaaac agaaaaaaga agcatttaac ttaaaattat  119460
ctcaagcttt agataaatta acgaagactg ttgattttgg atttaaaaaa tccatttcaa  119520
ttactgataa aatatcaagc atgctattta agtacaccgt cagtgctgct attgaagctg  119580
ctaaaatgac tgcaatgata ttggctgttg ttgttggaat agaccttttg atgattcact  119640
ttaaatactg gtcagataaa ttttcaaaag cctgggattt gtttagtaca gactttacca  119700
aattctctag cgaaaccgga acttggggtc ctttattaca gagcatcttt gattctattg  119760
ataaaattaa acaactttgg gaagcgggag attggggtgg attgacagta gctattgttg  119820
aagggcttgg aaaggttctt tttaatttag gtgaacttat tcaattaggt atggctaaat  119880
tatctgcagc aattcttcga gtcattcctg gtatgaagga tactgctgat gaagtagaag  119940
gaagagcatt agaaaatttc caaaattcta ctggagcatc tctcaataaa gaagaccaag  120000
aaaaagtagc aaattatcaa gataaacgaa tgaatggaga ccttggccca atagcagaag  120060
gactagacaa aatctctaac tggaaaactc gtgcatctaa ctggattcgt ggtgtagata  120120
ataaagaagc gctgactacc gacgaagagc gtgcggcaga agaagaaaaa ttaaagcaac  120180
tttcaccgga agaaagaaaa aatgctttaa tgaaggctaa tgaagctcgt gctgcgatga  120240
ttcgttttga aaaatatgcc gattcagctg atatgagtaa agactcaacg gttaaatcag  120300
ttgaagctgc ctatgaagac cttaaaaaac ggatggatga cccggattta aataattcac  120360
cggcagttaa aaaagaactt gctgctagat tttctaaaat tgatgctact tatcaagagc  120420
tcaagaaaaa tcagcctaat gccaaacctg aaacttctgc taaatcacca gaagcgaaac  120480
```

-continued

```
aagtccaggt gattgaaaag aacaaagcac agcaagctcc tgttcaacaa gcatctcctt  120540
cgatcaataa tactaataat gttattaaga aaaatactgt cgttcataat atgacacctg  120600
taacgagcac gactgctcct ggtgtatttg atgcgactgg agttaattaa ggaataatat  120660
ggcaattgtt aaagaaataa ctgctgattt aattaaaaag tccggtgaga aaatttcagc  120720
cggacagagt actaaatcag aagtaggaac taaaacatac acagcccagt ttccaactgg  120780
gcgtgctagt ggtaatgaca ctacagagga cttccaggta acagatctat ataagaatgg  120840
attattattt actgcataca atatgtcatc tagggattct ggaagtctta gatcgatgag  120900
atctaactac tcttcttcat cttcgagtat tttacgtaca gctagaaaca ctattagtag  120960
tacagtatca aaactatcaa atggattaat atcaaataat aattcaggaa caataagtaa  121020
atctcctatc gcaaacattc ttttaccgag atctaaatct gatgttgata catcatcaca  121080
tagatttaat gatgttcaag aaagccttat cagtagaggc ggaggtactg ctactggtgt  121140
gctaagtaat attgcttcaa ccgcagtatt tggggcactg gaaagtataa cacaaggtat  121200
aatggctgat aataatgaac agatttatac gacagccaga agtatgtatg gtggtgctga  121260
aaatagaact aaagtgttta catgggattt gactccacgt tcaacagaag atttaatggc  121320
tattattaat atctatcaat attttaacta tttttcttat ggtgaaacgg gtaaatctca  121380
atatgctgct gaaataaagg ggtatttaga tgattggtat cgttctacgt taattgaacc  121440
tttatctccg gaagacgcag ctaaaaataa aacactattt gagaaaatga catcgagttt  121500
aactaacgtt ctagtagttt caaacccgac agtttggatg gtgaaaaact ttggcgcaac  121560
atctaagttt gatggaaaaa cggaaatatt tggtccatgt caaatacaga gcattagatt  121620
tgataaaaca cctaatggta actttaacgg attagctatt gctccaaacc tccctagtac  121680
atttactctc gagattacta tgagagaaat tatcacgtta aaccgtgctt ctttatatgc  121740
ggggactttt taatgtattc tttagaggaa tttaataatc aagcaataaa cgcagatttc  121800
caacgtaata atatgtttag ctgcgttttt gcgacaactc catcaactaa aagctcttcg  121860
ttgataagtt caattagcaa cttttcttat aataacttgg gcctaaattc agattggtta  121920
ggattaactc aaggtgatat taatcaggga attaccacgc taattacagc tggcacacaa  121980
aaactgataa gaaaatcagg agtcagtaaa tatcttattg gtgccatgag tcaacgtaca  122040
gttcaaagtt tattaggctc atttacagtt ggtacatatt taattgactt ctttaacatg  122100
gcatataact catctggatt gatgatatac tctgtaaaaa tgccagagaa tagattatcc  122160
tatgaaactg actggaacta taattctcct aatattcgta taaccggaag agaattagac  122220
cctttggtta tttcatttag aatggattca gaagcttgta actatcgtgc aatgcaagac  122280
tgggttaact ccgttcaaga cccagtaact ggactgcgtg ctttgccaca agatgtcgag  122340
gcagatattc aggttaatct tcattctcgc aatggattac ctcatactgc ggtgatgttc  122400
acgatgcatt caatatcagt gagcgctcct gagttatcat atgatggaga taaccaaata  122460
actacatttg atgttacttt tgcgtacaga gtgatgcagg ctggagcagt tgataggcaa  122520
cgtgcgcttg aatggcttga atctgctgct ataaatggta ttcaaagcgt tctcggaaat  122580
agtggaggtg ttactggact atctaattcg ctttcacgac ttagtagatt agggggaact  122640
gcaggaagca tttcaaacat taatactatg acaggaattg tcaattcgca gagtaaaata  122700
ttaggagcaa tataacaatg gggaccgaaa ggtccatatt tttatttacg gaatgaaatg  122760
aaagcagcaa ctgaagcaac taaactgtct tcaatataaa cttcaatttt tacaggagct  122820
tctgactcaa atttacctgt tactacaccc tgaaaaatac tttcagtctg ttctggcttt  122880
gaaaaatttt cagaaggaaa aattccgaac tttttatctg ttccaaaaat tttgataaat  122940
tcatcgtaaa ccgcttcgtt aaaagcatta tcagcaggaa taacgccttc aactacaagt  123000
tcttgaccta aaaagcgtaa agaagatttc attttgtgtt cctcatgtta tgttagtaag  123060
actactataa cacaacacga gggacttgta aactacattt tgaacttttt agtacgcgta  123120
ataggcatgc gtcgatttta tactgtttca ttgtttgaag agcagtatca aaaacagcat  123180
taatgacacc aattggattt ccacccaagt ttttaagctt aactaatgat agtttctcat  123240
taacacctat cattacgata tgcatcattt tatcgcctgg tttaacgttt tatttgtatc  123300
accgccagag gtgtatgtac aaaatctaaa tccaggaagt acactttctt caccggcttg  123360
aatagcaaaa atttgtggta ttttatgctt aggatttaat gtaacaaccg gcgccgaagc  123420
gccgtcaaat aattctgtaa taagttccat gatttatcct tgaacgaact tgtaaggcat  123480
gtttgcaata tctatgcaag acgcaataat tccaagagat gattctactt tctgtttaac  123540
atttgatgaa acaaatgatg caaagtcaac tctatcttct atatcacctg tcattgtaac  123600
caattcacca gtttccatta aatggtctcc gtcatagatt accgattcgg tgagttcttc  123660
tgtggtcata acttcagctt gaataagctt gttgttagtt ttaactgttc catcattgta  123720
agatgcatcg gttattttat taactttgac cattaatcca cgtggcaaaa tgacttccat  123780
ttcatttgaa ggcgctaaac ttccaccggg taaaacaaca ttgaccttat cagccccagt  123840
aataacccat ccaattccaa ctaaattatc gctagaattt acaagtcctt catcagtttt  123900
atcaatagaa acgcttaaac gcttttcgtc tggtaaaaca cctatagatg aatcagtcat  123960
ccaagtacca aaaatatttg gatataatga tgttgacaca aagtttctaa aataaaaaac  124020
tcgatttttt accattgctt cgtatattga aggtaacatt cgttgtgaac gatacaaagt  124080
aataccttt ggtaatcgtt caccattttt aaaggctgaa tctaaattat caatagcttt  124140
ttctatgtca gatgctgtca aaatacttgt acgctcatct ggattatata atcccaaaag  124200
agcattattt atgtctacat atcctgaacc tacgtattca cgaattccgc gtttttgcgc  124260
tggtgtgtat ttagatgaat ctttattttc gactatagga tgtaatgacc atccagcggt  124320
aagagcatat ccacgtaatt ctcttcgaat aatctttgtt tttattgcat tccaagaatt  124380
ttgtactaac tcatttgcag catcttggtt taaatgcgaa tgtttgttaa tatttctttc  124440
aaaccaagca cccttatatt tttctaaagt atcatcgacg atagaagcaa tagtttctaa  124500
ggtttttatt gaagtaatag attcttttcg taatcttttct aaagctttat tttttatttc  124560
tgcgttaata atggattctt tatcttcagg aattatagaa gcttctctga atgccatccc  124620
agctgtaaca ctgctaagag cattctctag tgcaaatcct gaagtagaaa ttaccgttaa  124680
ttcattagaa tcagaaatta aaggcgcgtc cgctggttta tttaattcgg ccgctgaagc  124740
ctcaaatttt tgaaacattg gtgtttcaaa tctagaagat tccaatgact gactttgcgc  124800
aattgctcta cgggaaattt taactttaac gattacagct tggtcagaac gtttatcatt  124860
ttcttgcgca atagatgctg caattgcctc atttttagtt acttgagccc cagtatcttt  124920
attgatataa acatcaccga ccttcgattc aactttagta aagagctcgg tactaatttc  124980
cggaactcct ggaatgtctt ctagtgatac atttttgcga tgtataagaa tatatgcata  125040
ctttttatcg taatcccaga gttccttaag aaggacgtat ctaccacctg aacgactacg  125100
gataagtcta tcagcaataa cttgaatttg tcgagcttgg ccagcagttt tagacttaag  125160
aatacggagc atacaggcat caattttata ctggcgcatt gtttgcattg caacagtaaa  125220
```

aactgaattg atataattaa ttgggcttgg accaagacct tttaatttag caattgaacc 125280
tttagcagtt aatgtaaaag gaacaatatg catcatttta tcgcccatct ttaaatcacg 125340
attagtatca cctccagatg tataggtaca taaacgaaag cctggttgtt caattgcatc 125400
atcaacatga actgaaaaaa tttgcggtat tttcttcttt ggatataagt ttgtaattgg 125460
aagagtagta tcttcgtcaa ataattctgt aataagttcc atcatatcct ctctagtgtt 125520
tattctattc tatttataaa attaaaggcc cgaaggcctt taataatcta ttggtaagag 125580
agtacgatat atttcaaact ttggaccttt ttcataagca tcaaatgttt ctgtgaattt 125640
attataagca tatgcatcta taaattcaat catgatttgt gatacagaag tagaaacatc 125700
tccaccttct ttttgagcca cgacaattgt ttctaagtaa gctttcatag accagttacc 125760
tcatgaaaat caccaaatac atcttcgaat gtattagctt tagttttatc ttcacgtaaa 125820
cgaatcgcaa tcggaagaaa taatttaacg taatcagtgc ggccatcaga ttttaaccaa 125880
ccgttgcatt cgcactctag aatttttcca atataataat tttggttttc cataatgcga 125940
gtacggtcaa gttcatgcga ttttacaccg gctttatctt ttaagcctga accagcattt 126000
accttaattt ttccacactc tgactcaaga ataaatccac ccgctttagt agggtcttta 126060
cggtgaggat aaattcctac aatttttaaa tcaacatcaa ttacttcttt aaatttataa 126120
agattttttg aacgagcatt ttcccataat ccatcgatat ttttgagaat aataccttca 126180
agaccttggt caatatactt tttataaatt accttagctt catctaggtt atttactacc 126240
tggttttcaa ttaaaattac tttatcatat ccagatgtca tttgttctag tttagaaaaa 126300
cgtacatcat atttcaaacg aaatgcagga agactgtata tttctaccaa cgggacataa 126360
tcccagacct gaaacttcat gcattgtgct tctttttcag aaatggttcc ctttaaagat 126420
ttattggcga ttccattaga agcagtacgt gattcagcta cttcggcgaa ttctttagct 126480
ttactgtttt caggataagc atcaaaaaga aaatctaggc cttctggctc ctttttaact 126540
tgctcatggt ataccaattc gccatcaatc aacacacctt ctggatgaat ctggcgggct 126600
tcagcggtca ttttaattaa ctcttcctta agaagatcta atcctagata ttcattacca 126660
gctcgtgata aaagacgaac atcatctaat tcatcacctc taacttcagc aaaacaccga 126720
gctccatcag cttttaactg agcaaaggct ggaaatttga tattcttatt aatgcctttt 126780
tcatcataag aacttgcgag catttgaggt tgttcaggaa ttaaacctgg ccaaactttg 126840
tttgcaatag atactgaagc accacattca aggtctcgca tcatcactcg acgcaaaact 126900
tcaacatcat ctttttttacc atcggtgata tatccagtta attcctcaat tgctgcattt 126960
ccagtcaatt tccgagtagc taatgtgaat tcaatgaagt caagcatatc ggtaagagtc 127020
aacattccaa aactctgggt agcaatacca ggtttaggcc atttcttgat ataatactgt 127080
aacccacgag aataagtcag acgatatact cgtttaagca attcattatc tttattcttt 127140
tcaagaattg cttgcttctg tttagttgaa ccaatagatg ctatttcgtt cagaatttta 127200
agaatcattg ttcatccttt agagtttggt ttacagctct attataaatc aattcatcat 127260
taagctcagt caaagacctg tggtacgtgg ttctaacttt atttccttgc atccagtgct 127320
tgatataaat gaaaccttgc tctacacatt ttttaaaaat tcgttcgtct ttttgagctc 127380
ggaattctgg attgcatcta aaaaattgat ttacgtgacc gtaatcacgt gtagtattac 127440
cttcattttc ataaatagtg tgaacaacaa acattagaat gctccttgga aaatattatc 127500
accacaagta ggtctattat acaaatactc tataccgccg ggcttaatat agttccatgt 127560
ctgaaacgga tgcgtctgat atggatgata tggattataa ggattaaatc caggagttct 127620
ccaggtagtg ttccaaggaa aagaatcgtt tttaatcatc ttttcaatta catcttttat 127680
agctttttca ctatcaaaac tttctttatt ttcctttggt gaaaaaagct tattctctac 127740
atcgttccat gtataaactc gctgagcagt ttttggaata ttgtcacgct ctcctcgagc 127800
catccaatac acaggaacac gtaatatttc actcgcgtga tcgcagtggt gagcgagatc 127860
gtcaatataa caaattacgt tatatttctc ttttgctttt ttgaacaact cttcttttga 127920
agaatcatga ctacacatca gtacttctga gaaagcacca ggaaaaagag cattcaaatt 127980
aaattgacga tttaatagag cgtcaataga atcacccaat gctgtaacag caacaaaatt 128040
ataatcttct tttaatttgt taattacaca cagagcatct ttatatggag acaagtaacg 128100
aataaaaatcc gaacgattgt atttttcaat taacttgacg ccaagttctt catcacagtt 128160
aaagagttta ccaggagaaa taaatttctc atcttggatc atttttaaaa tatgttctaa 128220
cggaagatta tatttctgag caaaataagg aaggcctgat tgccagctta aacatactcc 128280
atcaatatca gttaaaatag taggcttcat agagagtctc ttaataggtt taacacatca 128340
ataaattcag cttcggttag tattgtatca tcttttgtta gaccactagc aatgctgtgc 128400
ttcaaaactt ttcctttcga ggcttgtaat gcatcacgaa agcccttgtt ttgaatcgct 128460
gcttcaaaat atgcatttgt gtataattct ttccacgccg gggagtatct tgaaaacgga 128520
actccaagcc aaaagagggt cccacggtcc tgagctctag cataagacct tccagcttgt 128580
tgggcggcaa gcccggataa cccaaatata cgacgttgtt gttcaacatt tttcacctta 128640
cacccttgga ggaatccttc aagacctcca aattgaatac catccataac gaaaggccat 128700
tgggcgaaat tacttaatgc acatgatggc cacctaaaat tgcttctaat ctctaactca 128760
gacattttca atgcttataa tttcaacatc agcccaatga ccatagcaag gaagacgaaa 128820
ttcaactggc cagttagggt ccctttctaa tataatagac tcaacttgtg gttcttcgtg 128880
ttcatcagta tacggatttt tatctgttac tttatatgtg accttaatgt actgaattcc 128940
aaaaatctta ttaattatat tcatactaat tcctttaatc cgtagatagg agataattca 129000
tcacccatac gaaggtcttc atttccatct acccaggaaa caatataagc ctcttttatt 129060
tgaataccac tccatttaaa tggaggtaga accttagaaa ttaatccagg tataccaact 129120
ccctttaatt caacagtttg acctaaaaag aatttcatta gaacctcatc tgaaaaccgt 129180
gcgatttaac attaccgccg ccaatatcag aaatgttaat ttcacgcgca attgaagggt 129240
caatgtcaat ttcacgattg agtttagtga tagctaaagt atcacgccca tttacagtac 129300
ggaactctaa aggacaaacc acatcaacgt agtttttaat cgattcgcta gtaagttgca 129360
aatgtgcagg aaggtcttta ggtgcctttg agaaaaccac ttcacagaaa tttttgcggg 129420
tatcaaaata agtagtcata aacataatat tttcctcagt aaggggctga agcccctcat 129480
tttattttaa atatcaaatt cattaagaac tacatcaaag attgcttcaa gatgctcagg 129540
tttagctctg ttactcagaa tatgacgaat ccaagtttta actaagagtt tacgattagc 129600
accattccag caaggatgag tccctaaatc gcgttggcgg aaatcatcat ccagagcgat 129660
tttgaagttg gaacctttca tcgtgattga aaccgtgata ccgttttcaa atcgcatata 129720
aacgtagtta ggagtcatat actgttcaat ttcgcatact gatccatttt gatgtttcca 129780
gaggcaaata gtatcaatag aacctgcaat accattagaa acatatttac gttcaaagtt 129840
aatgtagttc atttttattc tccgagatgt ttaattgcgg tacaggtata taatatcata 129900
tcctgtacca aagtaaacaa ttattttact actttccaat gctgcatgtc aagtttacca 129960

-continued acttttttca tcttctcaat taagcgttct gcacgttggc gagctgtaac ataatgccat 130020
tcgcctaatt cattttgttc aatttttcca acgattactg tattcaattc ataaatccaa 130080
ccagtaaaga aattatgaac ttgaattgta aaggtgaaat ctgttcccat accttctgtt 130140
gtttctactt caataatatc accttcaact gccattaaga accacatagt ttcatcatat 130200
ttaccattga agcatttagt tttaactgca gcgttcagat taatcgtttt cattttattc 130260
tcctttgttt gtgtaagata atactatcac aaaggaacta tactgtaaac aactttgtgc 130320
aatctttgga aaataaaaaa ggactcccga aggagtcctc aacttatgct ttctgcttac 130380
caaaacgaga agcatcatct cgaagaaccg cacgtgctcg gcgcatgatc ttctcaacag 130440
tttgattgat acgagagttc gacccacgct tgtagccagc gcgtttagaa tcaccaactt 130500
tcttttcaac tgctttcttt gctttagctt gttttgccat tataaattct cttttaaatg 130560
aaaatgcagg acttattggc attgcctgcg caagccctca aggggaacat aggtttttgg 130620
atatttaacg accaggataa ccataaaccc gtcatcattc acattcaaga ggtacaccgt 130680
aaaactgtcg gggtcttaaa actataatga ttcgcaaatc attaatcaga cagttcgacg 130740
gctcctcgat ttagctcaca ctaaggcagt gaatctccaa taaattactt cagtgttacc 130800
acaaagtgac gaactgcttt tcgtgcagca gaagccagag gcttagcata tttaagttca 130860
tctttttcct gaagctcagc agctaatgca gtttgagcag gattcagatg tttgaaataa 130920
cgcaggattt caagagcttc ggcttcaaca tcaatagatg cgccatagtt ttcgtgacca 130980
ttattccatg cgtttcgttg cagttcaaga gcgtgttgta attgtttaat catttaaaaa 131040
ttctcgttag agattaaaac tcggtagtca cgttcttctg aatttcatct tctttcgaca 131100
gatctctcag ttgtagacta ccacatagaa ttgttcggtt aacttattat tccgacaccc 131160
aattcatatt attatttata tcacttataa agacacggaa tagctttata gtgacaggta 131220
acgaattttt gtttaatttc ttttggctgc ttaagaccca gagctacaaa aggatgcgga 131280
acatttcgaa tttgaccaac tggaagagaa gtcaaatcac caacttcgca gaaaccttca 131340
ggaacatcag gaccgacaga gtgaactaca cacagttcag gaacttcacc ttgaacacgt 131400
ttaccgataa taagtcctga ttctgtaact tcttcatcac cggcttgtgc aggttcagaa 131460
actaaaataa catattcacc gacagcacga attggtagct gttgtacttc agacatcgtt 131520
tttccttttt gttaacagat gaattaataa taacaaatag ttcttaaagc atttatttac 131580
caataaattg aagcaaatgc tcaactttca taccattaac ggaaatcaat ttgtcaatag 131640
aaaaacctcg ccacgcacca agctcaacat caaatactgg aatcatgtca gtagattctt 131700
tccgagtaga ttcagtcaat ttgccagttt gcatggttgg cataaagtct gcatcacgag 131760
tacctttcat agtacgaata gtaccatcag acttttcaaa aactacgttt gaaacaccca 131820
tggacaattt agttttcaaa atttcacgaa ttgctacttt ctgctcagtt gtcagtttca 131880
tttatttacc tattacagtt ttaatatgag ttgttccacg ttctttaagg gtggaaagta 131940
atttttggca tttttctaaa tcagatttcc aactatatgg tctatcaata caaacccaat 132000
ttgtcttata atactgtttc catttagaga aaaaatattt cttatactct acagcaaatg 132060
agatgttctc gttagaataa gaactaattg ctgtgagttt taccaaacga aatttcatta 132120
ttcaccacag aattcgttga tattttccca gtttaactta ttcaagtttt tcttaggaac 132180
attaaacact tcaatacctg catttcgcag aatatcatcc caaccgggtt tatttttgtc 132240
gtatgtttca caataaacca gctttttaat accagattga gctatcgctt ttgcgcaatc 132300
tggacaagga gaaagtgtta catacatagt agcaccttca atagaagaac catttcgtgc 132360
agcaaacaaa attgcattta gttcagcatg aatttcattt ttagatgacc attccgagtg 132420
agcactacga tgttctttcg ccaaaacaaa acgatcagtt gaaccaaatg atacgcattc 132480
aggcttatga ccttgaatga tagcatgttt aggcttattc aacaaccatc cttgctcagc 132540
agcataatca caacagttca cacccccctgc gggtgaacca ttatacccag tagaaataat 132600
acgtccattc ttttcaatta ctgctcctac cttccaggag caacattttg attcctgcga 132660
tactaaatat gcaatttgaa gtactgtact cgctttcatt tcataatcac cagataagca 132720
gatttagcag tttcaacacg ataaatttcg tgacgaagtt tagttatact tttaataaca 132780
gaactaatta tattctgccc atctttaaag cggtttttct tatcaataaa aactgcgcca 132840
gtcatctttt tgtgaagctc aactggatac ttcgtcacaa taatagcatc atacacagaa 132900
ggatgaatac tattcaccag agtatcattc attaaagtta ttctaatgaa ctgtgctgtt 132960
tcagaatcaa gcgctctatg atcgccagta tcattttcaa gacaattatc aattatatca 133020
gttaaattca tcatagtacg ccatacaccc tttgtgcttc aactaatcca tcaaaatcca 133080
gtttaagatg cgatatttga tcgccatcac ctggattcac aattactaat actgaacgag 133140
gagtttcggt aataacacga accgatgttt caggaaatcg ttcagaaacc ttatttacta 133200
attcctgcgc aaatagttta actttttctt ggaattcctt taacagtaat cggtttttca 133260
cttagcaaca ttttgtttc ctcatttgtt ttggtagagc tataatatca caactctacc 133320
gtaaagtaaa ccattaaatc gctttgaatt ccgcagtttg agattcaaag cgaatatcgc 133380
ctttgataac aagctcagca tcaagaccaa atacgacaat gatatgcgcg gaacctggat 133440
acagtgtaat ggcaatagaa tccacctggt ctggaagcaa agtgttcaat acatgagtca 133500
cttgagcatg gattcgaagc tcagctgcgt tatcaagttt ttcaaacata ttattagcga 133560
taatttggct aaacactact tctacgattt tagagtaagt cggaaacata tttacctcac 133620
ataattttct tcaagccaat caataacatc caacgcatta tcaaaagttg aaccatctac 133680
tctgtcttct gtttcataat caagaacatc taggcctact cttccgtcaa caataggcca 133740
tagacaaaat agatatttct tttctttttc aattttatca caaagacgat aaatcttttc 133800
taggttattc ataagtttc catggtaaag gcagtttagt tttctttact actagttcaa 133860
catcgggatt cttttctctt aatttaagac attcctccca tgctctattt tcactagtaa 133920
atacacaaaa ttgcccatta ctagtaccaa ctaaaccgct atttacaata acaatagccc 133980
aagtttcatg gtgccaagcc attaaaaatc tcccgaagcg acttgccagc attcaacacc 134040
gatacgacgc cacatttcaa ctacttgagt tcggtcatca atagctaatt tcacgtcaaa 134100
atgcggtgca atgtgtttcc agaaaatttc ttctttaact acatcgtctt tacgggtatc 134160
gccttgttcg cgctgacatt gcataactaa tggaacgcca gcaatgtcct caacccattt 134220
acgggtcata cgataatatt tcgttgggtc ttctttagtt ccactttcac gacctgaaac 134280
gactacgatt tgataaccca taagagcata catcttagac agttcaacaa ccataggatt 134340
gataacatcg gtatcgcatt tttcaaggtc ataaggacca cgaccattca ttttagctag 134400
tgtaccatca acatcaaaaa taactgcttt tggtttacca ggagtcccat tatatactgg 134460
aagaccgaga tactctcgca tgcttttata cattgaacgt aaaacatcaa ttggtactgc 134520
tttagttccg cgttttgagt tacgtttaac caattcagtc caaggaacat caaacacttt 134580
atgttcaact ttccagccgt attctttggc aaaagtttcc catgctaggc gacgttcagg 134640
attcaggtta gtatctgaaa tgattactcc cttaacagaa tcgccaccgt acagaatact 134700

```
tttagctgta tcaaactgca taccagttac gataccttct ttctttttgg tatacttgta  134760
ctcatcgcgt tcttcatgcg ccataataga ttggcgatag tcatcacgat tgatattata  134820
aaacccggga ttcttagcaa taaattcacg agcccaagta ctcttaccag aaccaggaca  134880
gccaatagtc aaaataatct ttttcattta ttttttctca actaatgatt gaatataatc  134940
atgtaggtct ttagatgctt taccccactt attttgatat tcatttttga gattagcacg  135000
tgattgagct aataaaacat cattagttgg aggtaaagat tctaaccgct gaatctggcg  135060
tccataaatc attgcagcca tctcggattc ataaatcaat cctttgagat gttcaaattg  135120
atgccatgaa atcatttaca tttatcctct tttagctctt gacgataata acatrtcata  135180
gttttctggt catgtacata tcgttttaca tcattaagcc aaatacgaaa ttcctgagaa  135240
tcttcaaatg gcataccgac ccaggcttta ccatcaataa ctttaacttg ccaagatagt  135300
ttagcttcat catatgactt tatttgcaca ggccaattag gatgaactgt ttctttcttt  135360
acttctagag gctttgtcga acaaccaact agaagaccaa tagataatat tactgctgat  135420
agtttaatca tttagaaagg tcctggatgt cttctgcgaa cttgttgaag gagttgttga  135480
tttgtttttc aaccaatcct ggcttatgag ccaccacatc cgccttcttt gcatctttgc  135540
gcagtttttc attttcacgc tcaatagcag caattgcctc acgattttta ttattcatcg  135600
catcaatata attatactga attcgcaaat tatttaatgc taaggcgttt tcattggccg  135660
tttttgtaat ttcagtaact gatgtttcta atctttctac cttatgtttt aaaataatag  135720
atgttccgcc aaatgctatt acaagtaata gcaatccagc tgtaaaatta cttacatgca  135780
taaagtttta ataacctcta caatatcgtc ttgagaaaga ccgttaatta aaatatgatg  135840
ttcagctgga gatttagaaa ttttaaagca tgcctcaaca tcttctgcca tatccgatgc  135900
actacgattt ggattactaa taccaaggcg atgttttccc gtcaaaggat taacgatgat  135960
atagcatttg cagctattga tatgaacatt gggttgagtc tgattaatga acacttcaca  136020
atcatactta gcaagttgat tttctaaaaa gactttcatc tcttcaaccg catcaggaag  136080
catatcacgg gcttgctcaa gacgacgatt tcgatattct ttaatggtcg ttttccgctt  136140
gacttgctta gctaaatctt tcttaagacc agtgatatat ccaactcgac gatttccttt  136200
gaatacagaa atcccatctg tagtatcacc gtatgcttca acgaccattt cagtagtaat  136260
aagttgtaaa tccatcataa agtcctcatg ttatgtcagt aagactacta taacacaaca  136320
cgagggactt gtaaacaact tagtatcctt ctgggataaa tttttttataa tttttcaaaa  136380
aattctgttc gatttcacac atgacctttt cttgactatc gtacccctgg tataagctca  136440
tgatgatacc gaacaggtga tccattccag cacctttagc aacaccttgt gcttccattg  136500
cataagtctt tctatcctta ccgcaatgct tattatgaca gtcaagaact aaaaacagag  136560
ctcggtctaa gtacttcaga taagtcgttt caaatgcttc aatttttctg tatgaatatt  136620
catcgtcagc atacattgct ttaagatcat ctgatgcacc atcaataata gtcttaaaca  136680
atttttctgg attatctaat gaactttttg tactatgaag agacacgtac cagtcagact  136740
taattttaaa atgagaacca tctttcatca cagcaacata gccttcgatg ttttctgcat  136800
ttttagcttc ttctatccat ttagggctat cgatttcgta tcgttcaact agatacggac  136860
gaagagtagc atctttataa atatcatcgt atgaaatgta ttcacccgtt tcgttttcac  136920
gaacattcag taaaataatt ttcatctctt gataagcaag aacgattcta ttcgtcgggg  136980
caacgaattc gaagttagca gtaaatccat cttcagctaa ttctttaagt ctatcacgca  137040
accgatggtg attaatattc atcaaaattc cattagccat taaagcctgc tcagatttga  137100
ttgaaccctt tgatttgaac agaatttcat caccgtctaa ataagttgat accaaagacc  137160
cgtcttcttt tgttagaata taatcaacat cgtttaaatc gatattcatc gtgaacggat  137220
tttcattcaa gttaaaaaac ttttccatag gacgagaagc aattcttact ggtttttctc  137280
catccatttc aaacataatt ccacgacatt ctagtgcatc tggaagtaac caatcagaat  137340
aagatgcata attatatgag aaaattctgt aagttcttcc agatgcactt acatcatctg  137400
agtaaaaaaa cttacgctgc gaatccttac atagttccat taaattgtta aaaagttctt  137460
gcattgtgta tcctcttttg tgttttgaat atagtaccac actccatgtg gaagcatcat  137520
tttttcttgt gttgaatatt ccaaggcggg ttaaacagtt taatgaatag aggctcctct  137580
aagtcaatcg ttgcgattgt cattgtacct aactcatttg tcatagaaag attaaaacat  137640
tggcgggcgt aaaattcaac tttgcttcct tcctttagcg cagaatgaat taatgcagat  137700
ttagtagaat cagacgtttt gtctttgcgg ttaatagcag ttctataata gtttattctt  137760
ttacgtaaat ttttagtttt tccaatataa acaagctcat catttatagc aatagcataa  137820
attacgttat acttgtttgg aatagataat tgttttatac ttccattgtc gtctaattct  137880
agctcagtat atttaataaa tgaatattct gttgcaattt ctttcataat aaaatgggcc  137940
ttgcggccca ctccttaaaa gtattttttta aaactcatca taactttatc atcaacatca  138000
ttatcaatct gtgcaacaag gtaagatgac agttctactt cttgcggcgc ggattgaaca  138060
ttatcagaat taagatattc acgaatccaa ggatatggat gtttaaccgg agcatcggta  138120
attgggcatg gaagaccgca ctgtttcata cgagatacag ttaagtaatc aataaagctc  138180
cacatgctat ttgtatttaa tccaggaaca tcaccatctt taaataaatg aactgcccag  138240
tctttttcct ggcggttaac ttccatgaaa atatcaactg cttcttgttc acactcttgg  138300
gcaattttaa cccattcatc accatcagta ccggattgaa gttgacgaat aatatattgg  138360
gtgcctttaa ggtgaagctg ttcatcacgt gcaatgaact tcataatctt ggcattacct  138420
tccatgattt ccatgttctt atggaagtta aaggtaccgt atgttcgatt gagctcgcta  138480
attctcaacc cgttctctta tgaactgctg catgttacca tgcagtccag actatatcac  138540
aatcccggag ggattctccc catttcgagt cgcttgaccc tacgtccgaa gactagtcgt  138600
tgaaccttgt tttgcaattg tcgccgtgcc atcgtttata tgttgatggt gataaatctt  138660
tcttatcaca atatggacaa ttcaattgaa ttctatttgg atttaattta catctgtcat  138720
tatgttttag ataaaatcca ggacctttac caatgtgacc acagaaatca catgtgattt  138780
ctttttgtgc aggatgggtc ccgttcttaa ccatttctaa tgtttttgct gatgttcttt  138840
tcttatgttc ttccatcaga atctttaggt ataggtccgt tagcatctat ccaaattttt  138900
ctatagttca attgtgcatc ctcttaaaag tataatcata tttatattat actaattaaa  138960
ggtgcaagca aaaccttggc tgctagtttt ccataaagga ctttccagca attaaaggag  139020
ttttcgataa acgttaccgt ttaaaggcgc attttacgca aaagatacat aaaaacgaat  139080
agcttctaag gcattaataa cgtgcaaaca gaggtaaaga gatttcatca gatctcgttt  139140
agctctttgc tcaacgtctt tatcagctag aattagacct tggtctttat aatattcaac  139200
catgtcttta gcattttccc attcacgggt tttaaccaag acatcatcgt aatatcgccc  139260
aatggactca gcacgtttca taatagcttc atctaataca atctcatcaa acaccttcga  139320
tggatcagta taaagatttc gcatgatatg agtatatgaa cgactgtgaa tagtttcact  139380
aaaagtccat gtagcaaccc atgtatcaag gcttgggtct gaaattaatg acataagtac  139440
```

```
agcagatggc gcacgaccct gaatgctatc caaaagtgat tgatacttca ggttgttagt  139500
aaaaatattt tgctgatact gaggaagctt attaaattgc gcagcatcca tcattaagtt  139560
tacttcttca ggacgccaaa aaaaactgat ctgccgctca atgagttctt caaatactcg  139620
atgtcgttga atatcatatc gagctaaacc taatccagaa ccaaagaaca tcggttcatt  139680
caaaacatca actggatttg tattaaaaac tgtactcatt tagaatcctt aaatttacat  139740
ttatcataat gccatcttaa agcattgcct ttattaactt tcttaccaca gtgcgggcaa  139800
ggtggatact ctgctccttg tttagttctc aaagaaatca aatcacgggt ttctttagta  139860
tgaggaacat ctcttgtcgg agaaattgta ccatacatcg gattaagcac gccgacttta  139920
gcagcagcta tattcttttt agcttcttca gttttaggct ttctcatctt tttcttaggt  139980
ttcttcgctt ttagcccttc ctttggttgc cgccgatatt ttgtgtttgg tttcttctgt  140040
taaacgcaga cctgttttcg ctttttgaca ttttcagtct cgtttcttca gaaatgaccg  140100
tacctttgcg aaattgcgaa tttaacttct ttgcatgggc atatatttta gaatgaactt  140160
tataatgacg tttcttagtt cctttcatat tgcacatcat gaaaaatgcg aatataacag  140220
attttaccgg ataaatcttt gataaaatag catgcgctat aaaatgctct ctagctgtta  140280
attcaactaa atttctttta tcatcagaac ctcccatgca tctagggatt atatgatgtg  140340
tctctttata ttcggataaa ggttcccgag cctgagctcg ggaaattagg tcgttataga  140400
ttttttgata attcattaca atttacacgc tgcacaatca tcggctttag gagtttctat  140460
ttcataatca tcagtaccag aaccatcacg ggtattatga taatagaaat ttttaatgcc  140520
ataataccat ccgtatagca tgtcatcaat cattattgac attggaacct ttcctttttgg  140580
aaaaatctgc gggtcataat atgtattcgc tgaagctgat tgacataccc atttcagcat  140640
aatagctacc tgcgtaagat aaggtttatt acctttctta gctaatttcc atgtataatc  140700
atagaggtct atgttatgct caatattggg cacgacttga ttaaaggaac cctcttttga  140760
ttctttaaca cttaccggtc cacgtggagg ctcgtagccg tttgtactgt tagaaacttg  140820
ggaagatgac tcacatggca taagtgctga taatgtgcta ttacggatgc caaatagctt  140880
aaggtcttcc cgcagcgccg accagtcaca aacgtatttt ggagctgcga tttggtcaat  140940
ctttttattg taccagtcga taggtaattc gcctcgagac caacgagtgt ctgaataata  141000
ttccgaaggt cctttttctt tggcgagctt aatggatgct ttaatgagtc catactgtaa  141060
tctctcaaat agttcatgtg ttaaatcgtt agcatcttca taagaagcaa agttacttgc  141120
cagccaagct gcatagttgg taacacctac accgaggtta cgacgctttt tagctttttc  141180
tgcttcagga accggatatc cttggtaatc caacagatta tcaagagcac gaacttgaac  141240
ttctgccaat tcattaattt tatcttggtc ttgccagtca aaattatcta atacgaatgc  141300
agagagagta cacaatccaa tttcagcatc agggctattc acatcatttg ttggaatagc  141360
aatttcacag cacaagttac tctgacgaat aggtgccttt tcacgaataa acggagtata  141420
gttattcgta ttatcaatga actgcacata aatccttgct gttcctgaac gttcagtcat  141480
gagcaattca aatagttcac gggctttaat acgcttttta cgaatattag ggtctttttc  141540
tgctgcttcg tataattcac ggaaacggtc ttggtcttta aaataagaat aataaagctc  141600
gccacccatt tcatgcggac tgaacaaagt aatgtaatcg ttttttccaa aacgttccat  141660
catcaaatca ttcagttgaa caccataatc catatgacga atgcggtttt cttctacgcc  141720
tttgttattt ttcaaaacga gaagattttc aacttccaaa tgccaaatag gataataagc  141780
agtagcagcg ccgccacgaa ttccaccctg tgaacatgat ttaactgcag tctgaaaatg  141840
tttccaaaaa ggaataacac cagtatggcg tacttcaccc atgccaatct tagaaccttc  141900
ggcacgaatc ataccaacgt taataccaat tccagcgcgt ttagagatat attcaacaat  141960
tgaagcagaa gccttattga tagacttcaa tgaatctcct gcctcaataa caacacatga  142020
actaaactgt cgagtcggag tacgacaacc agccataata ggagttggca atgaaatctg  142080
tcgagttgat actgcttcat aaaaacggat aacatgtttt aatctatcaa caggttcatc  142140
ttgatgcagt gccattccaa tagtcataaa tgcaaactgt ggagtttcat aaatttgacc  142200
agtggtttta tctttaacta gatatttttc ttttaattgc attgccccgg aataagtaaa  142260
ttccatatcc cgttcgtgct taatttttga ttctaaaaat gtaatttctt ctgctgaata  142320
ttttgacaat aattcagggt cgtatttacc tgcatttaca caataagaaa tatggtcaat  142380
aaatgaacgt ggttcatact gcccataaac atgcttacga agagcaaaca ttaaacagcg  142440
tgcagctaca tattgataat caggttcttc aaccgaaata gaattcgcag cagccttaat  142500
gacaatagtc tgaatatcat cagttgtcat tccatcacgg agataagatt taatattttc  142560
atataattca taaggatcta ctgatgttcc ttcagctgcc caagataaaa ctttaataat  142620
tttttgtggg tcaaagctct gagaaacacc actactttttg ataacattaa ttaattgcat  142680
aagtcctcaa cttgaaaatc gtctttaaac aatcggttaa ctatatgagc tattatatca  142740
ccatgacacg gctttggttt acatgtgcat cctagcctca ttccacgtaa aggctctaaa  142800
tgtgctttag ttatttctcc ggatttaatt cgacgtataa aatctttttt gaataattca  142860
atggcagcct cccggctgcc agcatcttta ccgacgtaat ttccccaaaa tgtaccgcgg  142920
tgaatattaa catcaaagtc ggatttatat ttattcacta cccggcatag acggcccacg  142980
ctggaataat tcgtcatatt gtttttccgt taaaacagta atatcgtagt aacagtcaga  143040
agaagtttta actgtggaaa ttttattatc aaaatactca cgagtcattt tatgagtata  143100
gtatttttta ccataaatgg taataggctg ttctggtcct ggaacttcta actcgcttgg  143160
gttaggaagt gtaaaaagaa ctacaccaga agtatcttta aatcgtaaaa tcatatatcc  143220
tcgcaataat aaaattacac cgccatcttt cctttaatag gagggtgtga tacatagttg  143280
ttaagaacga aatctttagg cctaagttta agaacatatt ttaattgttc tttagtagaa  143340
agatatcgga atttataagg tagaccactt attaccagct cacaaagctc tttaggttca  143400
cgcctcaaaa tttctttaca ttgttctacg tgattcatat agatatgagt attaccacca  143460
gaaaatatca aatcccctgg aataagatta cacatcttag ctacaatatg aactaacgta  143520
gcatatgacg caatattaaa cggtagcatt atgttcagat aaggtcgtta atcttacccc  143580
ggaattatat ccagctgcat gtcaccatgc agagcagact atatctccaa cttgttaaag  143640
caagttgtct atcgtttcga gtcacttgac cctactcccc aaagggatag tcgttaggca  143700
tttatgtaga accaattcca tttatcagat tttacacgat aagtaactaa tccagacgaa  143760
attttaaaat gtctagctgc atctgctgca caatcaaaaa taaccccatc acatgaaatc  143820
tttttaatat tactaggctt tttaccttc atcttttctg atattttaga tttagttatg  143880
tctgaatgct tatgattaaa gaatgaatta ttttcacctg aacgatttct gcatttacta  143940
caagtataag cagaagtttg tatgcgaaca ccgcacttac aaaacttatg ggtttctgga  144000
ttccaacgcc cgtttttact tccgggttta ctgtaaagag ctttccgacc atcaggtcca  144060
agtttaagca tcttagcttt aacagtttca gaacgtttct taataatttc ttcttttaat  144120
ggatgcgtag aacatgtatc accaaacgtt gcatcagcaa tattgtatcc attaatttta  144180
```

```
gaattaagct ctttaatcca aaaattttct cgttcaataa tcaaatcttt ctcatatgga  144240
atttcttcca aaatagaaca ttcaaacaca ttaccatgtt tgttaaaaga cctctgaagt  144300
tttatagaag aatggcatcc tttttctaaa tctttaaaat gcctcttcca tctcttttca  144360
aaatctttag cacttcctac atatacttta ttgtttaaag tatttttaat ctgataaatt  144420
ccgcttttca taaatacctc tttaaatata gaagtattta ttaaagggca agtcctacaa  144480
tttagcacgg gattgtctac tagagaggtt ccccgtttag atagattaca agtataagtc  144540
accttatact caggcctcaa ttaacccaag aaaacatcta ctgagcgttg ataccactgc  144600
aaatccaaat agccattacg cacattaaac tgatagaaca tatgacaagg cggtaatgcc  144660
atatatttaa gttcagctgg attccatgca gaaacaattt gacgcctatc atttggcagt  144720
tttttaatac gatcaataac ttctataatt tggtctacac caccaaaatc acgccactgt  144780
tttccataaa ttggaccaag ttcaccgcta tggtatccta aatcttttgc ttgatttttcg 144840
taattttcat cccagactgt tttgccttgg attaacgaat cgtgttgaat taatcgtaaa  144900
tcattgacat ttgtgcttcc tgataaaaac catattagct cagcaatgca agctttccag  144960
gcgagcttct tagttgttac cgcaggaaaa cctttagtta aatcccagcg taatttagat  145020
ccgaacagag caattgttcc tgtgcctgta cgatcatcgg tttcataacc attttcaaaa  145080
atgtctttaa ttaaatcttg gtattgtttc atttatatac tgattccgta agggttgtta  145140
cttcatctat tttataccaa tgcgtttcaa ccatttcacg cttgcttata tcatcaagaa  145200
aacttgcgtc taattgaact gttgaattaa cacgatgcct tttaacgatg cgagaaacaa  145260
ctacttcatc tgcataaggt aatgcagcat ataacagagc aggcccgcca attacactta  145320
ctttagaatt ctgatcaagc atagtttcga atggtgcatt agggcttgac acttgaattt  145380
cgccgccaga aatgtaagtt atatattgct cccaagtaat atagaaatgt gctaaatcgc  145440
cgtctttagt tacaggataa tcacgcgcaa ggtcacacac cacaatatgg ctacgaccag  145500
gaagtaatgt aggcaatgac tggaacgttt tagcacccat aatcataatt gtgccttcag  145560
tacgagcttt aaaattctgg aggtcctttt taactcgtcc ccatggtaaa ccatcaccta  145620
aaccgaatgc taattcatta aagccgtcga ccgttttagt tggagaataa cggaatacca  145680
atttaatcat tacgtaaatc ctattttaat tgaaaacgaa tgcttacttg gataatttca  145740
atgacataca taatattttc ctcaaacaga ctttttcaca attttccaat cagctttaaa  145800
ctgctcgacg tcagaatggt aaatccaaaa tcctgcgctt tctccgtctt cataaagagg  145860
acatccatcg cattcatctt cccatcccat atcacgtaaa agatgttcag ctttttcaac  145920
aagttcagaa tctttaccga tgatattaaa ataccattta cctctaactt ctgaatcttt  145980
gatgctctgg cgttgtaatc tcattttatt ctccttagca agctttaatc aaaagatata  146040
aacagaccaa cataactgct gccataatat aaggtgcgaa cattttcttt tctccattag  146100
ttttgatagg gtaatagtat cacactacta ccctgatgta aactactttt tgaaagtttt  146160
tcgcaaaagt tcaatgattt catctacatt gttttcgtca acaatgcagt gaatttttgt  146220
tacgccagaa accttgtctt tgacttcatc ttcttcagaa gtcggttctt tatattcgcg  146280
gaaacaataa aactcttctt cactaagttc aaaataatca tcacccatac catcatcatt  146340
atagatttca ccattagcac aaatgatttc ggttacataa tcaaagccat ctaaacttga  146400
tattgattta acttcaaacc aaccgccatt ttcttgaatg atgccgacca tactagcatt  146460
tgatgaacta atatcaatga aagatttaat acgatgtgga tttaactcgt atttttttgcc 146520
gatttccatt ttgatttcc tcattttaat aggggcttga tagccccttg ataattattg   146580
ttcaatcagt cccatgtaaa attctgcgtc ttcagaatcc atgccatcac aatattcatt  146640
agccataaag cgggtgaggt cttcaagagg accttcaata acgatttgaa tactccaaaa  146700
cttagaatct tgcacgcttg tgatactaag ttcaggataa cgattacgaa taatctcttc  146760
aatatattca aaatcaacga tgtcaatatc aactttagcc atattatttt cctctttaat  146820
tattagcagt attgccgata gttgtatagt accataaagc tttatgcttg taaaccgttt  146880
tgtgaaaaaa tttttaaaat aaaaaagggg acctctaggg tccccaatta attagtaata  146940
taatctatta aaggtcattc aaaaggtcat ccaggtccgt gtcatcagca ctagatgaac  147000
taccagagct tgagctcata aaatcatctt cagtttttgt attgaagtca tcaacattga  147060
atgcatccaa atcatcagcc actttatcag ctttcttagc agcagttgca gcagcaccgc  147120
ccatcacagc agttcccata acttgaccga atttagtatt aagttcttca aacgatttga  147180
atttatcttt agaagtcatt tcagaaaggt caaccatttg ttcgaacagt tctttctgga  147240
aagattcatc gtcaatgttt ggaatcgcag attgattcag gaatttagat tcatcgtagt  147300
tactaaatcc agaaacttgt ttaactttca gtacaaagtt agcaccttcc cacggacaag  147360
ttacatcaac tggagtttca cccatttcaa catcaaccgc aatcattgca ttgattttat  147420
cccagatttt cttaccaaag cggtatttaa atactttacc ttcgttttct ggagcagctg  147480
ggtcttttac tacaagaatg ttagcccagt aagaagtttt acgtttaaca agactgtact  147540
ctttattgtc agtgttgtat agatcatttt tactgatgta ttgacatact gggcaagaat  147600
cgtaatcacc atgggtagat gaacatgttt caatatacca tttaccattt ttcttgaaac  147660
cgtgatttac aagaattgcg aatggtgctt gttcatcatt tttagacgga agaaaacgaa  147720
ttactgcttg accgttaccc gcattatcga gtttcagttt ccactcgcct ttatcttcag  147780
aagaaaaacc tttattgcca ttcagtttag ccatttgtgc agcgagttca gcagtagatt  147840
tacgtttaaa catttttatt tcctttttaa tttaatttaa ttaacagttg gtgctatgac  147900
actttacctc atagctggca taattcgcaa tactctgggt cttcgagagg tatccaacct  147960
gagttgaaat actttaccat cgatttagca gttgtatcag ttatatttat attaccttta  148020
actcttcgcc atccaggagt tttaccgtac agattagagg ataataataa cacataattc  148080
tcgtaagcaa tatgagataa tttccaagac tctatattag ctcgtgatgt tttccaaggt  148140
ctaaaatcgt cacggttcat ataattagcc aatctcatat gctctctaac ttccgggtct  148200
ttggctggat gagtttcacc actcacacca aatccaccac cagcatatac cagattaaaa  148260
tagtctggat tatctctggc atttacttca agttggtatt ttcgttctgc ttcaataaca  148320
tccaagtcat catcaatttg aattatttta acgctcggtt tttgaagcat tagcgcattc  148380
aaaaatcttt tttgtttaca tgagctccag tattcctttc cggaagagtc atatattatt  148440
ccgttctcaa atgagcaatt taatttacta ccgatatagt agtatggcgg agtcttattt  148500
ttgacacggt cttcaaatgt aaaccaatat actatattca tatcaatact tgcaagattt  148560
cacagtttca atgaaaacat ttttagcttt ctgtgaatca atatttaaaa tttttctata  148620
agcctttaac tttatagaat aattattcca gactaaatta tcagtctgtt catcatgttt  148680
atcaattata tttaaaaacg aatcaagcaa gataaacgtc tcaaacgaaa ttatgttcga  148740
ttgcagaagt ttaaaaatat aacttgattg aacttttgga ttatactcaa aaatttcttt  148800
aaaagcagaa acttcaactt ttttactaaa ataataaatg ttgcgaatat cttcttcaaa  148860
cttaaattta atttgcttta agcgtccgat atattcacga taaaacacaa gtgcatcagc  148920
```

```
gtcagagatg tcaccaatcc aagcatcttg gttagcaacc aaattgctta taaagattaa  148980
agcaagttcc tttaatttat atttttctga taacttctgg aaaaaatact tatcccttcg  149040
cttttgataa gcggcatcag acacccgcat gcaccaatta tacttaatta catcatactt  149100
tccattcata tgttgtttta tcattaagta taatttataa actgatttac catcaatgta  149160
tctttcacca ccagcaggca tgcggagttt aatcatagta gaaaatctaa tgtattagtt  149220
ttttcacaac gaacaacaga aggacgtaaa agattttcgt caatagcttc tgactgaatt  149280
ttttcaatta tacccgaagg aataaattta gcaaattgag tttcaggaat agaattttct  149340
tctaagaatg ctgttgtagc ttcaagataa ctcattccaa actcttctac catttttttca  149400
ataataaatc cattttcttg gcggtcaaga agctttgcta tttcatcctt ttctttctta  149460
attgaaagtt ctttttctga aagaccggtc tcatcgaccg gacgaatatc atttagagaa  149520
aactgtgtca taaagttcaa ctacctcttc agtttcagct tcaaacacat cacggttatc  149580
tttatgatac aaagctaata gacgattaaa catcttacca tcaacgccaa gttcatcttt  149640
agcacgaatt cgaatatctt taatcagttc attataaccg gaaattttca gtttatgatc  149700
agatgcttct ttaataaatt tagccaagtc ttcgccatgg atagcttcat caaattcaac  149760
catttctttt ttagccatta ttcacctcaa aattcattaa tgctattagt taatttagaa  149820
agacccgctt ttacaaaata tgaataaatt ttgccacgcg gtggtaattt atatgaatta  149880
tagtaattca caatgtttga agcaatatta tcaggaatat aatcaaaatc aattagaact  149940
aaattttctt tataacgatt atattcagat tcagtgagaa gcaccttagc ttgctcacgg  150000
tcattagcaa tagcttcaac gattgaagtt ttcattgaag gagttcgttc accttcaact  150060
ctggtaaacc aaaagtcaga tcgtacttta actgaagcaa cgttatcctt tttgtcgcct  150120
ttaaggattt tagtcataca gtcaatttca gcagaaccgc ttttaatttt aacccatttc  150180
ttatgcatcg gagaccattg cttaacattt ggatatttgt gaagctgagt aaagtcacca  150240
tctgacgaaa tgattaaaat cttatgtcct tctaaagaga actttttaac aagaacagca  150300
atgtggtcat ctgcttcata cttatcaata tccataacaa tgtatggcat ataagctttc  150360
aattcatcta taactttatg gctggattca aaataacctt cccagtccca agtagattct  150420
tctcgtgctt ttccacggtt tttcttataa taataagcga aatcacgacg ccaatatcca  150480
gatttcgcgt tatcaataca cagtacaatt ttagtgtatc caagcgtttt tgctttttttg  150540
acattaaact taattgagtt caatatcaaa tgacgaacca ttgataaatt aattttttct  150600
ttatctggga agtttaccaa agcagttgaa agcgcaattt gactaaagtc aattaagcag  150660
attccttctt tgtaatcttc atccaacatc atttctaaat ccatatgaac ctcgttcaat  150720
tagtgagatt tctattatat accatccaaa tcttaaagta aacaagtata aatacttatt  150780
attgaaaaca caataggagc ccgggagaat ggccgagatt aaaagagaat tcagagcaga  150840
agatggtctg gacgcaggtg gtgataaaat aatcaacgta gctttagctg atcgtaccgt  150900
aggaactgac ggtgttaacg ttgattactt aattcaagaa aacacagttc aacagtatga  150960
tccaactcgt ggatatttaa aagattttgt aatcatttat gataaccgct tttgggctgc  151020
tataaatgat attccaaaac cagcaggagc ttttaatagc ggacgctgga gagcattacg  151080
taccgatgct aactggatta cggtttcatc tggttcatat caattaaaat ctggtgaagc  151140
aatttcggtt aacaccgcag ctggaaatga catcacgttt actttaccat cttctccaat  151200
tgatggtgat actatcgttc tccaagatat tggaggaaaa cctggagtta accaagtttt  151260
aattgtagct ccagtacaaa gtattgtaaa ctttagaggt gaacaggtac gttcagtact  151320
aatgactcat ccaaagtcac agctagtttt aatttttagt aatcgtctgt ggcaaatgta  151380
tgttgctgat tatagtagag aagctatagt tgtaacacca gcgaatactt atcaagcgca  151440
atccaacgat tttatcgtac gtagatttac ttctgctgca ccaattaatg tcaaacttcc  151500
aagatttgct aatcatggcg atattattaa tttcgtcgat ttagataaac taaatccgct  151560
ttatcataca attgttacta catacgatga aacgacttca gtacaagaag ttggaactca  151620
ttccattgaa ggccgtacat cgattgacgg tttcttgatg tttgatgata atgagaaatt  151680
atggagactg tttgacgggg atagtaaagc gcgtttacgt atcataacga ctaattcaaa  151740
cattcgtcca aatgaagaag ttatggtatt tggtgcgaat aacggaacaa ctcaaacaat  151800
tgagcttaag cttccaacta atatttctgt tggtgatact gttaaaattt ccatgaatta  151860
catgagaaaa ggacaaacag ttaaaatcaa agctgctgat gaagataaaa ttgcttcttc  151920
agttcaattg ctgcaattcc caaaacgctc agaatatcca cctgaagctg aatgggttac  151980
agttcaagaa ttagttttta acgatgaaac taattatgtt ccagtttgg agcttgctta  152040
catagaagat tctgatggaa aatattgggt tgtacagcaa aacgttccaa ctgtagaaag  152100
agtagattct ttaaatgatt ctactagagc aagattaggc gtaattgctt tagctacaca  152160
agctcaagct aatgtcgatt tagaaaattc tccacaaaaa gaattagcaa ttactccaga  152220
aacgttagct aatcgtactg ctacagaaac tcgcagaggt attgcaagaa tagcaactac  152280
tgctcaagtg aatcagaaca ccacattctc ttttgctgat gatattatca tcactcctaa  152340
aaagctgaat gaaagaactg ctacagaaac tcgtagaggt gtcgcagaaa ttgctacgca  152400
gcaagaaact aatgcaggaa ccgatgatac tacaatcatc actcctaaaa agcttcaagc  152460
tcgtcaaggt tctgaatcat tatctggtat tgtaaccttt gtatctactg caggtgctac  152520
tccagcttct agccgtgaat taaatggtac gaatgtttat aataaaaaca ctgataattt  152580
agttgtttca cctaaagctt tggatcagta taaagctact ccaacacagc aaggtgcagt  152640
aattttagca gttgaaagtg aagtaattgc tggacaaagt cagcaaggat gggcaaatgc  152700
tgttgtaacg ccagaaacgt tacataaaaa gacatcaact gatggaagaa ttggtttaat  152760
tgaaattgct acgcaaagtg aagttaatac aggaactgat tatactcgtg cagtcactcc  152820
taaaacttta aatgaccgta gagcaactga aagtttaagt ggtatagctg aaattgctac  152880
acaagttgaa ttcgacgcag gcgtcgacga tactcgtatc tctacaccat taaaaattaa  152940
aaccagattt aatagtactg atcgtacttc tgttgttgct ctatctggat tagttgaatc  153000
aggaactctc tgggaccatt atacacttaa tattcttgaa gcaaatgaga cacaacgtgg  153060
tacacttcgt gtagctacgc aggtcgaagc tgctgcggga acattagata atgttttaat  153120
aactcctaaa aagcttttag gtactaaatc tactgaagcg caagagggtg ttattaaagt  153180
tgcaactcag tctgaaactg tgactggaac gtcagcaaat actgctgtat ctccaaaaaa  153240
tttaaaatgg attgcgcaga gtgaacctac ttgggcagct actactgcaa taagaggttt  153300
tgttaaaact tcatctggtt caattacatt cgttggtaat gatacagtcg gttctaccca  153360
agatttagaa ctgtatgaga aaaatagcta tgcggtatca ccatatgaat taaaccgtgt  153420
attagcaaat tatttgccac taaaagcaaa agctgctgat acaaatttat tggatggtct  153480
agattcatct cagttcattc gtagggatat tgcacagacg gttaatggtt cactaacctt  153540
aacccaacaa acgaatctga gtgcccctct tgtatcatct agtactggtg aatttggtgg  153600
ttcattggcc gctaatagaa catttaccat ccgtaataca ggagccccga ctagtatcgt  153660
```

```
tttcgaaaaa ggtcctgcat ccggggcaaa tcctgcacag tcaatgagta ttcgtgtatg  153720
gggtaaccaa tttggcggcg gtagtgatac gacccgttcg acagtgtttg aagttggcga  153780
tgacacatct catcactttt attctcaacg taataaagac ggtaatatag cgtttaacat  153840
taatggtact gtaatgccaa taaacattaa tgcttccggt ttgatgaatg tgaatggcac  153900
tgcaacattc ggtcgttcag ttacagccaa tggtgaattc atcagcaagt ctgcaaatgc  153960
ttttagagca ataaacggtg attacggatt ctttattcgt aatgatgcct ctaataccta  154020
ttttttgctc actgcagccg gtgatcagac tggtggtttt aatggattac gcccattatt  154080
aattaataat caatccggtc agattacaat tggtgaaggc ttaatcattg ccaaaggtgt  154140
tactataaat tcaggcggtt taactgttaa ctcgagaatt cgttctcagg gtactaaaac  154200
atctgattta tatacccgtg cgccaacatc tgatactgta ggattctggt caatcgatat  154260
taatgattca gccacttata accagttccc gggttatttt aaaatggttg aaaaaactaa  154320
tgaagtgact gggcttccat acttagaacg tggcgaagaa gttaaatctc ctggtacact  154380
gactcagttt ggtaacacac ttgattcgct ttaccaagat tggattactt atccaacgac  154440
gccagaagcg cgtaccactc gctggacacg tacatggcag aaaaccaaaa actcttggtc  154500
aagttttgtt caggtatttg acggaggtaa ccctcctcaa ccatctgata tcggtgcttt  154560
accatctgat aatgctacaa tggggaatct tactattcgt gatttcttgc gaattggtaa  154620
tgttcgcatt gttcctgacc cagtgaataa aacggttaaa tttgaatggg ttgaataaga  154680
ggtattatgg aaaaatttat ggccgagttt ggacaaggat atgtccaaac gccattttta  154740
tcggaaagta attcagtaag atataaaata agtatagcgg gttcttgccc gctttctaca  154800
gcaggaccat catatgttaa atttcaggat aatcctgtag gaagtcaaac atttagcgca  154860
ggcctccatt taagagtttt tgacccttcc accggagcat tagttgatag taagtcatat  154920
gccttttcga cttcaaatga tactacatca gctgcttttg ttagtttcat gaattctttg  154980
acgaataatc gaattgttgc tatattaact agtggaaagg ttaattttcc tcctgaagta  155040
gtatcttggt taagaaccgc cggaacgtct gcctttccat ctgattctat attgtcaaga  155100
tttgacgtat catatgctgc tttttatact tcttctaaaa gagctatcgc attagagcat  155160
gttaaactga gtaatagaaa aagcacagat gattatcaaa ctattttaga tgttgtattt  155220
gacagtttag aagatgtagg ggctaccggg tttccaagag gaacgtatga aagtgttgag  155280
caattcatgt cggcagttgg tggaactaat gacgaaattg cgagattgcc aacttcagct  155340
gctataagta aattatctga ttataattta attcctggag atgttcttta tcttaaagct  155400
cagttatatg ctgatgctga tttacttgct cttggaacta caaatatatc tatccgtttt  155460
tataatgcat ctaacggata tatttcttca acacaagctg aatttactgg gcaagctggg  155520
tcatgggaat taaaggaaga ttatgtagtt gttccagaaa acgcagtagg atttacgata  155580
tacgcacaga gaactgcaca agctggccaa ggtggcatga gaaatttaag cttttctgaa  155640
gtatcaagaa atggcggcat ttcgaaacct gctgaatttg gcgtcaatgg tattcgtgtt  155700
aattatatct gcgaatccgc ttcacccccg gatataatgg tacttcctac gcaagcatcg  155760
tctaaaactg gtaaagtgtt tgggcaagaa tttagagaag tttaaattga gggacccttc  155820
gggttccctt tttctttata aatactattc aaataaaggg gcatacaatg gctgatttaa  155880
aagtaggttc aacaactgga ggctctgtca tttggcatca aggaaatttt ccattgaatc  155940
cagccggtga cgatgtactc tataaatcat ttaaaatata ttcagaatat aacaaaccac  156000
aagctgctga taacgatttc gtttctaaag ctaatggtgg tacttatgca tcaaaggtaa  156060
catttaacgc tggcattcaa gtcccatatg ctccaaacat catgagccca tgcgggattt  156120
atgggggtaa cggtgatggt gctacttttg ataaagcaaa tatcgatatt gtttcatggt  156180
atggcgtagg atttaaatcg tcatttggtt caacaggccg aactgttgta attaatacac  156240
gcaatggtga tattaacaca aaaggtgttg tgtcggcagc tggtcaagta agaagtggtg  156300
cggctgctcc tatagcagcg aatgacctta ctagaaagga ctatgttgat ggagcaataa  156360
atactgttac tgcaaatgca aactctaggg tgctacggtc tggtgacacc atgacaggta  156420
atttaacagc gccaaacttt ttctcgcaga atcctgcatc tcaaccctca cacgttccac  156480
gatttgacca aatcgtaatt aaggattctg ttcaagattt cggctattat taagaggact  156540
tatggctact ttaaaacaaa tacaatttaa aagaagcaaa atcgcaggaa cacgtcctgc  156600
tgcttcagta ttagccgaag gtgaattggc tataaactta aaagatagaa caatttttac  156660
taaagatgat tcaggaaata tcatcgatct aggttttgct aaaggcgggc aagttgatgg  156720
caacgttact attaacggac ttttgagatt aaatggcgat tatgtacaaa caggtggaat  156780
gactgtaaac ggacccattg gttctactga tggcgtcact ggaaaaattt tcagatctac  156840
acagggttca ttttatgcaa gagcaacaaa cgatacttca aatgcccatt tatggtttga  156900
aaatgccgat ggcactgaac gtggcgttat atatgctcgc cctcaaacta caactgacgg  156960
tgaaatacgc cttagggtta gacaaggaac aggaagcact gccaacagtg aattctattt  157020
ccgctctata aatggaggcg aatttcaggc taaccgtatt ttagcatcag attcgttagt  157080
aacaaaacgc attgcggttg ataccgttat tcatgatgcc aaagcatttg gacaatatga  157140
ttctcactct ttggttaatt atgtttatcc tggaaccggt gaaacaaatg gtgtaaacta  157200
tcttcgtaaa gttcgcgcta agtccggtgg tacaatttat catgaaattg ttactgcaca  157260
aacaggcctg gctgatgaag tttcttggtg gtctggtgat acaccagtat ttaaactata  157320
cggtattcgt gacgatggca gaatgattat ccgtaatagc cttgcattag gtacattcac  157380
tacaaatttc ccgtctagtg attatggcaa cgtcggtgta atgggcgata agtatcttgt  157440
tctcggcgac actgtaactg gcttgtcata caaaaaaact ggtgtatttg atctagttgg  157500
cggtggatat tctgttgctt ctattactcc tgacagtttc cgtagtactc gtaaaggtat  157560
atttggtcgt tctgaggacc aaggcgcaac ttggataatg cctggtacaa atgctgctct  157620
cttgtctgtt caaacacaag ctgataataa caatgctgga gacggacaaa cccatatcgg  157680
gtacaatgct ggcggtaaaa tgaaccacta tttccgtggt acaggtcaga tgaatatcaa  157740
tacccaacaa ggtatggaaa ttaacccggg tattttgaaa ttggtaactg gctctaataa  157800
tgtacaattt tacgctgacg gaactatttc ttccattcaa cctattaaat tagataacga  157860
gatattttta actaaatcta ataatactgc gggtcttaaa tttggagctc ctagccaagt  157920
tgatggcaca aggactatcc aatggaacgg tggtactcgc gaaggacaga ataaaaacta  157980
tgtgattatt aaagcatggg gtaactcatt taatgccact ggtgatagat ctcgcgaaac  158040
ggttttccaa gtatcagata gtcaaggata ttatttttat gctcatcgta aagctccaac  158100
cggcgacgaa actattggac gtattgaagc tcaatttgct ggggatgttt atgctaaagg  158160
tattattgcc aacggaaatt ttagagttgt tgggtcaagc gctttagccg gcaatgttac  158220
tatgtctaac ggtttgtttg tccaaggtgg ttcttctatt actggacaag ttaaaattgg  158280
cggaacagca aacgcactga gaatttggaa cgctgaatat ggtgctattt tccgtcgttc  158340
ggaaagtaac ttttatatta ttccaaccaa tcaaaatgaa ggagaaagtg gagacattca  158400
```

```
cagctctttg agacctgtga gaataggatt aaacgatggc atggttgggt taggaagaga  158460
ttcttttata gtagatcaaa ataatgcttt aactacgata aacagtaact ctcgcattaa  158520
tgccaacttt agaatgcaat tggggcagtc ggcatacatt gatgcagaat gtactgatgc  158580
tgttcgcccg gcgggtgcag gttcatttgc ttcccagaat aatgaagacg tccgtgcgcc  158640
gttctatatg aatattgata gaactgatgc tagtgcatat gttcctattt tgaaacaacg  158700
ttatgttcaa ggcaatggct gctattcatt agggacttta attaataatg gtaatttccg  158760
agttcattac catggcggcg gagataacgg ttctacaggt ccacagactg ctgattttgg  158820
atgggaattt attaaaaacg gtgattttat ttcacctcgc gatttaatag caggcaaagt  158880
cagatttgat agaactggta atatcactgg tggttctggt aattttgcta acttaaacag  158940
tacaattgaa tcacttaaaa ctgatatcat gtcgagttac ccaattggtg ctccgattcc  159000
ttggccgagt gattcagttc ctgctggatt tgctttgatg gaaggtcaga cctttgataa  159060
gtccgcatat ccaaagttag ctgttgcata tcctagcggt gttattccag atatgcgcgg  159120
gcaaactatc aagggtaaac caagtggtcg tgctgttttg agcgctgagg cagatggtgt  159180
taaggctcat agccatagtg catcggcttc aagtactgac ttaggtacta aaaccacatc  159240
aagctttgac tatggtacga agggaactaa cagtacgggt ggacacactc actctggtag  159300
tggttctact agcacaaatg gtgagcacag ccactacatc gaggcatgga atggtactgg  159360
tgtaggtggt aataagatgt catcatatgc catatcatac agggcgggtg ggagtaacac  159420
taatgcagca gggaaccaca gtcacacttt ctcttttggg actagcagtg ctggcgacca  159480
ttcccactct gtaggtattg gtgctcatac ccacacggta gcaattggat cacatggtca  159540
tactatcact gtaaatagta caggtaatac agaaaacacg gttaaaaaca ttgcttttaa  159600
ctatatcgtt cgtttagcat aaggagaggg gcttcggccc ttctaaatat gaaaatatat  159660
cattattatt ttgacactaa agaattttac aaagaagaaa attacaaacc ggttaaaggc  159720
ctcggtcttc ctgctcattc aacaattaaa aaacctttag aacctaaaga aggatacgcg  159780
gttgtatttg atgaacgtac tcaggattgg atttatgaag aagaccatcg cggaaaacgc  159840
gcatggactt ttaataaaga agaaattttt ataagtgaca ttggaagccc ggttggtata  159900
actttcgatg agcccggcga atttgatata tggactgatg acggttggaa agaagacgaa  159960
acatataagc gagttttaat tcgtaataga aaaattgaag aattatataa agagttccaa  160020
gttttaaata atatgattga agcttctgtc gccaataaaa aggaaaaatt ctattataaa  160080
aaccttaagc ggttctttgc tcttttagaa aagcatgagc atttaggtgg tgaattccct  160140
tcatggcctg aaaaagaaca gaagccttgg tataagcgtt tattcaagca ttacgtataa  160200
atatcttaaa aggagggtct atggcagcac ctagaatatc attttcgccc tctgatattc  160260
tatttggtgt tctagatcgc ttgttcaaag ataacgctac cgggaaggtt cttgcttccc  160320
gggtagctgt cgtaattctt ttgtttataa tggcgattgt ttggtatagg ggagatagtt  160380
tctttgagta ctataagcaa tcaaagtatg aaacatacag tgaaattatt gaaaaggaaa  160440
gaactgcacg ctttgaatct gtcgccctgg aacaactcca gatagttcat atatcatctg  160500
aggcagactt tagtgcggtg tattctttcc gccctaaaaa cttaaactat tttgttgata  160560
ttatagcata cgaaggaaaa ttaccttcaa caataagtga aaaatcactt ggaggatatc  160620
ctgttgataa aactatggat gaatatacag ttcatttaaa tggacgtcat tattattcca  160680
actcaaaatt tgctttttta ccaactaaaa agcctactcc cgaaataaac tacatgtaca  160740
gttgtccata ttttaatttg gataatatct atgctggaac gataaccatg tactggtata  160800
gaaatgatca tataagtaat gaccgccttg aatcaatatg tgctcaggcg gccagaatat  160860
taggaagggc taaataatta tttgttcgta tacatctcta gatatcgata tacaccctca  160920
aaaccctcgt tgaattcgtc gatgagggtt ttcttatctt cttgagttaa ttcagaaaca  160980
attttacgga atgaattttg atttaacttt ctaccttcat gcgttactcc aatctcattt  161040
agaaatgcaa taaaattagc acgattctca acaatatctt ctctggaaaa tttaatcaaa  161100
atagatgcaa cagtaataat ttcacgaact gtatcaatgt ttttattcat taactatacc  161160
actcaattag ttgactttgt tataatatca tcagacgctt gatttgtaaa ctggtctgtg  161220
taattttctt caaaaaattt ttctacgaat tccttgaacg attcacgttc ctgagctaca  161280
ttatgctcga ttacctttc aagattatga ctcattcgaa ataatcttca atttcataat  161340
catggacata aatcattata gtttttaata catcatcaat attttttcct ggagctggaa  161400
ttacgtaaaa ataccctgct tttgagaggt ctttataagt tccaatcaag aaatcattat  161460
tctcaagatg taactcttca actaattcat tgacaattga atggtatagg tttggcagaa  161520
acttatatag cttttctaga atatcaattt tgaatgtata ttgaaccacg gactgagaat  161580
caataatcat agaccttccc cttatgtttc tgtttgcgat tagattcttt aaacgctttc  161640
ttcttatcct tatgaacaga agctttatta aaattatgct ttgcgactaa attgttcata  161700
gtgctgaatt acctctctta aacatttgca tgtgaatgaa aactttttag ctacaccaca  161760
ttcaaatata tgttctctta aatcgcgtgt atcggtatat cccatctcaa caataaaatg  161820
ccgtattaga tttttatctt tatcgtttag agaattaaaa taatcagatt ttgaattaat  161880
ttccctggcc aaattgaatc accttcagtt gacgttttaa ctcttttatc atctcttcgt  161940
tcatcgcaat ataaagatcg cgtagagcag gttttagcat tccatttact ggagaactaa  162000
atggacatac ataatctttt cctacgagct ttttagtgaa ttccatatca cagaactgaa  162060
atcccggctc attggtataa attccccaat tagttgacat cattttattg gcatattcca  162120
gtgcctggat ttgattcata attccatcaa tttgaaactt tttaatattc attagtaaag  162180
gtcctcagag taaagttctt tttcactacc acgttcaata cttacttgtc cagcgtaagt  162240
tgcaataatc attgcttctt cacgtgtcca ataattacta tattggtcaa taaacccttg  162300
gtcatcatca caaacttgct gagtaactaa ttgaggttta actacatcta aaacttctgc  162360
catatcttta gaataatgac gagcacctgg aataataaga gttcgtccat cttttaattt  162420
aaaacggttg gctgcgcaaa caattcgtcg ttgatacttt tggttttcat cccagtacgc  162480
agtctgccaa cagatttcag gaacttcttt cagaatatct tcttctgtgc atttataacc  162540
atgcgcttta aatttttcaa caagactttc tggagtttca cgagataaag gaacattcag  162600
catttttaaa cgattgataa atgggttcat ttaaaccatc ctttaatacg ctgccacaaa  162660
gttttctgtt gagctttgtt gacgccaatt gagcgaataa ccggttgaga ttcctggaat  162720
tctttataat cagcaaggta aatttcgtaa gctgcatccg taaatgaact tatcgctgcc  162780
ataaaattat tgcgaatacc tactggagca tctttacttt cacgaatgat catgtattta  162840
ccagtcttaa tctttacgat agttccaaga taagctccat ggtaccaaat atcccaaccc  162900
tcttgagtag gttctgcgca acgacgaagt tcattgacaa tttctaactt gtttattatt  162960
tattcctcac agttcagatg ctacagtgat tacagcttca atgttttctg ccgagcgttt  163020
aatgtcaaga tacacattac cgtttttagc gattttacat gacattccga tgtcagtaaa  163080
tttctgaata tgatgttcca tcattttgta tccaaaaatt cgcatatttc cattgttatt  163140
```

```
aatttcaaaa ttacgaattc cgttagtgcg tttttctaaa atagcaagat aattactacg  163200
ataaatttca accttttaa gaacaaatcc atttttatct aaaagtttta acatgaggtc  163260
tttatcttct tccatatcgg aagtaatctc gcgagcttta cgagttgctc gtttttcag  163320
cagttccgga gcattttcct gtgcatataa agttgctgca tttgaaataa tatcctgagc  163380
ttcaccagta atgattaatc catcaccaga tttctccacc aggccttttt taatcaatac  163440
cccaatatta ctattaacta ctgcgttacc taaatctgga tgcacctcac gaacttctgc  163500
agctgtaatg aaatctttct tagcaatggt aattaaaatc gtagcagttt tttcattcag  163560
aacatcgtta gaagctttga tgatgtaagt tactttagac attttctaat ctccgtaatt  163620
ctgtatcagt agttgatagt tgtatagtac cacagtatgc tttggttgta aaccgttttg  163680
tgaaaaaatt tttaaaataa aaaagggaga gcctcggctc tccctaaaat tactgcatga  163740
ctgtgataac tgtcatgata acacgttgaa ttccgaacgc aagaagacct cctgctacgg  163800
ctggaacaac gcctaaaccc gccagtaaaa tgctaccaga tactaatgca gcgcttgtaa  163860
taccaatgaa tggactcatt tgatttcctc taaatctttg gtgtattcag taactacatc  163920
agtagttttc caatattcgt tttcttcttt tttagcttta gcttcttcag caagtttctt  163980
tgcttcatcg gaagtcatat gaaaaatatt cattccaact agtttatcaa cataagaaga  164040
atacatatcg attttcgaaa gttcttcggt cagttcttta cgagttttac cctgtacaac  164100
aatttcacct gaaattactt tcttaatgaa atgtgctttg gcaaaggcta aacgaaaagc  164160
tgactcagtt tctttaattt tgttatcaat tcgtttttgg acataagttt tacgaacttc  164220
aacaaagtct ttaattaaat caactacgtt atcgtaaact tgcagctttc ctttctcatt  164280
aataaccgta atattctggg aacgacgctc aatcagtccg aagtctttca taatttttgc  164340
atggcgttct tcttcgttat cgctcaaaga atattctttg cggaatttaa ctttgaagcc  164400
aaaaccatgc tcaccacaag catcatccca tgtaatgaag cctttatttt caagtgggtc  164460
taagatttta ctcacataag tttcacgatc atacttatac ggaatctcag tgatatgcat  164520
ttgagttcgt gaagtaaact tatatgttcc acgaatttca tattgcccat caatttcaac  164580
gacttcacca cgaaattctg ggaattctac tttcggttta gttactttct ttccttgaag  164640
agcttgcagt acagctttct tgacagaaga aacactatga ggaagaatgt aagttgcata  164700
accagttgca ataccggaaa cgccattaag aagaacagta ggaataatag gcaaatagaa  164760
agcaggcgga atgtgttctt tatcttgatg taccggagca tattcagtat ctttatatac  164820
gttatagaaa tttttactta cacgagcaaa aatataacga cttgccgctg cctttttggac  164880
agtacgagaa ccaaagtttc cttgaccatc taacagagga aagttattat tccaagtatt  164940
agccatcaaa gcacctgcgt cttgtgcaga gttttcacca tgatgatatc caaggtccgc  165000
tacaccacct gcaatagaag cgagtttgtg aaacttatct ttatttcctc gtgccaaatc  165060
aagagctcga gcaataacaa atcgttgaac tggcttaaat ccatcaatca tatttgggat  165120
agcacgattt tcaaccgtgt acatagcata agccaatgct tcattatcaa tgatactttt  165180
taaatcgcga ttattcagtt gcataaattt accatactag tgaatgtagt gccataataa  165240
catcagaaat gaaaagcacg acttgaatta atccgaacat tactccgtaa tatagtgcta  165300
ccaataaagc agcaagggct aatgaatagc ccaagatttt cttaatcatt agataacaac  165360
acaaatgtta aatatgcaca catacctgg gctaaagctt gtgaaaacac actgctagca  165420
tcgatacaga tagttaaaac acatgctact atccaacaaa taaatgaaat aactcctaat  165480
aattttgcaa tattcatatt ttcctcactg gcgtccgaag acgcctttag ttttaagatt  165540
gttacgatag aactgcatca cgtgttcgtt atggaaatta ctcattaata tgcctgtaaa  165600
acaaatttaa agttatcagc caacatacgg ttcatttctt cgagtgtttg atactcagaa  165660
tgatgattac gagtaaacgc caaagctagc tgaccttttc caaatcccgt cgttagaggt  165720
ttcatcttag aagcaggcag ataaaacact gtgtatggaa cattgttatt tgcaatagta  165780
cgcgcaagtt gagaccggcg ttgacgaata tgacttaaaa ccgcactgaa tccttgctta  165840
gaacgctgat tacctacata aaatcgtgca gatacgcatg gattactaaa tggaccaccg  165900
agtttactca ctaaaaagta aaatccaggt ttagataaaa tatctttatg cggagttcct  165960
aaaaaccatt caccacccctt gattgtacca ataacagtag cgcctgcatc attcagatca  166020
gtaacagtca tatatttcat attaatttcc tctaaattat tttctactcc aaggccgcat  166080
gaatacacac ggccattaaa ttactcgtcg cagtcgacgc tcaattccca aaactcttct  166140
acagtataag tttcagtatc attttcaata cagaaacgtt cattactatt atttgctaaa  166200
gtagcattaa ctgtcatttt ttcgctagtg ctcttaagag gtgaaatacg aattaactga  166260
tcaccgttat ctaaacaaaa aatttcacca actttacat ctttaaaact tttcataatt  166320
cacctcaagg agtataaaat ccaaatgcag ttgttgacca tcccatccaa tatggaaaat  166380
ttacaccaat gtaaaacata agaatataaa accaaccgct cagcaaattc atcattttac  166440
accattccaa attgtttcaa ccacggattt taaaccattt tgatgaatat ccattcctac  166500
taccgccatc aaataaattc caactacaac tgaacctaag gcaaaaaatca gcatgaaaat  166560
gaataaagcc ggaaaaatat tatcgaaaaa ccattcaata aatgtaaaag cactgcgttt  166620
acgttcatat tttcctcaca taaatccaaa gtaaacgttt aatacatcaa tcattaaaac  166680
gattgggaat atactcaaaa ctattagtat tataactaca ttccatatag ctttaataat  166740
ctttttcatt ttctgttcct ccatagttga tagggtaata gtaccacgga agaacagtct  166800
tgtaaacaac ttttttaaaa atattcgtaa taaatgtgaa taccaactac taccgctgaa  166860
acctgtgcaa cccaccacgc acaagcaata agtacagaat tcaaaatttt cataataacc  166920
tcattacaaa agtaaatgtt aaacaaatta ctggaatact aattaaccaa acaaaacacc  166980
accataatga actcatagtt caatctcagc gattttcatt ttattctcca aatccgtatc  167040
agtagttgat agttgtatag taccacggtc cttgtggtat gtaaactgtt ttgtgaaatt  167100
ttttaaatgg aaagatacca tccgttgtag ttgcttttc ttacaacttt acgaaggtct  167160
tctctgtcac cgatgaactt cggagtgtac tggatgacac ctggatgaat ttctttagtg  167220
ttgaatataa ttatacagtc agcgacttga tgatttagaa tgggccctag atttattcca  167280
gaaccatatg gatactctcc gctgcatccc gttgttaccg aaatccaacg tgagtcagtt  167340
tgatgtgtct taacttctac acgaagcccg cagtattttg gatgagccaa tacatcccat  167400
gcatatgtgt acggatcatc gacatcctct tggcctttat tgacatatcc actcaaccaa  167460
tctgccacaa aaaactctgc gtacacagcg atacggcatc tttcgataac ttctgcctta  167520
tcttgatttg ggttttgttt taaagagtat cttgcagtat cagcaatttt gaccttcatt  167580
tcacaggtca agtcactgtt cgatagggta aatgtcggaa tctgaaatag tctctgtaac  167640
ccaggattcg ttttctgcat ttaaactttc ctttatgtcg gaatcaccga tattcatata  167700
aatcataatt tctcttaaaa caaaaggccg aagcccttta ttttacttga attgtgcaat  167760
tcttttctct agacattcag cataagattt cattgagatg aactgcgaaa gtagcagttc  167820
ttgctcaact gcgctaactg ttagaaactt tgcgctttct aaaaatttgc tcagtgcatt  167880
```

-continued

```
aattttgagc attaattgat cgtattcttc ttttactcgt gcttgataag ctaacataat  167940
tttccttagt taagggccga agccttattt aaattgttca gtaacgtctt caactacttc  168000
atattggcag gtacgcattt tagcatcgtt gtaatcaatc ggaattgata ctacatcgcg  168060
aggatgaact ttaactttta caactcggct ggttgaacta ccaaagtgac gaatataaga  168120
tttagaacac acatgcaaac cacgagaaca agtttgtgta tcatcgtcat tcacacgagt  168180
acgtggcatt ttaactactt tacccggact gttatcaaag gtgtttgagt gacagtcaaa  168240
gtaattgctg cgaactactt tccaagcata gaagtaacca tcttctgtaa tttcaatatc  168300
gtttgctacc aagaaatcaa agagtcgaga taccgctttt tggcttgggt tttccaacag  168360
attttccaag aacggaaaat aaaattcaaa gttttcgcct ttttccatcg agtcaagaat  168420
acgatcaacc aaaccagacc gcaattcaat attttgatag aacaagcttc caccttcaat  168480
tcgaacatcg ccggaaatat atttttcaac agcacgacga acattaattt tttgtgccgc  168540
ttcttccaac ttatccgcta caagcagatt aagaatttcc tggaagtttg aatgagtatt  168600
aggagttgcg ttataagtta cgccatcaac agtaattgaa atgaattttt tagatgcatt  168660
ccaaataatg tcagatttag caactggagc aataactgca tcgctattaa ctttaactgt  168720
aatatcaccg ctaatagtaa ctttagggcg tttagcttct tcagcatttt tcaaaacacg  168780
acggattgtg tcaaccgata caccttgcca atcagccaat tcctgttggg tgtaattacc  168840
acttgaatac agtttaacaa tttcagcttg ttcgtttttg gtcaggcatt taatattgta  168900
cat                                                                168903

SEQ ID NO: 6          moltype = DNA  length = 32
FEATURE               Location/Qualifiers
source                1..32
                      mol_type = other DNA
                      organism = synthetic construct
SEQUENCE: 6
cgaatgacca ggcatttacc gaccagccca tc                                32

SEQ ID NO: 7          moltype = DNA  length = 32
FEATURE               Location/Qualifiers
source                1..32
                      mol_type = other DNA
                      organism = synthetic construct
SEQUENCE: 7
agtgggaagg gttgcaggac accgtctttg cc                                32

SEQ ID NO: 8          moltype = DNA  length = 32
FEATURE               Location/Qualifiers
source                1..32
                      mol_type = other DNA
                      organism = synthetic construct
SEQUENCE: 8
ccgatgttac cttcctgaat caaatccgcc tg                                32

SEQ ID NO: 9          moltype = DNA  length = 32
FEATURE               Location/Qualifiers
source                1..32
                      mol_type = other DNA
                      organism = synthetic construct
SEQUENCE: 9
tgattgacgg ctacggtaaa ccggcaacgt tc                                32

SEQ ID NO: 10         moltype = DNA  length = 32
FEATURE               Location/Qualifiers
source                1..32
                      mol_type = other DNA
                      organism = synthetic construct
SEQUENCE: 10
gctgttaacg tacgtaccgc gccgcatccg gc                                32
```